US009308183B2

(12) United States Patent
Heers et al.

(10) Patent No.: US 9,308,183 B2

(45) Date of Patent: Apr. 12, 2016

(54) THERAPY FOR HYPEREXCITABILITY DISORDERS

(75) Inventors: Cara Heers, Monheim (DE); Thomas Stoehr, Monheim (DE); Bettina Beyreuther, Düsseldorf (DE)

(73) Assignee: UCB PHARMA GMBH, Monheim (DE)

( * ) Notice: Subject to any disclaimer, the term of this patent is extended or adjusted under 35 U.S.C. 154(b) by 1077 days.

(21) Appl. No.: 12/306,953

(22) PCT Filed: Jun. 29, 2007

(86) PCT No.: PCT/EP2007/005806

§ 371 (c)(1), (2), (4) Date: Dec. 30, 2008

(87) PCT Pub. No.: WO2008/000513

PCT Pub. Date: Jan. 3, 2008

(65) Prior Publication Data

US 2010/0324144 A1 Dec. 23, 2010

(30) Foreign Application Priority Data

| | | |
|---|---|---|
| Jun. 30, 2006 | (EP) | 06013655 |
| Oct. 12, 2006 | (EP) | 06021469 |
| Oct. 12, 2006 | (EP) | 06021470 |
| Nov. 22, 2006 | (EP) | 06024241 |

(51) Int. Cl.

| | |
|---|---|
| ***A61K 31/165*** | (2006.01) |
| ***G01N 33/68*** | (2006.01) |
| ***A61K 31/19*** | (2006.01) |
| ***A61K 31/195*** | (2006.01) |
| ***A61K 31/35*** | (2006.01) |
| ***A61K 31/4015*** | (2006.01) |
| ***A61K 31/4166*** | (2006.01) |
| ***A61K 31/53*** | (2006.01) |
| ***A61K 31/55*** | (2006.01) |
| ***A61K 38/04*** | (2006.01) |
| ***A61K 38/05*** | (2006.01) |
| ***A61K 45/06*** | (2006.01) |

(52) U.S. Cl.

CPC ............... *A61K 31/165* (2013.01); *A61K 31/19* (2013.01); *A61K 31/195* (2013.01); *A61K 31/35* (2013.01); *A61K 31/4015* (2013.01); *A61K 31/4166* (2013.01); *A61K 31/53* (2013.01); *A61K 31/55* (2013.01); *A61K 38/04* (2013.01); *A61K 38/05* (2013.01); *A61K 45/06* (2013.01); *G01N 33/6896* (2013.01); *C12N 2503/02* (2013.01); *G01N 2500/04* (2013.01); *G01N 2800/2835* (2013.01); *G01N 2800/2842* (2013.01); *G01N 2800/2857* (2013.01); *G01N 2800/302* (2013.01); *G01N 2800/52* (2013.01)

(58) Field of Classification Search

None

See application file for complete search history.

(56) References Cited

U.S. PATENT DOCUMENTS

| | | | | |
|---|---|---|---|---|
| 4,094,992 | A * | 6/1978 | Kaplan et al. | 514/620 |
| 5,378,729 | A | 1/1995 | Kohn et al. | 514/231.2 |
| 5,585,358 | A | 12/1996 | Bialer et al. | 514/19 |
| 5,773,475 | A * | 6/1998 | Kohn | 514/616 |
| 6,083,941 | A | 7/2000 | Farb | 514/177 |
| 6,277,825 | B1 | 8/2001 | Olivera et al. | 514/13 |
| 6,803,481 | B2 | 10/2004 | Selve | 560/157 |
| 7,416,864 | B2 | 8/2008 | Stoehr | 435/106 |
| 7,427,601 | B2 | 9/2008 | Stoehr | 514/19 |
| 2002/0052418 | A1 | 5/2002 | Shirvan et al. | 514/626 |
| 2002/0119944 | A1 | 8/2002 | Aguera et al. | 514/44 |
| 2004/0101582 | A1 | 5/2004 | Wolicki | 424/760 |
| 2004/0204495 | A1 | 10/2004 | Shirvan et al. | 514/616 |
| 2004/0220077 | A1 | 11/2004 | Selve | 514/1 |
| 2005/0085423 | A1 | 4/2005 | Selve | 514/17 |
| 2005/0106143 | A1 | 5/2005 | Giraudon et al. | 424/145.1 |
| 2005/0209163 | A1 | 9/2005 | Stoehr | 514/19 |
| 2005/0277596 | A1 | 12/2005 | Stöhr | 514/19 |
| 2006/0009384 | A1 | 1/2006 | Rudd et al. | 514/12 |
| 2006/0046957 | A1 | 3/2006 | Beyreuther et al. | 514/7 |
| 2006/0100157 | A1 | 5/2006 | Rauschkolb-Loffler et al. | 514/18 |
| 2006/0135437 | A1 | 6/2006 | Stoehr et al. | 514/19 |
| 2006/0252749 | A1 | 11/2006 | Stohr | 514/220 |
| 2007/0042969 | A1 | 2/2007 | Rauschkolb-Loffler et al. | 514/19 |
| 2007/0043120 | A1 | 2/2007 | Beyreuther et al. | 514/616 |
| 2007/0048372 | A1 | 3/2007 | Beyreuther et al. | 424/464 |
| 2007/0054962 | A1 | 3/2007 | Selve | 514/575 |
| 2007/0197657 | A1 | 8/2007 | Beyreuther et al. | 514/616 |
| 2008/0027137 | A1 | 1/2008 | Riedner et al. | 514/561 |
| 2008/0280835 | A1 | 11/2008 | Beyreuther et al. | 514/2 |
| 2008/0287545 | A1 | 11/2008 | Scheller et al. | 514/616 |

(Continued)

FOREIGN PATENT DOCUMENTS

| | | | |
|---|---|---|---|
| EP | 0 169 672 | 1/1986 | C12N 15/00 |
| EP | 1 537 862 | 6/2005 | A61K 31/165 |

(Continued)

OTHER PUBLICATIONS

Graves et al. "Neurological Channelopathies". Postgrad Med J, 2005; 81:20-32.*

(Continued)

*Primary Examiner* — Leslie A. Royds Draper

(74) *Attorney, Agent, or Firm* — Harness, Dickey and Pierce, P.L.C.

(57) ABSTRACT

The present invention is directed to the use of a class of peptide compounds for treating diseases associated with hyperexcitability. The present invention is also directed to the use of a class of peptide compounds for treating diseases associated with dysfunction of an ion channel.

20 Claims, 6 Drawing Sheets

(56) References Cited

U.S. PATENT DOCUMENTS

| | | | | |
|---|---|---|---|---|
| 2009/0018197 | A1 | 1/2009 | Rudd et al. | 514/563 |
| 2009/0018198 | A1 | 1/2009 | Stohr | 514/563 |
| 2009/0241205 | A1 | 9/2009 | Beyreuther et al. | 800/9 |
| 2010/0029543 | A1 | 2/2010 | Beyreuther et al. | 514/2 |
| 2010/0099770 | A1 | 4/2010 | Selve | 514/616 |
| 2010/0240576 | A1 | 9/2010 | Stoehr | 514/17.7 |
| 2010/0256179 | A1 | 10/2010 | Stöhr et al. | 514/327 |
| 2010/0256241 | A1 | 10/2010 | Stöhr et al. | 562/553 |
| 2010/0260716 | A1 | 10/2010 | Stöhr et al. | 424/85.6 |
| 2010/0273714 | A1 | 10/2010 | Stoehr | 514/17.7 |
| 2011/0082211 | A1 | 4/2011 | Selve | 514/616 |
| 2011/0130350 | A1 | 6/2011 | Riedner et al. | 514/21.91 |
| 2012/0225119 | A1 | 9/2012 | Beyreuther et al. | 424/456 |
| 2012/0238614 | A1 | 9/2012 | Stöhr | 514/424 |
| 2013/0251803 | A1 | 9/2013 | Cawello et al. | |
| 2013/0251813 | A1 | 9/2013 | Cawello et al. | |
| 2014/0066515 | A1 | 3/2014 | Heers et al. | |
| 2014/0088168 | A1 | 3/2014 | Stohr | |
| 2014/0128377 | A1 | 5/2014 | Stohr | |
| 2014/0128378 | A1 | 5/2014 | Stohr | |

FOREIGN PATENT DOCUMENTS

| | | | |
|---|---|---|---|
| EP | 1 541 138 | 6/2005 | A61K 31/165 |
| EP | 1 604 654 | 12/2005 | A61K 31/165 |
| EP | 1 604 655 | 12/2005 | A61K 31/165 |
| EP | 1 754 476 | 2/2007 | A61K 31/165 |
| WO | WO 00/00463 | 1/2000 | C07C 237/06 |
| WO | WO 00/51586 | 9/2000 | A61K 31/00 |
| WO | WO 02/15922 | 2/2002 | A61K 38/00 |
| WO | WO 02/42256 | 5/2002 | C07C 237/06 |
| WO | WO 02/074297 | 9/2002 | A61K 31/165 |
| WO | WO 02/074784 | 9/2002 | |
| WO | WO 2004/066987 | 8/2004 | A61K 31/00 |
| WO | WO 2004/066990 | 8/2004 | A61K 31/135 |
| WO | WO 2005/053667 | 6/2005 | A61K 31/165 |
| WO | WO 2006/037574 | 4/2006 | C07C 275/16 |
| WO | WO 2006/079547 | 8/2006 | A61K 31/165 |

OTHER PUBLICATIONS

Vicart et al. "Human Skeletal Muscle Sodium Channelopathies". Neurol Sci. 2005; 26:194-202.*

Centre for Genetics Education [Online]. "Autosomal Dominant Inheritance—Traditional Patterns of Inheritance". [Retrieved Mar. 22, 2012]. Retrieved from the Internet: <URL: http://www.genetics.edu.au>. 2007. pp. 1-4.*

Betts T. "Epilepsy and Stress". BMJ. Aug. 15, 1992; 305:378-379.*

Pusch M. "Myotonia Caused by Mutations in the Muscle Chloride Channel Gene CLCN1". Human Mutation. 2002; 19:423-434.*

Meyer-Kleine et al. "A Recurrent 14bp Deletion in the CLCN1 Gene Associated with Generalized Myotonia (Becker)". Human Molecular Genetics. 1994; 3(6):1015-1016.*

Ryan et al. "A Novel Alteration of Muscle Chloride Channel Gating in Myotonia Levior". Journal of Physiology. 2002; 545(2):345-354.*

Errington et al. "Seeking a Mechanism of Action for the Novel Anticonvulsant Lacosamide". Neuropharmacology. 2006; 50:1016-1029.*

Akiba et al. (2003) "Stable expression and characterization of human PN1 and PN3 sodium channels." Receptors & Channels 9:291-299.

Alekov et al. (2000) "A sodium channel mutation causing epilepsy in man exhibits subtle defects in fast inactivation and activation in vitro." J. Physiol. 592.3:533-539.

Amir et al. (2006) "The role of sodium channels in chronic inflammatory and neuropathic pain." J. Pain 7(5 Suppl. 3):S1-S29.

Andurkar et al. (1999) "The anticonsulvant activities of n-benzyl 3-methoxypropionamides." Bioorg. Med. Chem. 7(11):2381-2389.

Andurkar et al. (2001) "Synthesis and structural studies of aza analogues of functionalized amino acids: new anticonvulsant agents." J. Med. Chem. 44:1475-1478.

Backonja (2002) "Use of anticonvulsants for treatment of neuropathic pain." Neurology 59:S14-S17.

Backonja (2003) "Defining neuropathic pain." Anesth. Analg. 97:785-790.

Barela et al. (2006) "An epilepsy mutation in the sodium channel SCN1A that decreases channel excitability." J. Neurosci. 26(10):2714-2723.

Beyreuther (2004) "Pharmacology of SPM 927 and its relevance to clinical practice for neuropathic pain" Presented at Visiongain Pain Management, 2004.

Beyreuther et al. (2007) "Lacosamide: A review of preclinical properties." CNS Drug Rev. 13(1):21-42.

Bialer et al. (2001) "Progress report on new antiepileptic drugs: a summary of the Fifth Eilat Conference (EILAT V)." Epilepsy Res. 43:11-58.

Bialer et al. (2002) "Progress report on new antiepileptic drugs: a summary of the Sixth Eilat Conference (EILAT VI)." Epilepsy Res. 51:31-71.

Blackburn-Munro et al. (2002) "A comparison of the anti-nociceptive effects of voltage-activated $Na^+$channel blockers in the formalin test." Eur. J. Pharmacol. 445:231-238.

Brodie (1996) "Lamotrigine—an update." Can. J. Neurol. Sci. 23(Suppl. 2):S6-S9.

Cannon (2006) "Pathomechanisms in channelopathies of skeletal muscle and brain." Annu. Rev. Neurosci. 29:387-415 (PubMed Abstract Only).

Choi et al. (1996) "Synthesis and anticonvulsant activities of *N*-benzyl-2-acetamidopropionamide derivatives." J. Med. Chem. 39(9):1907-1916.

Citrome (2003) "Schizophrenia and Valproate." Psychopharmacol. Bull. 37(Suppl. 2):74-88.

Czech, et al. (2004) "Reduction of hippocampal collapsing response response mediated protein-2 in patients with mesial temporal lobe epilepsy." Neuro. Chem. Res. 29(12):2189-2196 (PubMed Abstract Only).

Dirksen, et al. (2004) "District effects on Ca2+ handling caused by malignant hyperthermia and central core disease mutations in RyR1." Biophys J. 87(5):3193-3204.

Ellerkmann et al. (2003) "Molecular and functional changes in voltage-dependent Na(+) channels following pilocarpine-induced status epilepticus in rat dentate granule cells." Neurosci. 119(2):323-333.

Elliott (1997) "Slow $Na^+$channel inactivation and bursting discharge in a simple model axon: implications for neuropathic pain." Brain Res. 754:221-226.

Erichsen & Blackburn-Munro (2002) "Pharmacological characterisation of the spared nerve injury model of neuropathic pain." Pain 98:151-161.

Errington et al. (2005) "Lacosamide has a unique molecular mode of action" Poster presented at AES Scientific Exhibit, Dec. 2-5, 2005.

Errington et al. (2006) "Seeking a mechanism of action for the novel anticonvulsant lacosamide." Neuropharmacology, 50:1016-1029 (PubMed Abstract Only).

Farber et al. (2002) "Antiepileptic drugs and agents that inhibit voltage-gated sodium channels prevent NMDA antagonist neurotoxicity." Molecular Psychiatry, 7(7):726-733 (PubMed Abstract Only).

Field et al. (1997) "Gabapentin (neurontin) and S-(+)-3-isobutylgaba represent a novel class of selective antihyperalgesic agents." Br. J. Pharmacol. 121:1513-1522.

Freeman (2005) "Autonomic peripheral neuropathy." The Lancet, Lancet Limited 365(9466):1259-1270 (PubMed Abstract Only).

Heers et al. (2006) "The preclinical profile of the novel anticonvulsant lacosamide" Poster presented at European Congress on Epileptology 2006.

Hovinga (2003)"Erlosamide Schwarz Pharma." IDrugs 6(5):479-485.

Hurley et al. (2002) "Gabapentin and pregabalin can interact synergistically with naproxen to produce antihyperalgesia." Anesthesiology 97:1263-1273.

Ilyin et al. (2005) "V102862 (Co 102862): a potent, broad-spectrum state-dependent blocker of mammalian voltage-gated sodium channels." Br. J. Pharmacol. 144:801-812.

Jain (2000) "A guide to drug evaluation for chronic pain." Emerging Drugs 5(2):241-257.

(56) References Cited

OTHER PUBLICATIONS

Jann (2004) "Implications for atypical antipsychotics in the treatment of schizophrenia: neurocognition effects and a neuroprotective hypothesis." Pharmacother. 24:1759-1783.
Jensen (2000) "Assessment and treatment of neuropathic pain." Eur. J. Neurol. 7(Suppl. 3):3-4, abst. MT-9.
Jurkat-Rott (2005) "Muscle channelopathies and critical points in functional and genetic studies."J. Clin. Invest., 115(8):2000-2009 (PubMed Abstract Only).
Kalso (2005) "Sodium channel blockers in neuropathic pain." Curr. Pharm. Design 11:3005-3011.
Kass (2005) "The channelopathies: novel insights into molecular and genetic mechanisms of human disease." J. Clin. Invest., 115(8):1986-1989 (PubMed Abstract Only).
Köhling (2002) "Voltage-gated Sodium Channels in Epilepsy." Epilepsia 43(11):1278-1295.
Kohn et al. (1988) "Marked stereospecificity in a new class of anticonvulsant." Brain Res. 457:371-375.
Lai et al. (2004) "Voltage-gated sodium channels and hyperalgesia." Ann. Rev. Pharmacol. Toxicol. 44:371-397.
Lehmann-Horn et al. (2002) "Periodic paralysis: understanding channelopathies." Curr. Neurology and Neuroscience Reports, 2(1):61-69 (PubMed Abstract Only).
LeTiran et al. (2001) "Functionalized amino acid anticonvulsants: synthesis and pharmacological evaluation of conformationally restricted analogues." Bioorganic & Medicinal Chemistry 9:2693-2708.
Lossin et al. (2003) "Epilepsy-associated dysfunction in the voltage-gated neuronal sodium channel SCN1A." J. Neurosci. 23(36):11289-11295.
Macres (2000) "Understanding neuropathic pain" www.spineuniverse.com/displayarticle.php/article1614. html.
Mar. (1985) Advanced Organic Chemistry: Reactions, Mechanisms, and Structure. New York: Wiley, pp. 16-18.
McCleane (2003) "Pharmacological management of neuropathic pain." CNS Drugs 17(14):1031-1043.
McDougall (2006) "Arthritis and pain. Neurogenic origin of joint pain." Arthritis Res. Ther. 8:220-229.
McGivern, et al. (2004) "Voltage-gated calcium channels as targets for the treatment of chronic pain." Curr. Drug Targets. CNS and Neuro. Disorders 3(6) 457-478 (PubMed Abstract Only).
McNulty & Hanck (2004) "State-dependent mibefradil block of Na+ channels." Mol. Pharmacol. 66(6):1652-1661.
Meinardi (1995) in Levy et al. "Use of combined antiepileptic drug therapy." Antiepileptic Drugs, 4th ed., chap. 6:91-97; Raven Press, Ltd., New York.
Meisler et al. (2005) "Sodium channel mutations in epilepsy and other neurological disorders."J. Clin. Invest., 115(8):2010-7, PMID: 16075041 (PubMed Abstract Only).
Morrow et al. (2001) "Antinociceptive properties of the anticonvulsant SPM927 (harkoseride) in rat." Soc. Neurosci. Conf. Abst. 508.
Parent, et al. (2006) "Prolonged seizures recruit caudal subventricular zone glial progenitors into the injured hippocampus." HIPPOCAMPUS 16(3):321-328 (PubMed Abstract Only).
Patel et al.(2001) "The effects of $GABA_B$ agonists and gabapentin on mechanical hyperalgesia in models of neuropathic and inflammatory pain in the rat." Pain 90:217-226.
Pollard et al. (2006) "Antiepileptic drug in development." Lancet Neuro. 5(12):1064-1067 (PubMed Abstract Only).
Priestley (2004) "Voltage-gated sodium channels and pain." Curr. Drug Targets—CNS & Neurol. Disorders 3:441-456.
Rainnie et al. (2004) "Corticotrophin releasing factor-induced synaptic plasticity in the amygdala translates stress into emotional disorders." J. Neruoscience 24(14):3471-3479 (PubMed Abstract Only).
Reckziegel et al. (1998) "Electrophysiological characterization of Na+ currents in acutely isolated human hippocampal dentate granule cells." J. Physiol. 509.1:139-150.
Remy et al. (2004) "Modulation of voltage-dependent sodium channels by the d-agonist SNC80 in acutely isolated rat hippocampal neurons." Neuropharmacol. 47:1102-1112.
Reynolds et al. (1981) "Single Drug or combination therapy of epilepsy?" Drugs, ADIS Int'l Ltd., 21:374-382.
Rhodes et al. (2005) "Sodium channel dysfunction in intractable childhood epilepsy with generalized tonic-clonic seizures." J. Physiol. 569.2:433-445.
Rogawski et al. (2006) "Diverse mechanisms of antiepileptic drugs in the development pipeline." Epilepsy Res. 69(3):273-294 (PubMed Abstract Only).
Rush, et al. (2006) "A single sodium channel mutation produces hyper-or hypoexcitability in different types of neurons." Proc. Natl. Acad. Sci. U.S.A. 103(21):8245-8250.
Sandtner et al. (2004) "Lidocaine: a foot in the door of the inner vestibule prevents ultra-slow inactivation of a voltage-gated sodium channel." Mol. Pharmacol. 66(3):648-657.
Sasaki et al. (2004) "Unexpected mexiletine responses of a mutant cardiac Na+ channel implicate the selectivity filter as a structural determinant of antiarrhythmic drug access." Mol. Pharmacol. 66(2):330-336.
Siep et al. (2002) "Sodium currents in striatal neurons from dystonic dt(sz) hamsters: altered response to lamotrigine." Neurobiol. Dis., 9(2):258-68 (PubMed Abstract Only).
Silver & Soderlund (2005) "State-dependent block of rat $Na_v$ 1.4 sodium channels expressed in xenopus oocytes by pyrazoline-type insecticides." Neurotoxicol. 26:397-406.
Sindrup & Jensen (1999) "Efficacy of pharmacological treatments of neuropathic pain: an update and effect related to mechanism of drug action." Pain 83:389-400.
Spampanato et al. (2001) "Functional effects of two voltage-gated sodium channel mutations that cause generalized epilepsy with febrile seizures plus type 2." J. Neurosci. 21(19):7481-7490.
Spampanato et al. (2004) "Increased neuronal firing in computer simulations of sodium channel mutations that cause generalized epilepsy with febrile seizures plus." J. Neurophysiol. 91:2040-2050.
Stables & Kupferberg (1997) in Avanzani et al. "Molecular and Cellular Targets for Antiepileptic Drugs", chap. 16, pp. 191-198; London: Libbey.
Stöhr et al. (2006) "Lacosamide displays potent antinociceptive effects in animal models for inflammatory pain." Eur. J. Pain 10:241-249.
Stoppini et al. (1991) A simple method for organotypic cultures of nervous tissue. J. Neurosci. Methods, 37(2):173-82 (PubMed Abstract Only).
Tan (2006) "Sodium channel variants in heart disease: expanding horizons." J. Cardiovasc. Electrophysiol. 17(Suppl.1): S151-157 (PubMed Abstract Only).
Vicart et al. (2005) Human skeletal muscle sodium channelopathies. Neurol Sci. 26(4):194-202 (PubMed Abstract Only).
Vreugdenhil (1992) "Enhancement of calcium currents in rat hippocampal CA1 neurons induced by kindling epileptogensis." Neuroscience 49(2):373-81 (PubMed Abstract Only).
Xie et al. (1995) "Interaction of the antiepileptic drug lamotrigine with recombinant rat brain type IIA Na+ channels and with native Na+ channels in rat hippocampal neurones." Pflügers Arch.-Eur. J. Physiol. 430:437-446.
Yang et al. (1994) "Human copper-zinc superoxide dismutase transgenic mice are highly resistant to perfusion injury after focal cerebral ischemia." Stroke 25(1): 165-170 (PubMed Abstract Only).
Rogawski et al. (2006) "Diverse mechanisms of antiepileptic drugs in the development pipeline." Epilepsy Res. 69(3)273-294 (PubMed abstract only).
Fisher, et al. (2003) "Trigeminal Neuralgia: current treatments and future developments." Expert Opin. Emerging Drugs 8(1):123-143.
Hovinga (2002) "Novel anticonvulsant medications in development." Expert Opin. Investig. Drugs 11(10) 1387-1406.
Doty, P., et al. "Lacosamide" (2007) *Neurotherapeutics*, 4:145-148.
Huang, C.J., et al. "Characterization of voltage-gated sodium-channel blockers by electrical stimulation and fluorescence detection of membrane potential" (2006) *Nature Biotechnology*, 24(4):439-446.
Kwiecinski, H., et al. "Treatment of myotonia with antiarrythmic drugs" (1992) *Acta Neurol Scand*, 86:371-375.

(56) References Cited

OTHER PUBLICATIONS

Lees, G., et al. "Stereoselective effects of the novel anticonvulsant lacosamide against 4-AP induced epileptiform activity in rat visual cortex in vitro" (2006) *Neuropharmacology*, 50:98-110.
Löscher, W.N., et al. "Morvan's syndrome: clinical, laboratory, and in vitro electrophysiological studies" (2004) *Muscle & Nerve*, pp. 157-163.
Stöhr, T., et al. "Lacosamide has a dual mode of actions; selective enhancement of sodium channel slow inactivation" (2007) *Journal of Pain*, 8(4):S32.
Stöhr, T., et al. "Lacosamide, a novel anti-convulsant drug, shows efficacy with a wide safety margin in rodent models for epilepsy" (2007) *Epilepsy Research*, 74:147-154.
Vetrugno, R., et al. "Continuous motor unit activity syndromes: a video-polysomnographic study" (2005) *Clinical Neurophysiology*, 116:2533-2541.
Office Action dated Feb. 11, 2004 issued in U.S. Appl. No. 10/344,885.
Office Action dated Sep. 11, 2006 issued in U.S. Appl. No. 11/149,181.
Office Action dated Sep. 21, 2006 issued in U.S. Appl. No. 11/145,965.
Office Action dated Sep. 27, 2006 issued in U.S. Appl. No. 10,466,295.
Office Action dated Nov. 28, 2006 issued in U.S. Appl. No. 11/002,414.
Office Action dated Dec. 27, 2006 issued in U.S. Appl. No. 11/342,140.
Office Action dated Dec. 28, 2006 issued in U.S. Appl. No. 11/089,441.
Office Action dated Feb. 5, 2007 issued in U.S. Appl. No. 11/149,181.
Office Action dated Aug. 8, 2007 issued in U.S. Appl. No. 10/466,295.
Office Action dated Oct. 29, 2007 issued in U.S. Appl. No. 11/342,140.
Office Action dated May 29, 2008 issued in U.S. Appl. No. 11/145,965.
Office Action dated Jun. 4, 2008 issued in U.S. Appl. No. 10/446,295.
Office Action dated Aug. 20, 2008 issued in U.S. Appl. No. 11/342,140.
Office Action dated Oct. 29, 2008 issued in U.S. Appl. No. 11/506,577.
Office Action dated Jan. 22, 2009 issued in U.S. Appl. No. 11/000,951.
Office Action dated Feb. 19, 2009 issued in U.S. Appl. No. 10/466,295.
Office Action dated Mar. 31, 2009 issued in U.S. Appl. No. 11/342,140.
Office Action dated May 12, 2009 issued in U.S. Appl. No. 11/506,577.
Office Action dated Jul. 22, 2009 issued in U.S. Appl. No. 10/466,295.
Office Action dated Oct. 21, 2009 issued in U.S. Appl. No. 11/342,140.
Office Action dated Dec. 17, 2009 issued in U.S. Appl. No. 11/506,577.
Office Action dated Feb. 3, 2010 issued in U.S. Appl. No. 11/507,110.
Office Action dated Apr. 15, 2010 issued in U.S. Appl. No. 12/188,419.
Office Action dated Aug. 19, 2010 issued in U.S. Appl. No. 11/507,110.
Office Action dated Apr. 7, 2011 issued in U.S. Appl. No. 12/304,023.
Office Action dated Jan. 10, 2012 issued in U.S. Appl. No. 12/304,023.
Office Action dated Aug. 15, 2012 issued in U.S. Appl. No. 13/442,212.
Office Action dated Jan. 7, 2013 issued in U.S. Appl. No. 13/442,212.
Office Action dated May 15, 2013 issued in U.S. Appl. No. 13/428,419.
Office Action dated May 20, 2013 issued in U.S. Appl. No. 13/442,212.
Office Action dated Jul. 29, 2013 issued in U.S. Appl. No. 11/342,140.
Office Action dated Sep. 9, 2013 issued in U.S. Appl. No. 12/304,023.
International Search Report and Written Opinion dated Jul. 8, 2008 issued in PCT Application No. PCT/EP2007/005806.
International Preliminary Report on Patentability dated Jan. 6, 2009 issued in PCT Application No. PCT/EP2007/005806.
Office Action dated Oct. 22, 2013 issued in U.S. Appl. No. 12/945,953.
Kubisch, C., et al. (1999), "KCNQ4, a Novel Potassium Channel Expressed in Sensory Outer Hair Cells, is Mutated in Dominant Deafness", *Cell*, 96: 437-446.
Olckers, A., et al. (1992), "Adult Muscle Sodium Channel α-Subunit is a Gene Candidate for Malignant Hyperthermia Susceptibility", *Genomics*, 14: 829-831.
Simon, D., et al. (1996), "Bartter's syndrome, hypokalaemic alkalosis with hypercalciuria, is caused by mutations in the Na—K—2Cl cotrasporter NKCC2" *Nature Genetics*, 13: 183-188.
Simon, D., et al. (1997), "Mutations in the chloride channel gene, CLCNKB, casue Bartter's syndrome type III", *Nature Genetics*, 171-178.
Vassilev, P., et al. (2001), "Polycystin-2 is a Novel Cation Channel Implicated in Defective Intracellular $Ca^{2+}$Homeostasis in Polycystic Kidney Disease", *Biochemical and BioPhysical Research Communications*, 282: 341-350.
Wang, Q., et al. (1995), "SCN5A Mutations Associated with an Inherited Cardiac Arrhythmia, Long QT Syndrome", *Cell*, 80: 805-811.

* cited by examiner

THERAPY FOR HYPEREXCITABILITY DISORDERS

CROSS-REFERENCE TO RELATED APPLICATIONS

The present application is the national stage under 35 U.S.C. §371 of International Patent Application No. PCT/EP2007/005806 filed on Jun. 29, 2007, which claims the priority of each of European Patent Applications No. EP 06 013 655 filed on Jun. 30, 2006, No. EP 06 021 469 filed on Oct. 12, 2006, No. EP 06 021 470 filed on Oct. 12, 2006, and No. EP 06 024 241 filed on Nov. 22, 2006. Each of the above referenced applications is incorporated herein by reference in its entirety.

REFERENCE TO A SEQUENCE LISTING

SEQ ID NO: 1 was submitted to the United States Patent and Trademark Office on a compact disc. The material on the compact disc is incorporated by reference herein in its entirety.

BACKGROUND

The present invention is directed to the use of a class of peptide compounds for treating diseases associated with hyperexcitability, such as diseases associated with a hyperexcitable tissue. The present invention is also directed to the use of a class of peptide compounds for treating diseases associated with dysfunction of an ion channel.

Certain peptides are known to exhibit central nervous system (CNS) activity and are useful in the treatment of epilepsy and other CNS disorders. These peptides are described in the U.S. Pat. No. 5,378,729 and in U.S. Pat. No. 5,773,475, which are hereby incorporated by reference.

WO 02/074297 relates to the use of peptidic compounds for the preparation of pharmaceutical compositions useful for the treatment of allodynia related to peripheral neuropathic pain. WO 02/074784 relates to the use of peptidic compounds showing antinociceptive properties for treating different types and symptoms of acute and chronic pain, especially non neuropathic inflammatory pain, e.g. rheumatoid arthritic pain or/and secondary inflammatory osteo-arthritic pain.

According to their mode of regulation, ion channels can be divided into voltage-gated ion channels and ligand-gated ion channels. Ligand-gated ion channels are also referred to as receptors. Examples for voltage-gated ion channels are voltage-gated sodium channels, voltage-gated calcium channels, voltage-gated potassium channels, and voltage-gated chloride channels. Examples for ligand-gated ion channels are nicotinic acetylcholine receptors, ryanodine receptors (calcium release channels), cyclic nucleotide-gated receptors, ATP-receptors, GABA-A receptors, glutamate-NMDA receptors, glycine-receptors, 5-HT3-receptors, and pH sensitive channels such as acid-sensing ion channel (ASIC), and TRP receptors.

Hyperexcitability is defined herein as an abnormal increase in responsiveness of a central or peripheral nervous system neuron to synaptic input. In addition, hyperexcitability is also referred to as an abnormal increase in responsiveness of any excitable membrane, such as a muscle cell membrane, to a physiological signal or to excitotoxicity caused by a pathophysiological signal.

Examples for hyperexcitable tissues are all innervated tissues such as central or peripheral nervous tissue, muscle tissue, and other organ tissue.

Examples for diseases associated with hyperexcitability are channelopathies, anxiety- and stress-diseases.

Hyperexcitability can be induced by dysfunction of ion channels. According to their mode of regulation, ion channels can be divided into voltage-gated ion channels and ligand-gated ion channels. Ligand-gated ion channels are also referred to as receptors. Examples for voltage-gated ion channels are voltage-gated sodium channels, voltage-gated calcium channels, voltage-gated potassium channels, and voltage-gated chloride channels. Examples for ligand-gated ion channels are nicotinic acetylcholine receptors, ryanodine receptors (calcium release channels), cyclic nucleotide-gated receptors, ATP-receptors, GABA-A receptors, glutamate-NMDA receptors, glycine-receptors, 5-HT3-receptors, and pH sensitive channels such as acid-sensing ion channel (ASIC), and TRP receptors.

Ion channel dysfunction may have genetic or other causes, such as tissue damage.

Diseases caused by one or more mutations of genes coding for ion channel subunits or proteins that regulate them are referred to as channelopathies. There are a large number of distinct dysfunctions known to be caused by ion channel mutations. They comprise a heterogenous group of usually hereditary disorders which in most cases are clinically characterized by episodes of disturbed excitability of nerve or muscle cells. The genes for the construction of ion channels are highly conserved amongst mammals and one condition, hyperkalemic periodic paralysis, was first identified in the descendants of Impressive, a pedigree race horse. Well known examples of identified channelopathies are diseases of the skeletal muscle (such as hyper-, hypo- and normokalemic (high, low and normal potassium blood concentrations) periodic paralysis, paroxysmal dystonia, myotonia congenita and paramyotonia congenita), central nervous disorders of excitability (such as episodic ataxias and several forms of inherited epilepsies), and cardiac arrhythmias (such as long QT syndromes).

Ion channels dysfunctions can also be caused by variations in ion channel genes that are not sufficiently severe to be classified as mutations, but instead are referred to as polymorphisms. Such polymorphisms may contribute to unique drug responses in carriers of these gene variants (Kass, R S, J Clin Invest (2005), 115:1986-1989).

Voltage-gated sodium channels are responsible for the generation and propagation of action potentials in excitable cells. The excitability of tissues depends mainly on the number of voltage-gated sodium channels that are available for activation. The fraction of sodium channels available for activation is regulated by fast inactivation, which occurs on a millisecond time scale, and slow inactivation occurring within seconds or minutes.

Mutations in genes coding for sodium channels are known to cause a number of characteristic diseases. Most inherited sodium channel mutations that are associated with human disease alter the inactivation process and hence alter the essential control of electrical-impulse duration that is effected by transition into the inactivated state (Jurkat-Rott, K, J Clin Invest (2005), 115:2000-2009). Most well characterised mutations are at the SCN4A sodium channel gene which codes for the alpha-subunit of the skeletal muscle sodium channel. Following diseases are listed in the OMIM database of NCBI for the SCN4A gene:

Cramps, familial, potassium-aggravated MIM: 603967
Hyperkalemic periodic paralysis MIM: 170500
Hypokalemic periodic paralysis MIM: 170400

Myotonia congenita, atypical, acetazolamide-responsive MIM: 608390

Paramyotonia congenita MIM: 168300.

Dystonia (literally, "abnormal muscle tone") is a generic term used to describe a neurological movement disorder involving involuntary, sustained muscle contractions. Dystonia may affect muscles throughout the body (generalised), in certain parts of the body (segmental), or may be confined to particular muscles or muscle groups (focal). Primary dystonia is caused by a pathology of the central nervous system, likely originating in those parts of the brain concerned with motor function, such as the basal ganglia. An example for dystonia associated with dysfunction of the voltage-gated sodium channel is paroxysmal dystonia.

Muscle weakness (or "lack of strength") is the inability to exert force with ones muscles to the degree that would be expected given the individual's general physical fitness. A test of strength is often used during a diagnosis of a muscular disorder before the etiology can be identified.

The term subsumes two other more specific terms, true weakness and perceived weakness. True weakness (or "objective weakness") describes a condition where the instantaneous force exerted by the muscles is less than would be expected. For instance, if a patient suffers from amyotrophic lateral sclerosis (ALS), motor neurons are damaged and can no longer stimulate the muscles to exert normal force. Perceived weakness (or "subjective weakness") describes a condition where it seems to the patient that more effort than normal is required to exert a given amount of force. For instance, a person with chronic fatigue syndrome may struggle to climb a set of stairs when feeling especially fatigued, but if their muscle strength is objectively measured (eg, the maximum weight they can press with their legs) it is essentially normal. In some conditions such as myasthenia gravis muscle strength is normal when resting, but true weakness occurs after the muscle has been subjected to exercise.

Myotonia is a neuromuscular disorder characterized by the slow relaxation of the muscles after voluntary contraction or electrical stimulation. Generally, repeated effort is needed to relax the muscles, and the condition improves after the muscles have warmed-up. However, prolonged, rigorous exercise may also trigger the condition. Individuals with the disorder may have trouble releasing their grip on objects or may have difficulty rising from a sitting position and a stiff, awkward gait. During pregnancy, symptoms of myotonia are more frequently experienced in women.

Myotonia can affect all muscle groups. It may be acquired or inherited, and is caused by an abnormality in the muscle membrane. Myotonia is a symptom commonly seen in patients with myotonic muscular dystrophy and channelopathies. Myotonia arising from channelopathies can be exacerbated by exposure to cold, by eating foods that are potassium-rich (such as bananas), and with exertion.

Myasthenias are a group of disorders which exhibit several striking features the essential one being a fluctuating weakness and fatigability of muscle. There is usually some degree of weakness at all times but it is made worse by activity. The weakness and fatigability reflect physiologic abnormalities of the neuromuscular junction that are demonstrated by clinical signs and special electrophysiologic testing.

Paralysis is the complete loss of muscle function for one or more muscle groups. Major causes are stroke, trauma, poliomyelitis, amyotrophic lateral sclerosis (ALS), botulism, spina bifida, and Guillain-Barré syndrome. Paralysis is most often caused by damage to the nervous system or brain, especially the spinal cord. Paralysis often includes loss of feeling in the affected area.

Paramyotonia Congenita (PC) is a rare congenital autosomal dominant neuromuscular disorder characterized by "paradoxical" myotonia. This type of myotonia has been termed paradoxical because it becomes worse with exercise whereas classical myotonia, as seen in myotonia congenita, is alleviated by exercise. PC is also distinguished as it can be induced by cold temperatures. Although more typical of the periodic paralytic disorders, patients with PC may also have potassium provoked paralysis. PC typically presents within the first decade of life and has 100% penetrance. Patients with this disorder commonly present with myotonia in the face or upper extremities. The lower extremities are generally less affected. While some other related disorders result in muscle atrophy, this is not normally the case with PC. This disease can also present as hyperkalemic periodic paralysis and there is debate as to whether the two disorders are actually distinct. Patients typically complain of muscle stiffness that can continue to focal weakness. This muscle stiffness cannot be walked-off, in contrast to myotonia congenita. These symptoms are increased (and sometimes induced) in cold environments. For example, some patients have reported that eating ice cream leads to a stiffening of the throat. For other patients, exercise consistently induces symptoms of myotonia and/or weakness. Typical presentations of this are during squating or repetitive fist clenching. Some patients also indicate that specific foods are able to induce symptoms of paramyotonia congenita. Isolated cases have reported that carrots and watermelon are able to induce these symptoms. The canonical definition of this disorder precludes permenant weakness in the definition of this disorder. In practice, however, this has not been strictly adhered to in the literature. Diagnosis of paramyotonia congenita is made upon evaluation of patient symptoms and case history. Myotonia must increase with exercise/movement and usually must worsen in cold temperatures. Patients that present with permanent weakness are normally not characterized as having PC. Electromyography may be used to distinguish between paramyotonia congenita and myotonia congenita. Clinicians may also attempt to provoke episodes or myotonia and weakness/paralysis in patients in order to determine whether the patient has PC, hyperkalemic periodic paralysis, or one of the potassium-aggravated myotonias. Genomic sequencing of the SCN4A gene is the definitive diagnostic determinant.

Some patients do not require treatment to manage the symptoms of paramyotonia congenita. Others, however, require treatment for their muscle stiffness and often find mexiletine to be helpful. Others have found acetazolamide to be helpful as well. Avoidance of myotonia triggering events is also an effective method of mytonia prevention.

Paramyotonia congenita (as well as hyperkalemic periodic paralysis and the potassium-aggravated myotonias) is caused by mutations in SCN4A. The phenotype of patients with these mutations is indicated in Table 1 below. These mutations affect fast inactivation of the encoded sodium channel. There are also indications that some mutations lead to altered activation and deactivation. The result of these alterations in channel kinetics is that there is prolonged inward (depolarizing) current following muscle excitation. There is also the introduction of a "window current" due to changes in the voltage sensitivity of the channel's kinetics.

TABLE 1

Mutations of SCN4A (adapted from Vicart et al., 2005). Mutation region nomenclature is: domain number (e.g., D1) followed by segment number (e.g., S4). Thus, D2S3 indicates that the mutation is in the 3rd membrane spanning loop of the 2nd domain. Some mutations occur between segments and are denoted similarly (e.g., D4S4-S5 occurs between the 4th and 5th segments of the 4th domain). Other mutations are located between domains and are denoted DX-Y where X and Y are domain numbers. C-term refers to the carboxy-terminus.

| Mutation | Region |
|---|---|
| I693T | D2S4-S5 |
| T704M* | D2S5 |
| S804F** | D2S6 |
| A1152D | D3S4-S5 |
| A1156T* | D3S4-S5 |
| V1293I | D3S4 |
| G1306V** | D3-4 |
| T1313A | D3-4 |
| T1313M | D3-4 |
| M1360V* | D4S1 |
| M1370V* | D4S1 |
| L1433R | D4S3 |
| R1448C | D4S4 |
| R1448H | D4S4 |
| R1448P | D4S4 |
| R1448S | D4S4 |
| R1456E | D4S4 |
| V1458F | D4S4 |
| F1473S | D4S4-S5 |
| M1592V* | D4S6 |
| G1702K | C-term |
| F1795I | C-term |

*Symptoms of both PC and hyperKPP (Periodica paralytica paramyotonica)

**Also diagnosed as a Potassium-aggravated myotonia

Diseases associated with hyperexcitability or/and diseases associated with dysfunction of an ion channel might be caused by genetic dysfunction of voltage- or ligand-gated ion channels, such as voltage-gated calcium channels, voltage-gated potassium channels, voltage-gated chloride channels, nicotinic acetylcholine receptors, ryanodine receptors (calcium release channels), cyclic nucleotide-gated receptors, ATP-receptors, GABA-A receptors, glutamate-NMDA receptors, glycine-receptors, 5-HT3-receptors, and pH sensitive channels such as acid-sensing ion channel (ASIC), and TRP receptors. Diseases associated with dysfunction of these ion channels include, among others, ataxias, myotonias, myasthenias, long QT syndromes, epilepsy syndromes, and hyperthermia.

Examples for further diseases associated with hyperexcitability that might be caused by other reasons than mutations and polymorphisms in genes coding for ion channel subunits or proteins that regulate them are anxiety and stress. Stress and other anxiogenic stimuli can cause hyperexcitability of amygdala neurones (Rainnie et al. J Neuroscience 2004 24(14):3471-3479). Since the amygdala is a key brain center for emotion acute severe or chronic mild stress can result in persistent changes in emotion as for instance found in patients suffering from post-traumatic stress disorder.

Lacosamide does not exert its effects on neuronal excitability by affecting fast inactivation gating of voltage-gated $Na^+$ channels (Errington et al., Neuropharmacology, 2006, 50:1016-1029).

SUMMARY

The present invention demonstrates that the compounds of Formulae (I), (II), or/and (III) as defined herein, in particular lacosamide, are capable of selectively enhancing slow inactivation of voltage-gated sodium channels while leaving activation and fast inactivation behaviour normal. This constitutes a novel mechanism of action of the compounds of Formulae (I), (II), or/and (III), which thus can positively influence diseases associated with hyperexcitability. Due to this novel mechanism of action, the compounds of Formulae (I), (II), or/and (III) can efficiently normalize excessive sodium channel function such as a reduced slow inactivation which is e.g. seen in mutated channels. Further, this novel mechanism of action can compensate excessive function of other ion channels such as voltage-gated calcium channels, voltage-gated potassium channels, voltage-gated chloride channels, nicotinic acetylcholine receptors, ryanodine receptors (calcium release channels), cyclic nucleotide-gated receptors, ATP-receptors, GABA-A receptors, glutamate-NMDA receptors, glycine-receptors, 5-HT3-receptors, and pH sensitive channels such as acid-sensing ion channel (ASIC), and TRP receptors.

The mode of action of the compounds of Formulae (I), (II) or/and (III) differs from that of common drugs used for the treatment of voltage-gated sodium channel associated diseases. Common drugs used for the treatment of voltage-gated sodium channel associated diseases often affect fast inactivation of voltage-gated sodium channels and therefore affect signal propagation in excitable tissues. In contrast, the compounds of Formulae (I), (II) or/and (III) cause a shift of the curve of slow inactivation to more negative potentials, which reduces excitability, but does not affect signal propagation.

Lehmann-Horn et al. (Current Neurology and Neuroscience Reports (2002) 2:61-69) report that the common mechanism for inexcitability in all known episodic-weakness phenotypes, such as episodic familial periodic paralysis, is a long-lasting depolarization that inactivates sodium ion channels. By the compounds of the present invention, inactivation may be restored at least partially in such patients.

The use of compounds of Formulae (I), (II), or/and (III) for the treatment of a disease associated with hyperexcitability or/and for the treatment of a disease associated with dysfunction of an ion channel has not been reported. Thus, the present invention concerns the use of the compounds of Formula (I), (II), or/and (III) for the preparation of a pharmaceutical composition for the prevention, alleviation or/and treatment of a disease associated with hyperexcitability. The present invention also concerns the use of the compounds of Formula (I), (II), or/and (III) for the preparation of a pharmaceutical composition for the prevention, alleviation or/and treatment of a disease associated with dysfunction of an ion channel.

DETAILED DESCRIPTION

Figure 1:
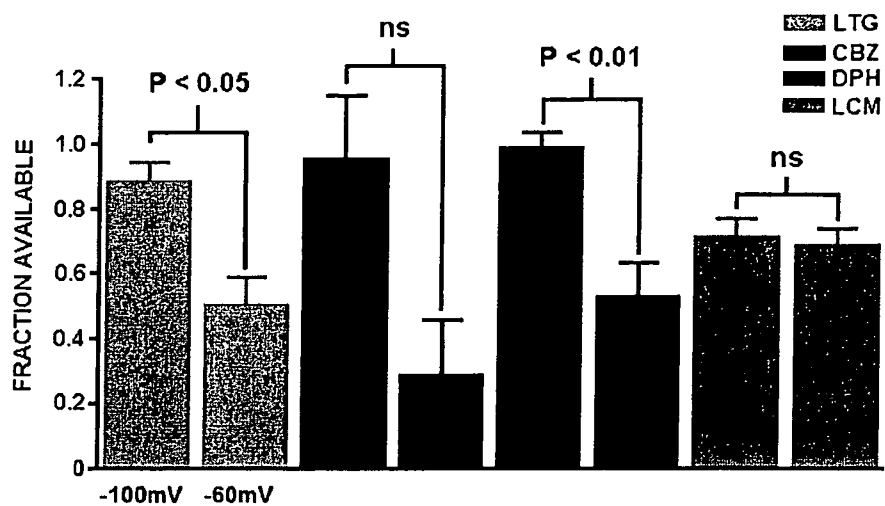
FIG. 1A is a chart showing a fraction of channels available after a repolarizing pulse of −100 mV and −60 mV, respectively.
FIG. 1B is a chart showing voltage dependency of slow inactivation in the presence or absence of lacosamide.
Figure 1:
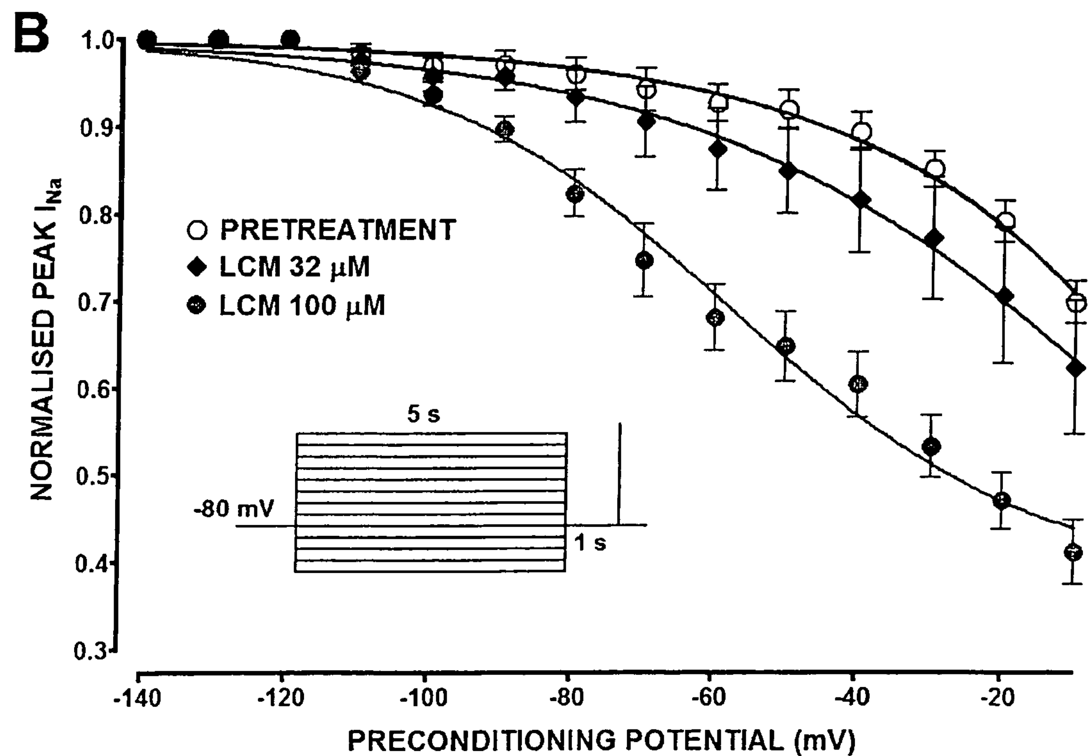

In the context of the present invention, hyperexcitability includes:

Hyperactivity associated with ion channels:

Lacosamide interacts with voltage-gated sodium channels in a novel manner (Examples 1 and 4): in contrast to all other drugs it enhances slow rather than fast inactivation of these channels. This is an efficient way to reduce pathological sodium channel hyperactivity e.g. induced by sodium channelopathies. By enhancing slow inactivation of sodium channels, hyperactivity of channellopathies associated with channels different from sodium channel may also be reduced.

Hyperactivity resulting in neurodegeneration:

Hyperexcitability e.g. as mediated by defective sodium channel activity can results in neurodeneration—a phenomenone called exitotoxicity. Lacosamide effectively blocks exitotoxicity (Example 3) thus preventing the toxic effects of hyperexcitability. Thus these effects can be discriminated from direct effects on hyperexcitability since in this case the consequences are affected and not the hyperexcitability by itself. Such effects are the underlying causes for many CNS diseases with ongoing neurodegeneration e.g. Parkinson's Disease, Alzheimers Disease, bipolar disorder and schizophrenia.

Behavioural hyperactivity (i.e. hyperreactivity)

On a behavioural level hyperexcitability can present itself as an exaggareted response to stress such as observed in disease like anxiety, post-traumatic stress disorder, or obsessive compulsive disorder. Behavioural hyperexcitability does not necessarily depend on cellular hyperexcitability as for instance observed in disorders like epilepsy and neuropathic pain. Lacosamide attenuates stress-induced anxiety (Example 2) demonstrating its ability to reduce hyperexcitability also on a behavioural level.

In one embodiment, the disease associated with hyperexcitability is a disease associated with a hyperexcitable tissue.

In another embodiment, the disease associated with hyperexcitability is a disease associated with hyperexcitability on the behavioural level (i.e. a disease associated with hyperreactivity).

In yet another embodiment, the disease associated with hyperexcitability is a disease associated with neurodegeneration, such as e.g. Parkinson's Disease, Alzheimers Disease, bipolar disorder and schizophrenia.

The disease associated with hyperexcitability may be a disease associated with dysfunction of an ion channel, such as a voltage-gated ion channel or a ligand-gated ion channel.

In one embodiment of the present invention, the disease associated with dysfunction of an ion channel is associated with dysfunction of a voltage-gated ion channel, selected from a voltage-gated sodium channel, a voltage-gated calcium channel, a voltage-gated potassium channel, and a voltage-gated chloride channel or with dysfunction of a ligand-gated ion channel, selected from a nicotinic acetylcholine receptor, a ryanodine receptor, a cyclic nucleotide-gated receptor, an ATP-receptor, a GABA-A receptor, a glutamate-NMDA receptor, a glycine-receptor, a 5-HT3-receptor, and a pH sensitive channel.

The disease associated with dysfunction of an ion channel may be associated with dysfunction of a voltage-gated sodium channel. The disease associated with dysfunction of a voltage-gated sodium channel may be a disease associated with altered inactivation of voltage-gated sodium channels in comparison to a healthy subject, in particular altered slow inactivation. The disease associated with dysfunction of a voltage-gated sodium channel may also be a disease associated with altered inactivation of voltage-gated sodium channels in comparison to a healthy subject in which fast inactivation of sodium channels is altered.

In the disease associated with hyperexcitability or/and the disease associated with ion channel dysfunction, the curve of slow inactivation of a sodium channel may be affected, in particular the curve of slow inactivation is shifted to depolarized potentials compared with the slow inactivation curve of a healthy subject. Such functional alterations may be reversed completely or at least partially by the compounds of the present invention.

The voltage-gated sodium channel may be any known type of voltage-gated sodium channels, in particular any type expressed in excitable tissues, such as muscle and nerve. Examples of genes encoding voltage-gated sodium channels or/and subunits thereof include SCN1A, ($Na_v$ 1.1), SCN2A ($Na_v$ 1.2), SCN4A ($Na_v$ 1.4), SCN5A ($Na_v$ 1.5), SCN8A ($Na_v$ 1.6), SCN9A ($Na_v$ 1.7), $Na_v$ 1.8 (SNS or PN3), and $Na_v$ 1.9 (NaN, SNS-2 or PN-5). The voltage-gated sodium channel may comprise a type IV alpha subunit SCN4A. The voltage-gated sodium channel may also comprise $Na_v$1.2.

The disease associated with dysfunction of an ion channel may be associated with an ion channel different from a voltage-gated sodium channel, such as a voltage-gated calcium channel, a voltage-gated potassium channel, a voltage-gated chloride channel, a nicotinic acetylcholine receptor, a ryanodine receptor, a cyclic nucleotide-gated receptor, an ATP-receptor, a GABA-A receptor, a glutamate-NMDA receptor, a glycine-receptor, a 5-HT3-receptor, or a pH sensitive channel.

Dysfunction of an ion channel different from a voltage-gated sodium channel might cause alteration of electrolyte composition in body fluids, in particular in the intracellular fluid or/and in the extracellular fluid, such as in the plasma, which alteration may for instance influence the activation or/and inactivation state of a sodium channel by altering the resting membrane potential. Alteration of electrolyte composition includes alterations of the $Na^+$, $K^+$, or/and $Cl^-$ concentration or pH. Dysfunction of an ion channel different from a voltage-gated sodium channel might also cause alteration of pre- or/and postsynaptic control, and alteration of synaptic transmitter release or/and postsynaptic transmitter action. Dysfunction of an ion channel different from a voltage-gated sodium channel might lead to a disease associated with hyperexcitability that can be prevented, alleviated or/and treated by a modulator of the activity of a voltage-gated sodium channel. A disease associated with dysfunction of an ion channel different from a voltage-gated sodium channel might be prevented, alleviated or/and treated by a modulator of the activity of a voltage-gated sodium channel.

Examples of genes encoding a voltage-gated calcium channel or/and a subunit thereof include CACNA1A (SEQ ID NO: 1), CACNA1S, and CACNB4. Examples of genes encoding a voltage-gated potassium channel or/and a subunit thereof include KCNA1, KCNQ1, KCNQ2, KCNQ3, KCNQ4, KCNE1, KCNE2, and hERG. Examples of genes encoding a chloride channel or/and a subunit thereof include CLCN1, CLCN5, and CLCNKB. Examples of genes encoding a ligand-gated ion channel or/and a subunit thereof include CHRNA4 (nicotinic acetylcholine receptor), RYR1 (ryanodine receptor).

In another embodiment of the present invention, the disease of the present invention is a channelopathy. The channelopathy may be associated with a dysfunction of a voltage-gated sodium channel, a voltage-gated calcium channel, a voltage-gated potassium channel, a voltage-gated chloride channel, a nicotinic acetylcholine receptor, a ryanodine receptor, a cyclic nucleotide-gated receptor, an ATP-receptor, a GABA-A receptor, a glutamate-NMDA receptor, a glycine-receptor, a 5-HT3-receptor, or/and a pH sensitive channel, as described herein, which dysfunction may be caused by a mutation. The channelopathy may be selected from familial potassium-aggravated cramps (e.g. MIM: 603967), myasthenic syndrome (e.g. MIM: 603967), hyperkalemic periodic paralysis (e.g. MIM: 170500), hypokalemic periodic paralysis (e.g. MIM: 170400), atypical, acetazolamide-responsive myotonia congenita (e.g. MIM: 608390), and paramyotonia congenita (e.g. MIM: 168300). The channelopathy may also be associated with at least one of the following mutations of the SCN4A polypeptide: I693T, T704M, S804F, A1152D, A1156T, V1293I, G1306V, T1313A, T1313M, M1360V, M1370V, L1433R, R1448C, R1448H, R1448P, R1448S, R1456E, V1458F, F1473S, M1592V, G1702K, and F1795I.

In yet another embodiment, the disease of the present invention, in particular the disease associated with dysfunction of an ion channel, is a muscle disorder.

The disease of the present invention may be a skeletal muscle disorder or/and a movement disorder, in particular a movement disorder.

The skeletal muscle or/and movement disorder may be selected from myotonias and paralyses, in particular selected from inherited myotonia and periodic paralyses, such as paramyotonia congenita, potassium aggravated myotonia, myotonia fluctuans, myotonia permanens, acetazolamide responsive myotonia, hyperkalemic periodic paralysis, normokalemic paralysis, paroxysmal dystonia, Morvan syndrome and Isaak syndrome.

Paralysis may be associated with loss of feeling in the affected area. Further, paralysis may be associated with stroke, trauma, poliomyelitis, amyotrophic lateral sclerosis (ALS), botulism, spina bifida, Guillain-Barré syndrome, or/and damage of the nervous system or/and brain, especially the spinal cord.

The skeletal muscle or/and movement disorder may also be selected from ataxias, in particular selected from episodic ataxia 2, spinocerebellar ataxia 6, and episodic ataxia.

The skeletal muscle or/and movement disorder may also be selected from myotonias, in particular selected from Thomsen myotonia, Becker myotonia, myotonia congenita, generalized myotonia, myotonia levior.

The myotonia may be associated with slow relaxation of a muscle after voluntary contraction or electrical stimulation. The myotonia may be selected from acquired and inherited myotonia. The myotonia may be caused by an abnormality in the muscle membrane. The myotonia may be associated with myotonic muscular dystrophy or/and a channelopathy (in particular a channelopathy caused by mutations in the chloride, sodium or potassium ion channels in the muscle membrane).

The myotonia may be exacerbated by exposure to cold, by a potassium-rich diet (such as eating bananas), or/and with exertion, e.g. prolonged, rigorous exercise.

The skeletal muscle or/and movement disorder may be a myasthenia selected from myokymias and hypokalemic periodic paralysis 1.

The muscle disorder may be a cardiac arrhythmia selected from long QT syndrome 3, Long QT syndrome 5, Jervell- and Lange-Nielsen syndrome, inducible long QT syndrome, long QT syndrome 1, and long QT syndrome 2.

The disease of the present invention may be an epilepsy syndrome selected from generalized epilepsy with febrile seizures plus (GEFS+), severe myoclonic epilepsy in infancy (SMEI), benign familial neonatal infantile seizures (BNIFS), intractable childhood epilepsy with generalized tonic-clonic seizures (ICEGTC), infantile spasms (West syndrome), generalized epilepsy associated with CACNB4 dysfunction, benign familial neonatal convulsions 1, benign familial neonatal convulsions 2, and nocturnal frontal lobe epilepsy.

The disease of the present invention may be a pain syndrome selected from erythermalgia and familial rectal pain (also called "paroxysmal extreme pain disorder").

The disease of the present invention may be a pain syndrome selected from dominant deafness, malignant hyperthermia 5, malignant hyperthermia 1, polysystic kidney disease 1, Dent's disease, Bartter syndrome, central core disorder, and cortical hyperexcitability associated with CACNA1A (SEQ ID NO:1).

In yet another embodiment, the disease associated with hyperexcitability may be a sodium channelopathy, such as a channelopathy selected from the diseases listed in Table 2a.

In a further embodiment, the disease associated with hyperexcitability is a potassium channelopathy, such as a channelopathy selected from the diseases associated with a potassium channel listed in Table 2b.

In a further embodiment, the disease associated with hyperexcitability is a calcium channelopathy, such as a channelopathy selected from the diseases associated with a calcium channel listed in Table 2b.

In yet another embodiment, the disease associated with hyperexcitability is a chloride channelopathy, such as a channelopathy selected from the diseases associated with a chloride channel listed in Table 2b.

In a further embodiment, the disease associated with hyperexcitability is selected from the diseases listed in Table 2c.

In another embodiment, the disease associated with dysfunction of an ion channel is a sodium channelopathy, such as a channelopathy selected from the diseases listed in Table 2a.

In yet another embodiment, the disease associated with dysfunction of an ion channel is a potassium channelopathy, such as a channelopathy selected from the diseases associated with a potassium channel listed in Table 2b.

In a further embodiment, the disease associated with dysfunction of an ion channel is a calcium channelopathy, such as a channelopathy selected from the diseases associated with a calcium channel listed in Table 2b.

In yet another embodiment, the disease associated with dysfunction of an ion channel is a chloride channelopathy, such as a channelopathy selected from the diseases associated with a chloride channel listed in Table 2b.

Table 2. Target diseases for selective enhancers of slow inactivation of voltage-gated $Na^+$ channels in excitable tissues TABLE 2a

| Dysfunction of voltage-gated sodium channels (sodium channelopathies)<br>AFFECTED TISSUE | | | |
|---|---|---|---|
| skeletal muscle | cardiac muscle | CNS | PNS |
| inherited myotonia and periodic paralyses<br>SCN4A ($Na_v$ 1.4)<br>(cf. Table 54-1 in "Principles of Neurology" & Lehmann-Horn and Jurkat-Rott www.channelopathies.org)<br>Paramyotonia congenita<br>Potassium aggravated myotonia<br>Myotonia fluctuans<br>Myotonia permanens<br>Acetazolamide responsive myotonia<br>Hyperkalemic periodic paralysis<br>Normokalemic paralysis<br>movement disorders:<br>SCN8A ($Na_v$ 1.6)<br>paroxysmal dystonia<br>(Siep et al., 2002)<br>Morvan syndrome<br>Isaak syndrome | cardiac arrhythmia<br>SCN5A ($Na_v$ 1.5)<br>long QT syndrome 3<br>(Lehmann-Horn and Jurkat-Rott www.channelopathies.org) | epilepsy syndromes<br>SCN1A, ($Na_v$ 1.1),<br>SCN2A ($Na_v$ 1.2)<br>generalized epilepsy with febrile seizures plus (GEFS+)<br>severe myoclonic epilepsy in infancy (SMEI)<br>benign familial neonatal infantile seizures (BNIFS)<br>intractable childhood epilepsy with generalized tonic-clonic seizures (ICEGTC)<br>infantile spasms (West syndrome)<br>(Meisler and Kearney, 2005) | pain syndromes<br>SNC9A ($Na_v$ 1.7)<br>erythermalgia (=erythromelagia)<br>(Yang et al., 2004)<br>familial rectal pain<br>(Meisler and Kearney, 2005) |

TABLE 2b

| Dysfunction of other voltage-gated ion channels (channelopathies)<br>AFFECTED TISSUE | | | |
|---|---|---|---|
| skeletal muscle | cardiac muscle | CNS | Others |
| Ataxias<br>Episodic ataxia 2 (CACNA1A)<br>spinocerebellar ataxia 6 (CACNA1A)<br>KCNA1 (potassium channel) episodic ataxia<br>Myotonias<br>CLCN1 (chloride channel) e.g. Thomsen myotonia, Becker myotonia, myotonia congenital, generalized myotonia, myotonia levior<br>Myasthenias<br>KCNQ2 (potassium channel) myokymia<br>Hypokalemic periodic paralysis 1 (CACNA1S) | Long QT syndrome 5 (KCNE1),<br>Jervell- and Lange-Nielsen Syndrome (KCNE1, KCNQ1),<br>inducible long QT syndrome (KCNE2)<br>long QT syndrome 1 (KCNQ1)<br>long QT syndrome 2 (hERG) | cortical hyperexcitability epilepsy syndromes<br>Generalized epilepsy (CACNB4)<br>Benign familial neonatal convulsions 1 (KCNQ2)<br>Benign familial neonatal convulsions 2 (KCNQ3)<br>nocturnal frontal lobe epilepsy (CHRNA4)<br>(Lehmann-Horn & Jurkat-Rott, 2000) | Auditory disorders:<br>Dominant deafness (KCNQ4)<br>Hyperthermia:<br>Malignant hyperthermia 5 (CACNA1S),<br>malignant hyperthermia 1 (RYR1)<br>Central core disease (RYR1)<br>Renal disorders:<br>Polycystic kidney disease (PKD1),<br>Dent's disease (CLCN5), Bartter syndrome (CLCNKB), |

TABLE 2c

| Other diseases due to hyperexcitable tissue (Hyperexcitability Disorders)<br>AFFECTED TISSUE | |
|---|---|
| CNS | PNS |
| Post traumatic stress disorder<br>(Centonze et al. 2005)<br>Alzheimer's disease, Parkinson's disease, Bipolar disorder and Schizophrenia<br>(Farber et al. 2002) | Peripheral nerve hyperexcitability syndromes |

REFERENCES

Farber, N B et al., Molecular Psychiatry (2002), 7:726-733

Lehmann-Horn, Jurkat-Rott www.channelopathies.org

Meisler M H, Kearney J A. J Clin Invest. 2005 August; 115(8):2010-7. PMID: 16075041

Siep E, et al. Neurobiol Dis. 2002 March; 9(2):258-68.

Victor M, Ropper A H Adams and Victor's Principles of Neurology. 7$^{th}$ edition, McGraw-Hill New York 2001.

Yang Y et al. J Med Genet. 2004 March; 41(3):171-4.

Based on the finding that the compounds of the present invention are capable of increasing slow inactivation of voltage-gated sodium channels and thereby act against hyperexcitability, it is concluded that the pharmaceutical composition of the present invention is suitable for the treatment of diseases associated with hyperexcitability, such as anxiety or/and stress.

Thus, in another embodiment of the present invention, the disease associated with hyperexcitability is a disease selected from anxiety, stress, posttraumatic stress disorder, obsessive compulsive disorder and peripheral nerve hyperexcitability syndromes. The disease may be stress-induced anxiety as for instance seen in post-traumatic stress disorder.

Hyperexcitability may cause neurodegeneration. Example 3 of the present invention demonstrates a neuroprotective effect of the compounds of the present invention. In one embodiment, the prevention, alleviation or/and treatment of a disease associated with hyperexcitability is effected by neuroprotection, in particular by short-term neuroprotection. In this embodiment of the present invention, the disease associated with hyperexcitability is a condition associated with neuronal damage or/and neurodegeneration. In particular, the disease associated with hyperexcitability is a condition associated with neuronal damage or/and neurodegeneration caused by a neurodegenerative disease or/and a psychotic disease. The neurodegenerative disease or/and the psychotic disease may be selected from Alzheimer's disease, Parkinson's disease, bipolar disorder, and schizophrenia.

In one embodiment of the present invention, the disease associated with hyperexcitability is not epilepsy, status epilepticus, pain, neuropathic pain, allodynia or hyperalgesia. In another embodiment, the disease associated with hyperexcitability is not an epilepsy related condition or a neuropathic pain related condition. In a further embodiment, the specific forms of epilepsy and pain as described herein are not subject of these disclaimers.

In another embodiment of the present invention, the disease associated with dysfunction of an ion channel is not epilepsy, status epilepticus, pain, neuropathic pain, allodynia or hyperalgesia. In another embodiment, the disease associated with dysfunction of an ion channel is not an epilepsy related condition or a neuropathic pain related condition. In a further embodiment, the specific forms of epilepsy and pain as described herein are not subject of these disclaimers.

In yet another embodiment, the disease associated with hyperexcitability is not amyotrophic lateral sclerosis or Guillain-Barré syndrome. In a further embodiment, paralysis associated with amyotrophic lateral sclerosis or/and Guillain-Barré syndrome as described herein is not subject of this disclaimer.

In a further embodiment, the disease associated with dysfunction of an ion channel is not amyotrophic lateral sclerosis or Guillain-Barré syndrome. In a further embodiment, paralysis associated with amyotrophic lateral sclerosis or/and Guillain-Barré syndrome as described herein is not subject of this disclaimer.

In a further embodiment, the disease associated with hyperexcitability is not Alzheimer's disease, Parkinson's disease, bipolar disorder, or schizophrenia. In a further embodiment, a condition associated with neuronal damage or/and neurodegeneration caused by a neurodegenerative disease or/and psychotic disease selected from Alzheimer's disease, Parkinson's disease, bipolar disorder, and schizophrenia is not subject of this disclaimer.

In yet another embodiment, the disease associated with hyperexcitability is not tinnitus or obsessive compulsive disorder.

The compounds of the present invention of Formulae (I), (II) or/and (III), in particular lacosamide, are well tolerated, which is an advantage over other commonly used therapeutics for treatment of diseases associated with hyperexcitability or/and of diseases associated with dysfunction of an ion channel.

The compounds of the present invention, in particular lacosamide, may be used in a first line treatment of a disease as defined herein. Therefore, the pharmaceutical composition of the present invention is suitable for a first line treatment of a disease as defined herein.

The compounds of the present invention may also be used in a second line treatment of a disease as defined herein. Therefore, the pharmaceutical composition of the present invention is also suitable for a second line treatment of a disease as defined herein.

Yet another aspect of the present invention is a pharmaceutical composition comprising at least one compound of Formulae (I), (II), or/and (III) as defined herein, preferably lacosamide, for the prevention, alleviation or/and treatment of a disease associated with hyperexcitability, as defined herein.

Yet another aspect of the present invention is a pharmaceutical composition comprising at least one compound of Formulae (I), (II), or/and (III) as defined herein, preferably lacosamide, for the prevention, alleviation or/and treatment of a disease associated with dysfunction of an ion channel, as defined herein.

The components of Formulae (I), (II), or/and (III) may also be administered together with a further active agent for the treatment of a disease associated with hyperexcitability, as defined herein.

The components of Formulae (I), (II), or/and (III) may also be administered together with a further active agent for the treatment of a disease associated with dysfunction of an ion channel, as defined herein.

A further aspect of the present invention refers to a pharmaceutical composition.

In one embodiment, the pharmaceutical composition comprises (a) at least one compound of Formulae (I), (II), or/and (III) as defined herein, preferably lacosamide, and
(b) at least one further active agent for the prevention, alleviation, or/and treatment of a disease associated with hyperexcitability as defined herein.

In another embodiment, the pharmaceutical composition comprises (a) at least one compound of Formulae (I), (II), or/and (III) as defined herein, preferably lacosamide, and
(b) at least one further active agent for the prevention, alleviation, or/and treatment of a disease associated with dysfunction of an ion channel as defined herein.

In the embodiments as indicated above, the compound of Formulae (I), (II), or/and (III) and the further active agent (b) may be formulated in one pharmaceutical preparation (single dosage form) for administration at the same time or may be formulated in two or more distinct preparations (separate dosage forms) for simultaneous or/and subsequent administration. The two distinct preparations in the separate dosage forms may be administered by the same route or by different routes.

Separate dosage forms can optionally be co-packaged, for example in a single container or in a plurality of containers within a single outer package, or co-presented in separate packaging ("common presentation"). As an example of co-packaging or common presentation, a kit is contemplated comprising, in separate containers, compound of Formulae (I), (II), or/and (III) and the further active agent (b). In another example, the compound of Formulae (I), (II), or/and (III) and the further active agent (b) are separately packaged and available for sale independently of one another, but are co-marketed or co-promoted for use according to the invention. The separate dose forms may also be presented to a subject separately and independently, for use according to the invention.

In one embodiment, the pharmaceutical composition comprises a single dosage form comprising at least one compound of Formulae (I), (II), or/and (III) and at least one further active agent (b).

In another embodiment, the pharmaceutical composition of the present invention comprises separate dosage forms comprising (i) a first composition comprising at least one compound of Formulae (I), (II), or/and (III), and (ii) a second composition comprising at least one further active agent for the prevention, alleviation, or/and treatment of disease associated with hyperexcitability, as defined herein.

In yet another embodiment, the pharmaceutical composition of the present invention comprises separate dosage forms comprising (i) a first composition comprising at least one compound of Formulae (I), (II), or/and (III), and (ii) a second composition comprising at least one further active agent for the prevention, alleviation, or/and treatment of disease associated with dysfunction of an ion channel, as defined herein.

In yet another embodiment of the present invention, the second composition (ii) comprising the at least one further active agent may be a commercially available composition.

The pharmaceutical composition of the present invention may be prepared for administration in mammals, such as in humans.

The pharmaceutical composition of the present invention comprising (a) at least one compound of Formulae (I), (II) or/and (III) and (b) at least one further active agent may be prepared for the prevention, alleviation or/and treatment of disease associated with hyperexcitability, as described herein.

The pharmaceutical composition of the present invention comprising (a) at least one compound of Formulae (I), (II) or/and (III) and (b) at least one further active agent may be prepared for the prevention, alleviation or/and treatment of disease associated with dysfunction of an ion channel, as described herein.

Yet another aspect of the present invention is a method for the prevention, alleviation or/and treatment of a disease.

In one embodiment, the method is a method for the prevention, alleviation or/and treatment of a disease associated with hyperexcitability, wherein the method comprises administering to a subject in need thereof at least one compound of Formulae (I), (II), or/and (III), in particular lacosamide.

In another embodiment, the method is a method for the prevention, alleviation or/and treatment of a disease associated with hyperexcitability, wherein the method comprises co-administering to a subject in need thereof at least one compound of Formulae (I), (II), or/and (III), in particular lacosamide, and a further active agent for the prevention, alleviation, or/and treatment of a disease associated with hyperexcitability in therapeutically effective amounts.

In another embodiment, the method is a method for the prevention, alleviation or/and treatment of a disease associated with dysfunction of an ion channel, wherein the method comprises administering to a subject in need thereof at least one compound of Formulae (I), (II), or/and (III), in particular lacosamide.

In yet another embodiment, the method of the present invention is a method for the prevention, alleviation or/and treatment of a disease associated with dysfunction of an ion channel, wherein the method comprises co-administering to a subject in need thereof at least one compound of Formulae (I), (II), or/and (III), in particular lacosamide, and a further active agent for the prevention, alleviation, or/and treatment of a disease associated with dysfunction of an ion channel in therapeutically effective amounts.

The at least one compound of formulae (I), (II), or/and (III), in particular lacosamide, may be co-administered with mexiletine, carbonic anhydrase inhibitors (such as acetazolamide or dichlorphenamide), benzodiazepines (such as diazepam, midazolam, alprazolam), SSRIs (selective serotonin reuptake inhibitors such as fluoxetine, fluvoxamine, sertraline, venlafaxine, mirtazapine), baclofen, quinine, phenytoin and other anticonvulsant drugs (such as lamotrigine, levetiracetam, topiramate, carbamazepine, oxcarbazepine, tiagabine, vigabatrine, zonisamide), tricyclic antidepressants (such as amitryptiline, imipramine, desipramine), nonsteroidal antiinflammatory drugs (NSAIDs such as acetylsalicylic acid, paracetamol, ibuprofen, naproxen), acetylcholinesterase inhibitors (AChE) inhibitors (such as tacrine, rivastigmine, galanthamine, donezepil), dopa decarboxylase inhibitors, dopamine agonists (such as ropinirole, pramipexole, lisuride, pergolide, piribedil), monoamine oxidase-B and COMT inhibitors (such as tolcapone, entacapone, apomorphine, rasagiline), atypical antipsychotic medications (such as clozapine, risperidone, olanzapine, quetiapine, ziprasidone, aripiprazole, and amisulpride), or potassium tablets.

The term "co-administration" refers to a plurality of agents that, when administered to a subject together or separately, are co-active in bringing therapeutic benefit to the subject. Such co-administration is also referred to as "combination", "combination therapy," "co-therapy," "adjunctive therapy" or "add-on therapy." For example, one agent can enhance the therapeutic effect of another, or reduce an adverse side effect of another, or one or more agents can be effectively administered at a lower dose than when used alone, or can provide greater therapeutic benefit than when used alone, or can complementarily address different aspects, symptoms or etiological factors of a disease or condition.

Co-administration comprises administration of the combination of the agents in amounts sufficient to achieve or/and maintain therapeutically effective concentrations, e.g. plasma concentrations, in the subject in need thereof. Co-administration comprises simultaneous or/and subsequent administration. Simultaneous administration comprises administration of the agents as a single or as different compositions.

The administration interval of the compound of Formulae (I), (II), or/and (III) and the further active agent may depend on the dosage forms. The compound of Formulae (I), (II), or/and (III) may be administered first, or the further active agent (b) may be administered first.

The compound according to the invention has the general Formula (I)

Formula (I)

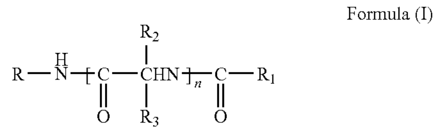

wherein

R is hydrogen, alkyl, alkenyl, alkynyl, aryl, aryl alkyl, heterocyclic, heterocyclic alkyl, alkyl heterocyclic, cycloalkyl or cycloalkyl alkyl, and R is unsubstituted or is substituted with at least one electron withdrawing group, or/and at least one electron donating group;

$R_1$ is hydrogen or alkyl, alkenyl, alkynyl, aryl alkyl, aryl, heterocyclic alkyl, alkyl heterocyclic, heterocyclic, cycloalkyl, cycloalkyl alkyl, each unsubstituted or substituted with at least one electron donating group or/and at least one electron withdrawing group;

and $R_2$ and $R_3$ are independently hydrogen, alkyl, alkenyl, alkynyl, alkoxy, alkoxyalkyl, aryl alkyl, aryl, halo, heterocyclic, heterocyclic alkyl, alkyl heterocyclic, cycloalkyl, cycloalkyl alkyl, or Z—Y wherein $R_2$ and $R_3$ may be unsubstituted or substituted with at least one electron withdrawing group or/and at least one electron donating group;

Z is O, S, $S(O)_a$, $NR_4$, $NR'_6$, $PR_4$ or a chemical bond;

Y is hydrogen, alkyl, aryl, aryl alkyl, alkenyl, alkynyl, halo, heterocyclic, heterocyclic alkyl, alkyl heterocyclic and Y may be unsubstituted or substituted with at least one electron donating group or/and at least one electron withdrawing group, provided that when Y is halo, Z is a chemical bond, or ZY taken together is $NR_4NR_5R_7$, $NR_4OR_5$, $ONR_4R_7$, $OPR_4R_5$, $PR_4OR_5$, $SNR_4R_7$, $NR_4SR_7$, $SPR_4R_5$, $PR_4SR_7$, $NR_4PR_5R_6$, $PR_4NR_5R_7$ or $N^+R_5R_6R_7$,

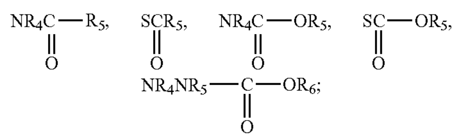

$R'_6$ is hydrogen, alkyl, alkenyl, or alkenyl which may be unsubstituted or substituted with at least one electron withdrawing group or/and at least one electron donating group;

$R_4$, $R_5$ and $R_6$ are independently hydrogen, alkyl, aryl, aryl alkyl, alkenyl, or alkynyl, wherein $R_4$, $R_5$ and $R_6$ may independently be unsubstituted or substituted with at least one electron withdrawing group or/and at least one electron donating group;

$R_7$ is $R_6$ or $COOR_8$ or $COR_8$, which $R_7$ may be unsubstituted or substituted with at least one electron withdrawing group or/and at least one electron donating group;

$R_5$ is hydrogen or alkyl, or aryl alkyl, and the aryl or alkyl group may be unsubstituted or substituted with at least one electron withdrawing group or/and at least one electron donating group; and n is 1-4; and a is 1-3.

In a preferred embodiment, the compound of Formula (I) has the general Formula (II), Formula (II)

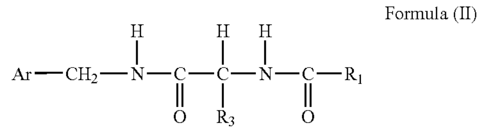

wherein

Ar is aryl which is unsubstituted or substituted with at least one electron donating group or/and at least one electron withdrawing group, preferably halo, more preferably fluoro;

$R_1$ is alkyl, preferably alkyl containing 1-3 carbon atoms, more preferably methyl; and $R_3$ is as defined herein.

In a more preferred embodiment, the compound of Formulae (I) or/and (II) has the general Formula (III), Formula (III)

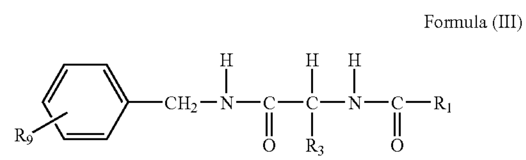

wherein $R_9$ is one or more substituents independently selected from the group consisting of hydrogen, halo, alkyl, alkenyl, alkynyl, nitro, carboxy, formyl, carboxyamido, aryl, quaternary ammonium, haloalkyl, aryl alkanoyl, hydroxy, alkoxy, carbalkoxy, amino, alkylamino, dialkylamino, aryloxy, mercapto, alkylthio, alkylmercapto, and disulfide;

$R_3$ is selected from the group consisting of hydrogen, alkyl, arylalkyl, alkoxy, alkoxyalkyl, aryl, heterocyclic, heterocyclic alkyl, N-alkoxy-N-alkylamino, N-alkoxyamino, and N-carbalkoxy; and $R_1$ is alkyl, preferably alkyl containing 1 to 3 carbon atoms, more preferably methyl.

The compounds utilized in the present invention may contain one or more asymmetric carbons and may exist in racemic and optically active forms. The configuration around each asymmetric carbon can be either the D or L form. It is well known in the art that the configuration around a chiral carbon atoms can also be described as R or S in the Cahn-Prelog-Ingold nomenclature system. All of the various configurations around each asymmetric carbon, including the various enantiomers and diastereomers as well as racemic mixtures and mixtures of enantiomers, diastereomers or both are contemplated by the present invention.

As used herein, the term configuration particularly refers to the configuration around the carbon atom to which $R_2$ and $R_3$ or H and $R_3$ are attached, even though other chiral centers may be present in the molecule. Therefore, when referring to a particular configuration, such as D or L, it is to be understood to mean the D or L stereoisomer at the carbon atom to which $R_2$ and $R_3$ or H and $R_3$ are attached. However, it also includes all possible enantiomers and diastereomers at other chiral centers, if any, present in the compound.

The compounds of the present invention are directed to all the optical isomers, i.e., the compounds of the present invention are either the L-stereoisomer or the D-stereoisomer (at the carbon atom to which $R_2$ and $R_3$ or H and $R_3$ are attached). These stereoisomers may be found in mixtures of the L and D stereoisomer, e.g., racemic mixtures. The D stereoisomer is preferred.

It is preferred that the compounds of Formula (I) are in the R configuration. It is also preferred that the compounds of Formula (II) are in the R configuration. It is also preferred that the compounds of Formula (III) are in the R configuration.

It is preferred that the compounds of Formulae (I), (II) or/and (III) in the R configuration are substantially enantiopure. As used herein, the term "substantially enantiopure" refers to a content of the R enantiomer of at least 99.5%. This corresponds to an enantiomeric excess (ee) of 99%. The respective quantities of R and S enantiomer may be determined by chiral column chromatography, e.g. by HPLC with "ChiralPak" as chiral, stationary phase.

The term "alkyl" (alone or in combination with another term(s)) means a straight- or branched-chain saturated hydrocarbyl substituent preferably containing from 1 to about 20 carbon atoms ($C_1$-$C_{20}$-alkyl), more preferably from 1 to about 8 carbon atoms ($C_1$-$C_8$-alkyl), even more preferably from 1 to about 6 carbon atoms ($C_1$-$C_6$-alkyl), and most preferably from 1 to 3 carbon atoms ($C_1$-$C_3$-alkyl). The alkyl groups include methyl, ethyl, propyl, isopropyl, butyl, isobutyl, tertiary butyl, amyl, hexyl, and the like. Further, alkyl groups also include halogenated alkyl groups up to perhalogenation, e.g. trifluoromethyl, if not indicated otherwise.

The term "alkoxy" (alone or in combination with another term(s)) refers to —O-alkyl and means a straight- or branched-chain alkoxy substituent preferably containing from 1 to about 20 carbon atoms ($C_1$-$C_{20}$-alkoxy), more preferably from 1 to about 8 carbon atoms ($C_1$-$C_8$-alkoxy), even more preferably from 1 to about 6 carbon atoms ($C_1$-$C_6$-alkoxy), and most preferably from 1 to 3 carbon atoms ($C_1$-$C_3$-alkoxy). The alkoxy groups include methoxy, ethoxy, propoxy, butoxy, isobutoxy, tert-butoxy, pentoxy, hexoxy and the like. Further, alkoxy groups include halogenated alkoxy groups up to perhalogenation, if not indicated otherwise.

The term "alkoxyalkyl" refers to an alkyl group substituted with at least one alkoxy group. The alkoxyalkyl groups include methoxymethyl ($—CH_2—OCH_3$) groups, methoxyethyl ($—CH_2—CH_2—OCH_3$) groups, ethoxymethyl ($—CH_2—O—CH_2CH_3$) groups and the like.

The term "N-alkoxyamino" refers to amino groups substituted with one or two alkoxy groups, e.g. $—NH—N(OCH_3)_2$.

The term "N-alkoxy-N-alkylamino" refers to amino groups substituted with an alkoxy group and an alkyl group, e.g. $—N(CH_3)(OCH_3)$, $—N(CH_3)(OCH_2—CH_3)$ and the like.

The term "N-carbalkoxy" refers to amino groups substituted with a carbalkoxy group, e.g. $—NH(C(O)—O—CH_3)$, $—NH(C(O)O—CH_2—CH_3)$.

The term "aryl", when used alone or in combination with other term(s), refers to an aromatic group which contains from 6 up to 18 ring carbon atoms ($C_6$-$C_{18}$-aryl), preferably from 6 up to 10 ring carbon atoms ($C_6$-$C_{10}$-aryl), and includes polynuclear aromatics. The aryl groups may be monocyclic, bicyclic, tricyclic or polycyclic and may be fused rings. A polynuclear aromatic compound as used herein, is meant to encompass bicyclic and tricyclic fused aromatic ring systems containing from 10-18 ring carbon atoms. Aryl groups include phenyl and polynuclear aromatics e.g., naphthyl, anthracenyl, phenanthrenyl, azulenyl and the like. The aryl group also includes groups such as ferrocenyl. Aryl groups may be unsubstituted or mono or polysubstituted with electron withdrawing or/and electron donating groups. A preferred aryl group is phenyl, which may unsubstituted or mono or polysubstituted with electron withdrawing or/and electron donating groups.

The term "aryl alkyl" as used herein alone or in combination with other term (s) means an alkyl group as defined herein carrying an aryl substitutent as defined herein. Preferred aryl alkyl groups are aryl-$C_1$-$C_6$alkyl, aryl-$C_1$-$C_3$-alkyl, $C_6$-$C_{10}$-aryl-alkyl, $C_6$-$C_{10}$aryl-$C_1$-$C_6$-alkyl, $C_6$-$C_{10}$-aryl-$C_1$-$C_3$-alkyl. More preferred aryl alkyl groups are phenyl-$C_1$-$C_6$-alkyl and phenyl-$C_1$-$C_3$-alkyl. Even more preferred aryl alkyl groups include, for example, benzyl, phenylethyl, phenylpropyl, phenylisopropyl, phenylbutyl, diphenylmethyl, 1,1-diphenylethyl, 1,2-diphenylethyl, and the like. Most preferred is benzyl.

The term "alkenyl" (alone or in combination with another term(s)) means a straight- or branched-chain alkenyl substituent containing at least one double bond and preferably containing from 2 to about 20 carbon atoms ($C_2$-$C_{20}$-alkenyl), more preferably from 2 to about 8 carbon atoms ($C_2$-$C_8$-alkenyl), and even more preferably from 2 to about 6 carbon atoms ($C_2$-$C_6$-alkenyl), most preferably 2 or 3 carbon atoms ($C_2$-$C_3$-alkenyl). The alkenyl group may be in the Z or E form. Alkenyl groups include vinyl, propenyl, 1-butenyl, isobutenyl, 2-butenyl, 1-pentenyl, (Z)-2-pentenyl, (E)-2-pentenyl, (Z)-4-methyl-2-pentenyl, (E)-4-methyl-2-pentenyl, pentadienyl, e.g., 1, 3 or 2,4-pentadienyl, and the like.

The term "alkynyl" (alone or in combination with another term(s)) means a straight- or branched-chain alkynyl substituent containing at least one triple bond and preferably containing from 2 to about 20 carbon atoms ($C_2$-$C_{20}$-alkynyl), more preferably from 2 to about 8 carbon atoms ($C_2$-$C_8$-alkynyl), and even more preferably from 2 to about 6 carbon atoms ($C_2$-$C_6$-alkynyl), most preferably 2 or 3 carbon atoms ($C_2$-$C_3$-alkynyl). The alkynyl group includes ethynyl, propynyl, 1-butynyl, 2-butynyl, 1-pentynyl, 2-pentynyl, 3-methyl-1-pentynyl, 3-pentynyl, 1-hexynyl, 2-hexynyl, 3-hexynyl and the like.

The term "cycloalkyl" when used alone or in combination with another term (s) means a cycloalkyl group containing from 3 to 18 ring carbon atoms ($C_3$-$C_{18}$-cycloalkyl), preferably from 6 up to 10 ring carbon atoms ($C_3$-$C_{10}$-cycloalkyl). The cycloalkyl groups may be monocyclic, bicyclic, tricyclic, or polycyclic, and the rings may be fused. The cycloalkyl may be completely saturated or partially saturated. Examples of cycloalkyl groups include cyclopropyl, cyclobutyl, cyclopentyl, cyclohexyl, cycloheptyl, cyclooctyl, cyclodecyl, cyclohexenyl, cyclopentenyl, cyclooctenyl, cycloheptenyl, decalinyl, hydroindanyl, indanyl, fenchyl, pinenyl, adamantyl, and the like. The cycloalkyl group includes the cis or trans forms. Cycloalkyl groups may be unsubstituted or mono or polysubstituted with electron withdrawing or/and electron donating groups. In a bridged bicyclic cycloalkyl group, the substituents may either be in endo or exo positions.

The term "cycloalkyl alkyl" as used herein alone or in combination with other term(s) means an alkyl group as defined herein carrying a cycloalkyl substituent as defined herein. Preferred cycloalkyl alkyl groups are cycloalkyl-$C_1$-$C_6$-alkyl, cycloalkyl-$C_1$-$C_3$-alkyl, $C_6$-$C_{10}$-cycloalkyl-alkyl, $C_6$-$C_{10}$-cycloalkyl-$C_1$-$C_6$-alkyl, $C_6$-$C_{10}$-cycloalkyl-$C_1$-$C_3$-alkyl. A more preferred cycloalkyl alkyl group is selected from cyclohexyl-$C_1$-$C_6$-alkyl and cyclohexyl-$C_1$-$C_3$-alkyl.

The term "halo" or "halogen" includes fluoro, chloro, bromo, and iodo.

The prefix "halo" indicates that the substituent to which the prefix is attached is substituted with one or more independently selected halogen radicals. For example, haloalkyl means an alkyl substituent wherein at least one hydrogen radical is replaced with a halogen radical. Examples of haloalkyls include chloromethyl, 1-bromoethyl, fluoromethyl, difluoromethyl, trifluoromethyl, 1,1,1-trifluoroethyl, and the like. Illustrating further, "haloalkoxy" means an alkoxy substituent wherein at least one hydrogen radical is replaced by a halogen radical. Examples of haloalkoxy substituents include chloromethoxy, 1-bromoethoxy, fluoromethoxy, difluoromethoxy, trifluoromethoxy (also known as "perfluoromethyloxy"), 1,1,1,-trifluoroethoxy, and the like. It should be recognized that if a substituent is substituted by more than one halogen radical, those halogen radicals may be identical or different (unless otherwise stated).

The terms "electron-withdrawing" and "electron donating" refer to the ability of a substituent to withdraw or donate electrons, respectively, relative to that of hydrogen if the hydrogen atom occupied the same position in the molecule. These terms are well understood by one skilled in the art and are discussed in Advanced Organic Chemistry, by J. March, John Wiley and Sons, New York, N.Y., pp. 16-18 (1985) and the discussion therein is incorporated herein by reference. Electron withdrawing groups include halo, including bromo, fluoro, chloro, iodo; nitro, carboxy, alkenyl, alkynyl, formyl, carboxyamido, aryl, quaternary ammonium, haloalkyl such as trifluoromethyl, aryl alkanoyl, carbalkoxy and the like. Electron donating groups include such groups as hydroxy, alkoxy, including methoxy, ethoxy and the like; alkyl, such as methyl, ethyl, and the like; amino, alkylamino, dialkyl amino, aryloxy such as phenoxy, mercapto, alkylthio, alkylmercapto, disulfide (alkyldithio) and the like. One of ordinary skill in the art will appreciate that some of the aforesaid substituents may be considered to be electron donating or electron withdrawing under different chemical conditions. Moreover, the present invention contemplates any combination of substituents selected from the above-identified groups.

The electron donating or/and electron withdrawing groups may independently be present in any one of the substituents in Formula (I), (II) or/and (III) e.g., in R, $R_1$, $R_2$, $R_3$, $R_4$, $R_5$, $R_6$, $R'_6$, $R_7$, $R_8$, $R_9$ or/and $R_{10}$ as defined herein.

The at least one electron withdrawing or/and at least one electron donating group is preferably selected independently from halo, alkyl, alkenyl, alkynyl, nitro, carboxy, formyl, carboxyamido, aryl, quaternary ammonium, haloalkyl, aryl alkanoyl, hydroxy, alkoxy, carbalkoxy, amino, alkylamino, dialkylamino, aryloxy, mercapto, alkylthio, alkylmercapto, disulfide, alkanoyl, amino alkyl, aryloyl, cyano, sulfonyl, sulfoxide, heterocyclic, guanidine, sulfonium salts, mercaptoalkyl, and alkyldithio.

The term "sulfide" encompasses mercapto, mercapto alkyl and alkylthio, while the term disulfide encompasses alkyldithio.

In the compounds of the present invention, the at least one electron withdrawing or/and at least one electron donating group is more preferably selected independently from halo, alkyl, alkenyl, alkynyl, nitro, carboxy, formyl, carboxyamido, aryl, quaternary ammonium, haloalkyl, aryl alkanoyl, hydroxy, alkoxy, carbalkoxy, amino, alkylamino, dialkylamino, aryloxy, mercapto, alkylthio, alkylmercapto, and disulfide.

Even more preferably, the at least one electron withdrawing or/and at least one electron donating group is selected from halo, $C_1$-$C_6$-alkyl, $C_2$-$C_6$-alkenyl, $C_1$-$C_6$-alkynyl, nitro, carboxy, formyl, carboxyamido, $C_6$-$C_{10}$-aryl, quaternary ammonium, $C_1$-$C_6$-haloalkyl, $C_6$-$C_{10}$-aryl $C_2$-$C_6$-alkanoyl, hydroxy, $C_1$-$C_6$-alkoxy, $C_2$-$C_6$-carbalkoxy, amino, $C_1$-$C_6$-alkylamino, $C_1$-$C_6$-dialkylamino, $C_6$-$C_{10}$-aryloxy, mercapto, $C_1$-$C_6$-alkylthio, $C_1$-$C_6$-alkylmercapto, and disulfide.

Even more preferably, the electron withdrawing or/and electron donating groups may also be independently selected from halo, $C_1$-$C_6$-alkoxy, nitro, carboxy, formyl, carboxyamido, quaternary ammonium, hydroxy, amino, mercapto, and disulfide.

Most preferred electron withdrawing or/and electron donating groups are independently selected from halo such as fluoro and $C_1$-$C_6$-alkoxy such as methoxy and ethoxy.

The term "carbalkoxy" as used herein alone or in combination with other term(s) means an —CO—O-alkyl, wherein alkyl is as defined herein, taking into account that the —CO—O— group provides one carbon atom in addition to those of the alkyl group. The carbalkoxy group preferably contains from 2 to about 20 carbon atoms ($C_2$-$C_{20}$-carbalkoxy), more preferably from 2 to about 8 carbon atoms ($C_2$-$C_8$-carbalkoxy), even more preferably from 2 to about 6 carbon atoms ($C_2$-$C_6$-carbalkoxy), and most preferably from 2 to 3 carbon atoms ($C_2$-$C_3$-carbalkoxy).

The term "alkanoyl" as used herein alone or in combination with other term (s) means an alkanoyl group —CO-alkyl, wherein alkyl is as defined herein, taking into account that the —CO— group provides one carbon atom in addition to those of the alkyl group. The alkanoyl preferably contains from 2 to about 20 carbon atoms ($C_2$-$C_{20}$-alkanoyl), more preferably from 2 to about 8 carbon atoms ($C_2$-$C_8$-alkanoyl), even more preferably from 2 to about 6 carbon atoms ($C_2$-$C_6$-alkanoyl), and most preferably from 2 to 3 carbon atoms ($C_2$-$C_3$-alkanoyl). The alkanoyl group may be straight chained or branched. The alkanoyl groups include, for example, formyl, acetyl, propionyl, butyryl, isobutyryl, tertiary butyryl, pentanoyl and hexanoyl.

As employed herein, a heterocyclic group contains at least one heteroatom in the cyclic structure, preferably one, two, three or four heteroatoms. The at least one heteroatom may be independently selected from sulfur, nitrogen and oxygen. The heterocyclic groups contemplated by the present invention include heteroaromatics and saturated and partially saturated heterocyclic groups. The heterocyclics may be monocyclic, bicyclic, tricyclic or polycyclic and may be fused rings. The heterocyclics also include the so-called benzoheterocyclics. Heterocyclic groups may be unsubstituted or mono or polysubstituted with electron withdrawing or/and electron donating groups. The heterocyclic groups preferably contain up to 18 ring atoms and up to a total of 17 ring carbon atoms and may be unsubstituted or mono or polysubstituted with electron withdrawing or/and electron donating groups.

More preferably, the heterocyclic group may be independently selected from 5 or 6-membered monocyclic heterocyclic groups and may be unsubstituted or mono or polysubstituted with electron withdrawing or/and electron donating groups. The heterocyclic group may also be more preferably selected independently from furyl, thienyl, pyrazolyl, pyrrolyl, methylpyrrolyl, imidazolyl, indolyl, thiazolyl, oxazolyl, isothiazolyl, isoxazolyl, piperidyl, pyrrolinyl, piperazinyl, quinolyl, triazolyl, tetrazolyl, isoquinolyl, benzofuryl, benzothienyl, morpholinyl, benzoxazolyl, tetrahydrofuryl, pyranyl, indazolyl, purinyl, indolinyl, pyrazolindinyl, imidazolinyl, imadazolindinyl, pyrrolidinyl, furazanyl, N-methylindolyl, methylfuryl, pyridazinyl, pyrimidinyl, pyrazinyl, pyridyl, epoxy, aziridino, oxetanyl, azetidinyl, the N-oxides of the nitrogen containing heterocycles, such as the N-oxides of pyridyl, pyrazinyl, and pyrimidinyl and the like. Even more preferably, the heterocyclic moieties are those aforementioned heterocyclics which are monocyclic.

The heterocyclics may also be more preferably selected independently from thienyl, furyl, pyrrolyl, benzofuryl, benzothienyl, indolyl, oxazolyl, methylpyrrolyl, morpholinyl, pyridiyl, pyrazinyl, imidazolyl, pyrimidinyl, and pyridazinyl. Especially preferred heterocyclic are independently selected from furyl, oxazolyl, pyridyl, pyrazinyl, imidazolyl, pyrimidinyl, and pyridazinyl. The most preferred heterocyclics are independently selected from furyl, pyridyl and oxazolyl.

The monocyclic 5- or 6-membered heterocyclic groups in the compounds of the present invention are preferably of the Formula (IV):

Formula (IV)

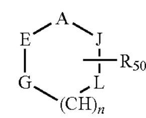

or those corresponding partially or fully saturated form thereof, wherein n is 0 or 1; and $R_{50}$ is H, an electron withdrawing group or an electron donating group;

A, E, L, J and G are independently CH, or a heteroatom selected from the group consisting of N, O, S; but when n is 0, G is CH, or a heteroatom selected from the group consisting of NH, O and S with the proviso that at most two of A, E, L, J and G are heteroatoms.

When n is 0, the above heteroaromatic moiety is a five membered ring, while if n is 1, the heterocyclic moiety is a six membered monocyclic heterocyclic moiety.

If the ring depicted in Formula (IV) contains a nitrogen ring atom, then the N-oxide forms are also contemplated to be within the scope of the invention.

When $R_2$ or $R_3$ is a heterocyclic of Formula (IV), it may be bonded to the main chain by a ring carbon atom. When n is 0, $R_2$ or $R_3$ may additionally be bonded to the main chain by a nitrogen ring atom.

The term "heterocyclic alkyl" as used herein alone or in combination with other term(s) means an alkyl group as defined above carrying a heterocyclic substituent as defined above. Preferred heterocyclic alkyl groups are heterocyclic-$C_1$-$C_6$-alkyl, heterocyclic-$C_1$-$C_3$-alkyl, wherein the heterocyclic may be a preferred, more preferred or most preferred heterocyclic group as defined herein.

The term "alkyl heterocyclic" as used herein alone or in combination with other term(s) means a heterocyclic group as defined above carrying at least one alkyl substituent as defined above. Preferred alkyl heterocyclic groups are $C_1$-$C_6$-alkyl-heterocyclic, $C_1$-$C_3$-alkyl-heterocyclic, wherein the heterocyclic group may be a preferred, more preferred or most preferred heterocyclic group as defined herein.

The preferred compounds are those wherein n is 1, but di (n=2), tri (n=3) and tetrapeptides (n=4) are also contemplated to be within the scope of the invention.

In the ZY groups representative of $R_2$ or/and $R_3$, in the formula (I) or/and (II), Z may be O, S, $S(O)_a$, wherein a is 1-3, $NR_4$, $PR_4$ or a chemical bond; and Y may be hydrogen, alkyl, aryl, aryl alkyl, alkenyl, alkynyl, halo, heterocyclic, heterocyclic alkyl, alkyl heterocyclic, and Y may be unsubstituted or substituted with at least one electron donating group or/and at least one electron withdrawing group, provided that when Y is halo, Z is a chemical bond, or ZY taken together may be $NR_4NR_5R_7$, $NR_4OR_5$, $ONR_4R_7$, $OPR_4R_5$, $PR_4OR_5$, $SNR_4R_7$, $NR_4SR_7$, $SPR_4R_5$, $PR_4SR_7$, $NR_4PR_5R_6$, $PR_4NR_5R_7$ or $n^+R_5R_6R_7$,

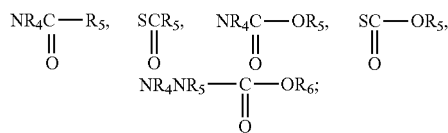

wherein $R_4$, $R_5$, $R'_6$, $R_6$, $R_7$, are as defined herein.

The ZY groups representative of $R_2$ or/and $R_3$ in the Formula (I) or/and (II) may be hydroxy, alkoxy, such as methoxy, ethoxy, aryloxy, such as phenoxy; thioalkoxy, such as thiomethoxy, thioethoxy; thioaryloxy such as thiophenoxy; amino; alkylamino, such as methylamino, ethylamino; arylamino, such as anilino; dialkylamino, such as, dimethylamino; trialkyl ammonium salt, hydrazino; alkylhydrazino and arylhydrazino, such as N-methylhydrazino, N-phenylhydrazino, carbalkoxy hydrazino, aralkoxycarbonyl hydrazino, aryloxycarbonyl hydrazino, hydroxylamino, such as N-hydroxylamino (—NH—OH), alkoxy amino [$(NHOR_{18})$ wherein $R_{18}$ is alkyl], N-alkylhydroxyl amino [$(NR_{18})OH$ wherein $R_{18}$ is alkyl], N-alkyl-O-alkylhydroxyamino, i.e., [$N(R_{18})OR_{18}$ wherein $R_{18}$ and $R_{19}$ are independently alkyl], and O-hydroxylamino (—O—$NH_2$); alkylamido such as acetamido; trifluoroacetamido; alkoxyamino, (e.g., $NH(OCH_3)$; and heterocyclicamino, such as pyrazoylamino.

In a preferred ZY group, Z is O, $NR_4$ or $PR_4$; Y is hydrogen or alkyl.

In another preferred embodiment,

ZY is $NR_4R_5R_7$, $NR_4OR_5$, $ONR_4R_7$,

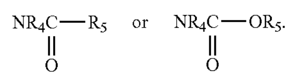

In a more preferred that ZY is $NR_4OR_5$, or $ONR_4R_7$.

Another more preferred ZY is N-hydroxyamino, N-alkylhydroxyamino, N-alkyl-O-alkyl hydroxyamino, O-alkylhydroxyamino, N-alkoxy-N-alkylamino, N-alkoxyamino, or N-carbalkoxy.

In Formula (I), R is preferably aryl or aryl alkyl, more preferably R is aryl alkyl, wherein R is unsubstituted or substituted with at least one electron donating group or/and at least one electron withdrawing group. R may be phenyl or benzyl, most preferably benzyl, wherein R is unsubstituted or substituted with at least one electron donating group or/and at least one electron withdrawing group. If R is substituted, R is preferably substituted on the aryl ring. In this embodiment, the at least one electron donating group or/and at least one electron withdrawing group is preferably halo, more preferably fluoro.

In Formulae (I), (II) or/and (III), $R_1$ is H or alkyl. More preferably, $R_1$ is alkyl, preferably containing from 1 to 6 carbon atoms, more preferably containing from 1 to 3 carbon atoms. Most preferably the $R_1$ group is methyl. $R_1$ may be unsubstituted or substituted with at least one electron donating group or/and at least one electron withdrawing group.

Further, it is preferred that one of $R_2$ and $R_3$ is hydrogen. It is more preferred that $R_2$ is hydrogen. Other preferred moieties of $R_2$ in Formula (I) are aryl such as phenyl, aryl alkyl such as benzyl, and alkyl. It is to be understood that the preferred groups of $R_2$ may be unsubstituted or mono or poly substituted with electron donating or/and electron withdrawing groups. It is preferred that the at least one electron withdrawing or/and at least one donating group in $R_2$ is independently alkoxy, N-hydroxyamino, N-alkylhydroxyamino, N-alkyl-O-alkyl hydroxyamino or O-alkylhydroxyamino, and especially methoxy or ethoxy.

In Formulae (I), (II) or/and (III), $R_3$ may be hydrogen, an alkyl group unsubstituted or substituted by at least an electron donating or/and at least one electron withdrawing group, an aryl group unsubstituted or substituted by at least an electron donating or/and at least one electron withdrawing group heterocyclic, heterocyclic alkyl, or ZY.

It is preferred that $R_3$ is hydrogen, alkyl unsubstituted or substituted by at least an electron donating or/and at least one electron withdrawing group, aryl which is unsubstituted or substituted by at least one electron donating group or/and at least one electron withdrawing group, heterocyclic, heterocyclic alkyl or ZY, wherein Z is O, $NR_4$ or $PR_4$; Y is hydrogen or alkyl; ZY is $NR_4NR_5R_7$, $NR_4OR_5$, $ONR_4R_7$,

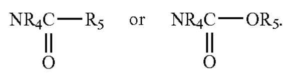

It is also preferred that $R_3$ is alkyl unsubstituted or substituted by at least an electron donating or/and at least one electron withdrawing group; or Z—Y, wherein Z—Y is as defined herein.

It is also preferred that $R_3$ is alkyl unsubstituted or substituted by at least an electron donating or/and at least one electron withdrawing group; $NR_4OR_5$, or $ONR_4R_7$, wherein $R_4$, $R_5$ and $R_7$ are as defined herein.

It is also preferred that $R_3$ is $CH_2$-Q, wherein Q is alkoxy especially containing 1-3 carbon atoms; or $R_3$ is $NR_4OR_5$ or $ONR_4R_7$, wherein $R_4$, $R_5$, and $R_7$ are as defined herein.

$R_3$ is also preferably alkyl which is unsubstituted or substituted with at least one alkoxy especially containing 1-3 carbon atoms.

$R_3$ is also preferably $CH_2$-Q, wherein Q is alkoxy preferably containing 1-3 carbon atoms, more preferably Q is ethoxy or methoxy.

$R_3$ is also preferably $NR_4OR_5$, or $ONR_4R_7$, wherein $R_4$, $R_5$ and $R_7$ are as defined herein, and $R_4$, $R_5$ and $R_7$ are as defined herein, e.g. N-alkoxy, N-alkoxy-N-alkylamino or N-carbalkoxy.

$R_3$ is also preferably heterocyclic, heterocyclic alkyl, or aryl, which may be unsubstituted or substituted with at least an electron donating or/and at least one electron withdrawing group. A most preferred heterocyclic in $R_3$ is furyl or oxazolyl.

$R_3$ is also preferably selected from the group consisting of hydrogen, alkyl, arylalkyl such as benzyl, alkoxy, alkoxyalkyl, aryl such as phenyl, heterocyclic, heterocyclic alkyl, N-alkoxy-N-alkylamino, N-alkoxyamino and N-carbalkoxy.

It is to be understood that the preferred groups of $R_3$ may be unsubstituted or mono or poly substituted with electron donating or/and electron withdrawing groups. It is preferred that the at least one electron withdrawing or/and at least one electron donating group in $R_3$ is independently alkoxy, N-hydroxyamino, N-alkylhydroxyamino, N-alkyl-O-alkyl hydroxyamino or O-alkylhydroxyamino, and especially methoxy or ethoxy.

$R_4$, $R_5$, $R_6$, $R'_6$, $R_7$ and $R_8$ are preferably independently hydrogen or alkyl.

$R_4$, $R_5$, and $R_7$ are preferably independently hydrogen or alkyl preferably containing 1-3 carbon atoms.

The most preferred aryl is phenyl. The most preferred halo is fluoro.

In the compounds of Formula (I), R is preferably aryl alkyl, wherein R is unsubstituted or substituted with at least one electron donating group or/and at least one electron withdrawing group.

In the compounds of Formula (I), $R_1$ is preferably alkyl which is unsubstituted or substituted with at least one electron donating group or/and at least one electron withdrawing group.

In the compounds of Formula (I), $R_2$ and $R_3$ is preferably independently hydrogen, alkyl which is unsubstituted or substituted by at least one electron donating group or/and at least one electron withdrawing group, aryl which is unsubstituted or substituted by at least one electron donating group or/and at least one electron withdrawing group, heterocyclic, heterocyclic aryl, or ZY; wherein Z is O, $NR_4$ or $PR_4$; and Y is hydrogen or alkyl; or ZY is $NR_4NR_5R_7$, $NR_4OR_5$, $ONR_4R_7$,

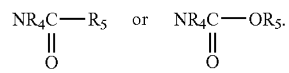

wherein $R_4$, $R_5$ and $R_7$ are as defined herein.

In the compounds of Formula (I), the preferred groups of $R_2$ and $R_3$ may be unsubstituted or mono or poly substituted with electron donating or/and electron withdrawing groups, such as alkoxy (e.g., methoxy, ethoxy, and the like), N-hydroxyamino, N-alkylhydroxyamino, N-alkyl-O-alkyl hydroxyamino and O-alkylhydroxyamino.

In the compounds of Formula (I), the at least one electron donating group or/and at least one electron withdrawing group in $R_2$ or/and $R_3$ is preferably independently hydroxy or alkoxy.

It is more preferred that in the compounds of Formula (I), $R_2$ is hydrogen.

In the compounds of Formula (II), $R_1$ is preferably methyl.

In preferred compounds of Formula (II), $R_3$ is hydrogen or alkyl unsubstituted or substituted by at least one electron donating group or/and at least one electron withdrawing group; or $R_3$ is heterocyclic, heterocyclic alkyl, or Z—Y, wherein Z—Y and heterocyclic are as defined herein.

In other preferred compounds of Formula (II), $R_3$ is an alkyl group which is unsubstituted or substituted by at least one electron donating group or/and at least one electron withdrawing group, $NR_4OR_5$ or $ONR_4R_7$, wherein $R_4$, $R_5$ and $R_7$ are as defined herein and wherein the at least one electron donating group or/and at least one electron withdrawing group is preferably selected from hydroxy and alkoxy.

In further preferred compounds of Formula (II), $R_3$ is $CH_2$-Q, wherein Q is alkoxy preferably containing 1-3 carbon atoms, more preferably methoxy, or $R_3$ is $NR_4OR_5$ or $ONR_4R_7$ wherein $R_4$, $R_5$ and $R_7$ are independently hydrogen or alkyl containing 1-3 carbon atoms.

In other preferred compounds of Formula (II), $R_3$ is —$CH_2$-Q, wherein Q is alkoxy containing 1 to 3 carbon atoms.

In the compounds of Formula (II), Ar is preferably phenyl unsubstituted or substituted with at least one halo, preferably with at least one fluoro. More preferably Ar in Formula (II) is unsubstituted phenyl.

In preferred compounds of Formula (III), $R_9$ is hydrogen or fluoro, $R_3$ is selected from the group consisting of methoxymethyl, phenyl, N-methoxy-N-methylamino, and N-methoxyamino, and $R_1$ is methyl.

The most preferred compounds of the present invention include:

(R)-2-acetamido-N-benzyl-3-methoxy-propionamide;
(R)-2-acetamido-N-benzyl-3-ethoxy-propionamide;
O-methyl-N-acetyl-D-serine-m-fluorobenzyl-amide;
O-methyl-N-acetyl-D-serine-p-fluorobenzyl-amide;
N-acetyl-D-phenylglycine benzylamide;
D-1,2-(N,O-dimethylhydroxylamino)-2-acetamide acetic acid benzylamide;
D-1,2-(O-methylhydroxylamino)-2-acetamido acetic acid benzylamide;
D-α-acetamido-N-(2-fluorobenzyl)-2-furanacetamide;
D-α-acetamido-N-(3-fluorobenzyl)-2-furanacetamide.

It is to be understood that the Markush groups of $R_1$, $R_2$, $R_3$, R and n as described herein can be combined and permutated. The various combinations and permutations not explicitly disclosed herein are contemplated to be within the scope of the present invention. Moreover, the present invention also encompasses compounds and compositions which contain one or more elements of each of the Markush groupings in $R_1$, $R_2$, $R_3$, n and R and the various combinations thereof. Thus, for example, the present invention contemplates that $R_1$ may be one or more of the substituents listed hereinabove in combination with any and all of the substituents of $R_2$, $R_3$, and R with respect to each value of n.

More preferred is a compound of Formula (I), (II) or/and (III) in the R configuration, preferably substantially enantiopure, wherein the substituent R is benzyl which is unsubstituted with at least one halo group, wherein $R_3$ is $CH_2$-Q, wherein Q is alkoxy containing 1-3 carbon atoms and wherein $R_1$ is methyl. Preferably R is unsubstituted benzyl or benzyl substituted with at least one halo group which is a fluoro group.

Depending upon the substituents, the present compounds may form addition salts as well. All of these forms are contemplated to be within the scope of this invention including mixtures of the stereoisomeric forms.

The manufacture of compounds utilized in the present invention is described in U.S. Pat. Nos. 5,378,729 and 5,773,475, and in the international application PCT/EP 2005/010603 the contents of which are incorporated by reference.

The compounds utilized in the present invention are useful as such as depicted in the Formulae (I), (II) or/and (III) or can be employed in the form of salts in view of its basic nature by the presence of the free amino group. Thus, the compounds of Formulae (I), (II) or/and (III) form salts with a wide variety of acids, inorganic and organic, including pharmaceutically acceptable acids. The salts with therapeutically acceptable acids are of course useful in the preparation of formulation where enhanced water solubility is most advantageous.

These pharmaceutically acceptable salts have also therapeutic efficacy. These salts include salts of inorganic acids such as hydrochloric, hydroiodic, hydrobromic, phosphoric, metaphosphoric, nitric acid and sulfuric acids as well as salts of organic acids, such as tartaric, acetic, citric, malic, benzoic, perchloric, glycolic, gluconic, succinic, aryl sulfonic, (e.g., p-toluene sulfonic acids, benzenesulfonic), phosphoric, malonic, and the like.

The physician will determine the dosage of the present therapeutic agents which will be most suitable and it will vary with the form of administration and the particular compound chosen, and furthermore, it will vary with the patient under treatment, the age of the patient, the type of malady being treated. He will generally wish to initiate treatment with small dosages substantially less than the optimum dose of the compound and increase the dosage by small increments until the optimum effect under the circumstances is reached. When the composition is administered orally, larger quantities of the active agent will be required to produce the same effect as a smaller quantity given parenterally. The compounds are useful in the same manner as comparable therapeutic agents and the dosage level is of the same order of magnitude as is generally employed with these other therapeutic agents.

In one embodiment, the compounds of the present invention are administered in amounts ranging from about 1 mg to about 100 mg per kilogram of body weight per day, or in amounts ranging from about 1 mg to about 10 mg per kilogram of body weight per day. This dosage regimen may be adjusted by the physician to provide the optimum therapeutic response. Patients in need thereof may be treated with doses of the compound of the present invention of at least 50 mg/day, of at least 200 mg/day, of at least 300 mg/day, of at least 400 mg/day, or of at least 600 mg/day. Generally, a patient in need thereof may be treated with doses at a maximum of 6 g/day, a maximum of 1 g/day, a maximum of 800 mg/day, or a maximum of 600 mg/day. In some cases, however, higher or lower doses may be needed.

In another embodiment, the daily doses are increased until a predetermined daily dose is reached which is maintained during the further treatment.

In yet another embodiment, several divided doses may be administered daily. For example, three doses per day, or two doses per day, or a single dose per day may be administered.

In yet another embodiment, an amount of the compounds of the present invention may be administered which results in a plasma concentration of 0.1 to 15 μg/ml (trough) and 5 to 18.5 μg/ml (peak), calculated as an average over a plurality of treated subjects, intravenous administration in emergency treatment might result in peak plasmid levels of up to 30 μg/ml.

The compounds of Formulae (I), (II) or/and (III) may be administered in a convenient manner, such as by oral, intravenous (where water soluble), intramuscular, intrathecal, rectal (e.g. suppository, gel, liquid, etc.) or subcutaneous routes. In particular, the compounds of Formulae (I), (II) or/and (III) may be administered orally, rectally or/and i.v. In emergency treatment, the compounds of Formulae (I), (II) or/and (III) may be i.v. administered.

The pharmaceutical composition of the present invention may be prepared for the treatment regimen as described above, in particular for the treatment with doses as described above, to effect plasma concentrations as described above, for administration periods or/and administration routes as specified in the embodiments of the present invention as described above.

The compounds of Formulae (I), (II) or/and (III) may be orally administered, for example, with an inert diluent or with an assimilable edible carrier, or it may be enclosed in hard or soft shell gelatin capsules, or it may be compressed into tablets, or it may be incorporated directly into the food of the diet. For oral therapeutic administration, the active compound of Formulae (I), (II) or/and (III) may be incorporated with excipients and used in the form of ingestible tablets, buccal tablets, troches, capsules, elixirs, suspensions, syrups, wafers, and the like. Such compositions and preparations should contain at least 1% of active compound of Formulae (I), (II) or/and (III). The percentage of the compositions and preparations may, of course, be varied and may conveniently be between about 5 to about 80% of the weight of the unit. The amount of active compound of Formulae (I), (II) or/and (III) in such therapeutically useful compositions is such that a suitable dosage will be obtained. The compositions or preparations according to the present invention may contain between about 10 mg and 6 g active compound of Formulae (I), (II) or/and (III).

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier.

Various other materials may be present as coatings or otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations. For example, sustained release dosage forms are contemplated wherein the active ingredient is bound to an ion exchange resin which, optionally, can be coated with a diffusion barrier coating to modify the release properties of the resin.

The active compound may also be administered parenterally or intraperitoneally. Dispersions can also be prepared in glycerol, liquid, polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions (where water soluble) or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersions and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of preparing sterile powders for the manufacture of sterile injectable solutions, the preferred methods of preparation are vacuum drying, or freeze-drying optionally together with any additional desired ingredient.

As used herein, "pharmaceutically acceptable carrier" includes any and all solvents, dispersion media, coatings, antibacterial and antifungal agent, isotonic and absorption delaying agents for pharmaceutical active substances as well known in the art. Except insofar as any conventional media or agent is incompatible with the active ingredient, its use in the therapeutic compositions is contemplated. Supplementary active ingredients can also be incorporated into the compositions.

It is especially advantageous to formulate parenteral compositions in dosage unit form or ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specifics for the novel dosage unit forms of the invention are dictated by and directly dependent on (a) the unique characteristics of the active material an the particular therapeutic effect to be achieved, and (b) the limitations inherent in the art of compounding such as active material for the treatment of disease in living subjects having a diseased condition in which bodily health is impaired as herein disclosed in detail.

The principal active ingredient is compounded for convenient and effective administration in effective amounts with a suitable pharmaceutically acceptable carrier in dosage unit form as hereinbefore described. A unit dosage form can, for example, contain the principal active compound in amounts ranging from about 10 mg to about 6 g. Expressed in proportions, the active compound is generally present in from about 1 to about 750 mg/ml of carrier. In the case of compositions containing supplementary active ingredients, the dosages are determined by reference to the usual dose and manner of administration of the said ingredients.

As used herein the term "patient" or "subject" refers to a warm blooded animal, and preferably mammals, such as, for example, cats, dogs, horses, cows, pigs, mice, rats and primates, including humans. The preferred patient is a human.

The term "treat" refers to either relieving the pain associated with a disease or condition, or to providing partial to complete relief of the patient's disease or condition or to alleviating the patient's disease or condition.

The compounds of the present invention are administered to a patient suffering from the aforementioned type of disorder in an effective amount. These amounts are equivalent to the therapeutically effective amounts described hereinabove.

EXAMPLES

The present invention is further illustrated by the following example and figures.

Figure Legends

FIG. 1A: Fraction of channels available after a repolarizing pulse of −100 mV and −60 mV, respectively. LTG: lamotrigine, CBZ: carbamazepine, DPH: phenytoin, LCM: lacosamide.

FIG. 1B: Voltage dependency of slow inactivation in the presence (LCM) or in the absence (PRETREATMENT) of lacosamide. Cells were held at −80 mV and depolarised for 10 seconds to −10 mV, followed by a recovery interval of 1.5 s prior to a test pulse. The recovery interval of 1.5 s was used to completely allow the recovery of fast inactivation making occupancy of the slow inactivated state the sole determinant of the second test pulse amplitude. The test pulse was used to measure the peak available current.

Figure 2:
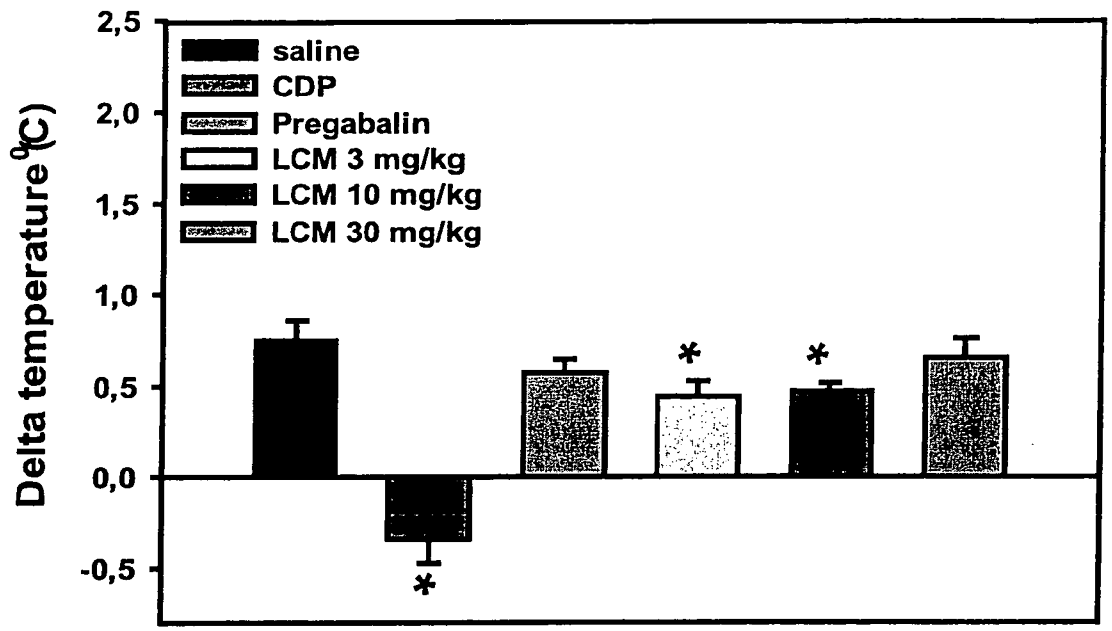
FIG. 2 is a chart showing an effect of chlordiazepoxide, pregabalin and lacosamide on stress-induced hyperthermia in mice.

FIG. 2: Effect of chlordiazepoxide (CDP), pregabalin and lacosamide (LCM, 3-30 mg/kg) on SIH. Data represents mean±SEM of 11-12 mice/treatment group. *: significantly different from saline, P<0.05.

Figure 3:
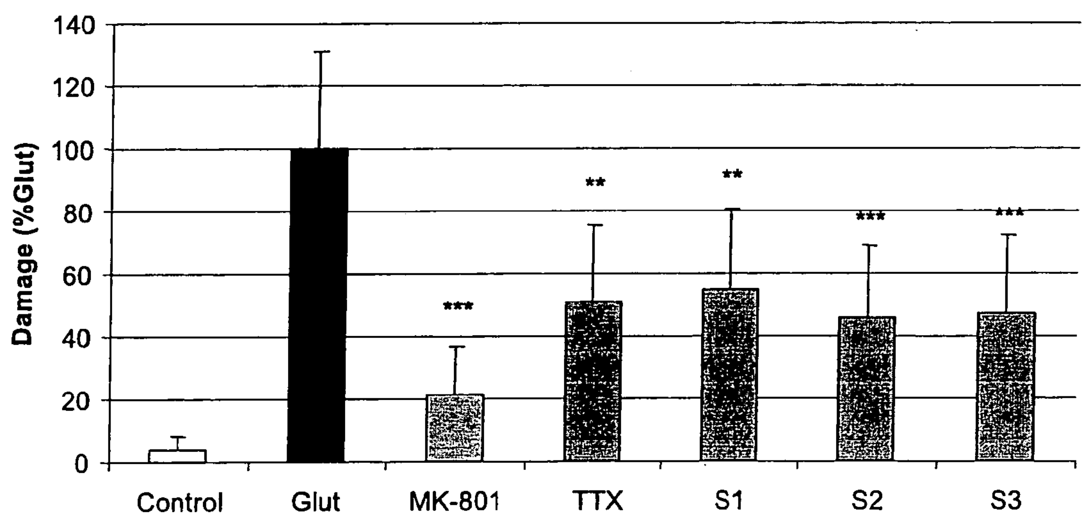
FIG. 3 is a chart showing effect of lacosamide on neuronal damage in CA1-CA3 after glutamate excitotoxicity (Glut), as assessed by densitometric quantification of propidium-iodide uptake.
Figure 4:
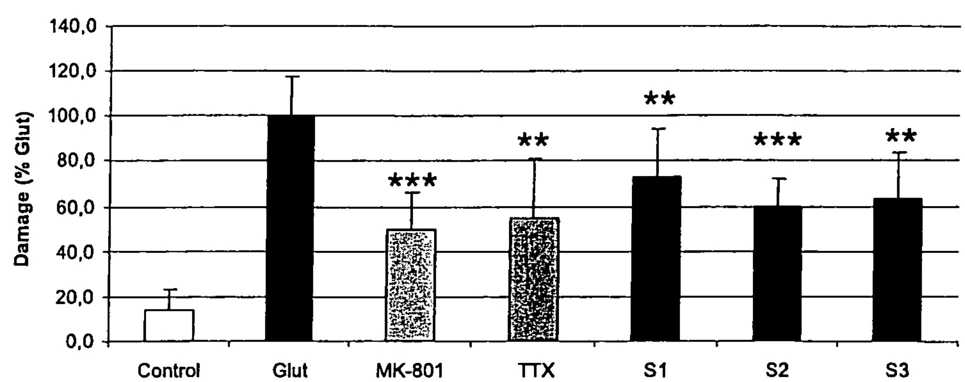
FIG. 4 is a chart showing effect of lacosamide on neuronal damage in CA1-CA3 after glutamate excitotoxicity (Glut), as assessed by colorimetric quantification of LDH release 24 hours after Glut onset.

FIGS. 3 and 4: The effects of lacosamide on neuronal damage in CA1-CA3 after glutamate exitotoxicity (Glut). 2 h before Glut (15 mM for 24 h) cultures were treated with vehicle (Glut), 10 μM MK-801, 1 μM Tetrodotoxin (TTX), 1 μM (S1), 10 μM (S2) and 100 μM (S3) of lacosamide. Compounds were present from 2 h before until 24 h after Glut onset. Neuronal damage was assessed by densitometric quantification of propidium-iodide (PI) uptake (FIG. 3) or by colorimetric quantification of LDH release (FIG. 4) 24 h after Glut onset. Glut damage was set to 100%, data are given as % of Glut damage. Data were combined from 2-4 independent experiments Data are given as mean value plus STD (*p<0.001 vs Glut; p<0.01 vs Glut. Tukey test post hoc after 1-way ANOVA).

Figure 5A:
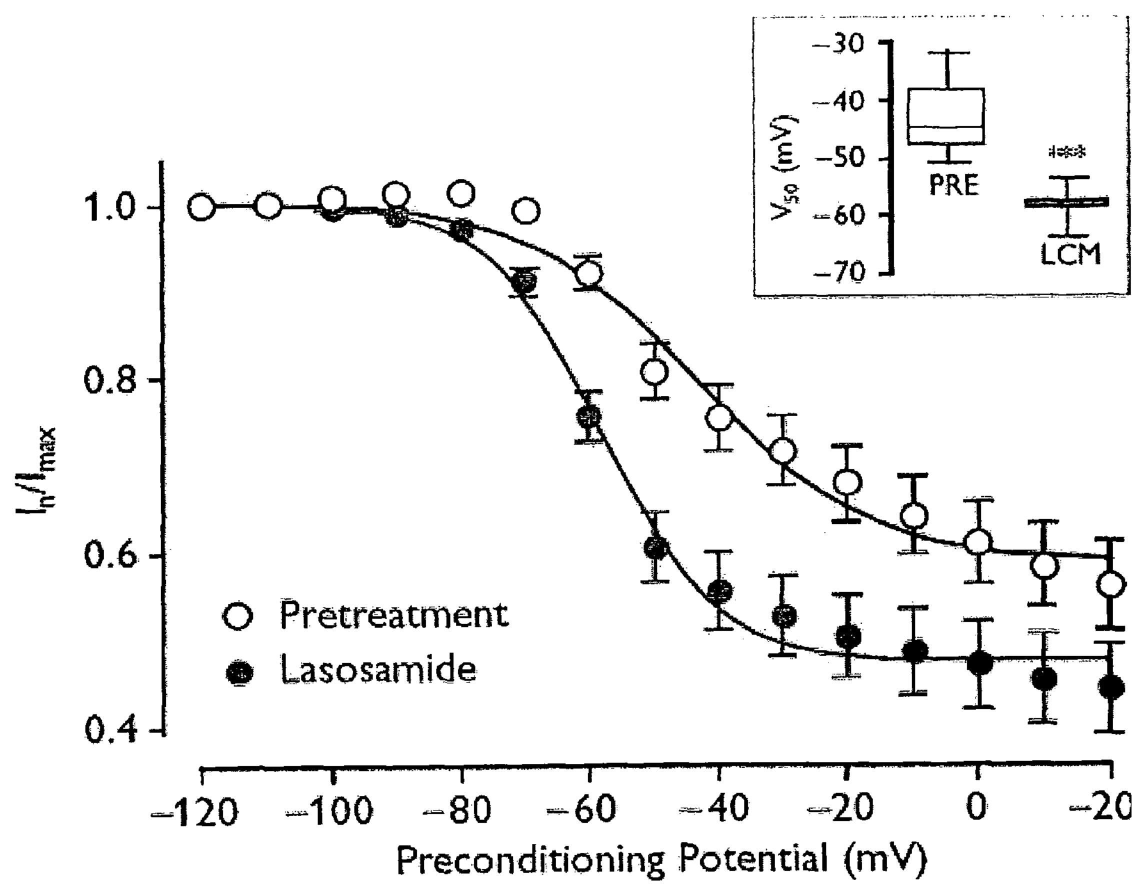
FIG. 5A is a chart showing that lacosamide shifts the slow inactivation voltage curve to more hyperpolarized membrane potentials in *Xenopus* oocytes expressing the alpha subunit of the rat type II sodium channel.
Figure 5B:
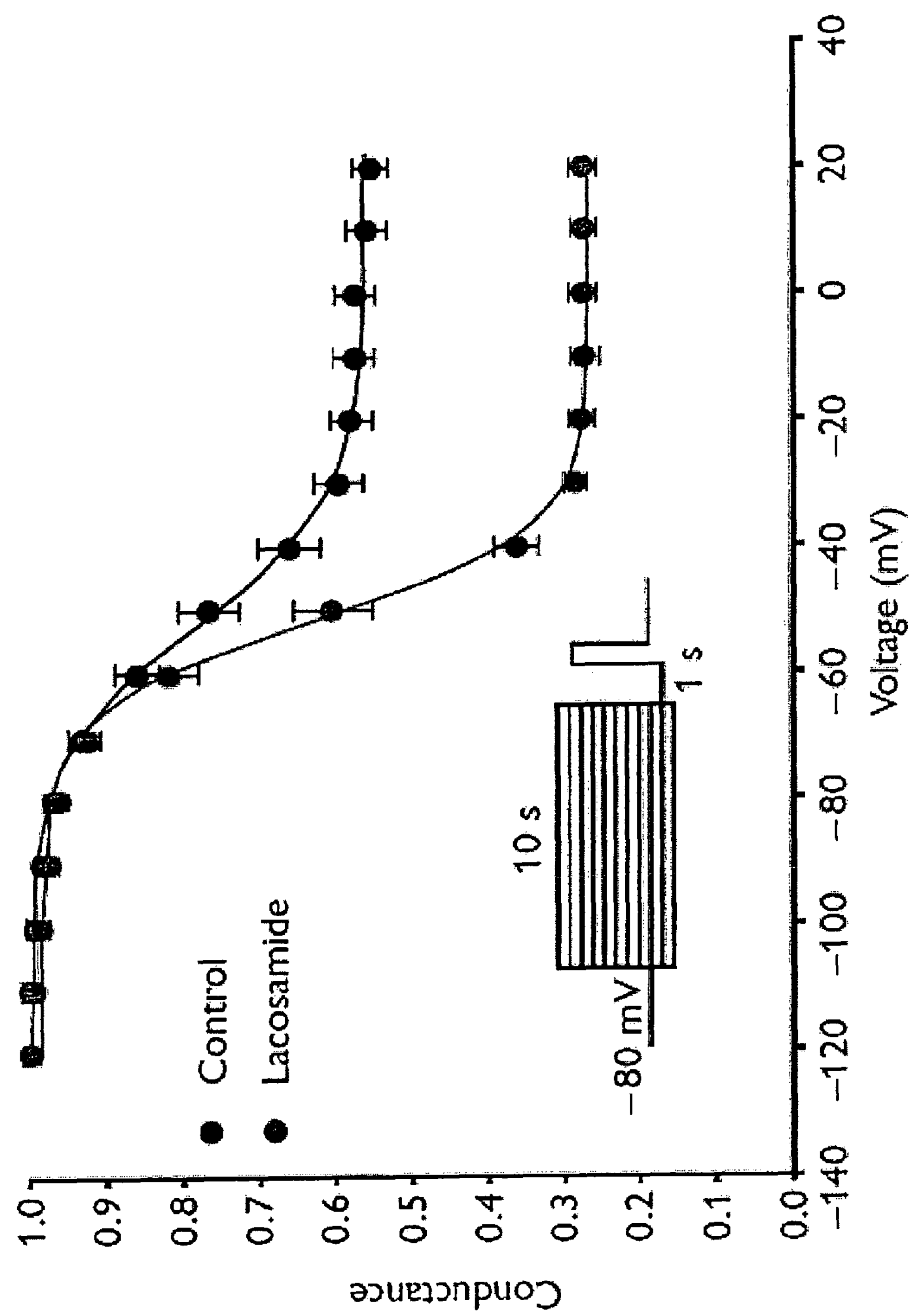
FIG. 5B is a chart showing that in rat dorsal root ganglia, lacosamide at 100 μM increases the maximal fraction of slowly inactivated TTX-resistant sodium current.
Figure 5C:
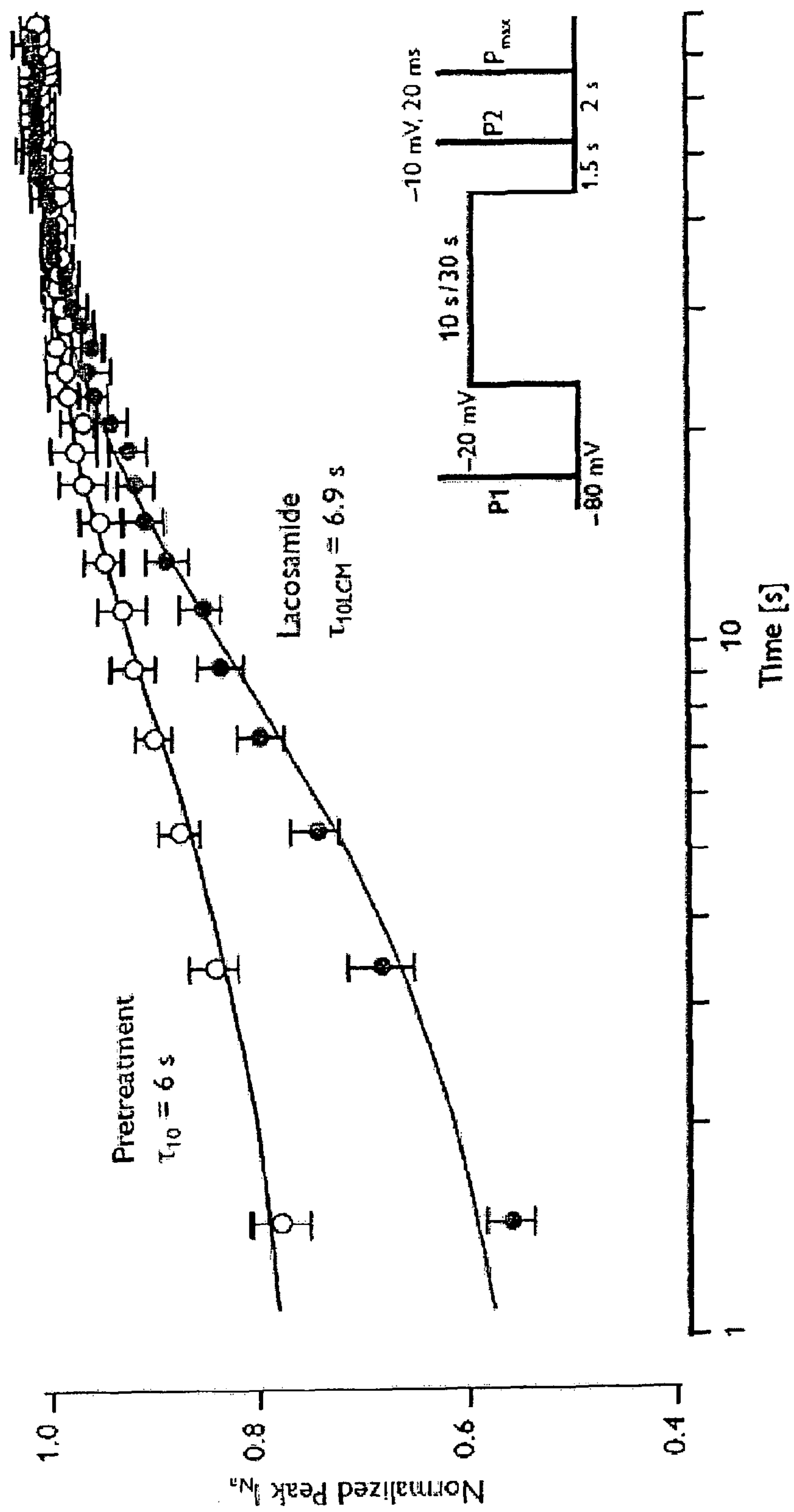
FIG. 5C is a chart showing that lacosamide does not delay recovery from slow inactivation.

FIG. 5: Lacosamide shifts the slow inactivation voltage curve to more hyperpolarized membrane potentials in *Xenopus* oocytes expressing the alpha subunit of the Rat Type II Sodium Channel (FIG. 5A). In rat dorsal root ganglia, Lacosamide at 100 μM increases the maximal fraction of slowly inactivated TTX-resistant sodium current (FIG. 5B). Lacosamide did not delay recovery from slow inactivation (FIG. 5C).

Example 1

Initial studies indicated that lacosamide does not produce changes to the processes of fast inactivation gating of sodium channels in a manner that was consistent with the effects of existing antiepileptic drugs. This was evidenced by a very limited effect of lacosamide upon action potential firing evoked by brief depolarising steps or ramps. The lack of effect of lacosamide upon fast inactivation has been further supported by experiments performed upon *Xenopus* oocytes expressing only sodium channel alpha subunits. Again, as was observed in neuroblastoma cells, lacosamide did not produce shifts in the fast inactivation voltage curve or retard recovery from steady state fast inactivation. Contrary to the lack of effect of lacosamide, both of these gating processes were considerably changed by carbamazepine, lamotrigine and phenytoin.

In the oocyte expression system lacosamide was however, still able to produce rapid and profoundly voltage dependent inhibition of sodium currents. Sodium channels in mouse neuroblastoma N1E-115 cells undergo the physiological process of slow inactivation in addition to fast inactivation when exposed to periods of prolonged depolarisation. Sodium channels in the fast inactivated conformation can be reactivated by a 500 ms hyperpolarizing pulse. A following test pulse will reveal selectively the amount of slow inactivated sodium channels.

Thus neuroblastoma cells were maintained at a holding potential of −60 mV to induce fast and slow inactivation and depolarised by a 10 ms test pulse to 0 mV to measure the amount of available channels. This protocol was repeated in each cell with a 500 ms hyperpolarizing pulse to −100 mV prior to the depolarising test pulse in order to selectively remove fast inactivation. In all cells tested carbamazepine (CBZ), lamotrigine (LTG), phenytoin (DPH) and lacosamide (LCM, all drugs tested at 100 μM) produced a reduction in current when the holding potential was −60 mV. For CBZ, LTG and DPH application of a 500 ms hyperpolarizing pulse to −100 mV reversed the blocking action on the channel, with the fraction available being 0.94±0.19, 0.88±0.06 and 0.99±0.05 respectively compared to control values (FIG. 1A).

In comparison to the results of the clinically used sodium channel modulating anticonvulsants, the inhibition produced by LCM was not altered by the hyperpolarizing prepulse i.e. by the removal of fast inactivation. This indicates that whereas the classical sodium channel modulating anticonvulsants lamotrigine, carbamazepine and phenytoin selectively act on fast inactivation, lacosamide exerts its effects on sodium currents exclusively by enhancing slow inactivation.

In order to assess concentration-dependent effects of lacosamide on the entry of sodium channels into the slow inactivated state, cells were held at −80 mV and depolarised for 10 seconds to −10 mV, followed by a recovery interval of 1.5 s prior to a test pulse to measure the peak available current. The recovery interval of 1.5 s was used to completely allow the recovery of fast inactivation making occupancy of the slow inactivated state the sole determinant of the second test pulse amplitude. When neuroblastoma cells were depolarised for 10 seconds the peak available current was reduced to 0.73±0.01 that of the preconditioning test pulse. Lacosamide enhanced the entry of sodium channels into the slow inactivated state in a concentration dependent manner (% of channels in the slow inactivated state: VEH: 27%. LCM 32 μM: 37%, LCM 100 μM: 50%, LCM 320 μM: 62%). Lacosamide (100 μM) more than doubled the reduction of sodium channel availability that resulted from entry into the slow inactivated state.

The time constant for the physiological entry into slow inactivation was 12.0 s. In the presence of the drug, channels entered the slow inactivated state faster (i.e. time constant for entry 4.8 s).

As with its more rapid counterpart, the extent that sodium channels undergo the process of slow inactivation at steady state is dependent upon membrane potential. Voltage dependence of slow inactivation in N1E-115 cells was evaluated and revealed physiological slow inactivation at potentials more depolarised than −80 mV. However slow inactivation was only 30% complete at the maximum conditioning pulse of −10 mV. Lacosamide shifted the slow inactivation voltage curves to more hyperpolarized membrane potentials in a concentration dependent manner. The first significant change in channel availability in the presence of 100 μM LCM was noted at a conditioning potential of −80 mV; more hyperpolarized than the typical resting potential of many neurons. LCM application significantly increased the maximal fraction of current made unavailable by depolarisation across the range of potentials between—80 mV and −10 mV (−10 mV, CONTROL 0.70±0.02, LCM 0.41±0.04). Lacosamide (32 μM and 100 μM) produced a shift of the $V_{50}$ for slow inactivation to more negative potentials (FIG. 1B), i.e. lacosamide shifts the slow inactivation voltage curve for sodium channels to more hyperpolarized potentials. Thus, at the given steady-state potential, the amount of sodium channels which are available for activation is reduced by lacosamide.

The following effects of lacosamide upon sodium channels were identified in rat cortical neurons, NIE-115 cells and *Xenopus* oocytes:

- Lacosamide did not modulate synaptic transmission under normal physiologic conditions.
- Lacosamide indiscriminately attenuates the rate of synaptic traffic in cultured neurons in a stereoselective and concentration dependent manner.
- The frequency of miniature excitatory post-synaptic potentials is not reduced by lacosamide.
- Lacosamide produced no effect upon resting conductances.
- Lacosamide did not block sustained repetitive firing.
- Lacosamide inhibits slow prolonged bursting in cortical neurons.
- Lacosamide inhibits prolonged sustained repetitive firing on action potentials.
- Lacosamide does not shift steady state fast inactivation voltage curves.
- Lacosamide does not change the rate of sodium channel fast inactivation.
- The rate of recovery of sodium channels from the unavailable slowly inactivated state is not changed.

In summary, these experiments demonstrate that lacosamide selectively enhances slow inactivation of voltage-gated sodium channels while leaving fast inactivation normal. This constitutes a novel mechanism of action which can efficiently normalize excessive sodium channel function as e.g. seen in mutated channels.

In particular, by its effect on slow inactivation of sodium channels, lacosamide is suitable for the prevention, alleviation or/and treatment of diseases associated with hyperexcitability. Further, by its effect on slow inactivation of sodium channels, lacosamide is suitable for the prevention, alleviation or/and treatment of diseases associated with dysfunction of an ion channel.

Example 2

Lacosamide in an Animal Model for Stress-Induced Anxiety

In this study the effects of lacosamide in an animal model for stress-related anxiety were tested. In this animal model, stress is induced by the measurement of rectal temperature. The stress-induced hyperthermia (SIH) test is based upon the principle that mice have a natural hyperthermic response to stress, which reflects the level of stress-induced anxiety. The effects of lacosamide in this model were compared to that of the reference compound chlordiazepoxide (CDP) which is used clinically as first-line anxiolytic treatment. In addition, the novel anticonvulsant drug pregabalin which is also developed for generalized anxiety disorder was used as additional reference compound.

Materials and Methods

Adult male 129SVEV mice (8 weeks old) from Taconic Laboratories (Germantown, N.Y.) were used in this study. The mice were housed in standard polycarbonate cages with filter tops. Four animals were housed per cage and food and water were provided ad libitum for the duration of the study except noted otherwise. Prior to initiation of the study, the animals were examined to assure adequate health and suitability; the animals also received two days of handling prior to test to minimize non-specific stress associated with the test. Mice were maintained on a 12/12 light/dark cycle with the light on at 6:00 a.m. The room temperature was maintained between 20 and 23° C. with a relative humidity maintained between 30% and 70%.

Chlordiazepoxide (CDP 10 mg/kg; batch number 94H1023, Sigma) was dissolved in sterile water. Lacosamide (batch number WE11837 (537.1008,SIFA)) and pregabalin (batch number HS3730) were dissolved in saline. All drugs were administered i.p. 60 min prior to testing.

The test involves two measures of rectal temperature repeated in the same animal with a 10-minute interval. On the day prior to testing, the mice were brought to the experimental room one hour before scheduled lights out and singly housed overnight with food and water ad libitum. On the morning of the experiment, animals were first injected with either saline, CDP (10 mg/kg) or with lacosamide (3, 10 or 30 mg/kg). One hour following injection, each animal was removed from the holding cage and held in a supine position and his rectal temperature was measured by slowly inserting a rectal probe into the animal's rectum at a length of approximately 0.5 cm. The rectal probe is attached to a PhysiTemp digital thermometer (Fisher Scientific) which provides temperature readings at 0.1° C. accuracy. The probe remained inside the animal for approximately 5 seconds or until body temperature reached stability. This temperature was recorded as the baseline rectal temperature (T1). The animal was immediately placed back to the holding cage and after a 10-min interval the 2nd rectal temperature (T2) was taken using the same procedure as in measuring T1. Upon completion of the two rectal temperature measures, the animal was returned to the home cage and then later returned to the colony room. Before each insertion, the rectal probe was cleaned with an alcohol pad and lubricated with sterile K-Y jelly. All SIH studies were conducted between 8:00-11:00 a.m.

All data was analyzed using one way analysis variance (ANOVA) followed by Fisher PLSD post hoc analysis. Outliers above and below 2 standard deviations from the mean were taken out from the final analysis.

Results

One way ANOVA found a significant treatment effect. Fisher PLSD post hoc analysis revealed that the reference compound CDP (10 mg/kg) significantly decreased the temperature of the mice compared to the saline-treated mice (FIG. 2). Similarly, at doses of 3 and 10 mg/kg, lacosamide significantly attenuated SIH compared to saline (Figure below). No significant effects of either pregabalin or lacosamide (30 mg/kg) were found on SIH.

Conclusion

Lacosamide is effective in this animal model for stress-induced anxiety. Thus, the compounds of the present invention, in particular lacosamide, are suitable for the prevention, alleviation, or/and treatment of a disease associated with hyperexcitability, such as anxiety or/and stress.

Example 3

The focus of the present study was the analysis of potential neuroprotective effects of lacosamide in rat hippocampal slice cultures after glutamate (Glut) exposure as a model for a excitotoxic injury. Lacosamide was administered 2 h before insult and present until the end of the experiment at 24 h after insult. Quantitative analysis of necrotic cell death was performed by propidium iodide (PI) uptake (neuronal cell death in area CA1-CA3) and lactate dehydrogenase (LDH) release (cell death in whole slice). Lacosamide showed a protective effect against necrotic cell death after Glut. Due to the neuroprotective effects found in this study, lacosamide is predicted to be effective for treatment of disorders associated with excitotoxic insults.

Experimental Methods

Model System: Organotypic Hippocampal Slice Cultures (OHC).

Organotypic slice cultures and among them, hippocampal slice cultures represent in vitro models that keep the different cell types and retain the complex three-dimensional organization of the nervous tissue. Since OHC combine the accessibility/speed of an in vitro system and the retained 3-D structure of the respective tissue found in vivo they represent an excellent model system for the quick evaluation of the effect of compounds on cell proliferation/differentiation in the CNS. OHC greatly reduce the number of experimental animals and time needed. Furthermore they are perfectly suited for detecting metabolism-related effects, pharmacotoxical mechanisms and even for assessing effects on overall function.

Injury Model 7-8-week OHC interphase cultures were prepared according to Stoppini et al. (1991, J Neurosci Methods, 37(2):173-82). OHC (400 μM slice thickness) were obtained from young animals (rats; postnatal day 7-9); for the first 2 days the cultures were maintained in medium supplemented with 25% horse serum to facilitate recovery. After that serum-free (Neurobasal) medium was used throughout the experiment. Serum free cultures are better suited for the analysis of exogenously applied factors since unwanted effects of serum components are excluded. On d11 cultures were incubated with 2.5 μM PI for 12 h followed by pre-selection to make sure only high quality slices (no PI uptake, no anatomical damage) were used in the experiments. After 12 d OHC were treated with lacosamide (1, 10, and 100 μM), a vehicle control (DMSO) and a reference substance 2 hrs before the insult. 24 h after onset of insult the cultures were analyzed. OHCs were continuously exposed to lacosamide from 2 h before until 24 h after the neurological insult. Thus lacosamide was present during all stages of the test.

Glutamate induces excitotoxic (necrotic and apoptotic) cell death by acting on all glutamate receptor subtypes: kainate, NMDA and AMPA receptors. OHC were treated with lacosamide or either one of the two neuroprotective reference substances—the NMDA antagonist MK-801 (10 μM) or the Na-channel blocker TTX (1 μM). Two hours afterwards, OHC were subjected to excitotoxic insult by administration of 15 mM glutamate for 24 h.

Quantitative Assessment of Damage

PI-Uptake (Necrosis)—Assessment of neuronal damage. 22 h after the respective insult, cultures were stained with propidium iodide (PI) for 2 hrs (PI uptake/incorporation serves as a marker for cell degeneration). Fluorescent images were acquired semi-automatized (Nikon motorized stage; LUCIA software) and analysed by densitometry to quantify necrotic cell death (LUCIA Image analysis software). Damage was analysed only in the CA area (CA1-CA2-CA3) thus representing neuronal damage. PI staining proved to be not suitable for reliable cell death analysis in the AD. In order to combine data from individual experiments the densitometric mean value of the respective insult of an individual experiment was set to 100% damage. All other data are given in % of insult damage.

LDH Release (Necrosis)—Assessment of general cell death. Medium samples for this analysis were obtained from the same cultures used for PI-uptake studies. 24 h after insult aliquots from cell culture medium (1 well is shared by 2-3 slices) were collected, frozen and kept at 4° C. Subsequent sample analysis of LDH activity was performed using the CytoTox96® (Promega Corp) colorimetric cytotoxicity assay. Measurements were performed on a Magellan Plate reader (492 nm vs. 620 nm). This assay detects LDH release from all damaged cells thus representing an assessment of general cell death in the slice culture. In order to combine data from individual experiments the mean value of the respective insult of an individual experiment was set to 100% damage. All other data are given in % of insult damage.

Experimental setup and area of analysis. On d12 in vitro only high quality slices were selected and treated with lacosamide (1, 10 and 100 μM) 2 h before insult onset. lacosamide was present from 2 h before until 24 h after insult onset. 24 h after the insult the assay was terminated and cultures used for analysis: 1) Culture medium samples were obtained for LDH release measurement. 2) PI uptake was analysed in the cultures. Neuronal damage was assessed by densitometric quantification of PI uptake in area CA1 and CA3. In all figures error bars indicate standard deviation. Data were analysed by one-way ANOVA followed by Tukey all pairwise multiple comparison post-hoc test. Statistical significance is defined as * $p<0.05$,  $p<0.01$, or * $p<0.001$.

Results

Effects of Lacosamide After Glutamate (Glut) Insult

Neuronal Damage. As assessed by densitometric PI uptake analysis lacosamide had a statistically significant effect on neuronal damage in all CA subfields (combined CA1, CA2, CA3) 24 h after Glut (FIG. 3). This was true for all three concentrations of lacosamide tested ($p<0.01$ S1 vs. Glut; $p<0.001$ S2 and S3 vs. Glut). The reference substance MK-801 (10 μM) provided significant protection against Glut-induced neuronal damage ($p<0.001$ for MK-801 vs. Glut). The second reference substance Tetrodotoxin (1 μM TTX) showed also a neuroprotective effect after Glut ($p<0.01$; TTX vs. Glut). The extent of lacosamide mediated neuroprotection was similar to that of TTX but smaller than that of MK-801.

Overall Damage. As assessed by colorimetric measurement of LDH release, lacosamide had a statistically significant effect on overall damage 24 h after Glut (FIG. 4). This was true for all three concentrations of lacosamide tested ($p<0.01$ S1 and S3 vs. Glut; $p<0.001$ S2 vs. Glut). The reference substance MK-801 (10 μM) provided significant protection against Glut-induced cellular damage ($p<0.001$ for MK-801 vs. Glut). The second reference substance Tetrodotoxin (1 μM TTX) showed also a protective effect after Glut ($p<0.01$; TTX vs. Glut). The extent of lacosamide mediated cellular protection was similar to that of TTX and MK-801.

Discussion and Conclusions

This study was designed to investigate the potential protective effects of lacosamide after a neurological insult in-vitro. As endpoints two different readouts were used: Specific neuronal necrotic damage in the CA region was quantified by densitometric PI uptake analysis and general cellular necrotic damage was assessed by measurement of LDH release from the whole slice. High glutamate levels (Glut) caused massive neuronal necrotic cell death (CA1 more affected than CA3). Administration of the NMDA antagonist MK-801 reduced the neuronal damage by app. 80% and overall damage by app. 50%. This indicates that MK-801 provided protection for neurons but not for glial cells. The Na-channel blocker TTX provided app. 50% of neuronal damage reduction and app. 20-40% of general damage reduction. Lacosamide showed a significant protective effect on neuronal (CA1 and CA3) and general necrotic damage after Glut. Lacosamide significantly reduced Glut-induced necrosis by app. 40-50% and overall damage by app. 30-40%. According to these data lacosamide seems to have an anti-necrotic effect in a model of excitotoxic insult (Glut).

Thus, the compounds of the present invention, in particular lacosamide, may be suitable for neuroprotective prevention, alleviation or/and treatment in particular in a neurodegenerative disease or/and psychotic disease.

Example 4

The lacosamide-induced shift of the slow Inactivation voltage curve to more hyperpolarized membrane potentials (see FIG. 1B) and/or the increase the fraction of slow inactivated sodium channels has been observed in different cell systems. FIG. 5A shows this pronounced shift of the voltage curve in *Xenopus* oocytes expressing the rat type II sodium channel alpha subunit ($Na_v1.2$) in the presence of 100 μM lacosamide. In rat dorsal root ganglia 100 μM lacosamide markedly increased the slow inactivation of TTX-resistant sodium currents (FIG. 5B). Although lacosamide (100 μM) significantly increased the fraction of sodium channels slowly inactivated by a 10 s depolarizing pulse the half-life for channel recovery (ι) was not significantly changed (FIG. 5C).

The invention claimed is:

1. A method for alleviating and/or treating a myotonia in a subject in need thereof, comprising administering to the subject lacosamide or a pharmaceutically acceptable salt thereof.

2. The method of claim 1, wherein the myotonia is a disease associated with dysfunction of a voltage-gated ion channel.

3. The method of claim 1, wherein the myotonia is associated with a mutation at SCN4A or CLCN1.

4. The method of claim 3, wherein the myotonia associated with a mutation at SCN4A is selected from the group consisting of paramyotonia congenita and potassium aggravated myotonia.

5. The method of claim 4, wherein the potassium aggravated myotonia is myotonia fluctuans.

6. The method of claim 4, wherein the potassium aggravated myotonia is myotonia permanens.

7. The method of claim 4, wherein the potassium aggravated myotonia is acetazolamide responsive myotonia.

8. The method of claim 3, wherein the myotonia associated with a mutation at CLCN1 is selected from the group consisting of myotonia congenital, generalized and myotonia levior.

9. The method of claim 8, wherein the myotonia congenita is Thomsen myotonia.

10. The method of claim 8, wherein the myotonia congenita is Becker myotonia.

11. The method of claim 1, wherein the myotonia is selected from the group consisting of paramyotonia congenita and potassium aggravated myotonia.

12. The method of claim 11, wherein the potassium aggravated myotonia is myotonia fluctuans.

13. The method of claim 11, wherein the potassium aggravated myotonia is myotonia permanens.

14. The method of claim 11, wherein the potassium aggravated myotonia is acetazolamide responsive myotonia.

15. The method of claim 1, wherein the myotonia is selected from the group consisting of myotonia congenital and myotonia levior.

16. The method of claim 15, wherein the myotonia congenita is Thomsen myotonia.

17. The method of claim 15, wherein the myotonia congenita is Becker myotonia.

18. The method of claim 1, wherein lacosamide or a pharmaceutically acceptable salt thereof is administered in a dosage amount of 50 mg/day to 1000 mg/day.

19. The method of claim 1, wherein lacosamide or a pharmaceutically acceptable salt thereof is administered in a dosage amount of 200 mg/day to 600 mg/day.

20. The method of claim 1, further comprising administering to the subject at least one further active agent for alleviation and/or treatment of a myotonia.

* * * * *

SEQUENCE LISTING

<160> NUMBER OF SEQ ID NOS: 1

<210> SEQ ID NO 1
<211> LENGTH: 307019
<212> TYPE: DNA
<213> ORGANISM: Homo sapien

<400> SEQUENCE: 1

```
tgtatagggg cttcatggtc aaagtgtgca aagagaacaa tcacaaatca tcatgacaag     60

tggtgctgct tgggctgtac ttcaggagca tcacgaattt tttttttttt ttttgagaca    120

gagtctcact ctgtcaccca ggttggagtg cagtggcatg atctcagctc actgcaacct    180

ccgcctcctg gattcaagtg attctcttgc ctcagcctcc cgagtagctg ggattacagg    240

catgcaccag catgcccggc taatttttgc attttaagta gagacagggt tttaccatgt    300

tggccaggct ggtctcgaac tcctggcctc aggtgatctg cccaccttgg cctcccaaag    360

tgctgggatt atagtcttga gccaccatgc ccagcctaca aatatttttt atttaagtag    420

gcagcacaca caaaactgca caaatcagtc acgtgcagct cagtgaaaag gtacaaaatg    480

aacaaaactt aaaaagtgag cacacccatg ccactgtcac ccagatggag atgcttccag    540

aatgtatccc tttaccctca aagcgactac tcctttgact tctaaaggtg atcagtgttg    600

ctcatttttt aatgttatta tttacttatt taatttttta aaagaagaga ttgggtctca    660

ctctgtcgcc cgggctggag cacagatcat gtagctcact gcaagcctcg aattcctggg    720

ctcaagccat cctcctgtct tggcctccag agtagctggg aatcaggata cctgggacta    780

caggtgtgca ccattttttt ttaaacttta tataacagga attatacacc atgttctgtt    840

ctgtgtctgt cttcttgggt tcagcatgga gtttgtaaaa ttcatccatg cacctgtgtg    900

tagctccata ttgtcctttc ttattgctgc ataaaattcc atgttctaca gtgtatttat    960

ccattacggt attttggaaa tttccaactt ttagcaagta tgaatagtgc tgcacattct   1020

agggcatata tcctcatttc tcctgggtgt atacccagga gtgacattgt tgggtcatag   1080

gatactcaaa tggccatgtt aatagaaatg accaaaaagt tttctttttt atgtgtttgt   1140

tgtcgttgtt tgtttttttga gacttgactg tctcccacac tggagtgcat gatcttggct   1200

cattgcagcc tcaaactcct gggctcacac aatcctccca ctttggcctc cccagtagct   1260

gggactatag gcatgcacca ccatgctcaa ctaatttatt tatttcctga ccttttcttt   1320

tctttttttct tttctttctt tctctttctt ttctttctct ctttcttctc ttttctttct   1380

ctctttcttt ccctccccc tccctccctc cctccctccc tcccttcctt ccttccttcc   1440

ttttgtagag gcagggtctc actatgttgc ccaggctgct cttgaactcc tgggctcaag   1500

cagtcctcct gcctctgccc accaaaatac taggattaca gatgtgagcc actgcaccca   1560

gccaacggtt ttccaaagtg gttgtaccaa attcccctct gtccaacaga atacaagagt   1620

cagaaatggg ttcagatcca cgttagtgac cttgggaaag tttttaagtc tccctcaccc   1680

tcagtgtttg catctgttcc acggggctgc tgtgaagact cagtgggaga tttaccctgg   1740

caggagctcc atcagtgaga tgtcactctt tcctgaaaaa ctctggggtc ttcacagatc   1800

tatgcaggta atgctcctgc tctaaaactg aataatcttc tcagagaggt ccatcagaac   1860

aaatgataag ttcaactcag ctcctctcat atgactggtt cttcccatct gaacacatgg   1920

gctcgcttct tgtttcatat tagttgctgt tcacctttta tatctgaaac aatgtcaagt   1980

acaaaaatca ctgatatttg gtgagcgcct taaaagcccc tccttctccc tgaatcccac   2040

acaattctat ctccttgcaa ttccaatcac tcttggttta atcatttcat ccatatcgtg   2100
```

```
acaagttaga aaatcttgaa agtgctatgg ggcaatgtat aatagttggt gcattggcac   2160

agaacgggga ctttatataa agacatatca tctttccaga gtgttccaaa agaactcgaa   2220

tattgatatg tgtgtgtggg gtggcgaggg gggaagggaa ttaactagga tttaactagc   2280

taaggcttga aagaatattt gcctttttca tccttttccc attcctctcc atttggcctt   2340

tctgcgtata caagctccat gaaaattcaa tggtttcttg gtacattgaa tttgcaagac   2400

agtttgatga catcttataa gcttgaagat atgaatacct tgtggaccca gacattccac   2460

acctaaggct attcctagag acatgcattc ttatctgcac caaaggtacc tgaggcagta   2520

atgtttaata gccccaactg gaaaaaaaac agatacccat caacaagatg atggataaac   2580

aaattgtggc atattctctt gatgaaatac tatacagcag tgaaagtgaa tgaatcacag   2640

ccatgtgtga caacaaacag gtgaattttt ctaaaattcg aaacagatta ggatgtatga   2700

atcttgtttt ttttgtttgt ttgtttttgt tttgttttgt tttgtttgac agagtctcac   2760

tttgttgccc aggctggagg gcagtggttt gatcttggct cactgcaaca tcctggactc   2820

aagggatctt cccatctcag cctcctaagt agctgggact aggttcacat caccatgcct   2880

ggttaatttt tattttaaaa aaggtttttg gagagacagg gtcttgctat attgcccagg   2940

cttgtctcaa acccctggcc tcaagcaatc ctcatgctct gcctcccaaa gtgctgggat   3000

tacaggcgca gacaccgtgc cctgccagat gaatcttaaa gacataatgt tgaaccgaag   3060

aaacaagaaa ctgtagaata tatactatat gattattcca tttatataaa agcccaaaag   3120

aagcaaagta aaattgtatt ggttaggaac gcataataag gtagtcaaac tttttttaaa   3180

aaagcaagat atgaatacca taaagtcagg tagcgattat tgctggaata aggggctgtg   3240

taagcgtgtt ggcaaagggg gttctgcaga ggtggtgatg ttccatttct agccctagac   3300

ttgatttcat gagtgttcat ttcagaccaa tttcttaact ccgtaccttt atgttttatg   3360

catttttctt tgtgcttatt gaatttcacc acacaaaaag cagaatggga agtaatcaaa   3420

gtggttctgg agagacgtga gtatcaagca aactatacca cccagaaccc ctatccagcc   3480

aactaggacc tggttaatta tttcctcctg ggagttcaga cttgtcacct ctggggtctc   3540

caaggtagaa taaaccttta attccaactt gcaggagtcc ttgtgatttg aaacgttcac   3600

agaagtaacc ccaaaccact ctctccactt tcaaaaatgg tcttttgcta aacagagcaa   3660

atttgtttag agactgacga atcgcacctc tagacacaaa tccccttctc ttttctgtct   3720

tttaagtttt tttcctgcct ccatcctgcc ttctccttgc aagatgctgg ggagcgtccg   3780

gctgtctgca accgaaatgg aacggggtgg aaaacaggct ttcctcccag gggaggagga   3840

agcaccccaa ttccccoctc cctgcctccc aaccatgcga cgctcccctc tctcccccac   3900

aaactccgct gagcccggta cccccgcgcc tccacgagcc tccacgattg gtcgcgggcc   3960

ctcatgtgtc gacactctgg gtgggtcctt ctactgttaa actcatcaat tgctcccctt   4020

ttccgtttgc tggccagtgg ttcagacctt tgcgcccatt ttttttcct ctttaccttc    4080

ttctacccgc aaccctccac accagtctta ttttagcaaa acctagagaa ggaggaggtg   4140

gagggatttg gagggtggag aggcattgcc gcatccaggg gcagctattg agtggctaag   4200

cggagggcgc atacctctct ctctctctct tttcccoctg ttgggaattt tcaggatttc   4260

actgctgcaa tttaacccca agatgaggca ccattgagcg aaacgctgtg cgcacataca   4320

cactcacact tcctccggga gcagaagagg cagccgttgg tgattcagga agaaaaaaaa   4380

ttttttttt ttttttaaa cctggaccct gcggtgtgaa gactccttag gaaccctctg     4440
```

```
gagcgtctta ctccccttcc ctcctctttc ccttcccttt catcttcttt gtttttattt   4500
tattttattt ttggagctac agatctttca gcatttttaa ggtctaggaa ctccagcaaa   4560
acagaagggc acttaatttt tttttttttt ttttttgccc tccccaccca gacctgggtt   4620
tcgtctttct ttatttttaa atatatatat atttttttat tttttatttt ttattttttt   4680
ttaatgggcc gagcgcactc cttttgcaag atgccagcct gacccggacc tcggaggaat   4740
ttgaagcttc cactgcgtcc cggggggggc gtcctttgca aaccgttcgc gtcttaaagg   4800
gggtgtgcgt tgggtggatt tttttttttt aactgtctct tttttttttt ttccggagtg   4860
ggtggactgg ggattgcctg gattccttcc tcggttattt tttgcctcgc ttctctctcc   4920
cctccccccct cctccccggg cccccgcgcc ccgcccccgc accctcctcc cgcccctcct   4980
tctccggggt cagccaggaa gatgtcccga gctgctatcc ccggctcggc ccgggcagcc   5040
gccttctgag cccccgaccc gaggcgccga gccgccgccg cccgatgggc tgggccgtgg   5100
agcgtctccg cagtcgtagc tccagccgcc gcgctcccag ccccggcagc ctcagcatca   5160
gcggcggcgg cggcggcggc ggcgtcttcc gcatcgttcg ccgcagcgta acccggagcc   5220
ctttgctctt tgcagaatgg cccgcttcgg agacgagatg ccggcccgct acgggggagg   5280
aggctccggg gcagccgccg gggtggtcgt gggcagcgga ggcgggcgag gagccggggg   5340
cagccggcag ggcgggcagc ccggggcgca aaggatgtac aagcagtcaa tggcgcagag   5400
agcgcggacc atggcactct acaaccccat ccccgtccga cagaactgcc tcacggttaa   5460
ccggtctctc ttcctcttca gcgaagacaa cgtggtgaga aaatacgcca aaaagatcac   5520
cgaatggcca tatcctttg cccgaacccc agcagcagct gcgcctcccc ctcctccctc   5580
cgcctcccct cttccaggct gggagagaga cccgggggtt gatgggaggt ggggaggagg   5640
ggggtcttcc aggggctggg agagggggca ccgggaggag tgtgaaagaa tctctccacc   5700
ccgagctggg ttgagctacc ctggaggctt gggaatgggt ttgtgggggg ctggggggtg   5760
ggcagcggag agtggatcct tcccaaggac cgactctaga atgagatctg gggcctgggg   5820
tcgtgcagga gccttggtgg gggctttcga gccaagtccg gagggtttgg agttctacgg   5880
agtgagcttg gagcgggctc gggcctgggc gcttctggcc agggcagggg aactatgggg   5940
gccttggttg ggttttcttg gccgtcgctc actggagtcc acgcagggga agctggacag   6000
cctctccact actgctttcc ccaaggtggg gggccgccgc acttttaggg cagggcgctt   6060
gggggctccc agggctaaga gcaagaggga gtccatgtgg ccttcacact gagaagccag   6120
cactggccga agtgagtacc ccagggtggg ccgctgttcc tatctggaga ggatagtgat   6180
gggctggggg gcgcttatgt ttccctcatg tgtgcaggtc ccattgcctt taaccgctga   6240
ttggggaacc tcatcatctt tgggggtgtc gagaaagaga tcccacttgc tttatctggg   6300
cccctggcct gggaagacct gatctggaca ctttcagtaa gaaagacagg gcaacagcaa   6360
atgaggtggt gggtccattt tagagcacca tgtccagctt ttcctacccc gagtagccga   6420
gagggaacac caggagaatc agcacccatg tggacatctt aggtaggtaa atgcctttta   6480
aatttttttt tttttaatca aagatccaga ggaaaaaggt gaagcccaca ttttcttctg   6540
tggagatgct atcaaaatgc agatcttctg tgtttcttta aatccctgcc tgcttgaaat   6600
aaaccttgag gagggcttaa catctatcga gatgtaggca ggcaagggtg ggtaattagt   6660
cgggctttct agcagttatc taagcatgac ccagattcca ggagggggga cacaccctgc   6720
tgcccaggct ggctggccac tgtgccatgc ccagatgtgc cgcttctccg cacagttcca   6780
accagctgcc ctctgtgtaa aaatgaacgg gctggatggg tccctggggc tcagcgatga   6840
```

```
gtcccctatc ccttttgtat gtggttttgc agttatagac taaacggggc tgggccctgt   6900
gtggtctccg gggggttgctg tttgaggagc atggcgggtg gtagagggac tcacttcagg   6960
ggggttcaaa atcgagcctg gcgcttggat cctgggtgct gggattgcaa cagagggcac   7020
tgaggttttg gagtgtgtga gtggtctact ttgagggtgg ggaaaattaa gaagttcagc   7080
agaggtgctt ttgaggggag catacctcta actacgatgc catctccgtt ggtgcccaaa   7140
gcaggtgcca ggtctttgct tcctaagttt cagactctta aagaggctgg ttcttaaggt   7200
tagcaattcc tcaccatccc aggcccattg aagtgctcag ggtggcttg attactctgc   7260
ctatcaacag agtgaggagt gggagtgcct tgcaggagga cagggtattc atgggtgcac   7320
acccagttag ctccaggagt gagagggctt tgctcggctg acaggtttcc tcattgaaaa   7380
tggctttaga tcgccttctg gagcctggat ttggagactt ctaagaggaa aggaaggagg   7440
tggggagccc ttctgctgtg tccttagctt acctctgtcc agcctgaatc ctgcagattg   7500
gagggctgtt gggggagagg gggattgcag tggcccctcg gaagggggaa tcgtgggaga   7560
gggaggcagg tgaattgcga gtgttgcttg ccacttcatc tattctctgg ccagctcgcc   7620
cggggctttc ttgctcttat gatgagtttg tgcattatgc tctctgcaga ctgtttttgt   7680
tctctttgac ccgaggtaac aaacacatta tacagcccta ctctggaagg gaaaactccc   7740
cacctcacaa tctgtcatcg agctgggtca tccaggactg agctttctct gtcctggatg   7800
gagcggaggg cggtggcggg gtgggtggga gggttggaga tgagagggga tggacagaga   7860
cctggggagg gaggtagtga ataaaagaat tcaggccagt gtaaagagaa agacacgtgg   7920
aatgtcagag tcacgatacc agggcagaac attctacttt ttaatctaaa tatttctgcc   7980
attaaaaaaa aatgtttcag catatcctga gagtgaaaaa aaaagtgtgt aggtacttaa   8040
ataaagtcta atatatgtac aggcaagtac atatattcag atgcatagat ttttacaaaa   8100
tgaacacacc cacgtatcca gcacccaggt cccgatcagt gccctggaag tccccctccc   8160
cataccgcct cctagttgct cccccaacaa gggtaccgct cacctgactt ctaaggttca   8220
ttttgcctct tttaaacatg taaatggagt cacacagtac gttcttttgc cactggcttc   8280
ttttgctcac atctgtgtat gtgactctac tacaatctat ccattctact gttgatgggc   8340
atttgtgtca tttctgtttg tgccactggg aacattcttg tgtcttctat tatttttttc   8400
ccacagttct cttagatagg agtggaatcg cccctgctac tttttgatgc atgtgttgtg   8460
ggatgtgtat ttggaaatgg tgttgactaa gggttgcagg tcgatatgga aagcaggttc   8520
ctccctgtct tgtttaagag aagtgagtga atgatccatg aacttgtcgg tatgctcaca   8580
gggcctaaga gtgctacttc caaatgtaaa ttctggcatg gtacactggt gaaggatgca   8640
gtcttgcttt ctccacactc ggggcaattt gtcactatga tttcttcctc tttcatccct   8700
cagtgggtca aacttgaagc catcaatgac aattaagaat cctcatttat ttcatttttt   8760
cccctcttcc taagtgagga aacccaaatg gaagtctttg atgttcaaat ttacattgcc   8820
gtgtttttct catgccaggc agcaagccgt cttgaccaca caccttggtt tcatgttttc   8880
attgactgga attgtgattc aaatagggcc atgagggtct ctgatgattg ccgaagagct   8940
cagatctgtc agctcaaaaa ggagcatctg tcagccttcc tagagttccc tccccactta   9000
atgccactca ctccttctac caagtgccaa ggtgaatgtc atctttccag ccctccctgt   9060
gccaccaggt ctcccactga acatgatgta gaaactcagg ccatcggagg aacactggaa   9120
gcaggtcagt gtattatcac gcacagttgc ctgaattaca cgtagaattc cagcttttca   9180
```

-continued

```
tccggtttgc agaaatctta acaagacacc taaagtcaca ttgacatcag gtgacatcac   9240
tttgacatct gtggacattg gctgattggc actcctctca ttttttttt ttttttttt   9300
tttaagaaaa gctctctaaa gagaaacttt ctgcatgaga agcgctggga gacatgggag   9360
caggttatca gactcttggc ctgtcctgag agatagaatg ttctagaagg tactgccgta   9420
gagggcagga tggtgtcact tacgtgatcc ttgtactaga ccggcttggc tggtatttcc   9480
agaggagcaa aattctgcga agtaaaattt agcacggctt ttccaatggg agtattttca   9540
aaaagggtgc aatttcttat ccacaattcc ccaatccaaa aagctccaaa aaccaaaaga   9600
cgagctcata tagaggtaaa acctaacctg aactgacttc agtttgaagt cttaatttac   9660
agttttcatt cattctactt ggtgtgcatt tgagtatgtt ttgcagcaga aatgttagat   9720
gtgcttgatg atgaggtgct gcttcagctc ctgactgtta ggtctgcatt gtagtcctgt   9780
caaactttca ggtgtatgga agttgtcttg ttaacaggat ggttctggtc cagcaggatt   9840
tgggtggggt ctgggattct gcttttctag ctagcttcta gggattcccc atgtggtaag   9900
ttcatgggct agggttggag tatccaggtt agatcataga gacatcttgt tatcattttt   9960
cttttcctta aaaatcaggt ttataggggc cgggtctggt ggttcacgcc tataatccca  10020
gcactttggg aggctgaggc cggtggatca tgaggtcagg agttcgagac cagcctggcc  10080
aacatggtga aaccccgtct ctactaaaaa tacaaaaatt agccaggcgt ggtattgtgc  10140
gtctataatc ccagctactc gggaggctgg caggagaatc atttgaacct gggaggcaga  10200
ggttgcagtg agccgagatt gcaccactgt acttttttt gagactctgt ctcaaaaaaa  10260
aaatagattt attgatgtat aatttatttg tagcaaaatt caccctttg acatactggt  10320
ctgcaagctt tgacaaatgg atgtagttgt ggccaccacc caaatcaaga tatgggacag  10380
tttcatcaac cctaaaatac ccccacagtg cccctcttga gtcagcaccc cacttctcca  10440
gcccccttcaa ccactgatct gttctccatc cctacagctt tgccttttgc cgaaggtcat  10500
ataaatgtaa tttcacagta tatagccttt tgaatgtgga ttcttttact cagactttga  10560
gattcattca tgctgttgcc tgtgacagta gcgccttcct ttttggtgtt gagcaggatt  10620
ccatgatatg gatggaccag agtttgcttc ccagccgaag gacattggga tgcttccagt  10680
ttcaatgatt atgaatagag ctgctataaa cattggctta tgggttttag tgggaacatt  10740
tcatttcata catttcattt ctcttgggta aattaaccca ggagtgagat tgctgagttg  10800
tgtggtaggt gtatgtttaa ttttataaga ggctctcaaa ctgttttcct aagtggttgt  10860
accattttac attcccatct ttgcaatgcg tctaaaagcc ctgagttctg aattccaaag  10920
cacgtctggc ctcgatggct taggattaag gatgtggatc tatggaaagg agtggaagta  10980
atagtgttaa atcccggtca gagaaataag aaagattaag gatgtcattc aaagctatgt  11040
gcctgcacta gagagagaga aagaaggggt tctcttgggt ggggttccac ccctccctgg  11100
tagttctacc attccccagg aaaaagtcaa gctctgaggc tgtgagaccc atgatcttta  11160
ccctgttctt caccactgca accccagtgt gtgggacaaa gcaggcgtcc tataaacgtt  11220
tgctgagcaa atgagaaaag gtacctgtct tcacccatta actaaattgt ataacatcta  11280
tctgatctac ccttgtgcca acgttttagg attttgatgg gttttagttg caggggggttg  11340
agagactgtc catgagatta tcagaccaat gaaagtttct gaaatgttag tgcttgagta  11400
gattggatgc agcggcccct tgagaatgaa gtctttcttc agggacttgg agtgggaggc  11460
atctgttggg tgcgtagggc ttatgcttcc ccctccctgt ttcccccccca gtagcaagca  11520
cacatataca ctttctcagc aataaaaagc accgccggga aggtggactc catccagaaa  11580
```

```
tgatcagagc ctaagagccg tgcagtaacg catttccgag aatgccagct cagctcctga  11640
gaaaagggcc ggatgggatg gtgcctgctc tgaaagaggg cagagaggag agggaaaaca  11700
ctccggactc tgggtcagac tggcccaggt tcacattatt caccagccat gttatcttgg  11760
gcaccagagc ctatttcttg acatgcatga tgaggatatt ccttctagta gcatctccct  11820
tggagggctc tcaggagatt aaatggggtc gtgcgtgaaa aatggccagc acagtctcca  11880
gcacagagaa aaaccccaaa acgccagagc cgtaatacta tggagtcatt taggttccag  11940
tgttcttttt ttggaaaccg gccagaaaag aggctttctg ggtgggaatg ggagcgaagt  12000
gccccccccc accacccccct gcgactggtc agtgtggatt gattaacctg atcgtggcgc  12060
tctttaaagc cacctttgga cattttgcat tctccgttct ctctggaagc tttcagggga  12120
aaaaaaattc gtggccactt gacccatttt tctattccct tgagtctaag gtaaaaatta  12180
attctctttc ctcctttggt ccctccctct ctctgtgggt gacaaggtga gggagtttta  12240
aagtatataa ttagcttccc tcttcccctt ttgcactccc tgtctcttcc tttggggccg  12300
gtcgagagtg cagcccagga tggccacccc aggtgtccac tgcaaactcc acagaaaaac  12360
tttgctcaac ttttggttta gaatttaggt accccccctcc ccttccaaac tttggtcttc  12420
tttctcctca ctccctaaaa aaataggaaa aacaaggaac attcctggcg agggaaccat  12480
gagtgggcac agcaacttag gtttcaaaaa ccactgggcc tcagttctta tctgagtagg  12540
gtgacccttc agccagggtt gcctgggact atcctgggtt tagcatctct ggaaactcac  12600
agtcctgggc aaactgggac gctggtcacc ctaatggtga gttcttaaca cctgagagag  12660
aagaatggtg caagagatgg tgccgttgac caagaaaggg ggagagtcag ttacttattc  12720
cctctgaaaa gccaagactt tttattggaa tgaatgcagc ttttagaagc cgtctttaag  12780
gcagctaata caagagagat tccagctatg aagggaaatg cctgagttaa gtccggatca  12840
agttttgaca tctcgcttcg gtcagacacg gctttatctg ccgttcagac tgggagcagc  12900
cgtgagtctt ccttaaaggt gcctgttgct caggcggcac ctgcagttag aaattagcag  12960
cctcccaccc ccagccccca aataacagga ttcaagagtc ccctctctga agccatgagg  13020
gaaacccaac ttagtcaccc acttgccagt aaataatatt catgctgtta agttctgttc  13080
tcattttagg cctatgtgta aaaaatatat gtaattttaa actgattttt aaagtatttt  13140
catacgaaca gcatttgcag gagggcgaag tctggatgtt acctttttgt aaaagtggat  13200
ggatttgtct tcaatgagac tctggggcag acttaaaact tggcccgcag tggtgttaca  13260
tggattctga tcttccagag tctgtcacgt tcttttatct ccatgatctt tattatcttc  13320
tttattgaga atgatgggca tggtgtgtgt gggtgggagg gctatgctga ccatcactgc  13380
agtgaaatgt gttcgtggca tgttgtggcg tctgcatagg aatgtgtctg tttgattaac  13440
agcacaagca gtggaggctg taaggaggaa aagaggaggg aaggtgatat tggatggagg  13500
ggagacatat agagcttggg aacagtccac cctggctgca aatctcagct ccagctcaca  13560
gttgtggagc ctcagtcttc tcctctgtaa aacggggaca gtagtcctat gtccgaggaa  13620
ttgtaagaag gttaaaagat actgtaccca gaaagcacat ggcatatata atcatcctgt  13680
gaagtagcca actcaatgaa ttttatttta tttattttga gtcagagtct cactctgtca  13740
cccaggctgg agtgcagtgg catgatcatg gctcactata gcctcgacct cctaggctca  13800
agcgatcctc ctgccttagc ctcccgagaa gctgggacta taggcatgca ccaccgtacc  13860
cagctttaac aacataaatt tatatatata tatatatata tatatatata tatatatata  13920
```

-continued

```
tatatatata tatatatatt tttttttttt tttttttttt tttttttttt ttgagatgga  13980
gtttcattct tgttgcccag gctggagtgc aatggcgcga tctcggctca ctgcaacctc  14040
cgcctcccgg gttcaagcag gacgatgggc atttgggatg tttctagttt ggggtggggg  14100
attgtttgtt tgtttgctgt tatgaacaat gctgctgtaa ggaatcaata attttgaatg  14160
aatgaattcg aggtgttaat tttagtctgt gtacttggaa atctagcttc acctagaatc  14220
agctgagatt catcagcatt tatggcagga gctaagacat ttcacagctt actcatcatt  14280
ttctctaaga ggctgggtca accggttagc tcttggtcct gcttgtattc tgagagtcag  14340
aacctgtggt ttagacactg gcaattgata tggttgtaga gaagcagcat ggttgagttg  14400
agagcatgga ttctggagct aggtggctgg ggttcaaatc ccagctctac tagtcactgg  14460
ctgcgtgatc ttgggcaagt cacttaagtg ttctgtgctt cagtttccca gtctgtccca  14520
gtggtgattc taatagctcc atggggatcc taatagctcc tatctgggag gattaaatga  14580
gttaatacat ctgatgttta gagtggtgcc tgacacttag gaagcactat atgtgtttat  14640
acatggaaga gtggatagat ggatggactt atgtgggtgg ccatatttgg gcttctctga  14700
tccactgctg agaatagtgt gtggcacaca gtaggtgctg cataagtgtt aatattctgc  14760
tctttcttgc caagtctctc aactcccttg atctctgtta tttttggcgt ctgtgttgtt  14820
aacccattct tctgaatgat cagctgaatc actgttgctc caatatataa gccaaggaga  14880
acacaatcac aaggtctcat tgattgtcca tactagaatt ccatgattcc taggcccaag  14940
taggattttc cccacgtctc agcaatcctt cttccatgtt tctaatcttt ttctctcatt  15000
tgttatgccc cattgccaga ctctccaatc tccccacagc ttccccttcc tctaactata  15060
ctgtctctag tcttaccttc tccctaaggg caccgtcttt gaagacatca aatacttcag  15120
agcaccaaat ataggttagc ttctctgagg gccttacaag gacatggagt gtttgggtct  15180
tacacaaatt ggaatggtca gaaatgttta gagacttgag ttgtctttga aagagttgtc  15240
agaatgcaaa tttttgactt gtggcctgtt tctgatcaca acgcagtctt ttaagttatg  15300
gatcatagct ggatgtttgt ggtttagagg ggatggaggc atcctctgca gttagtgttg  15360
gatgtctggg tggatggatg gatggatgga tggatggatg gatggatgga tggatggttg  15420
aacagatgca tggatgagtg gatggatgga tggatgggat gaaggaagga aggaaggatg  15480
ggtgattgga gggtaggtgg gtggataagt agattggtag atgactcgat gggtgggtgg  15540
acaaatggat gggtgaatgg atgactggat ggatgactgg atggattggt gtatgagtga  15600
atatatggct ggatgaataa ataggcagat gactagactg gattgagggg taaaaatatg  15660
gatgactgga tgggtggatg agtggatgat agatggttga atgggtgggt ggatgggtgg  15720
atgttggata taagggtgta tggtagggta gctgtctatg tgtgggtctc cctgatattt  15780
ggtgttctgt ttgacttggg aatgaccaag tctctccgct taccacctta tttgtacctt  15840
ttccagtatc aagtgaattt tgcacacttt tgtaaaaatc aataagattg tatgtttagg  15900
actttgggag gccgaggcag gcagatcaca aggtcaggag atagagacca tcctggctaa  15960
cagggtgaag ccccatctct actaaaaata caaaaaatta gccaggcgtg gtggcgggca  16020
cctgtagtcc cagctacctg ggaggctgag gcaggagaat ggcatgaacc cgggaggtgg  16080
agcttgcagt gagccaagat catgccactg cactccagct tgggcgacag aacgagactc  16140
catctcaaaa taaataaata aataaatatt atatgcttag gttttaccta tgtaattaga  16200
aagctccttg agggtagggg acagtgattt gccttcctca catcccccca aagttcctgc  16260
actatatcat gcataagtat ttaattgagt aatggtgagg aaagtaaaca gtgttattga  16320
```

```
acaaagatta ttaaaattct ggaaacacct ggttttgttt cagcactggg actgaaagtg  16380
gaattccttg gattttgctc cattggtgga taggatagca tgtggtggtg gactggtaga  16440
ctctttctct tccaagcaga ttgggtaaat gccccagatt cttacccact agtcagagat  16500
tacagattac tgattgatat ggtttttctc tgtgtcccca cccaaatctc atctcaaatt  16560
gtaataccca catgtcatgg gagggacctg gtgaaggtga ctggatcatg gggtgattt  16620
cccccatgct gttcttgtga tagtgagttc tcatgagatc tgatggtttt aaacttgtgt  16680
gggcctcttt cctctctctc ctctcctgct gccatgtaag acgtgccttg ctttcccttt  16740
gccttctgcc atgatttgta agtttcctga ggcgtcccca gccatgcaga actgtgagtc  16800
aattgaacct cttttcttta taaattactt ttatagcagt gtgaaaacgg actaacacac  16860
tgatgtagca aggtccttta aggccccatg tgatctggtc cctgttttgt ctttgatctc  16920
atctctttca ttgtctacct tcctttcatt gtctattctg tctcagccct gctgaccatt  16980
ttactcacac ccatgtcatt tgcattacat gacattcctt ctgttcagca taagctattt  17040
cctctgcctg catcactgtt tctccaggtc tccccatggc taactccttc tcttcattta  17100
ggtctcagcc caaaagttac ctcctccaag aggcctatcc ttttcattta ctgaacatct  17160
catgtacaaa aaagaatata aaatatatgt atactctctc atccacaaaa aaatctctga  17220
agacatttta atgtatttca tcccatacct ttttatgcat gtaaactttt aggaacacat  17280
ttccatgcca ctaggtatcc ttgaaaaaat aagggccacc atgtatagtt gcacaggttg  17340
tgcactgcac aaagatagca tgtcacatat cttaagtatc atggagcttg tatgtctact  17400
atttcagtac cccagctgat aaaagcttaa gtatcttgtt ctagcaagat gaagctatta  17460
tgacaatttt tgacagagaa aggggtgttt tgtttaagtt cacaatcaga gaaatgggtg  17520
tcttgtttaa tttcacaacc agagaaaggg gtgtcttgtt taaattcata cagtggtgct  17580
gtatgggttg gtggcaaccc cagaaaagac tgttgttaat atctgataat gttccacttt  17640
atacgtgtat tatattcatg taacaatctc tggctgtttg ttttgccatt ataaataaca  17700
gtgcagtaaa catctttgtg tgtgaatctc tgtccaaggt tctgatagtt ttctgaatga  17760
aattcctgtc tatatatggc actccaagcc cataattgaa actctgctgt taccactttc  17820
tttgaatctg tagaaggaat tttgagaaca ggtgactggt atattcagga tgttgatgac  17880
aaggaacaga gaaagaacag ttaaatggtt tggaattttt cctgggctgc atgtaaagca  17940
gtgcttttga actgggagca atttttcccc caaggggact tttggcaatg tctggagacg  18000
tttttggttg tcacgaatgt agggggaggg ggcaagatgc tactggcatc tggctggtag  18060
aaaccaggga tgcagttcag catcttaaaa tgcacaggac agcctttctc agtaaagaat  18120
tatccagctc caaatgtcag taataccaag gttgagaaat cttgatgtaa tcgatgtcat  18180
gggtttcttc aagaggagtg ggtggattta gggtttttgg gtgacttaaa tttaatttac  18240
agtttgtctt cctagctggg tgtctaagcc agctttctgt gaactttaga tcccacacaa  18300
gaagcaacag gcttgctacc gacagattcg ttgatgtaaa tatagatgag tgtatagaag  18360
gaaatctcac ccagagctgg aaaatgttgg aatgaaaact gcggcggcct ccccttctct  18420
ctccttcccc ttctgttgcc ctgtttgaaa atcgtgcctt actttctttg gtctcctggc  18480
atggtgaatg ctgctggtat ggactgtgtt tctatatccc cttgatcccc acacccttag  18540
gaacgtacag gagagagacc ctggagcata tcagcttaga gatggagggg aatgggaagg  18600
agtgcgttca ttcattcata aatgttgact gagcacctac tgtatgctag gtgaatggga  18660
```

```
ggacgtgagg gcagggaggt gacaaggttg gcttattctg ggctttgtga actatggtga  18720
ggattttgtt tttttccaaa ggaaatggaa taaccactcc ttttttcccc ccgatatacc  18780
taaacttttt gattttcata acaaaaatgg gcttcctttt gtatatttgt tttgagacca  18840
gccgtttttc caccaacact gatcacactg cagtgagcat cctggtagag aagtctttgc  18900
acacttctgt cactgtttcc ctaggacaga ttcctggaaa tggtatggca aggttgtatg  18960
tcaggctttt gggccaggtt gcaagaaaca ggaagtctgt gccctttcaa attccaaggt  19020
cccctttccc tgacgacgtg gcccaatcag gcttgccctc ccttgatttt acatcttcac  19080
caatcagata agtgaaagtg aaatcctgtt gtggtatcct gtgcatttct ttggtgactt  19140
aagacataga gcattttcca gatctctgtg ggctgtttgg atatcctttc ctctgttttc  19200
tcaggcacat tctttaccga tgtctttgag ggattgagca agtttctgtt gaaattgagg  19260
catgtcatgg ctctgtgtgg ggcttgaggc agtccagtgt agtggaggga gggaggctgt  19320
ggagcctggc tgcctaggtt caaataccaa ctctgcttat ttccattcat atcattttag  19380
gcaaatcact tagccccctg ggcctgcctt tcctcatcag taaaagtggt ataacattag  19440
tgcctgcatt gtggggtggt tgtgaggaaa gcagcactca aaacagtacc tgacacacag  19500
tgggtgccaa ataagagtct gatgtattag tgttataggt atcggcctcc tccctcccca  19560
gtgcaatagt gtgtgtgcgc ctctgtgtac ctctgttggt gctgacaagc ccttttttaaa  19620
atttagaggt gaggtctcac tctgtcccct aggctggagc acagtggtgc aatcatggct  19680
cactgcagcc tcaaccgcct gggctcaagc aatcctccca gcttagcctc ctgagtagtt  19740
gggactatcg gtgtgcacca ccacacctgg cccttagaca gcccctttat ttcaaagcga  19800
aatggcagcc acaagattta gtgcaagctc tccaagcttt aggaccagct gcaactcctc  19860
taactgacca aacaggatcc cccatgtccc caaccccccaa aacctgatga aaagcaaaca  19920
gaccattttc cacattcatg acggaaaggc ccttttcttg gctcctgccc ttgctcatgt  19980
caggatttca ctccatccct gataaagagg aagcaccatg tcccaggagg acatggaaac  20040
tctctgcttt gtggtgaata gttacagtaa cagtagctcc tctctgtggg gagcttatga  20100
gcccctaagc tttatagaac tgccctggca gtttatgaga acttcatccc agcccccaga  20160
gctcatggca cttatttttg cccccagttt gcagatgtgc acactgagac tcagagagct  20220
aacactgctt gccaaggtca cacatctagc aaatggagaa actttatgag acaggtgaag  20280
gcacagcaag gataaaaacc cagagggaaa aatactcaag ttttctccgg gaaaccattt  20340
gcattccaga gaggttggtg tgcgagtggg caagagatgt cgcgggacga tggttaaggg  20400
acagagtctg agctcaacta ggactaggtt tcttcctttc cttccttcct tcctttcttc  20460
cttccttctt cctttccttt gtctttctct ccctcccttc cttcttcctt tccttccttt  20520
cctttctctt tccctccctc cctcccttcc ttcttccttc cttactcctt tccttccttc  20580
ctcctttcct tcctttcctt tctctttccc tccttccctc cctcccttct tccttccttt  20640
ctttccttcc ttcctttttc ctttctcttt cctttctttc ctttccttcc ttcctctctt  20700
cttccttctt ttctttcttt cttttctctt tctttctttc tttctttctt tctttctttc  20760
tttctttcct ttctttctct ctctctctct ttctttcctt ctttctcctt ccttccttcc  20820
ttcttttctt ttcttttcct ttctttttctt ttgtttttg agatggagtc tcgctctgtt  20880
gcccaggctg gagtgcaatg gcacaatctc agctcactgc aacctctgcc tcccggttca  20940
agcaattttc ctgccttggc ctcccaagtg gctgggacta caggcacgcg ccaccacacc  21000
cagctaattt ttgcattttt agtagagatg gagtttcacc atgttggcca agctggtctc  21060
```

```
gacctcttga cctcgtgatc ctcctgcctc agcctcccaa agtgctggca ttacaggcgt  21120
gagctaccac gcctgggcta ggactaggtt tctatcggtg gtgtggcttt tgggaagcta  21180
cctaatctta accactctgt ttcgtcatct ataagataag cagtgtagca ttttcttgca  21240
ggaatgttgc aaggattaag tggatggtga ctgtaaaaca tcatgcgtgg cacatagtaa  21300
attctcagca ggtagtcatt gctggtcatt tacttttctc taatgaccag caagctctta  21360
atttcctcct tggcatgggc actgggacgt agatggacaa aacacagaga gaaataaaca  21420
cacggacaaa aatccccgcc ctggtgtggc tgatattctg ggtggggaga gagagggagt  21480
ccaaggacca gataaacagg taaaggatag tttgagtgtg gtaagtacta aggctcaaaa  21540
ataaagatct cccaggtgat cttagctgca tttggaggtg acaggagata caactgagaa  21600
actgagatag gaggaaaccc aaggggagat gtgggcttga tttagggtga tctgaggagt  21660
aggagaagtc aggggctggt gtggggaggc tctgatggtt ctctctgggg agtgaagcag  21720
ggattcgttg gggagaccca aggggacagg tgaaggcccc tgaacaggtg gccagtgctg  21780
agaaaggaaa ggtggaggac ccaagtgagt tcctaatttc ttcattgctc ccctaaggtg  21840
tttgtctcac ccttggccat agtcttggat cacttacaga tgcagaccag gctgggctca  21900
atggcttgtg cctgtaatcc cagcactttg agaggctgaa cccaggagtt tgagagcagg  21960
ctgggcaaca tggtgaaacc ccgtctctac aaaaaaatac aaaaattggc cgagggtgtt  22020
ggcacatgcc tgtagtccca gctacttggg aggctgaggt aggaggatct cttgagcccg  22080
ggagacctat gctgccaaat aaggtaggca gtagccacac atggctattg caattttaga  22140
aattaattac aggccacatg tggtggctca cacctgtaat cccaacactt tgggaggccg  22200
aggcgggcag atcatgaggt caggagatcg agatcatcct ggccaacatg gtgaaacccc  22260
atctctacta aaaatacaaa aattagctgg gcatggtggt gcacacccgc agtcccagct  22320
actcgggaga ctgaggcagg agaattgctt gaacccagga ggcagaggct gcagtgagct  22380
gagattgcac cactgcactc cagcctgggc aacagagaga gactccgtct caaaaaaaaa  22440
aaaaaaaaaa aaaaaaagaa aagaaaagaa attaattaca ataaaaacag tccctgagtt  22500
tcactggcca catttgaagt gcccgatgac cctgtgtggc ttagtgacca ctgtgctgaa  22560
tagtgcagat ctagagcatc ctactggaca tgttgccagg gtccctgaac caacagaatt  22620
agcatctcct gggagcttgt tggaaatgca gaatctcatc ccctacccca gacctgctca  22680
atcccaatct gctcttcagt gagattcctc aggtgatctt gactgcacct tctaatcact  22740
tggaagcttt aaaaatgctg aggctgggca cggtggctca cgtgtgtaat cccagcactt  22800
taagaggcca aggcgggtgg atcacctgag gtcagaagtt tgagaccagc ctggccaaca  22860
tggtgaaact ccatctctac taaaaattac aaaaattacc caggtgtggt ggcacacacc  22920
tgtagtccca gctacttggg aggctgaggc aggagaactg cttgaacctg ggaggtggag  22980
gttgcagtaa gctgagatgg cactgctgca ctccagcctg ggtgacagag tgggactctg  23040
tctcaaaaaa aaaaaaaaaa aaaaaaaaaa gaaaagaaaa aggaaaatgc tgatgcccca  23100
agctccaccc ccacagatgc tggagagatt tgtccagggc ttcccctgga gtggggaatg  23160
tttgaaaact ccccaagggt ttctaaagtt cagccagagt tagcagaaag cccattaggt  23220
ggctaagcag gtagactgaa gttggagctg tgtgaccttg ggcaagccac ttaccctctc  23280
tgaaccacaa gctcccttct ctctaaaact agagacctgc tggcacctcc ctcccagggc  23340
tgtgagaagt aaatgatggg atgattcaaa gtgctgagta gggtcagatg cagtggctca  23400
```

```
cacctataat cctagcactt tgggacgctg aaatgggagg attgcttgaa gccaggagtt  23460
tgagaccagc ctgggcaaca tttaaacatt acccaggtgt agtggtgcat gcctgtagtc  23520
ctagctgctt gggaggccga ggtgggggga tcccttgagc ccaggagttc aaggctgcag  23580
tgaacaatga tggtgccact gcactccagc ctgggggaca agagtgagac cctatttcta  23640
aaaaagaaag aaacccaaaa tgctgagcga gtgccttgga ttgatagtaa gcagtgcctg  23700
tgtaataagc atgaatttta aaaaatgagg tcagcagcct tagagctaat ggttaatggg  23760
tttgggtgtg ggattttttt ttttttaatt tttaaaacat tgagataaaa ttcccataac  23820
ataaaattga ccattaacca ttttaaagtg tacagtttgg tggcatttaa tacactcagt  23880
gttgtgcaac catcacctct ctgtagttca aagaccccaa aaaggagacc ccgtactcac  23940
tgagcgctca ctccctgtct ctccccgctc ccccagcccc tggcaactac taatcttctg  24000
tctgtataga ttgacctatt ctgattttgg gggtttttga actcgccttc cctggctgac  24060
aacctctcgc catccaggtg agactgtgtg aaagcccagc tccctgcatt tctgggtctt  24120
cctctcccca ctgggggctg cccccacctg tttccccctc tgggcaccct ggttctactc  24180
atcagcctgg cttaatccca gcagcaggtc catgttctgc tctcctgtgg ctgccacaaa  24240
tgagaggttt catctcagct gggtttctcc tagttaaata tttaataaat aagacctaca  24300
acttgtgatg ctgggagtgt ttgatagtga aattaatgat ggggagagag tggcaggcgg  24360
cccacaggtc catgctggag ctgggatgag gcgccctggg caggcgtccg tgccactgat  24420
gcttgggaac cacggtgggc catgccatcc catttccccc agccagggcc tctttttttag  24480
cactgtgtcc agcacagggt agccacctga taaataagtg ttaaaagaaa gagaggctgc  24540
gtgtgtaggg aagaaggaag agacagagga gacaaagagg agacacagag agagagagag  24600
agatgagaga gaaagaaaag tggaaggtga gaaagagaca gagatggaag gggagagaag  24660
gacctggatg gaggaagtgc aaggaaggca atggtgaggg aaaagagaga gagacaaaga  24720
tggaagggat gaaggagagg gagagatatg gaggtagaga aagagagaca gaaagaagag  24780
agagaatatt gcttcttgta tcttcccctt ctcctgttat ccttgaccat cttattattt  24840
ttttcttttt tctgtctctc cagttctcat ttccttaccc tcgccgtctt gccaactcgt  24900
catctctttt catttcctgt gtctatgtta tcttttaatt ttctgtctgg gtattttccc  24960
cttttctctt tctcagcata aactgttggt tggtgtatgt gtcttctttc ttttttagtc  25020
tttaactgac gtgtgtgtgt atgtgtgtgt gtgagagaga gagagacaga cagacagaga  25080
gagagagaga gagacagaac aaacctagag agcagtgtag gaacatagat gaacatttta  25140
aagaccaaac catgaagcgt acacccattt tacccaggtc aagagccaca gggccaccat  25200
cagattctcc ctcatgctca tcctcaatca cagccactcc ttccctcctg gaggaaccac  25260
tattggagat tgtatgggaa ccattcgctt gctttcttgt gtggttgtac cacctaagta  25320
cgcatcctga agcaatatag tcagatatta tgtggttttg agttttatat gaataaaatc  25380
atgtgagagg agttgttttg tattttgctt cattggtttg cagttacctt tgtgagattt  25440
catcctcatt gtggtcactg cagctccttc atgatcttgt ttattcattg atgatgagca  25500
tgtgactttg ttctcttttg ggcactggca taagcagctt tgttggttgt ttatggattc  25560
tgctgctcgc ttgcaggggt ctctctggag cacatcgctc tgtgtgaaat tgttggatac  25620
taagatttgt acattttcac cttgactaaa cactgccaaa caattttcca aagtgcttgt  25680
gctaatttac actcctgccg gtggtgggtg agcattcaag atgcttcaca accttgccaa  25740
cacttggtat tgtcaggttt ttaagttata gcctttctca tggtgatttc tcattgtgat  25800
```

```
tttagtttgc atcccccgat tgcaaattag agtgaacata gtttaaaata tttattgact  25860
attcaagctt gctttttttgt gaagtgcctc tacatgctct gtccattttt gattaggtca  25920
cttttaaaaa aaaaatattg atttgtgggt gatccttaca tagcctggaa actgattctt  25980
catcattata tgttgtgcaa tattttctct tggcttggct tttgatcttt tttataatgt  26040
cttttgatca ccaacagttc ttaattttga tgtggttgat tttagaaatc ttttccttta  26100
tagtttgtgg gctttgtatc ttatttaaga aaatcatttc taccctgagg ccatggatat  26160
attttatgtt atttctgaaa gttttacagt tgtgttcact gtatgtcttt aatcagcttg  26220
ggattgattt ttatatgtgg tggtaggtag gggtccaatt tcctttttat tccataagaa  26280
ttgtcccagc atcatttatt aaaaagccca ttcttgcccc aatgatctgc aagacaacct  26340
cttgactgtt taacttttac cttctttcat ctggtctgtt tttatactca acctttgaag  26400
ccacaaatat ttattgagtg ccaactgtgt gccaggcact gagttacagt gacggatatg  26460
acagatgcaa tcatggcttt catggagttt acagtctggc aaggatgaca tgtaaatagt  26520
tattactact tataatttaa aatgttatag gccttgcaaa aagggacaag tctggcttgc  26580
tctaaaagaa acatgtgaaa caacatcttc cagggaagtg ctgataaact gagtctttag  26640
tgggcctctg ctattgtagg ggtgggaatg gtggaaaaga tgttttggcc acagggaaca  26700
gcatgtgcaa aggtcctgtg gaaggtgctt aggagtttga tatttatcct aaaggcactg  26760
tcaggctact gaagcagtaa tacaatgatt ttatgtctgt gaatagttcc actggttgct  26820
gcatggagaa tgtattggaa tacagcaaga ataaaaagcc atgagaccaa ttaggaaatg  26880
atttcactca ttcagggaag tgtgccttgg gctggcatgg tggctgtgga gatggaaatc  26940
attgatcaga ttaaaagaaa ttttgagctg gcatgatttt tcccctctct cccctctctc  27000
tatctctgtt tcttttctgg ttgtgttttc tgggtgagaa aagcagtttg tgatcctgcc  27060
aagggtatgt gctctggagg atgtatttgc cacagatggt ctttggaatt ctggccaaga  27120
gagtcactgg acagcccctg gcccccaggg tttctggagc caattcaaca atgactgttt  27180
attaacaaca gcaaggatga gttgctagcc tttccttcag agcacctttt aactgttacc  27240
ttactttgtt acccaaaccg acactatgga attggtgggg gagaagtgga agggttttta  27300
tctccatttt ttatagaacg gggggaagtta attggcactc ttgaaatcat acaaaagatg  27360
ttggtttcag gattggtttc tggactttca gcccaatccc aattactcaa gctcacacac  27420
ccaatcccca aacatactct tttgcaaata atttccctac tgaggtgctc ctggccaatt  27480
taaaaggtcc ccatttcctt gcctataaaa tgggaattaa agtaaaaata tctacctgtt  27540
gacttgctgt gaggtcagtg ggcctgacac atggtgtgga ctcattatat ttacctatgt  27600
gaatccctta gttcccttta cttggaagag gtggaaaact caaaggggct taaacaagaa  27660
gtggggattg tattggctca tgagactgaa gagtctcagg agtgtccagc ttcaggcttg  27720
tttggatcta gggatcagat aacaccatta ggcctctgtt tctgtttctt ggctctactt  27780
tttgcagctg gctccattat ccatgactta gctgcacttc cagccctcca gtctgcccaa  27840
gaccatattc agagagagat tcttctctct ttttcagcta tcttcccgga attttcagca  27900
aatgctttct tgcttttgat tggctgttgc tgaggtcgtg tgctcatgcc agaaccaatc  27960
actgtgggga aatgggaggt ggagaacggg gtgctctgat tggcttaggc ttgggtcaca  28020
tgactttatg gagttggggt ggagccaact tctccaagtg gggaagagca gtcttcttaa  28080
aggtgtatta ggatatgctt gctgctgtaa caagcaaccc ccaagtctgc agtagcttaa  28140
```

```
ggcaatacga atgtacttct cactcaccct aaatccaatc agataatcag caagtggcat  28200
tccatgtggt gatttcagga cccggctctt tccatctgtg gctccaccat cccctaagat  28260
cagaaagtcc ttcacttccg gcctgtagga aaagagtatg aaggctcaca caggaagttt  28320
tgggaggcca catatagaag tagtgaacct tacttctgcc tgcattctgt ggactggaat  28380
ttcatcccat ggtgtatgag agagggtccc agtaggaaac ggaagacaca gaccaagaat  28440
caaattaaga gatagcttaa gaatcaaatt aagagatagc ttacaaaggt gtgggccctt  28500
actgaaatag agaaggagga agagaggaag gaggcagaga cagagagaga ctgagactca  28560
caaagacaca cacacacaca cacacacaca cacacacaca cacacacaca caagttgaga  28620
gaaagaaggg gggagagaaa gagagagagg gagcatttcc taacaggaag ctggcagaat  28680
aaatgtcccc cattgtccaa agccagaggg ctgggagccc agtgagccca tccacacagg  28740
tcagcccccc atgtgacagt cctagaaggg taaagaagga aggagagtgg atttggggta  28800
atggaagaca gccaataccc atggtccatc tgactgcagg gggaactgag aaattcagtc  28860
catggagaag aaggtttagt ggacacgtca ctttgtcttt ttcacaaagt gaaactaggt  28920
tctcaggtgg aaaaaagaaa aagaaggttt gccttgctgc tattcttttt ttttttttga  28980
gacggagtct cactctgtca cccaagcggg agtgcagtgg cacgatctcg gctcactgga  29040
agctctgcct cctgggttca cgccattctc ctgcctcagc ctcccgagta gctgggacta  29100
caggcaccca ccaccacgcc cggctagttt ttttgtattt tagtagagac ggggtttcac  29160
tgctagccag gatggtctcg atctcctgac ctcgtgatcc gcccgcctca gcctcccaaa  29220
atgctgggat tacagacgtg agccaccgca cccggcctcc ttactgctat tcttattatt  29280
ggtggtagca gtggtggtga tggttattgg ttcttagttc cctctacatg ccagtatctg  29340
ctctcttctt tttttctccc ttacttcttt ccttgttctg caaattcttt ccctttaagt  29400
gaaaatcttt ccgtgttctc caagggagat aaattctatg ccaagcttga gtgtggggtc  29460
ctctgcttgg atagctgtct tctccaggag atgaggtaga actgagatag tgggggtctc  29520
tgcaggcagt ctgtgcccct ggcaagcccc tcaccttaac ctgaggctgg gtggggaaag  29580
atgccttgat ggagtcagaa cagaaagcaa gtgatcgctg cctgaaccaa gcagtcactt  29640
tcctggaggt gaaacctaga aacggtccct caggctgggt ccagggaggt ggacttgggt  29700
cccaggggca ggaagcaacc tgcccctcac ctgctcctac ctctttgtag cctatcttgg  29760
caaccagaag taggtataca agtgacgttg aagctgggca tgttaacaat ggtgtgagcc  29820
cgcctgactc caatctggtc cagctgtact ggccgtgcat cctcatctcc agcccccagg  29880
gtcagcccag cggctgtaac aatggtctgt cccctccccg ccccacccac ttctttgaac  29940
tcctccaagg atctgtgatg atagggctgt cactgtctta gcttccacca ttcaagctta  30000
accggccttc ttcccctcca tggagaacgg aagagcaacc cctcattgcc tctggcagct  30060
gaccagcagg tccctgcctt ctgcccactc ccaggtctag gacaatgagg tgagaggtag  30120
acaggaccaa gttccccagt gctgtcttct aggtccacct atcatgagag ccgtgattcc  30180
tagtttttat caccctctcc ccaactttgc cagctctcca cttctggcag tggtggctgc  30240
ccatgacttc accttcccgt gcctcagttt cctcatctgt aaaataagga cagccatggt  30300
aatgagagtt ctggtcaata tgccaggcac ctcgcttgca tcaatttagc tcatcctttc  30360
agtgccctga ggggtgggta ctgttatcat cccgtgtaac aaaaagagaa aaccgaaaca  30420
gagagagaga ctcactatct gaggtcttgc acccctcaag caacaaaagt gggatttcag  30480
cctaggctat ctagattcgg agtccacggt ctcaatgaat aataacaaca ataataatat  30540
```

```
tgtcctaatc tgatgagttt ttgatcagat tcaatacaag agcataggca gaaaagctta  30600
gcccagtgcc cagcacatgg taagaactca gcatgttatt tataatagta ataaaccatt  30660
ttatgttatg taattatata ttcatagata aatatagttg actcttgaac aacatagggg  30720
ttggggcaat gacctcctgt gcagtcaaaa atgtgtgtgt aacttttttt ctctattttt  30780
tagaaatttt aaaattagag acaaggtctc gcttttgttg ctcaggttga tctcgaactc  30840
ctgggctcaa gtgatcctcc tgcctcagcc tctcaaagtg ctaggattac aggtgtgagc  30900
ccccgcaccc agcctgtgta taacttctga ctcccccaaa gcttaactac taacagtcta  30960
ttcttgacca gaagccttac cagtaacata aacagtcgat gaagacagat tttatatgtt  31020
atatgcatta tatactgtat tcttacaata aagtaagcta gggaggagaa agtattattt  31080
taagaaaatc ataaggaaga gaaaatatat ttactattca ttaattggaa agggatcatt  31140
ataaaggtct tcatcctcat tgtcttcaca ttaagtaggc tgaagaagag gaggagttgg  31200
tcttgttgtc tcaggggtgg cagaggtgga ggtggaaggg gaggccagaa agacaagcac  31260
gcttggtgta actgttattg gaaacaaatc tacataagtg gacccataaa attcaaacct  31320
gagttgttca ggggtcaact atatatgcta caaatacgta atatgctaat atagttgtat  31380
gttattgtta tagtacgggg atcagaaaat gttttctgca aaggattagc tagaaaatgt  31440
ctagtaaata ctgtctcttt gggaccactc tactctgcca ttatagcaaa ggcagctaca  31500
ggcaatacgt aaatgaatgg gcatggccat ttgccaataa aactttgttt acacaaacaa  31560
gccatgggcc agagtttgtc aacggctggt atagtatatg ttattatata ttagctttac  31620
tttttctgtt gctttgttta tgttcttctt tgcccttcct ttcttaaagg ccagcctttc  31680
tttctctctg ttggtctgtc ttttaggaca gcatggcagg ccactgggac atgggctctc  31740
ctgactccag gcttgtttgt ctgataagac atgaagagtg aaggtggcag gactctgagc  31800
tcaggcctgt cctcctcctc ttccctctct tcgtttttttc tttcctcttt cctcttttct  31860
tcccaagctc cagaagttgc cattttcctt tcccattgct gattttctct gccttgggag  31920
aaagcccgag aagatcactt ggaaaagccc acgagcatct ctggcctcac tcacccagct  31980
cctgccattg tctttactct tcctcagaca caccaggcac agtcctacct cagggccttt  32040
gcactggctg tttcctctgt ctgcattgtt cttctctcag gtgacctcat ggcttctccc  32100
tcctctcctt caggacttca ctcaaaggcc accttctcag catttgcctc ccgcccttct  32160
gccttatttt cccctttgga acttttcacc ttcttactta ctcatctgtc tgctatctgt  32220
caccctacat cactatgatc tccacaaggg aaggtgattt tattcgtttt ttgttctgtt  32280
ttgttgaaga tgaggttttg ctcttgttac ccaggctgga gtgtggtggc acgatctggg  32340
ctcactgcaa cctccacctc ccggattcaa gtgagtctcc tgcctcagcc tcctgagtag  32400
ctgggattac aggcacccac caccatgcct ggctaatttt tgtattttta gtacagatgg  32460
ggtttcacca tgttggccag gctgatctca aactcctgac ctcaggtgat ccacccacct  32520
cagccttcca aagtgctggg attactgtga gccaccacac ctgatctttt ggttttaccc  32580
accaatgtgg actagaacag cctagatcag caggtggcat gcagtaagca gttgataaat  32640
atgtgttgga tgagtgagca ctgtggcttc tgtcattctg ttgctcaata gcattcatct  32700
ggaaataacc acagtttgtt tatccattta cctgttgatt ggcatttctg ttgattctcg  32760
tttgggccat tatgaacaaa gctgctgtga aatacttata cctttgccca attcttcact  32820
tggtgaaccc ttataaatcc tttaggccag gtgtggtagc tcacgcttgt aaccccagca  32880
```

-continued

```
ctttgggaag ccgaggtagg aggatcgctg gaggccagga gttcaaaacc agcctgggta  32940
acatagcaag acccgtctct acaaaaaaat aaaaaattgg ctggacgtgg caatgcatgc  33000
ctgtagttcc agctacttag gaggctgagg tgggaagagt gcctgagccc aggagttcaa  33060
gaccgcagtg agtgatcgcg tcctgcactc caggctgggc gatagagtga gaccctgtct  33120
gtaaaaatga cagcaacaac aacaataata aaacctttag gtttcctctt aaaaggaaca  33180
tccttagagc ttttcctgac ccagcaactc accccaagtc tgaattagac ttcaccccat  33240
ttctttcata acatttatca caatgacatg tttattttgt gggggcgggt ggcattctgg  33300
ccagaactgt cgacttccag agtgaaaata cggaagaacc aaataaaaca caacacacac  33360
atttgcacag cagctcgagg gaggtgctta gttctttgag tttccaagaa cagagagacg  33420
aagatttgtc tggggaggaa aaatcaggga ctgcttcttg gaggaggtgg actgttgctg  33480
ccccatccac ccacacattt gcagatgtgg tgatgagaag atgactgtca cgaggtctct  33540
gagcccaggg ggcccatggt tgagtgcaaa gatagtgggg ttgacaaata atcgtcgtat  33600
aacaaaagaa aagccaccac agttgcataa tggaaaggcg gcttctatag aacattcaga  33660
tcatagttga aggcatgtca cactgtgtta ctcagaggcc actgtcagag ccaaaagtga  33720
gagtggatga gagtttgggc aggaaacaac tgaaccagat acagcatcac ctccatgagg  33780
gctcagcttt atctattttg tcttctgttg catccccagc ccttagaaca ctgcctggtc  33840
catctttgct gtgtgaataa taataaggaa cgatcgctgt gttgagtttg ggctgtgaat  33900
tcagacagtt tgctgctgca tacctgatta tgagtctcag ttttcctcct ccataaaatg  33960
ggcaaaacag tccttgcctc atggggctgt gcatttgttt agcaaacact gaaggagtat  34020
acatggtggc caaggcactc ttcaagacac aggaagcaga caaaagtccc tgccctctgg  34080
gagcttacat gctcatgggg agagatgtat gataagaaac aaaaatagta ggtaagttgc  34140
atagtacttt agaagattat aagggtaatg ggaagagaac agcagagaaa gggctgggga  34200
ggcagttgct gtattagata gagctttatc gaggcgatgg cattggagcc aagacttgag  34260
gaagctgtga ggatgtctag agaaagaagg aacagctggt gcaaaggccc tgaggtaggg  34320
gtatatgtga catgtgtgac agtgaggagg cagatgtggc tgaagccagt gagcaagaga  34380
gagggaaggt gcaaggataa ggacagagag gtgacgggac aggttttgga gggccttatg  34440
ggctgcgggg aggactttgg cttttgctct gagggagctg ggagccacgg agggcttttg  34500
agcagaggag ggacgtgacc tgactcagat attcataggc tcctctggct gctgtgaaaa  34560
gaacagactt tgaaggttgg gggcaggcag ggcagaagct ggggaattag gaaggaggtg  34620
acagtgttgg tcctggcagg taatagtggg ggtggaacca ggttgttgtc tgtggagata  34680
ataatgagtg gctggattct ggttataatt tttaagtttt tttattgtga taaaatgaat  34740
ttttttattg tgataaaatg aaatttacca ctttgaggtg tgcaattcca cagcacttac  34800
tacagtcacc ctgttatgca acagtcacct ctatttaatc tcagaacatt tcatcccccc  34860
taaaggaaac cctgcaccca ttagtagtta cttccagttt ctcccttccc ccagcttctg  34920
gaaactacta attctggata taagttgaaa gttgaccagt aggatttcta ggcagacagg  34980
tggtgagggc tcaatgcatt catgcacaga aagtactcag gtggcatatc ataggtgctc  35040
aaaactgaaa tggtgatgat gagttggcaa tgatggtgag tccttccaga atccctgctc  35100
tagtgctaaa ctgacctacc tggctgtgta gaattctcac ctgctggccg ggagggtggc  35160
agaaccagga tcccttctta cttccagtct ggcttgggtt agggataggg gaggaatgat  35220
cagaagaacc aagctagcac catctgttct ggaacatcat ccaactcttg tccagatttc  35280
```

ccagaactga gcaggaaaat gtccagggag gaacagtgca gctgatggaa gtcctggtaa 35340
gccctggccc cagcttcctg agctgctgtt gcaccaacta gcatttgttg gaccttcagt 35400
ctgagccaag atggcagctt cagaggaaga acaagaagtg tacaagtttc tttcatggtt 35460
gtgtccccgc ctccttatat agcctcatat aaacccctgc actatcccgt tactgtttgc 35520
ctctccctga aaagagtgta aaactccccc actttttccc tacttttcac aatgtgtttt 35580
ggtttctaaa gatgaaactc ctttaattat gttctggttg taattttctg gctcctttta 35640
tttctccctt acttgatgta ttattttccc ttgttccttc tgccccctgc ctccattgat 35700
gtttctcttc actgctatct agatttaatt ctcaactcct gccaagttca gggtgatagt 35760
gcaaaaagac atggaccatt tagtcttgaa ttcaggtccc acttctgaca ccttcaaagc 35820
tgctttactt tgggcaagtc atatgatctt cctgaggggg tatcctttac cttgttcagc 35880
taacatttct tgtttttctc tgggcacaga gtagagtgtc attttcccca cctccctgaa 35940
gttaggtatg gctgtgtgat ttggtttcat caatgaaatg tgaggggaag tgacgtgagt 36000
ccttccggac agaagcctta agggtgagca tgggattcac catgtttcct ttttcctgcc 36060
tccactgtca tggatgcaca aagatggacc ctctctcaaa gtaagtgctg gagagaggat 36120
gacatagatc agtccccatc ccacttcata gcatgagtag aaaaatagac ctggggtgtg 36180
ttcaaccact gagatctggg gattgtttgt tactgcagca ggacatagac taggctgact 36240
gtatacctca ttatctgcat tttggggctg atatctaatc acagtgtctc caggaagatt 36300
atgttgatgt atgttttagg gatggatatt catattttcc tataagggct caataggttt 36360
ggaaatgtca catgcatgta aacttctgat taacaaatat ttcttgcttt ccaatttctt 36420
cctatagtgc ttctaatttt cctgtttttc aatcttgaat aaaatgtgag aagtgtttga 36480
cttctccttc gaggagatta atggtttcta aagcctgggg cattgattta gtcattctca 36540
acctccttgt ttctatgacc tttttttctc cttctctggt cacttagtgt ctgctaaggg 36600
gtgaaggaat gtctgtttta actcattgca tttttttttt ttttgagacg gagtctccct 36660
ctgttgccca ggctggagtg cagtggtgtg atgttggctc actgcaacct ctgcctcctg 36720
ggttcaagtg attctcctgc ctcagcatcc caagtagctg ggactacagg tgtctgccac 36780
cactcccggc taatttttgt atttttagta gagacggggt ttcaccatat tggccaggct 36840
ggtctcgaac tcctgacctt gtgatccgcc cgccttggcc tcccaaagtg ctgggattac 36900
aggcgtaagc caccacacct ggcaaactct ttgcattttt aactcttgac atcttcatct 36960
tctttttccc acctcccctt tgcctgttcc tcccctgctc accccaccag ggagtttata 37020
atcaggttct agaacctgca atgtttttct gttgttgtct tccatcttcc ttgagtctta 37080
tgggaatcgg ccatagtcgc aaattaacaa atagctctga agcgcctcaa gcttggaggc 37140
atttcctttt gctcacctaa gcaagatcct ggagctgttg caaatatcct gccccctact 37200
gtaaatctgt cttcatggtt gtaagagatt cagtcggggt cagtgaagac ccgagcagga 37260
gatcttggcc gaggctcctt gatgttctgt ctgcgctggg tgttgtcata ttgattaagc 37320
tcctgggact gctgccagca gcctctagga ttaaatcaat agagtttgca aaagtaaaag 37380
cttcttttgg agacacagaa tatgtgggtt tattttttaa tgataaagct tcaaggagaa 37440
tcttcatgga tggcagaacc agtgatggaa aaggcgaggc agacccaaat atttggggaa 37500
gtgcagtggg gagcaagtga gggaggtttc attgggaggc cggggctttc cagaaaatct 37560
gtttaactgg agttgctaat gcaacagctc agagttagaa gtgaaggtgg aagatgcaag 37620

```
aaggactgcc gctgagatgt aaagagaaat gaaggagagg tggatccatt tgctcattca  37680
ataaacattt tgggaggcag gggggtgggg gggagcctgc catgtgcctg gaactgggat  37740
gtacatggtg gggacatgac agtgggcagg acagatgtgg ttcctcctgg ccctcctgga  37800
acttgtaaca ggaaaagaag gcataaaata aggaataggc aaatacagac ataattacta  37860
attgtggtaa gtgtttggga gaaaaccagc agggtcctgt gtttgtttcc tagggctgcc  37920
aggacaaatt gccatgaact atatggctta aaacaacata aatatattgt cacccagttc  37980
tgaaggctgg aagaccaaaa tcaaggcatc agcagtgctg agctcccttg gacggctcta  38040
gagaagaatg cttccttgat tcttccagtt tctggtagtt gttagcatac attggcttga  38100
ttggcttgtg gctgcatcac tgcagtctct gcctctgtct tcacatggcc ttctccttca  38160
tgtcagtgtc ttctcttcct cttctctctc tctctttttt tttttttgt cagggcctca  38220
ctctgtcacc ctgtacaaga gtacagcagt gcaattatag ctcactgcaa ctgctgcttc  38280
ccagcatcaa acaatcctcc cacctcagcc tcctgagcag ctgggactta caggcgtgca  38340
ccaccatact cagctaattt ttaaattttt gatagagatg ggatctcact atattgccca  38400
gactggtctt gaacttctgg gctcaagtga tcctccctcc tcagcctccc gaagtgctgg  38460
gattacaggt gtgagccact gcacctggcc tcttctgtct cttataagga tctttgtcga  38520
tggattttga gcccgtcaga taatccagga caatctcatc ttgagatctc taatttaatt  38580
atacttgcag aggccgtttt actaaataag gtcatggcca gaggctccag aggctaaagc  38640
atgggtatga ttgcaccact gcactttagg ctgggtgaca gagcaaggcc ccatctctga  38700
aaaataaaat aaaataagta acctactaca ggccctttgc gtagaggata attagaagta  38760
caggggtacc acgtaagtga agacctgaag gttgttaagc acagagcaga gtgtgaacag  38820
aatgagacag agggaggaag agaatcccag gcagagggaa cagcatgtgc aaaggccctg  38880
gggaaggaac aagttcatca tgttaaaaat gagccagtgt agctagagtc tgatgagcaa  38940
agggactcac aggtgggaag acacccaaga agttggcaga gacaggtcac acaagacctt  39000
ctaggtcaag ttccggaggt gaactttatt ctacatgcaa tgagaagtcc tcagagaagc  39060
ttaagtggga tgggacagaa ctgctttact ttaaatatat atacatatat acaaacatat  39120
aatattacat atataaagca tatatatgta tacatatata catatctatc tacctgtcta  39180
tatatttttt agctgggcat ggtggctcac acctgtgatc ctagcacttt gggaggctga  39240
ggtgggagga tcacttgagc ccaggagttc aagaccagcc tgggcaacat agggagaccc  39300
catcactaca aataaaaata aaaattaaaa attagctggg tgtgatagtg tgcacctgta  39360
gtcccagcta cccgggaggc tgaggtagga ggattgctgg agccccaaag gttgaggctc  39420
cagtaagccg tgattgtgcc cctgcactct agcttgagca acagagtgag atcctgtctc  39480
aataaaataa tttttgtatt gaggtgaaat tcatgcaaca taagttaacc attttaaaat  39540
gagcaattca gtggcattca gcgcattcac aatattgtac aacctccacc tctttctagt  39600
gctgaaatat tttcatcacc acccctccag aaaaccctgt atccatgagg cagttgctcc  39660
tcatcctccc ctcccggtat ccccccaacc cccaccactc ctggtaacta caaatttgtt  39720
ttctgtttct atggatttac ctatactggc tctttcatat aaatgaattc aggcactgtg  39780
tgacctttcg tgtctggctt ctttcactta gcataatgcc ctggcttctc tctggagaat  39840
gaaatggata gaccactttg gagtctactg agattataga tatttctgtg ggaagggaca  39900
gtggcttgac cttgggtggt gctgaagagg caatgctgag caggaggatt caaagtctaa  39960
tttcggaagt agaattggtg gggtctgatg atacatcagc tgtaggggga ggaagatgta  40020
```

```
ggaactggga aggtctctta gggtaacctt acctgattga gctccttact aggcagctgg  40080
tggtacaatt cataacaaag gttaatagag aaagagacat gggattaggg agggaatgga  40140
agagtttggg ccttggacac tgtagtggtt tgaatcctgt ccaccaaaaa ttcagatgca  40200
tttggaactt cagaacctga gacctcattt gaaagtagga tctttgcaga tgtcattgag  40260
tcagggattg agatgaggtc atcctggatt acagtggact cgagattcca tggtaagtgc  40320
ttttatatga gaaggtacag gggagaaagt catgtggcaa tagaagcaga gaatggagtg  40380
ctgcagccac aagccaaaag acatgtagag gcaccaaaag cgggaagagg caaggaagga  40440
tcctccccta gagcctttga agggaaaccc cctaatttca gaaccttgcc tccaggatga  40500
cgagagaata aatttctgtt gttttaagcc acccaatctg tggcaatttg tcatgactgc  40560
cctaggagac taatatagac actcctatga gatgctctaa gaagacacag agtggtatag  40620
ctattgctaa gaccacacac tgtagcaggg aggaaatcaa atggagaaat gccccaactc  40680
cccctcctct ctgatctctt gctggtgcct cccgttggcc aagccaaccc agaaggcaga  40740
agatgtggtg gagggcagcg ttgcagggct tggatgatgc agtcacagaa gtcagccctg  40800
cctctaccag gatgccaaac agggcaatga gtggatattt tagggagaaa gggcaacaag  40860
agaatggcaa aatacatcga aatgcatgca agctctagaa agaggataga gatagataaa  40920
gggtgattac ctaggattaa gccccaggga agaccaacat ttagagattg gatagaaaaa  40980
gaggagcaaa aagggaagat tgagaagtag agaccaggag gataggagga aaactagaac  41040
aacattaaga agggcatggt caagtaatct gggcacagaa aaatggccct gggatttggc  41100
agcctggggg tctttggtga tcctctttgg aagagttttg gttgagtgat gggggctaga  41160
aaccagcctg gggagggtag gagaagaatg tgcagtgagg aagtggcagg aacacgtgaa  41220
ggcaactctt catgaagggg agtagagaaa ttggttggtg gctgaaggaa aattttcagt  41280
caagggtgga ggttttaatg atggaagaat attgatttct gtaaattggg tcattcccat  41340
ccattatacc aatatgcacg ggtgtcttct ctgatatagg atgctgggat tctcaaatgc  41400
ccatttgagt ttagcatcat gaatttaatg tcaccagccc agatagttga tctcattcag  41460
gaatgctcca ctgcccaggt atggggaagg caactagttg agttcatgca gggatggatt  41520
ttttccagga gagaaacagg aggcaagaaa gtgcgatata atcaacctat gtaaggttga  41580
caaggcagga gagggtcctg agaaatggcg gggtcagtgg gttgcagggc tcgatgggat  41640
ggacgttggt ttgcatttaa gggagttagt gagctgggag gtggttaaag aggaggtggt  41700
tcagccgggc gcggtggccc acacctgtaa tcgcagcact ttggggagcc gaggcgggcg  41760
gatcacaagg tcaggcgatc gagaccatcc tggctaacac ggtgaaaccc tgtctctact  41820
aaaaatacaa aaaaaaaaaa aaaaattagc caggcgtggt ggcgggcgcc tgtagtccca  41880
gctactcagg agcctgaggc aggagaatgg cgtgaacccg ggaggcggag ctgctgtact  41940
ccagcctggg cgacagggcg agactccgtc tcaaaaaaaa aaaaaaaaaa aaaaaaaaaa  42000
gaggtggttc aagacaagga tgctggaaac aggtgttttg gaggtggctg gtgtagcttc  42060
tgagcatgca tagctggagt ggcttggagg agacattggt tattgatgaa gaggtaggga  42120
catcctccag tgatcaagga agcaggggac cagcatggac aatggtctct ccacagggaa  42180
attggaggtc atcaaatgtt aacaggttcc gtcggagtct tagctcccag cttctgtttt  42240
cctgtggatc tcaggatctt ggctgctggt gctacctctg actttggact tcccattgag  42300
cccagcagca ctgggaggga ccttcatggc attggctggt ttaaggaaga cttccttggc  42360
```

```
tttgctgact ttcttggggg ccttcttggc tacacctgct tttgagggag ccctcctcac  42420
ctcacctgac ttcttggggg caccttttcc accttatctg agttgggaag gtctttcttt  42480
gattctcttg ctttcttggg gcccttctca ctggtttttc tgggggccat gatggtggac  42540
atattccaga gctgagcttt ccttttgttc ttaggaacta atttgaggct gccagtggcc  42600
ccaccttggt cttagagttg atggtctgca gggaatttcc aggttaaagg tttttttattt  42660
gtttgtttaa ttttgagaca gagtcttgct ctgtcaccca ggttggagtg cagcggcacg  42720
atcttggctc actgcagcct ccgcctcctg ggttcaaaca gttttcctgc ctcagcctcc  42780
taagtagctg ggattacaag cacgcaccac catgcccagc taacttttgt atttttagtg  42840
gagacagggt ttcaccatgt tgaccaagct ggtctcaaac tcctgatctg aagtgatccg  42900
gccaccttgg cctcccaaag tgctgggatt acaggtgtga gccactgcgc ctgacctcca  42960
ggtttaagtt taaaccatga agtagatgga ctgtgtagag agagaccagg gaaatggagg  43020
attttactga ccactgaaca gggatgtcac tattgccaga gaggaaaagg attcccccctt  43080
ggtagagtga acatataagg gaaagtggtt gaaaattgaa tcaggagaca gagacctcac  43140
accactcaga ggtccctaga gaactttact gacctagaaa aaaagataaa cagggagaag  43200
gtcttcagtt cttgtttgga atctgacact gaagcatcct cactcctcac tctcttcccg  43260
accccgagag tctgaaattg attaatactt tttgtttaaa acttggcttg ttgttttgtt  43320
ttttctttct gttttcatca aggatctttt attttacttt tgtgtatttg tgtgttttcc  43380
atgagtcatg ttaattcttc catgtttaaa ctttttggcc cagaggaatt tatacattta  43440
aattatggat ttaatttcag aaggtacata cacacacaca cacacacact cactcatctc  43500
actttttaaa aactgtaaaa tatagccctg taaatatcca gaaaatatct aatgtgggcc  43560
gggtatggtg gctcatgcct gtaatctcag cactttggga ggccgaggtg ggtggatcac  43620
ctgaggtcag gagttcgaga ctagcctggc caacgtggtg aaaccctatc ctcactaaaa  43680
ataaaaaaat tagctgggca tggtggcagg tgcctgtaat cccagctact cgggaggatg  43740
agacaggaga atcacttgaa cccaggaggc agaggctgca gtgagccgag atcaccccac  43800
tgcgccccag cctgggcgac agactgagac tctgtctcac aaaaaaaaaa aaagaaaaga  43860
aaaagtcagt gtgcatcccc tctgacatcc agcaacttca catcttggaa tttatgctgc  43920
aggaaaatta tcacaagtgc acaaggatgt atggtgagat agttattatt atcattttaa  43980
aagatagggt ctcactgtgt cacccaggct ggagtgcagt gaagtgatca cagctcactg  44040
cagccttgac cttctgggct cgagtgatcc tcgtgcctca gcctccccag tagctgggat  44100
tacaggtgtg agccaccatg cctggcatcc ccctttttttt aaaaaaaggt tttaattatg  44160
aaaagaatat gggcttgttg ttttgtgtgg ttttttaaaa gcttaaaaaa tgtgtagtgt  44220
gtcatttaga aggtgaaaag cccttacccc atcccacctc ccagagataa cctctgctag  44280
caatttcgtg tttgtctttc aaatttttttc ccacacacat tctttgtact ggctgcttcc  44340
cctcctgggt tactcttctc ccagacagaa acagggctca ttcccttgcc tcctccagct  44400
tttattaaaa cattaacttc cctgtagctg gatgcagtgg ctcacgcctg taatcccagt  44460
gttttgggag gtggggaggc aggaggatag cttgagccca ggagtttgag actagcctgg  44520
gcaacatagc gagacccatc tctacaaata aataaataaa taaataaata aataaataaa  44580
taatggaaat ttaaaagaga gagggaagga ctcttgaaaa ccgtccatat catgcttctc  44640
taaatggttg agggctcaga ggaaaaaaaa tcagcaattt cacatcacgg aatttattct  44700
gcagaaaaat tctcacaagt gcacaaggat gcgtggtcag atgatgatga tgatgattat  44760
```

```
tattattatt attgaagaaa gtagcagcag cagcagcagt attttaaaag acagagtctc  44820
ggatgggcat ggtggctcac gcctgtaatc ccagcacttt gggaggttga ggtgggcaga  44880
tcacttgagg tcaggagttc gagaccagtc tggccaacat ggtgaaaccc caactctact  44940
aaaaatgcaa aaattagcca ggtatggtgg tgggtgcctg cagtcccagc taccagggag  45000
gctgaggcac gagaatagct tgaacccagg aaatggaggc tgcagtgagc caagatcgtg  45060
ccactgcact ccatgcactc cagcctgggt gctgacccag gttaggtgca agactccgtc  45120
ttaaaaaaaa agaaaaggaa aaaaaaaaaa aaaggacaga gcctcactgt gtcgcccagg  45180
gtaaagtgca atgagtaaag gcccatgatg ggaaccctga ggagagagtc aaggggaaag  45240
aaaaaaaaaa aagcaaaacc aaaatggaat ttaaaaaaaa tcaggtgcaa tttgcataac  45300
agaaaattaa ccattttaaa gtgaacggct ctgtggcatt tactgcactc caactgttat  45360
gtaactacca cctctgtcta gctccagaac attttcacca cccctaaagg agaccttgta  45420
cccattaagc agtctctctc cttctcccct ccccaccacc ttcctccagc ctctggcaac  45480
cacccatctg cattctgtct ctatggattt acctattcta ggtagtcaac aggatgagat  45540
atcccaaaag tccatccatg gatgaacaga taaaccaagt gtgatatgcc ttcctcagat  45600
attagtctgc cttaaaaagg aatgaaatac taatctttgc tacaacatag atgaacctca  45660
aaaatatgat gtggctggac acagtggctt acacctgtaa tcccagaact ttgggaggct  45720
gaggtgggcg gatcgcttga gcccaggtgt tcaagaccac cctgggtaac atagcaaaac  45780
tccatctcta caaaacaatt tacaaaaaac tagccaggtg tggtgacatg tgcctgtagt  45840
cccagctatt caggagactg aggcgagagg atcgattgag cccaggaggc cgaggctgca  45900
gtgagccatg atcataccac tgcactccag cctaggcaac agagtgagac cctatctcaa  45960
aaaacaaaac aaaacaaaac aaaaaagttg atgctgagtg aaagaagcca gacacaaaag  46020
gcaacatcgt gtttaattcc atttacatga aatgtccaat gaagattttt tttggcaaca  46080
tttattttga gtataatatt cagtgagtgg accacacata tgcatgcact gcagtatgtt  46140
cttggaaaca tttcagattt gagaggtctg ttcagctatg atgacggtag gtattgtccc  46200
ttccctccct ccttgaagaa aaggaactaa ggctggacgc ggtggctcat gcctgtaatc  46260
ccagtacttt gggaggctga ggtgggcaga tcacttgagg tcaggagttc aagactagcc  46320
tggccaacat ggtgaaacca tgtctctact aaaaaataca aaaaattagc caggtatggt  46380
gctgcacgcc tgtagtccca gctactcggg aggctgaggc aggagaattg ctcgcaccca  46440
ggaggtggag gctgcagtca accgagattg caccattgca ctccagcctg ggtggcagag  46500
caagactctg tctcaaaaag aaaagagaag agaagagaaa agaaaagaaa ccaaaagaaa  46560
aggaaagaaa agaaaaggaa ccaagaccta gaagggcaaa aataggaaaa gttggccggg  46620
cgcagtggct cacgcctgta atcccagcac tttgggaggc caaggtgggc agatcacaag  46680
gtcaggagat cgagaccacc ctggctaaca cggtgaaacc ccgtctctac taaaaatact  46740
aaaaattagc cgggcgcggt ggcaggcgcc tgtaatccca gctactcggg aggctgaggc  46800
aggagaatgg cgtgaacctg ggaggcggag cttgcagtga gccgagatag caccactgca  46860
gtctggcctg ggcgaaagag caagactcgg tctctaaaaa aaaaaaaaaa aaaaaaattg  46920
gaaaagttat ttactattag cagcaattgt cataaagtaa tgaacattta ttgcatgatt  46980
acaatgagat aaattgtatc ctgtttttat aagcatatta agttttcttt tttaaaaaaa  47040
tgtatgtatt tatttatttt aagagatagg gtcttgctct gttgcccaga ctggagtgcc  47100
```

-continued

```
atggtatgat catagctcaa tgcagcctca aattcccagg ttcaagcaat cttcttgcct  47160
cagtctctcg agtagctagg actacaggca tgtgccaaca tgcctggcta gttttcttat  47220
ttttaaatgt atttttgtag agacaggatc ttgctgtgtc gcccaggctg tcctcaaact  47280
cctggcctca agcgatcctc tgccttggcc tcccaaaggg ctgagatgat aggcatctac  47340
ctctgcattt ggcccacatt aaattttcta gtcatcatgg gaaccaaaat aaacaatata  47400
aaacactcac attccttgag cacttactat atgcagggcc ctgtaataga ttattgtgtg  47460
tatcagctca ttccattctc acacaaccta tgaggttgat gctattttct accttttata  47520
tatgaggaaa ctgaggctca gagaaggaaa ctgccttgcc caaggtcaag gccacgtctg  47580
atccccaaat cctttcaact cctctgcact actatttttt agtgcagata ttgccagttt  47640
tctaagcaga agcatgattt agcagccctg agtagacttc tcatttcaga accaaagtgt  47700
tggacattgt tggataatat gaaaaacaaa tgacacacaa acctatttga tactgttttt  47760
aattttctct tcatttgatt ttcctgatga catgattaat ctttttttgcc tctaccctgt  47820
atgtgaaatg taggtctttg cagatgtctc agagagtgtt aatagttgct gctggttttg  47880
ttttctctcc ccggggattc ccatccctgg gtgcaagtga aattaaactt gtgcctcttt  47940
gccgctggcc gtggtgctga aaacatcccg ggcagcgcta gggttgccct tgttagcatg  48000
ccatccctgc taagagtctt aggctgatca gcgagtggag agatcttttc caggcttcat  48060
tttggttaga actgtgtgtt gaagatttta aagcccatgt ctgggaactg gagactgttt  48120
ggattgtttg aagttgaaat agtcatgaat aattcctact tgagatgggc ttatgagggc  48180
gtggactagc atgcaatggt tggcctttac taaactgtgg ccattggttg ggacttgggt  48240
gaggtgtaac ccatttggtc taatccatat ggttagggcc ccaagtgcac ctgcattcta  48300
ttttttttt tttttaaata aaggcaaacc catctatctt ctaaccagga tagctcctga  48360
gtggtctttg gggaccacca gcttaaaagc atagactgtg ggctgggcac agtggctcat  48420
acctgtaatc ccagcacttt gaaaggccaa ggtgagagga tcgcttgagc ccaggagttc  48480
aagaccagcc taggcaacat ggtgagaccc tcatctctac aaaaatgtta aaagttagcc  48540
aggtgtgttg gcatgcacct atagtcccag ctactcagga ggctgaagtg ggtggatcgc  48600
ttgagcctgg gaggtcaagg ctacagtgag ctgtgatcgt gccactgtat ttcaccctgg  48660
gcaacagagc aagaccctaa ctcaaacaaa caaacaaaaa aaggcataga ctgtggagtt  48720
gggcagacct gggtgtgagc cccagctctg ccagtacctc ctatgtgacc ttgaaaattt  48780
gtttaatctc tctgagcctg gattttcttg tgtggaaaat gaggcttacc acagaaccca  48840
ccttgtagaa atgttgcaag gaattaactg aaacaaagtg cttaccacgg tatctgccca  48900
aagaagcagt tggaaacaag gcagctgtaa ttatggtcgc tgtgcttgtt aatggcccca  48960
taatagttga tcatattgca gagtgaaatt ggggtatgtg tttaatggac caaggaatat  49020
gtcttaaacc catatatcta gggttctggt accctctact ctttttcctg gtgattgtga  49080
tgagcatgga acttacatga aaatgaggtc tgtttggctt cttcacacaa gctcaatgac  49140
ctggctaact gctacaagta tctgtttcct tagaacccac ccatcagcag tccccatagt  49200
ggagacaagg tcacaaagag ttgacaaacc tgatttgatt tccgcaccaa ccacaggagg  49260
cttgaaatga gatgagggtg aagggcacca cagagggatg caaggattac ttggacactg  49320
caaggtcttg ctaagggatg ggaaccatca gccacgccca ctttgagaat tttccttcat  49380
gttctgaatc tgaagagcaa ggtcctgttc tcagatgcaa gccctccttc ttccctacgc  49440
agagtcaaac ttggtctttt ccagggtcac atacagcctc tctctggggc ctctgcaggt  49500
```

```
cctgatcaat ttcattgtgt atagagctct gtgtctcctc acctgcctgc agggctgtct  49560
gctatcctga cttccgagag ccatttcgga agccagcttt tcctcccatc agggatgctt  49620
ctcttctttc agcccccgcc ccgctttggc ctcctaggat ggctgatttt tctggatccc  49680
gctgacacag gtgctttctc tccgagccaa tcagggagca gaaaggctca gctcagctaa  49740
cagaggcatt gctcaccgca gctgtgagtt agaactcagg ctttctaaat cgggaggatc  49800
aggcatgact tgaggttggg ctgagaaagc ctcgcctgcc ccccagctcg actacccagt  49860
gaaacctttg gcttctgcct cgggcgaggc atctcttacc atgccaagaa ctcagcagcc  49920
catctttctt tcatctgggc accaagtaca tcattgcata tttcaggggg tttcattgtg  49980
tccttaacat gctcatggag acttggcttg agatgaagtc ggggtttcta ggcagcagga  50040
cccatgtccc cttccttcat ttcctccacc ggtgattttt gttttgtttt gttttgtttt  50100
gttttgtttt gttttgtttt tgagacggag tctcgttctg ttgtccaggc tggagtgcag  50160
tggcgttatc tcggctcact gcaaactctg cttcccgggt tcaggtgatt ctcctgcctc  50220
agcctcccaa gtagctgaga ttacaggcgt ctgccactat gcccagctaa tttttgtatt  50280
tttagtagag acggggtttc accatgttgg ccaggctggt ctcgaactcc tgacctctgg  50340
tgatccaccc gcctcggcct cccaaagtgc tgggattaca ggtgtgagcc accgcaccag  50400
gcccttccac tggtgttttt tgagcatcta ctatatagag aatgctctcc tgggcacaga  50460
ggatgaagca gtgaacaaag tagacaaaaa atccccacgt gcatagagtg tgcagtctcg  50520
tgggagagac agggaacaag ataaagaagg aaaaaaatag cagatgcttg actggggacg  50580
gggactaaag aaagaaaaaa ataagcaggc taagggggtt gatggatgtg acctttgagt  50640
aaaggcctaa aggaagtgag ggagggagtc atgtggatgt ctggggaaag actattccag  50700
gagaatgaac agcaggtaca aaggcccctg ggtacaaatg tgcctgggga gtttggggaa  50760
taaaagggag gccggcgttg ctgtagctga gtgactaagg gagagaatag aggagatgag  50820
gggagggagg taatgggagc aggtcatgca ccttgctggt gctggaagga ctttgttttt  50880
gcttttgagt gagatgggat ccatgggaag gctttgaata cttccacatg cattaggctg  50940
aaattttctt ttctgctttt gtcgcattcc aacattgctt ttatttcatc aaaatcttcg  51000
gtttcttctc aggctcttta cccaagtggg agcagaaggc tggtacccag ggctgttcag  51060
ttctccccct ggggtcagaa cgtggaggag aaagcttgga ggagaaacag gaacccccac  51120
ctctttctgg atgactcaaa accgcaatta cctgagctcc tcctcctatc cctgaaatag  51180
aggcacttag cacttcctaa acttcccggt gcacacaaat cccctggcga tctttttaaa  51240
tgcaggttct gactcagcag gtggatgcaa ggtctaaggc tgcattccta accggtgctg  51300
gttctgggac cacactttga gtagcaaggg tctgaggtca ttgttgcaga tgtccatctg  51360
gggcatgtct gtggacactt gcgggggtgc gggtgagcag agggaggggg gatgatgttg  51420
gaaaagcagt gtgagtatct gtgtttgata agaagtaaga aaatgaagca aggtgggaga  51480
gtagaacctc tttattttg cctacgtgct aaggttttat tgccataccc agagagccct  51540
gggtctgaaa tccaggcaac actggccagt tgaaaccctg atattgcagc ccataaaagt  51600
gctgcatgct gcatggtgga cttctgggac tcttcctgga accttcagtg ccagagccgg  51660
tccaaaggaa gtcacatccc tgccattgag gggcaggaga ccagggaacc ggaggagtgg  51720
gatggcagaa gcgcgtgtaa ggaggctgag ttggcaggga gagaaagcga agtcagcttc  51780
aaatcatagc gagaggagac cagggaaggg cttggcgttg ctgctctgtg tacaaatatt  51840
```

```
gtctcttatt ttccaggctg cagggtgagg cagagtggag tatttgtgca acacagccca  51900
gctttgttct ctgggctcct aatgcctgtc agctcagagg cagaaagcca atcagagatg  51960
atcgtcggca aggccggctt ttgttggctc cccaaattgc cctgagtctc ggattttgct  52020
tttcagagtg tgctttcagc tggaggcaaa ggctgaagct ggtgacaaaa ggaagcctgg  52080
ttttcctggc tttccgagac ttttactgag gggtttcta tttcagactc cgttttccca  52140
cctggaaagc aggttccact ctccctccgg cctggaaggg atggttttat ggtgcttcca  52200
aaatgccaaa cctaactcca gggcagaaga ggagactgaa accaattaat tttccaaagg  52260
ttagagctac gaggagggga gaggtttagc atggtcaagt tccccaagac atactaattg  52320
atctctctac agaatgcggg atttcagtgc ccccagggga cactcagcaa tgtttagaga  52380
ccacttgagg ttgtcatcac tggacaggag gggctgctac tggcatctag cacacacagg  52440
ccagggatac tgttgaacat gctgcagtgc ccagacagcc ccaccaagga gaatgatcca  52500
cccctaaacc tagtgctgag gttgggaaat cctgctccgg agtaaccaac accctatggc  52560
tttttcactc aagcagccgc ttctccagcg cttacacctc ctcagagatt gccagatcca  52620
tatgcagagc ctgttggcgt gggacacttc tgaggggtgt ggcagggaga cagcggacat  52680
tcccatttac cagctgatca gcaggttagg agctaatatg aaatgaacaa gatagaccct  52740
ccccacctgc cctgcagatc ctctggtggg acactaggga gggaggcctc ctaaacccaa  52800
atgacagttc ccaggatgca gggaggagtt tacctatgca aactggagag aatgcaaatg  52860
gggcatctag agatacttac tggacgaccc ctcccctgcc tcgggtcttg gaagaacaga  52920
ttctcagagg tctgccctga tcactgtaat ttttttttta ttgaggtaaa attaatataa  52980
cacaattaac cattttaaag tgacatttag ggctgggcac agtggctcat gcctgtaatc  53040
cccgcacttt gggaggctga ggaagaaagg tcgcccagga gttcaagacc accctgggca  53100
acaaagtaag actctgtctc ttacaaaaaa aaaattaggc acacatggtg ttgtgcacct  53160
gtagtcccag ctactcagga ggctgaggca ggaggatcgt ttgagcctag gaattcaagg  53220
ctgcggtgag ctatgatcat gccactgcac tccagcctgg gtgacagagc aaaattgtgt  53280
ttctttaaaa aaataaaagt aaaaataaat aagaaaagaa aggagagggg aggggagagg  53340
cgtttagtac actcacaatg ttgtgtaact gtcaccttca tctagttcta aaacattaag  53400
cagccactcc catttccctt gccattcccc aggaacaaca aatctgctgt ctgtctctgg  53460
atttgcctgt tcgggatatt tcatatacat ggaatcatac aatatggggt attttatgtc  53520
tgcttctttc gcttggcata atgttttcaa ggttcattcc tgttctatca tgtatcagta  53580
cttcattcct tttttttttt ttttttgaa acggagtttt gcttttgttg cccaggctgg  53640
agtgcaatgg cacaatcttg gctcactgca acctccgcct cccgggttca agcaatcctc  53700
ctgcctcagc ctcctgagta gctgggatta caggcatgcg ccaccacacc cagctaattt  53760
tgtacttttt ttagtagaga tggggtttct ccatgttggt catgctggtc ttgaactccc  53820
aacctcaggt gatctgcctg cctcggcctt ccaaagtgct gggattacag gcgtgagcca  53880
ctgcacccgg cctacttcat tcctttttat ggctgaatac tattccattc tatgagtaga  53940
ccacattttg tttatccatt cacccactgg tgaaatttag gttgtttcca tcttttggct  54000
gttgtgaata gtgctgctgt gaatatttgt gtatgagtgt tcgttggaat acctgtctta  54060
cgatcctttt gtgtttatac cttggagtgg agttactgtg tgtcacatgg taactctgtg  54120
attaactttt tgaggaacca aggaatggtt ttctatggca gttgcactgg tgttttttg  54180
ttgttgttgt ttttgttgtt gttgttttga gacagggtct cactcccatt gcccaggctg  54240
```

```
gagtgcagtg gtgcagtcat ggttcactgc agcctcaacc tcctggggct caagcaatcc  54300
tctctcctca gcctcccaag tagctggcac tacaggcctg cgccactatg cccggctaat  54360
ttttcatatt ttttgtagag atagagtctc agtttgttgc ctaggctggt ctcggactcc  54420
tgtgctcaag taatcctcct acctcggcct cccaaagtgc tgggattaca ggcatgagcc  54480
accgcatctg gccagctaca ccattttata ttcccaccag catgagggtt tcaatttctt  54540
cacatcttca ccaacacttg ttttctgttt gtttgtttgt ttttaatagc tatcctagtg  54600
gatgtgaagc agtatcccgt tggggtttga tttgcacttc cctgatcact aataccctca  54660
tgtacatatt ggccatttga ctgtcttctt tggagaaatg tctattccag cctcctgtcc  54720
atttttcaat tggattatct ttttgttgtt gtgttgtaaa tgttctctct ttattttttta  54780
ttttttttgag acagagtctc gctctgtcgc ccaggctgga gtgcagtggc acgatcttgg  54840
ctcactgcaa gctccgcctc ccaggttcac gccattctcc tgcctcagcc tcccgagtag  54900
ctgggactac agatgcccgc taccacgccc ggctaatttt ttgtattttt ttagtagaga  54960
tagggtttca ccgtgttagc caggatggtc tcgatctcct gacctcatga tccacccgcc  55020
ttggcctccc aaagttctgg gattacaggc gtgagccacc acacctggcc gtaaatgttc  55080
tttatatagt actagaccct tatcagatac atgatttgca aatagcttct cctattctgt  55140
tacttgcctt ttaactttct tgataacgtc ctttgatgca caaaaggttt aaattttgat  55200
aaagcccagc atatctgttt tttcttctgt ggatcatgca ttaggtgtca aatctgatca  55260
taatgtttta tttatttatt tacttattta tttattattt tatttatttt tgagatggag  55320
tcttgctctg ttgcccaggc tagagtgcag tggcatgatc tcggctcact gcaacctcca  55380
cctcccaggt tcaagcgatt ctcctgcccc ggcctcccaa gtagctggga ctacaggtgt  55440
gtaccaccac gcctggctaa tttttgtatt tttagtagag acagggtttc accatgttgg  55500
ccaggctggt ctcaaagtcc tgaccgcaag tgatccaccc accgcagcct ctatctattt  55560
ttaatttatc tctttttttt tttttttttt tgagacaggg cctccttctg tcacccaggc  55620
tggagtgcag tggtatagtc attgtacact gcagcctcta cctcctcggc tcaagcaatt  55680
ctctcgcctc agcctcccaa gtacctggga ccacaggtgc ctgccatcat gctggccctg  55740
ccaccatatt tgaaattgca gccctgaccc cttccactgt ctatagtctt caccatctta  55800
ctacataaca tagcatatat gatgtactgt ataacatggt atatgcagtg tactgtatag  55860
catagtatac atgatgtagt catctcattt atttgcttct cctctgggaa gcaggaggaa  55920
gcttctcctc ttgtctgctt tgctctcaac tgtgtcccta gcccagaaca gagtctggca  55980
cacagcaggt actgaatgaa tatgtgttca gtgaatattg tgggtgagat agaaggtgaa  56040
tatccacatt tccctttaga agtcacctga tctgggtttg agatctgcag ggatctactc  56100
cagacaggag aacgaataat tccacctgtg ctgatgagtt ggaaggatct agagggcttg  56160
agatctttcc actggggtca gtgggggtgg gtgcacctcc aacacccttc ttttctttga  56220
acaagatttt tccttaattc cccaatactc cctttgaata tatgatttta gccaccatca  56280
tagcgaattg catcgtcctc gcactggagc agcatctgcc tgatgatgac aagaccccga  56340
tgtctgaacg gctggtgagt gatgtctttt ctcagggtct tctccttggc tttagcagga  56400
cattaatttt tgggggagtg gagcagggca cagaggaggc tctcagtcct ggagcccaga  56460
gccagatcat gggaagccta aatttccttt tcattttttc ttgaaccaga gtctcgctct  56520
gtcacccagg ctggagtgca gtggttcagt catagctcac tgcagcctcc acctcctggg  56580
```

```
ctcaagccat cctcccactg cagcctcctg agtagcaggg actacaggtg ccaccatgcc  56640
cagttaattt tcttattttt atcttttttt gtagagatgg ggatctcact aggttgctta  56700
ggctggtctc aaactgccca ctttggcatc tgacataatt tcaggcagta tactcaaatg  56760
aacattgtta atgttaataa ttatgtcttg gccagacact gtagctcatg cctgtaatcc  56820
cagcagtttg ggaggccaag gcaggtagat cacttgaggt caagagttcg agaccatcct  56880
gaccaacatg gtgaaagccc gtctctacta aaaaaataca aaattagctg gatatggtgg  56940
tgcacacctg taatcccagc tacttgggag gctgaggcag gagaatcgct tgaacccggg  57000
aggcagaggt tgcagtaagc caagatcgca ccattgcact ccagtctggg caacaggagt  57060
gaaactccat cttggtgggg gggaggcgaa aaaaaagaaa caagaatatt acaaaggata  57120
cagatgaaga gatgcaaagg gtgagatata ggagaagggt gtggctggca gcttctaggt  57180
agcttcagga gggggactgg tcaccagaaa gaccaaggca tgattcgagg gttgcgactt  57240
tcagccccac cccccaacct ctgggagggc agaggggctg aaaatcaagt tgatcaccaa  57300
cggtcaatga tttaaatcca aacctctaat catgccttgg ttttcccggt gaccaacccc  57360
catcctgaag ctacctagaa gctgccagcc atcagtcaat ccttagcctg caaaaagaca  57420
tccctttgga gatcccaagg gttttaggag ctgtacacca ggaaacagtg tcaaagacca  57480
aacatacatt tcacaatgtc acagtcttct aaaaactata actagcctag caaacctatg  57540
atttctagat ctttgcattt tcacttaaaa taaagctaaa taaaaagcgt ccattgaaag  57600
actggtaagc aagtagaagt accagtggca agctaatgtg gaaaaaaaaa atcattcagg  57660
cagagtgaaa atgattgtag ctcgagaaac gttgctgtaa cagatgggaa aacattcaca  57720
ttggggctct gatggagaag agcttgtagc ttaatttcaa atatgataga ttagcagctg  57780
gaagccagaa ccagccggag gttctgcaga ggaactggag gtgaggatac tggccactta  57840
tcagccagta cagaagtcct attccaaacc tttaacaatc tacatgccag ctgagaacca  57900
tcctaagggg tcagatttag gagtgaggtc aatgcacaag ctctagcctc aaataccttg  57960
aacgctgcat gtgacaagta aattctctaa accaatgctt tccattagaa ctttctgcag  58020
tcacagaaat gatctccatc tgccctgtcc aataggattg tcacttgaaa tgtagccagt  58080
gtgactgcag aactgtgttt tttattttat tgcatttaaa ttaattttaa ttgaaatagc  58140
cacatgtggc ctgtgactgt cgtattgaat aagacaggtg caaacaaata attctgttta  58200
gctgagtgat atgtgaggtt ggcccaaaag gaatgaagga ggaaggtgcc ttctctaggc  58260
attggctttg ctcgcaaaag gctttggaca agagaactct gcaagaggca gtgaggggtg  58320
gtgagtgcag gagggtcagg ggaagtgaga gggtgatagg tactgatttc taggtgggct  58380
ggttccctga tcttgtcaac atctgcccag cccaagacgc tgaccttgcc ttctctccct  58440
tccaggatga cacagaacca tacttcattg gaattttttg tttcgaggct ggaattaaaa  58500
tcattgccct tgggtttgcc ttccacaaag gctcctactt gaggaatggc tggaatgtca  58560
tggactttgt ggtggtgcta acggggtaag tggcgcgtgc tatacgcttt ggatttaact  58620
agctgaagga ttacgaggct tttggttggt gtggtccggg ccaggctcag gaaggctgag  58680
cccttgtgtt ctccctcccc ttgttatgcg cctgcctcct ttctgccaac accccacctc  58740
catgtctcag ctgtatatta cagcagatgc tttctgttac aattaaaata atagctcatt  58800
attgttggct gcttccagag tgctttatgc ccattctcta atttaatcct tgcaacaacc  58860
cactgaatta ggaaatatta atattcccat ctgaccactg aggaatcaga aactcagagt  58920
gtaacttgct taaggccacc cagcaagtaa gtgatggaac tgggagatga acagaagatt  58980
```

```
atgcattcca gaactcaagg ttttaagtgt tgtacgtgca tgggtctctt gatttgcttg  59040
aggatatctt gcttttattt caacttggtg aatgtttttt gagaatgtct gggtgcaagg  59100
gattgtgatt atgacaaagg agaaaagcaa gctaaataag gtacagttac tgtcttcaag  59160
gagttttcag atccatatat gatgaactgt ggttgaaatg tgtatatgct ttcctctaag  59220
caccctgtat gaggtagcac ttgctggtat aacaaaagat ccaaagctag gaaatgactt  59280
aaacacggca gaagtttatt tgtcactcat agaaaattca aaattgagct gggtgtggtg  59340
gtgcatgcct gtaatctcag cactttggga ggctgaggtg ggaggatcac ttgagctcag  59400
gagttcaaga ccagcttggg caacacagtg agaccacccc cccatctgta aaacataaaa  59460
taaaataaaa attaaccagg catggtggta catgcctggg agaattgctt gagctcagga  59520
gttggagggc acagtgagct atgatcatcc aaccgtgctc cagcctgggc aacagagcaa  59580
gaccccatct cgaaaaaaaa aagtccaaaa taattgttcc tagttgacag gctcatctcc  59640
tccaatgact gacggaccct gacccttgcc atattgtggc tcttcattgt cagcccacat  59700
catccaataa ctccatgctt gtctgtatca aaccaggaag gagaagtgag catagaaggt  59760
gatacttgga aaggtttatg agtttggaag gggtgtgacc catacctgtt ccattcatat  59820
cctattggct agaactcggt cacatgacca cacatcactg caagggaagc tgggaagtat  59880
cagattgtgc ttagaagaaa agggaaatgg atttggagaa tgacctacta gtctgtcagg  59940
gaccttaaaa actttttatta gattccagta gggacattag tatctggtac caatggctgg  60000
ttcctcctct tcccactctc tactctcctc tcagctaagt ctgggctctt ctattctaag  60060
acccttcttc actggacacc tttttcatag taatcattta caggatcata gctttccatg  60120
ttttgttgct gctccaggtt ctgtctctct tggcggatgt gatgggttgc agcacccaca  60180
ctgtgctggc cgggctctca caatgcagat ttgtttcaga gcaatgttgc ctctcacaga  60240
aggagctgtg gcctattggg ctgtttctgt agaggccttc agatgtcagc agtctgttgt  60300
aaggactctg ggctagctct catgggcttg ggtgttcaca gagggatctt tgttggctgt  60360
gctcacagtt cggtggcttg ggaccttggt gggttccaag ggcatattat ggtactgggc  60420
acttttctct tagtctacta ggaaactcat ctagaaacag cctagtggct aacttttttta  60480
ttgtttaaaa aatgtaaagc tgggcagggt ggctcatgcc tgtatcccag cacattggga  60540
ggccaaggtg ggaggattgc ttgggcccag gagtttgaga cgagcctgag caacatagca  60600
agaccacatc tccacaaaat aaaaattaaa agtgtataaa gctgggtaca gtggcacatg  60660
cctgtaaccc caattactca ggaggctgga gagagaggat tgcttgagcc taactagttt  60720
gagaccagct tgggtaacct agcaagatcc catgcaaaac taagtagaga ataatagagc  60780
aaacacctgt gtatacattc atttattcaa tgactattta ttgaacactt ctgtgtgcca  60840
ggtcctgttc taggctctgg gacacagcag taaacaaaat agaaaaatcc cctgtcctca  60900
tggagctgag agtctactga tggagatgga cacaattgat gaatgaatct agtgtgtcag  60960
atggcggtga ggggtacaga ggaaaaataa agcaggggag ggatgggatg tgtggcaggc  61020
aggggtgagg ggtgctggaa gccagggaag acttcactgg gcatgtgaca tctgaatgaa  61080
aacctaaggg aggtgagtga gtgagccatg aggagagctg gaacagagtg tcaggcaaag  61140
ggaacagcca gtgcaaaggc tctgaggctg gactgtatct gacatgtttg atcaacagta  61200
agaagaccca catggctaga gaaggtgacc agaagaatgg ggagaattgg ggatagagaa  61260
gtaatggagt aacctgctat caaaacacaa cctttctctt tttttttttt tttttttttt  61320
```

```
tgacaagagt ctccctctgt cacccaggct ggagtgcagt ggtacaatct cagctcactg  61380
cagcctctgc ctcccagttt caagtgattc tcctgcctca gcctcccaag tagcttggat  61440
tacaggcgtg taccacaaca tctagctaat ttttgtattt ttagtagaga cgggtttacg  61500
ccatgttggc caggctggtc ttgaactcct gacctcaagt gatccacctg gcatggcctc  61560
ccaaagtgct gggattacag gcgtaagcca ctgtgcccag caaaacaaaa cctttctaac  61620
ctttctaatc cctgttttct ccctccctag acccattcct ttctctcccc catccagggg  61680
cactttcctg aattttatgt ttattatttg catttatgta ttcacacttt ggctgcctaa  61740
gtatataaga aatatatgct acctattttt acacttcaaa atatttttta aatagcatca  61800
gagtgagaat agtttacact ttgactacat gcatagataa gaaatatgtg ggctgggaat  61860
ggtggctcac acctgtaatc ctagcaattt tggaggcaaa gatggaagga ttactttagg  61920
ccagaagttt gagaccagcc tggccaatgt agtgaaaccc tgtctctaca aaatgaaata  61980
aaatgtaata aaatattcag ctgggcatgg tggtgtgctc ctgtggtccc agctactcag  62040
gaggccaagg cgggaggatc acttaagccc ataaggtcga cgctgtagtg agctatgact  62100
gcactccagc ttgggcaaca gagcaagacc ctgtccctaa aaaatgtttt ttgttgttgt  62160
tgttgttttt tgtttttttg ttttttttaat aaaggccagg tgtgatggct cacacttgta  62220
agcctagcac tttgagaggc cagggcagga agactgcttg agtccaggag tttaagacca  62280
gcctgggcaa catggtgaaa ccccatctat aaaaaaaatg caaaaaaatta gccaggcatg  62340
atgacgcacg cctgtagtcc cagctactca ggaggctgag gtgggaggat cacgtgagcc  62400
caggaggtcg aggctgcagt gatccgtgat tgcaccactg cactccaggc tgggcaacaa  62460
agtaagacct tgtctcaaaa aaataaaata aaataaaaaa taaaaaaaag aaaagagaaa  62520
gaaaaaaaga gatatgtggt actgtttttc aaacttcaca tttctctaac ctgacttttg  62580
tgttcaacat gagataaatc tgattaataa aaatagtttc catgcatcca ttttcatgac  62640
tgcatagtat tctgtggtag gagtatgctg ccgtgtattt atctatttgg attgtttcca  62700
gctttgggct attttgaccc aaagtgtccc tgctttctcc caagtgagtt tctctagggc  62760
acgtacccag gagtggaact gctgagttgt atactgtgtg catcctcagc cccactaggt  62820
attgccaaat tgctctgcaa agtggttgtg ccaattcatg ctccctgggg gctggcttct  62880
gctggctgag gctggcttga ccttgctggc aggaaggagc cttaaaaatc cctgtgtggt  62940
ttttttgtt ttacttttat tttaagttta ggggtacaag tgcagatcta ttacatgggt  63000
aaacttgtgt cttgggggtt tgttgtacag gttatttcat cacccacgta ttaagcctag  63060
tacccattag ttatttttct tgatcatctt cctcctcccg ccctccaccc tccaaaaggc  63120
cccagtgcgt gttgttcacc tctgtatgtc catgtgttat catcatttag cccccactta  63180
gaacacgcag tatttggttt tctgtttctg cattagtttg ctaaggataa tggcctccag  63240
ctccgtccgt gttcctgcaa aggacatgat cttgttcttt ttcttggctg catagtattc  63300
catggtgtat atgtaccaca ttttctttat ccagtctatc attgatgggc ttttgcagcc  63360
ctgttttttt tttttttca taataacacg gttatgggaa cacttaggga agctcatata  63420
ttattgagca gtgtgatggt taatattgag catcaacttg atcagcttga aggatgcaaa  63480
gtcttgttcc tgggtgtgtc tgtgagggtg ttgccaaagg agattaacat ttgagccggt  63540
gaactaggag aggcagactc acccccaatc tgtgtgggca ccatctaatc agctgccagt  63600
gtggccagaa taaaagcagg cagaagaagt tggaaagagt agacttgctg agtcttctgg  63660
ccttcatctt tgtcctgtgc tgaatgcttc ctgccctcta aaatcagatt ccaagttctt  63720
```

```
cagcttttgg actcatggac ttacaccaat ggttagccag gagctctcag gcctttggcc  63780
acagactgaa ggctgcactg tcagcttccc tacttttgag gtttgaggac tctgacggat  63840
ccaccactgg cttccttgct cttcatcctt cagatgggct atcgtgggac tttaccttgt  63900
gattgtgtga gtcaattctc cttataaact ccctttcata tatacatcta tcctgttagt  63960
tttgtccctc tgaagaacct tgactaatac agacacctag tgggtcccaa taagtgatca  64020
ttaaactgaa ggcagtcatt cagtaggtca gtttgtcact tgtgtttgta tctccctgct  64080
tacaacaagg tggcctttct tctagtttcc tgtcatctga tggaagagat tctagactca  64140
ttcctctaga ggagaaatac ttcatctaga acagataggt cctaagggtg agagctcatc  64200
gttgggatga atgaacccac tgaaatttta tgcaagaaga aaattgtgta tatgtatatt  64260
tttttttctg gtctgtagtt tttattagat tctcagggaa tcctgatcct atcatgaaga  64320
ccttctattc tagattgggt tcctttcaca tccccttctc ctttcttgtt gaattctcca  64380
tgcatttctt tcacttgctt ttcttgctct tatttctctg gtagtcagtt atcctttttg  64440
tctggtggtt ctatctcctt caaatgaggc acattgctca aattttatta ctccaaattc  64500
caaggtgctg tttagtgtcc tgttgggttg taagctagga acagggaggg gaaagtaaaa  64560
cattctgcat gagctgggtg cagcgggcaa gcacctggaa ttccagctac tggaagctga  64620
ggtgggagga ttccctgagc ccaagggttt aaggccagcc tgggcaacaa agtgagattt  64680
tgtcttaaaa aaaaaaaaaa tcccagctgg gctctgtggc tcatacctgt aatcccagca  64740
ctttgggagg cagaggcggg cagatcgctt gaagtcagga gttccagacc agcctggcca  64800
acgtggtgaa accccatctg tactaaaaat acaaaaaaaa aaaaaaaaaa gcctggcatg  64860
gtggtgtggt gtgcactggt aatcccagtt atttgggagg ctgaggcagc agaatcactt  64920
gaatccagga ggcagaggtt gcagtgagct gagattgtgc cactgcactc catcctggat  64980
gacagagtga gactctgtct caaaaaaaaa aaaaaaaaga aagaaaaaac acgcgcgcac  65040
acacacacac atcatgcaga cctagccttc tgccaatgtc aatggtagag aaacacagta  65100
gacacttaat tctatgtttc agagaggagg ggactcaaat atattaattt gacattgaga  65160
cagtgatgac tttaatgagt actttctttc cttttttttt ttttttttt cgggacagag  65220
tgcagtggtg ggattttggc tcactgtagc ctccacctcc tgggttccag cagttctcct  65280
gcctcagcct cctgagtagc tgggactaca ggcatgcact gctgtgcctg gctaattttt  65340
gtatttttag tagagacggg gtttcacact atcagccaga ctggtctcga actccggacc  65400
tcaggtgatc tgcccacctc ggcctcccaa agtgctggga ttacaggcat gagccaccgt  65460
gcccggccta atgagtactt tctgattaac ctgttgccct ctcagattcc tgaagcaaac  65520
cacagcgtta aaacgtgatt cattttgtgt ggaccaccac ggtgtttacc ttcttcttgg  65580
gtgaagtttg gtggaaaaga tcttaccccg gacatctgtt tgttctttgt aactcagagc  65640
ctcagagaaa tcctaacttt ataatgttgt caaacccttg taaggcatgt ttttattgta  65700
tttgtgttct gatcatgaaa ctgaaaatgt gtaagaggaa gatttcagaa gcttggctgt  65760
atgtctgaga tgacagttct tttactgtca ttctcaaata tatataaata ttgaagagat  65820
caaataacac aaatcgtgca tgttaagaaa agagactgtg aacctcacca gagaggggtg  65880
agcacaattt tttttctttt ttattcacag ggttagcact gtccctttca cataataaat  65940
gctcagtaaa ataaatggtt gttaagccgg aaaagggtaa cacttctgat aatgagtgtc  66000
ctgggaaatt tactaagctg tttagaagat gggaccaaca cactgataga aatagtcaga  66060
```

```
tagtccagaa gtctatggca gatgccctga acatcagatg agatataaga cagagaagct  66120
ctgggtcttt gccagctctg acattttatg actctatgaa acggaaggtt ccttttttaga  66180
agggtctata aactgtctca ggctttgggc cattttgttg aagatcagag gcaaggaaaa  66240
gacacaacta cacaggaacc atcagggaaa gatgttgttt tttggtcttg aagcatcatt  66300
gaattttttt ttttttttt gagacggagt ttttctcttg ttgcccaggc tagagtgcaa  66360
tggcatgatc tcggctcact gcaacctccg cctcccaggt tcaagtgatt ctcctgcctc  66420
agccttctga gtagctggga ttacaggcat gtaccaccaa gcccgggtaa tttttttgta  66480
tgtttagtag agacgaggtt tctccatgtt ggtcaggcta gtctccaagt cctgccctca  66540
ggtggtccgc ccacctctgt ctcccaaagt gctgagatta caagcgtgag ccaccgcacc  66600
gggccgcatc attggatttt aaggctccat ggattctggc aggtccagcc cttctgtttt  66660
actcacaaac aagtggtttg tccaaagtca cacagagatg gtggcaagag atctagaata  66720
agaaggtgtc ttcaagtcat ggagccagga accctggctt tttgggcaat ggaagtggta  66780
taaatgttta atatcacccc tcaggttctg ccactagagc ccagctctct cttccttcct  66840
cttgcccccct gactagccta tggcctcttt ccagagaata agaaagggat cctcagagaa  66900
taatcccagt tcctcgcttt ttattatata gttgaggaaa ccaagtctca gaggggtcag  66960
tgtcttgacc atacacctct catgtcctct ctcctttttg attaattgaa taaatacatg  67020
tagttgcttc ttacctcctt tctttcttca cccctgcccc atgcacctgc tcttagttgc  67080
cttcacatgt aaacagcatt ccaacaacaa caacaaaaca caaccagcat tctaactcat  67140
gagaccagca acagttccta taaataccag cagcatttta ttttaatgtc tctctgcagt  67200
agtttctccc ctccatggat cagtcatcct tggtaccaaa aggattcccc actgtgacac  67260
aaatgctttt tgtcattctc agtgagttat accattgaga gagcatcgat ctttttattg  67320
ttcaaagctt ttggttgtca tgatatttgc tggaccatgt ttcaccagga accacatcac  67380
ttcctagcag caggagctat tttcttccat cttctaacaa caccagcagt gacagtgata  67440
ataatgatgt tagctgccat ggtcgttatt cttatcattt attgagtact tactatgtgc  67500
cagggactac attaagagtt ttatgtgtat tatcacattg agcctcgcta gcctttgtac  67560
agatgaatct gaggctcaga gaggttaagc tgctcacaag ggagtcacac agctggtaag  67620
gggtggatca ggatctcagc ctctctgcta ggacacttct ctaaacctag aataatactg  67680
ggcctgtgtt aagttcagca aagagctgta ttcaacccag tgtccttagg aatgtaatgc  67740
ctgttattaa caacagtggc aacattgata agctgaaact tatgaggtgc ttacaatatg  67800
atatactata tattatatac atacataggc acccacctat aatctcagca ctttaggagg  67860
ccaagtcagg aggatcactt gagcccagga gttcgagacc agcctgagca gcatagcaag  67920
atcctgtctc tgtaaaaagt ttattttttc agttggccag gtatgttggt acatgcctat  67980
agtcccagct aatgaggagg ctgaggcagg aggattgctt gagcccagga atttgaggct  68040
gcagtgaact atgatcacac cactgcactc cagcctgggt gacagagcaa gactgtctct  68100
aaaaataaaa ataaaaataa aattatttca actctcaagg ttaaataaat actattatta  68160
ttcccattta cagatggagc aactgaggct caaagacatt aaatgcttac tgtcttagtc  68220
tgttttctgt tgcttatagc agaacacctg aaactgagta atttataaag aaaaagcaat  68280
ttatttctta cagttatgga gactggaaag tttaagatca aggctgcatg agctataatg  68340
cacacacact attgcactcc aggctgggtg acagggtgag accccgtgtc aataaataat  68400
aatataaaat aaataaaaca aatttcaaca tgagttttgg aaggtttgaa atattcaagc  68460
```

```
cagagcatct gtctcataag tggtggaccc aggatttgaa ctaaggcaga tctggatcta  68520
gaacccattt tcttgaatcc tacgctattt ctctaaggtc aagtttgcca aggaaaataa  68580
acttgagaat ttgaatagag ctctctgaca tgggaagtca gggtgatcct tccttcccct  68640
ccctgatctt gggttccact atggctgggg gaaaacagga gcagaagaga tttcaagaaa  68700
tgagagattg gcctagcgcc atggttaaga cctggacttc agagtcagag gaagctcctc  68760
cctctatgac agtgagaatg tgggttgaac tcactgaacc tcagttttct cacctggaaa  68820
aagggagtaa aactagtgcc tagctcctag ggtttgcatc acacacgaaa gttggtgaac  68880
tgaaggaaaa aaacttaaat tcttgtgggg gagcatgtga tagatgctac aaattctcca  68940
tgccttattt acctagctta cgtctaagtt cacctgcagc ttcctcttgg tacactccca  69000
tctctctaca tctctgttgg agggcagtct ctggcatcac agagtttgct gagccagatg  69060
cttaacaacc tcggtagcat ccctcaacca gtgagctagg gagtcagtgt ataaataccc  69120
tggcttcccc attgctcagt gggaaaacac tgaaatatgt tatacagcat catagaggtg  69180
cctcagtaaa attgaatcct agttgttcac ataaaaccca ttcactagtg tacccttac  69240
caatctctct cttcctcatt cctcacttgt aattccttgc attacctccc aaattaacca  69300
ttggacccta gtttttgcct tggggtctac tcggcgctaa ctcaaggagc ggaagttgga  69360
agcttagcgg gttacaggtt tcagcaccct ggacagctcc cagcacaccg tattgtgcta  69420
aaatgttctc ttccctccct ctgcctccag ctggggtgga gagggactga gtaaaggcca  69480
gatggccagg tgaccttgtt ccatactgag cttcttggcc attttccctg tggggctgga  69540
gaagaccttg ccatccatct ctccgcaggt ttgggggccg actgaggtct tgttttctcg  69600
aattgctatg acaaatgcca gcctgcctcc aaggggcatc tgtcccactg cctctacagt  69660
ttgcatgcct aatgactcct ctcctctcac cagggcaggg aggtggctgc ctggtgggcc  69720
gcttgaagcc gggagaccaa gatcatgcca ctggactcgc aacaaaccga gactcttttt  69780
ttttttttt tttcctcgag acagggtctt gctctgttgc ccaggctgga gtgcagtggc  69840
gcgatcttgg ctcactgcag cctccgcctc ccaggttcaa gcactcccac ctcagcctcc  69900
caagtagctg ggattacagg cgcacaccac catgcctggc taatttttgc atttttagta  69960
gagaggggt ttcaccatgt tggccaggct gatctcgaac ttctcccctc aggtgatcca  70020
ctcgccttgg cctctcaaag tgctgggatt gcagctgtga gccaccatgc ctggccaaca  70080
gaataggact ctgtctcaaa aaataatttt ttttaaacat tgctttgcaa cccagctgct  70140
tcttgtgcag gcatctctaa atgaggacag ccagtctaca tagacacgta aggaagcata  70200
gtggttaaga cctggtcttt ggggttagag tggattccca acctgactcc actgtttcca  70260
agctgtgtga ccttgggcaa gttactgtac ctccctgaat cttccatttc ttcatctgga  70320
aaatgagagt agtagcatcc cctgacttgg tggggcatgg tggctgatgc ttgtaatcca  70380
aacactttgg gaagccaagg tgggtgaatc gcttaaactt gggagttcaa ggccattctg  70440
ggcaacatgg tgaaactcca tctctacaaa aacaaaacaa agcaaaaatt atctgggtgt  70500
gatagtgtgt gcctgtaatt ccagctactc aggaggctga ggtgggagaa tcacttgagc  70560
ccaggaggtc aagtctgcag tgagccgtgc ttgcaccact gcagtccaac agagcgagac  70620
cttgtctcaa acaaacaaaa caaaacacaa aacaacaaca aaatactacc accttatgga  70680
gttgttttca aggttcaatg agttaatgtc tgacccatgc tgggctgggt ttatggatgt  70740
tacttgccca gggacagtct gaagaaagag aaagtgatat agtccattgg gcctcagctt  70800
```

```
cctcatctgt ggaatgggaa taataattgc acctacctca aaaggtaaaa gtcagtgaga  70860
tacatataag gcattcagaa caaaaactgg cacagaataa gtgctcaatt atattagcta  70920
ttgtaagact aataactatc attataatga tgataataat tattactact tccccaggcc  70980
cagttccata gaccagttag ttaactgtag ggaacgtttg ctattattag ttgggttccc  71040
aatatctgac ctccctttcc aatttaggga gaatcctccc ctttctataa agtactgctg  71100
gtctatggga tcccaccctc actaataagt tgaaggtgaa agggattcat tgtcacccca  71160
tcacctggta gtcagggcat gtgatttaaa caaccagggc caggcgcagt ggctcacgcc  71220
tgtaatccca gcactttggg acgccaaggc aggaggatag cttgagccaa gcccaggagt  71280
ttgagaccag actgggcaac atagtgagac ccctatctct taaaaatttt ttaattagct  71340
gggggtggta gcacaggctt gtagtccccg ctactcagga ggctgaggca ggaggattgc  71400
ttgagcccag gaggtcaagg ctgcagtgag ccgtgatagt gccactacac tccagcccag  71460
cctgggcaac agggcaagat cctgtctcaa aaaacaaact aataaaaaac tcaaccagtc  71520
acgttttcct acccaggaat ttgaaaatgg accaagtgat ccaaacatga tggtttggac  71580
tctttcatgg cctcctgcta caggagaagg tcaggctggc tacattgttc ctgctgattt  71640
cccaaatccc ctcttctggc cccctgttga ttatctgagt ttcctaaaaa tcccttttat  71700
gcctaagata gccggtcagt gtttggtttt gcaatcaaga acccagactg ggccaggcac  71760
ggtggcccac gcctgtaatc ccagcacttt gggaggccga ggcgggcaga tcatgagatc  71820
aggagatcga gaccatcctg gctaacgtgg tgaaaccccg tctctactaa aaatacaaaa  71880
caaaaaaaaa aaaattagcc aggcatgatg gcggtcacct gtagtcccag ctactgggga  71940
ggctgaggca ggagaatggc gtgaacccgg gaggcggagc ttgcagtgag ctgagatggc  72000
accactgcac tccagcctgg gcgacagaac gagactccgt caaaaaaaaa aaaagaaaaa  72060
agaagaaccc agaacccaga ctgatcctga gacaaagatt tgagggcaac gaatcacgag  72120
gtcaggaaat cgagaccatc ctggctaaca tggtgaaacc ccgtctttat taaaaataca  72180
acaaattagc tgagcgtggt ggtgggcgcc tgtagtccca gctactcggg aggctgagga  72240
aggagaatgg cgtgaacctg ggaggcggag cttgcaataa gccaagatcg caccactgca  72300
ctccagcctg ggtgacagag caagactcca tctcaaaaaa aaaaaaaaaa aatttgagga  72360
caagtggttt gtttggcaat accaggaaac aggggaacag gatagtcaga aaagaaagag  72420
aaagctgggc atggtggctc actcctgtaa tctcagcact ttgggaggcc aaggcaggtg  72480
gatcacctga ggtcaggagt ttgagaccag cctggccaac atggtgaaat cccgtctctg  72540
ctaaaaatat aaaaattagt cgggtgtggt ggcgtgcacc tataatcaaa ataaaataaa  72600
atcaggatat tttattttaa aactctgtct tagtgtaact catatttacc tcttctgtat  72660
gctcctttgc atcagttata tattgccata atacggctgt gtaacaaaca atccccaaga  72720
cccagtggct tataatgaca agcatttatt tagctcatga ttctgaaggg tggcagttta  72780
ggctgggccc agttgggtgc tttatctggt ctcagttgag ctcattcatg catctttggt  72840
cagctgcggg tcagctgggt ggctcttctg tttggctgtt agctggctgc agactggtcc  72900
aggatgacct cggctggaat gactgtgctc cactccctat ggtctttcac cctccagcag  72960
gctagcctga gctagttcac atggcagctt ttcatcctcc agcaggctag cctgagctag  73020
ttcacgtggc agcaatggga ttctaagaga aagaggaagt gttcagcctt cttaagggct  73080
agtcccagga atggcacaac atcgtgttgg ccactgttgt ccaaagcaag caatgaagct  73140
ggtccagatt caaggaatgg ggcaacagag cccatctggt atttacctgg ggccactggg  73200
```

```
gccccattcc tgttccctgg ggccttttgc cctgacttct gtgggccctc agagcatatt  73260
ttcagattcc tttccatccc tgaccctcag caatcaatgt agatgacgtg tcattactgt  73320
gtcacttgca cagagaaaag gaggaaaaaa tgtcagcaaa aactctgctg agagcagagg  73380
gcccatcata cagcaagctg gaaagaaaag tgggaatgat tacacagcct cctcagatgc  73440
ttccagcttt tatcaaatct cactgtgata tctgagttct gaaccctcac aggtggttgg  73500
cgtgcaaggg aagagatttc ttgtctgcca tgctgacatg cacagacacg caacctggct  73560
ccctctgtcc actggggctt tggattttgt ttgttgaaat gttacccact cctgatcaga  73620
gctggatgga aacctggctc tgattccatt ggctcagggg ctcaggtggg ggcagaggcc  73680
aggctggttg ggtgtctatg tggagacctt aactcttctc cctcccgccc caactctttt  73740
tgtttctttt tttttttttt tttttttttg agatggggtt tcactcttgt tgcccaggct  73800
ggagtgcagt ggcgtgatct tggctcactg caacttctgc ctcctgggtt caagcaattc  73860
tcccacctca gcctcctgag tagctgggat tacaggagca cgccaccata cctggctaat  73920
ttttgtattt ttagtagaga cagggtttcg ccatgttggc caggctggtc ttgaactcct  73980
gacctcaggt gatccaccct cctcagcctc ccaaaatgct gggattagag gcgtgagcca  74040
ccacacctgg ccctttcttc ttcttagctg cctccacctc tcttcccttc tgcagtgtta  74100
ggtttatgga aaccgaggcc ggcgtagaga tcaacttcag agagcatgaa ctgagcatct  74160
gctgggtctt agatccttta catagcttat catcttcaaa ccttctcaca gttctgtgtg  74220
gctagagcca ggatttggac acagctctgc cccactgtag aaccaggctt ccttctgtcc  74280
actgtcaaat tttagaggga gaaaataggg aaagggacac cagccttctc cacgagcagc  74340
ttctgcccac tcaccccagg gactttgcac atgctgtgtg cctgtgtctg agatatgctc  74400
cctcctctgt atctgcttaa ttcttaccca gacatgatac ataaagtatt taacatccag  74460
gtggcaggga caccagctaa cctgaaaaga ggttcccctg ttgtgccaca tgtgtactca  74520
ttgtttgctg cattgtgggg gcagtccagg ggccttgaag aggggccaag gtgccaaagg  74580
ggcactctca ggcctcaagg aagtacatgt ttactgatat gatactgtct cttcctccag  74640
gaaggaagcc ttccctgatc tccccactgc atgcccacta tgataccagt ttaggtcccc  74700
tctttatggc catctgtggc atcagtgtga atcctcttaa tgttgtctat ttggttaatc  74760
atctgtctcc ttcctctggg gggtaaagac agaaccacag agcctcgtgt agaacttgag  74820
aatggggttc agtaaaaatc tgttgaatgc ataaatgggt gattgagtga atgaatgaat  74880
gagtgaatga atgagtgagt ggatgaatga atgagtgaat gaatgagtga gtgaatgaat  74940
gaatgagtga attaatgaat gaattcatag ctgataatac aggcttcatg gcttttgtta  75000
ggcttgccca gacattgcta ggggatggac agaaggaaga agagctatac ttaattccag  75060
tcctgttgtt ctgtagcagg aggagaaaaa cagggactgc ccagcctgct ctgggtggat  75120
tcaggagcag ctgaggttcc tctcttattt gcaaacaggg aattcaaaaa gccccaacct  75180
cagaatcaca ctcgcctcag cagctgtacc agccaagggg acaatgtggg aagccttggg  75240
caccaggaat gctgagtgct tcgaaaaagc gaaggctcag ggaacaatcc ctgatttttc  75300
attcccttgt cctttctgaa gaaacaggca aaggcaggcc aggcacggtg gctcacacct  75360
gtaatcccaa cactttagga ggccgaggct ggtgaatcac ttgaggtcag gagttcaaga  75420
ccagcgtagc caacatcatg aaatcccatc tctactaaaa atacaaaaat tagctgggtt  75480
tggtggtgca tccctgtaat ctcagctact cgggaggctg aggcatgaga atcacctgaa  75540
```

```
ctggggaggt ggaggttgca gtgagctgag tctgcgccac tgcactccag cctggatgac  75600
agagtgagac tccatcttaa aacaaaacaa aacaaaaaca agtaaagcct tgtgtgtttt  75660
taaattgtag gttcagcagc aaagctctgt aataaggagc tggaccctgc agtcagacag  75720
tcatgggctt ctccagtgcc cagccgagtg acccgaggga gttatgataa acaccaacat  75780
tcatccacaa tttgtaccta gtgctattct caatatcttg agtaaattat ctcatttaat  75840
cctccaggca catctttctt ggtaggtgcc gtcattgtcc ccagtgtaca tctgggaaaa  75900
tgaggacagg ctggcagagc acccttcctg ctcacctctg ctgctctgct gacctctggc  75960
aagactgttg tctctctgag cctcagtttc cccatctgaa aattggggcc tgtattagcc  76020
cgttctcaca ttgctataac gagatgcttg gctggggctg ggcgtgatgg cttatgcttg  76080
taatcccagc actttgggag gctgagttgg gcagattggg agtgtgagac cagcttgggc  76140
aatatagcaa gaccccatct cttctaaaaa aaaaaaaaaa ttagccaggc atggtgatat  76200
gcacctgtaa ttccagctac ccaggaggct gaggcaggag aattgcttga acccaggagg  76260
cagaggttgc agtgagccaa gattgcgcca ctgcactcca gcctgggaga cagagtgaga  76320
ctccatctca aaaaacaaat tatttttaaa aaattaaaaa aaaaaatgcc tggctgggca  76380
cagtggctca cacccataat cccagtactt tgggaggcca aggtgggaag attgcttgag  76440
cccaggagtt ccagaccagc ctgggcaaca cagtgaaatc ctgtctctac taaaagtaca  76500
aaaattagcc aggtgtggtg gcacgcgcct gtggtcccag ctactcagga gggtgaggtg  76560
ggaggattgc ttaagcctgg gaggtcaagg ctgcagtgag caatgattat gccactgcac  76620
tccagcctgg gcgacagagt gagaccttgt aaaaaataata ataataataa taaataaata  76680
aaaaccctga gactggggta atttataaag aaaagaggtt taattgactc acgattctgc  76740
aggctctaca gaaagcatgg cagcatctgc tcagcttctg ggaaggcctc aggaaactta  76800
caatcatggc agaaggtaaa gctggagcag gtgtcctcac atggccagaa caggaggaag  76860
agagagagtg gggagatgct acacaccttt aaatgtccaa tctcacaaga actcactcac  76920
gatctcgaga atagcaccaa ggcggaaatc tgccccccatg atccaattac cttccaccag  76980
gccccacctc caacattggg gattacaatt cgccataaga tttggttgcg gacagacaca  77040
gatccaaagt acattaaaag taatggcaaa aaccacaatt acttttgcac caacctaata  77100
tctcaggggc tcattgtacc tatttcacag gacaaatgaa ggtatcagta ataacagtag  77160
cctgtagtcc cagctattca ggaggccgag acaggaggat cacttgaacc caggaggtcg  77220
aggctgcagt gagctatgat cacgccactg cactgcaccc tgggtgacag ggcgaaaact  77280
tatctctaaa aataataata acaacaacaa tagtgaacac agatataaca tgtgtgtggc  77340
caggctgtgc ccttagggct ttgcagggat tatttcattc actctcaatc tccccatttt  77400
acagatgaga aaactgacgt tcagaaaagc tagaggactt gccccaagcc acacggctag  77460
gaagtggtgg aattggggtt taaatgagga agcttgactt cagtgtcgaa gctcttaact  77520
gccacactca atacatggag tagaggttgc tgattctgtg attatctgat tctggaaagt  77580
aaagaccctg tttccagacg tttgctgctt gacttagttc ccaggggatg gccactggat  77640
gatgcagtgt tgcccaggag aggttagcta gacacactgc aaccattcca ttgctaatac  77700
ttatacttgc tcttgttctg ctgggtgcta tgcagggaag ggctgtctga gccctttgca  77760
agaattctcc cattggtgcc tcccagagat tctgaggttg gggctttttg catcccttat  77820
tagcagatga gacaccaaag cccaggtcaa taatctgacc tgcatccccc gcctaccagc  77880
cagaccaagg tcacttcccc acaatgcagg ccctgatcca aggctctggg tgcaaaccag  77940
```

```
tttccatgtc cctgggggtc catcttcttc agctgacttt tttttttttt tttttttttt  78000
gagacagcgt cttgctttgt tgccgaggct ggagtgcagt ggtgtgatca tggcttattg  78060
cagccttgac ctcccaggct caagcaatcc tcccacgtca gcctcctgag tagctaggac  78120
tatgggcaca cgccatgatg cctgggtaat tttttttttt ttttttttga gacagagtct  78180
cgcactgtag cccaggctgg agtgcagtgg cgcaatctcg gctcactgca agccccatct  78240
cccaggttca tgccattctc ctgcctcagc ctctcgagta gctgggatta caggtgcctg  78300
ctacctcgcc tggctaattt tttgtatttt tagtagagac ggggtttcac cgtgttagcc  78360
aggatggtct ccatctcctg acttcgtgat ccgcccacct cagcctccca aagcgctggg  78420
attacaggca tgagccagat gcctggctaa tttttaagtt tttttataaa ggcggggtct  78480
tgctatgttg cccaagctgg tctcaaactc ctggcctcaa aaagtcttcc tgcctcagcc  78540
tcccaaagtg ctaggattac agacatgagc cactgcaccc agcctgactt tttttctaac  78600
tgaaaaatta attatatata ttcatggagt acaatgggat gttctgatat atgtttacat  78660
ttttgaatga ttaaatcaag ccaattaaca tatccactac atcgcatact tatttttttgt  78720
ggtgagaacg cttaaaatct actcttttag caattttgaa atatacaata ccttatgttg  78780
tatattacat tatgttgtat agtacgttga aacatacact acaatacgtt atcattaatt  78840
gtggtcacca tgctgtgcaa aagatctcta aaacgtattc ctcctgtctg actgaaactt  78900
tgtatccttt gcctaatatc tccccaatcc ctccaccacc agcccctggt aaccaccatt  78960
ctctctgctt ccatgggttc aaattttttta tttttgaaa tttttaattt ttatttattt  79020
atttatttat ttatttattt atttttgaga tggagtctcg ctctgtcacc cagtctggag  79080
tgcaatggtg ccatcttggc tcactgcaac ctccgcctcc tgggttcaag cgattctcca  79140
gcctcagcct cccgagtagc tggggttaca ggtgcttgcc accaggcccg gctaattttt  79200
gtatttttag tagagacggg gtttcaccat gttggctagg ctggtctgga actcctgacc  79260
tccagtgatc cacccacctc ggcctcccaa agtgctgaga ttacaagcgt tgagccactg  79320
cacctggcct aaaatttttt tttttttttt tttttttgag acggagtctc actctcttgc  79380
taggctggag tgcagtggca tgatctcagc ccactgcaac ctcagcctcc cgggttcaag  79440
cgattctcct gcctcagcct cctgagtagc tgggactaga ggtgtgcacc accacgccca  79500
gctaattttt gtatttttag tagggacagg gtttcaccat gttggccagg atggtgtcaa  79560
tctcttgatc tcgtgatctg cctgcctcgg gcttccaaag tgatgggatt atgggccacc  79620
acgcccggcc tcaaattttt tagagctcac atataagcga gattgtgtac tatttgcgtt  79680
tctgtgtctg gcttgtttca tcttagtata atgtcctcca ggttcatgca cgttgtcgca  79740
aaagatggaa tttgctcctt tttaaagact gaatagtact tcattgtgta catatacacg  79800
ccatattttc ttcatccatt cctttactga tggacatttg ggttgtacct gcatcttggc  79860
tattgtgaag agtgctgtca tgaacatggg tgtgcagctg actctgaggt gttagaggga  79920
ttacagctcc tccaaaagac caccgtcacc caaacctgct cctcctgccc tattttctgt  79980
ttaggtaaag gcggctttaa ccccctgcag tgctctggcc tcagacctcc agatcttcct  80040
ctatgcctct atgcctcttt ttctccaccc cctgcatcca atctgttagc acatcttatt  80100
ggctctacct tcagaatcta cccagaatcc accacccacc tctcaccacc ttcacagccc  80160
caccccggtc cagccccccat ctttgctggc ctggactaaa ccagttgccc ctccacccca  80220
atctggtctc ttaacttcag tccttgcccc acccccagga ctgttcccca cacagcagcc  80280
```

agagggcacc tgtgagccac tgagtcagga cctggctcct ctttgctcac aacctcactt 80340
ggagaaaaag cccaaattct cctcacaggg acccacaaac tctgcccctg tgatccccca 80400
tccccctcta ttcccactct cctctccact cactcggctt cagctacaca agttccctgc 80460
tgtcccttac acaccaagca ctccccagcc tcagggcctt tgcacaggct gttccctctg 80520
cctggaacac tcttccccca gatatctgct tggctccccc ctcacttcct ttgggtcttt 80580
gctcaagtgt ccttctaaca tgtaactgcc tcacctgcac tgtgccaccc cactccccgc 80640
ctctaggctt aatttccctc tacacccctg aagagcatct gccaagctat atttacttgt 80700
ttattggtta ttgccaatcc cctgccccca ctagaatgcc agctccatga gggcagggac 80760
ttctgtctgt tttgttcact gctattcccc cagagcctag aacacagcct ggcacatagt 80820
aagtattcac taaataattt gtaatatgaa ttgtgccagt aaaatcttcc aggggcatca 80880
agcccctgcc atgactaggt ggtaacatcc tcacccccctg tccatgtgct atctcctcct 80940
gacctgcttg tctcattgtt ctaatggtgg ctcacgcctg taatcccagc acttggggag 81000
gccgaggcgg gcagatacct gagttcagga gtttgagacc agcctggcca acatgatgaa 81060
accctgtctc tactaaaaat acaaaaatta gctgggcgtg gcattgcacg cctgtagtcc 81120
tagctactcg agaggctgag gcaggagaat cgcttgaacc cgggaggtgg aggttgcagt 81180
gagctgagat catgccattg caatccagcc tgggccacaa gagcgaaact ctgtctcaaa 81240
aaatatatat atatatttca ttgtggtaac atatgcataa cataaaatgt accatttttt 81300
aagtgtttag ttgagcggcg ttaagtacat tcatattgtt gtgcaaccag gaccgccatc 81360
catctccaga acttttgcat cttgcaaaac tgaagctctg cccccaggaa actctcactc 81420
cccgctcccc cttcccctct ccccgactcc cccttccccc ctccccactc cccccaccct 81480
actccacact ccccactccc ccagcccctg gcacccgccg ttctagtttc tatctctgtg 81540
aatttggcta ctttgggtcc cccctgtgag tagaatcata cagtatttgt ctttttgtga 81600
ctggtttgtt tcgtggagca taatgtcctc cagtctcatc catattgtag catgagtcag 81660
aatttccttc ttttccaggc cgaatcgtat tccattgtgt ggatggacca cactttgctt 81720
atctgttcat ccagatgggc acttggcttc cacctttttgg ctattgtaaa taatgctgct 81780
gtaaacctgt gtgtacaaat agctgagtcc ctgctttcaa ttcttttgga tatagaccca 81840
gaagtggaat ttttttaaa tcaagatttg acccactggg gcccttagag gtctcattgg 81900
ctctgaagct ttttttttt ttttttttg gacgctttga aactaaaaat aggagtgagg 81960
ggcacagtga ggggggcaca catctctcgt gtcagcgttt tttaaaaaca ccccgggagg 82020
aagatgtgtg aaatccctcc cttccccccg ctcccacccc ctccaagatc tcaaaatacc 82080
tcttgtttta ggaagcggct gtgacatcag gcaggcagcg tgtggcatct gagacacaat 82140
atcgcaagtg gctgggagcc cagagaaacc aggacaggcg tgctggggat gtggactaga 82200
gatggagcta attttagtgg ctgaagaggc tgcaagaaga gagagaaaga ggggtgtgtg 82260
tgtgtgtgtg tgtgtgtgtg tgtgtgtgtg tgtacgcaca gtgatagagg ctggaggggg 82320
agaaatgaca gataaatcag cttgggcaaa gaaagctaat gggcagagga gcgagaccca 82380
gctcagaagg tggtcagcaa atctaaagat gtgtgcccga gggtcaaggt ggtgggggga 82440
ttcataggca agtggtagag aggctattcc atttgcagag gctctctctg tttgaggcgt 82500
gattcacctg tgccgtcctc aaggccattc tgagaacacc actgttgttt tcctcctttt 82560
atgagtaggg aaactgaggc attgaactgc ttctattctt cagtaagaag caggggggaac 82620
atatggtaga agcaaagaaa tacaaacatg agggctctcg ggtctacgt gattggctgt 82680

```
gacatccatg agagcggatc gcaggttgaa ggaaacactg gtggcagaaa gtagctgaac  82740
atttggattt gggaatccca gtggacgtgg cgaaaattct ggcttttccc ttcacaggct  82800
gcggggccac tctgacctgc ggtttcctta tctgtgaaat ggaacgatgc cacctgtctc  82860
agcgttgttt tgaggatgcg aggagatgat ccgtgtaata tgcccactag gggcctgct  82920
ccagggtaga ttctcagcaa atggtagtca tggtttttgt tacatttggg gatattggca  82980
ggtaaaaagg aaatacttca ttcattccaa aattgctcac tgaggttcta ctatgtgcta  83040
ggccctgatg acacatcggt caacaagaca ggcctgcttt ctgcccttgt aaaacttcag  83100
ttcaactgca ttgcactcat cagcctaata atccaggtaa attgtgatga gaataacaac  83160
tagcatttac tatgagccct ttacaaatat taacccattt aatcttctaa agagcctata  83220
agataagagc tcttgccctg cgcagtggct cacgcctata atcccagcac gtcgtgaggc  83280
caaggcaggt ggatcacctg aggtcaggag ttcaagaata gcctgaccaa cagggtgaaa  83340
ccctgtctct gctaataata caaaaattag ccaggcatgg tggcaggtgc ctgtaatccc  83400
agctacttgg ctgaggtagg agaatcgctt gaacccagga ggcggaggtt gcagtgagtc  83460
gagatcactc cactgcactc caagagtgaa actctgtcac acacacaaaa aaaaacaacc  83520
tgttattatc cacattttac ctatgaggaa accgatgccc agagaggtta agtaactgtc  83580
caaaggtcac acagctacgg agtggtagag ctgggattca gacccaggag tgtgatccca  83640
gagtgtgtgt gtatgtttgt ttgtttgttt gtttgtttgt ttgtttttac cactgtgttt  83700
tcctgcttct gcaatagaag taatcaccag taacactgag cagttgttat gtgccatgcc  83760
cttaacacac atctccttgg atctttggaa agaatcctaa aagggttgtt tttcatgatc  83820
cacattttat ggagagagag agatcaaagc atagagagag gaagtaactt gcccaagatc  83880
ctgcagctga agactctagg gttgcaaatt tgggacggcc ctggaccctg cattccagct  83940
tctagcagct catagggga actctttatt tatttattta tttatttatt tatttattta  84000
tttattttga gatggagttt cgctcttctt gcccagcctg gaatgcaatg gcatgatctc  84060
ggctcactgc aacctccgcc tcctgggttc aagtgattct cctgcctcag cctcctgagt  84120
agctgagatt acaggcatat gccaccacgc ctggctaatt taattttttt tagtagagac  84180
ggggtttctc catgttggtc aggctggtct cgaactcctg acctcaggtg atccgcccat  84240
ctcggccccc caaagtgcta ggaatacagg cctgagccac cacgcatgcc ctgggggga  84300
ccacttttat cggtgcattt cttccatttt ccctgtgtct gtgtaaagat aaacaccccc  84360
aagcccttg actatgaact gtgggccata attagttaat ggaaggtaaa tgttttagag  84420
acggaaattg ctgtgccatt tttccccgct aggcattgtt gcctgcatgc taatgcaaca  84480
caatgtgcct ttcttctgtc aggcattttt agacaaattc tattttccct aaaatatttt  84540
gccaaagaaa atagcaaatg gggaagacat tcagaggctc aggcagagag aggacaccat  84600
tcccttgggt ttaaacagaa tggcagagtg gataacagca cagatcttga gttaggtgga  84660
tgccaatttg tgatttattt cccagcaaac caagatgctg gctctctgtg tgcctcagtt  84720
tacttatttg tcaaatgagg agaataatgg tacctgtctc tcaccagctt accagttgcc  84780
tctttagcta tgtctaatct gctattaacc acgcccacta tgtctttaat tccaagtatt  84840
agaattgttt tcttcctaca agctgtctga tctttttttaa tcctgcttca tcttttgcag  84900
tattgttttc ctacagcagg atttctcaac cttggcacaa ttgacatttt gggctaggta  84960
attcttggcc gtgagctacc accctgtgct aagatactta gagcatccct ggcctctcac  85020
```

cctactaaat gccagtagca gcccctcccc agttgtggca gccaaaaatg gctcagacat 85080
tgccaaacga aatgtcccat ggagggtaga aacgccccca cttgagaatt gttctatagg 85140
tattttcaag catgtcttac atttctttaa gtataatatg caaaagaaaa ggctaaatct 85200
aaaaaaagcc cataatatgc gaagaatttt tataatcagt gtccaataac ttaagtatct 85260
aaaattgtta tggctttttt tctgctgtct cttgtttcct gtgattcctc attctggtgc 85320
cttgttttct tgaatgtctt gttatctttg gttgtgtgaa gctcattttc catgggacac 85380
tatttttgt tttgttttgt tttgagacag agtctcgctt ggttgcccag gctggagtgc 85440
agtggtgcaa tatcagttca ctacaacctc agcctcccag gcccaaatga ttctcctgcc 85500
tcagcctcct gagtagctgg gattacaggc gtgtgccacc acacccagct aattttttg 85560
tatttttagt agaggcaggg tttcaccacg ttggccaggc tggttttgaa ctcctgacct 85620
caagtgatca acccgcctcg gcccccaaa gtgctgggat tacaggtgtg agccaccgtg 85680
cccggcatcc atgggacact gttgaaggga gttcattgag gcctgcgatg aaggcgaacc 85740
ctccatggac aatttgcatt tactttttcc aggtgtctgg gaaactccca gtctaggacc 85800
atcttagact tttagaccaa caatgtgttg agaatttagg tcaccagtgt ctgcaaaagc 85860
cagcttgtgg ttataatttc tcaaaaactt ttgtttttct ccttttctgc aaagtgccaa 85920
agtaacttcc tcaaaaatct ctgggaatgg aaagacggga gtaaattaac ttcaggtttc 85980
ttacctgaaa gtgatagcct attggggccc catcctactt ggggagtggt gtgtctcctt 86040
tgagactttc taacacgtgt gtaccctgga ctttgcccca cccctgctcc ctaggaggcc 86100
ataaaacttg aagcagcagt tccatgggtt agacagatgc ccttggggca aaagtggttt 86160
taatgctctg gtagatgctc aggttacctc tgggaaattc ttgacttcac ttatttattt 86220
ggggctgata actactaatt gtcaggcctt tcttgtttca acaacatgga cttcagattt 86280
tatgcaggat ttgtcatcgt tttcagcaag agagtcagtc ttattaccca gcttactgca 86340
ttagaaatag atgtctgggc caggcgcagt ggctcacacc tgtaatccca gctgtttggg 86400
aggctaaggt gggcggatca tgaggtcagg agttcgagac cagcctggcc aacatggtaa 86460
aaccccatct atactaaaga tagaaaaaat tagctgggtg tggtggtgcg tgcctgtaat 86520
cccagctact tgggaggctg aggcaggaga attgcttgaa cccgggaggc agaggttgca 86580
gtgagccaag atcgcaccac tgcactccag cctgggtgac aggacgagac tctgtctcaa 86640
aaaaagaaat agatgtctgt tgtgtggatt atttaaaaga gtagatggcc aagaactatg 86700
acttatgcct gtcatctcag cactttgaga ggctaaggtg gagggatcac ttgaggccat 86760
gagttagaga ccagcctggg aaacatagca agacccccat ctctgcaaaa gtaaaataaa 86820
ataagttagt gtgcatgatg gtgcaggcat acctctagtc ctagctactc aggaggctga 86880
ggcaggagga tcacttgagc ctaggagttt gaggctacag tgatctatga tcatgccact 86940
gcactccagc ctgggtgaca gatcaagacc ctgcctctaa aacataaaaa taaatacaaa 87000
ttaagttaaa aaataaaata aataagtaat agaacatcca gcacagttct tggcatgcat 87060
tgactgttgt tgtttgtttg tttgtttgtt tgtgacggag tctcactctt gttgcccagg 87120
ctggagtgca atggcatgat cttggctcat cataacttcc acctcccagg ttcaggtgat 87180
tctcctactt cagcctcctg agtagctggg attacaggca cgtgccacca ctcctagctg 87240
ttttgttttg tttgtttgtt tgttttgtat ttttagtaga gatggggttt ctccaagttg 87300
gtcaggctgg tctcaaactc ctgacctcag gcgatctgcc agcctcggcc tcccaaagtg 87360
ctgagattac agacgtaagc caccacgcct ggccagctgt tttgattgtt aaatgaaggt 87420

```
ggtatgaaag ggaaggaaga acagtgacat ttgcaaggga cactccctgg agggcagggc  87480
aagggggctg tggaggggag aagtcagaga gtatgataca ggttgccttg ggtgatgttt  87540
tagattttag ccaacattgg caaagagcct catttatctc tcagagtagc tctggctact  87600
ggaaatgctg cacaacttca ggcggacttt ctagaagaaa actcttggcc aggtgcagtg  87660
actcacacct gtaatcccaa cactttggga ggctgaggca ggtggatcac ttgagctcaa  87720
gagtttgaga ccagactggg caacgtggca aaacctcatc tctacaaaaa aaaatacaaa  87780
aattaaccag gcgtggtggt gcatgcctgt atcccagcta cttgggaggc tgaggtggga  87840
ggattgcttg agcctgggga ggtggaggtg gtagtgagcc aagattgcac cactgcactc  87900
ccatttgagt gacagagcaa gaccttgtct caaaaaagaa aaaaagaaaa gaaaagaaaa  87960
gaaaattctc tctgggattc aatcctggcc cacacagcat tggcttcact tcacctcctt  88020
ctcccctgag atacacagca ccattccccc aagcttcatc aacttaatct ctgatctggg  88080
tgctgtgact tgtccccatt cctggccaga atttaaggta gggatgaacc cactagccct  88140
ccatcacgca ctctgccata aaagcacacc acgtgctgat tgctgtcttt ggtctccttt  88200
ctgccttgcc ctctagactc tgagctgctt ggagacagag gccagttttg tccatctcca  88260
aatcccctaa agtcctgtgg ccagcaagca ggtaggacat ctgaaagttc gtcagagagg  88320
gaattgcttt tctcttgaga tgcaactaga acaagaatct tattgacctg gagtagcttc  88380
aaggttgtaa gagtatgtgt cagggttctc caagaccact ctcaggtttg aaggtttgct  88440
aaaagggctc acgggaccca gaaaagctgt gaaattcagt tatggtttat tacagtggaa  88500
gaatacagat aatacagatt aaaatctgca aagcaaaaga tgcacaaggc aatgtccagg  88560
ggagatcagg catgagcttc cagctgttca ctcccagtgg agttatgcaa acagtgctca  88620
attctcccag caatggtgtg tgacaatgta cagtgtaccg ccaaccagag aagctcacct  88680
gagccttggt gtccagggtt tttattgggg ctcagttaca ttgacatgga gcacccatgt  88740
gactgacttt aactgctggg tctccagcac actccaagat caaactgata ccgtgtgtcc  88800
cagggcccca gctgaacaca aacaggcagt caccatagat cccattgtga gcataagcta  88860
ccaggcatgg cccaaagccc tagatataca gatattcttt ccaggagcca gccaagggcc  88920
agtccttcct ttggaatatg cagagtttga actccccaac cccaaggagt taactcttta  88980
ctacacagaa tataaatctc accaagtctt tcttcttgtc aagtcctctc aaggtgaccc  89040
attgctttta gcagtgtctt tgagaccctg cgtcatctgg ccttgaccca tatcacctgt  89100
gttatctctc cactctagct acattgaact tttctttttt gagatgtggt ctcactccat  89160
cacccaggct gaagtgcagt ggtacagtca cagctcactg cagcctcaaa ctcctgggct  89220
caagtgatcc tcccacctca gcctcctgag tagctgagcc cacaggtgca tgccattaca  89280
cccagctaat atttttattt ttagtaaaga tgggttctca ctatgtttcc caggttggtc  89340
tcaaactcct gggctcaagc agtcctccca tcttggcctc ccaaagtatt ggcattacag  89400
gggttagcca ccacatccag cccattgaac tttttaagga tcccctagca tcctatactt  89460
tctgtcactg gatagccttg gaattatttt tccttctttt tgaaatactc ttcttctttc  89520
cacccttttgc tgtcaagtct cagaataggc attatttcct ccaaaaaccc tctcctgacc  89580
ctccaaatct ggatgaggac acttcctttg cccagagagc acctgtttta atcctctcag  89640
gtggctataa taaaatacct taaactgggt ggcttataca cctcagaaat ttattttcca  89700
cagttctgga ggctgggaag atcaaggcac tgacagattt ggtgtctgat gaggggccat  89760
```

```
ttcttgtttc gtagaagggg tcttcctact gcatctttcc atggtgaaaa gagttgaggc  89820
agctctctga aacctctttc atgagagcat gaatccctct gtcttcatga tctaatcacc  89880
tcccaaaggc cccacttcct aatatcttca cattggtgac taggtttcaa catatgaatt  89940
tgagaaagac acagacattc agaccatagc agtgctcttc caccaggttt tttatccccc  90000
tgtattataa ttgaggttta aattatctgc tttccttccc ttagattgta agctccatga  90060
gagcagggcc ctacccatcc agtcattgtc ctatccccca tgactacaac ttcctgggta  90120
cataattaat atttattata ttatgtagca aaggtatgct gccatactaa gagacccaaa  90180
aggccaccgg attaaaacct taaagaaaaa aaaataattt ctctcctata atagctgcaa  90240
ggttagccat gcaggttggc agggaagctc acttccacaa agtcactcag ggattcaggc  90300
tcctgttgcc ctcttctttt ctaccaccaa atgatcttca gcaccatttg cacaatcaaa  90360
acttaactgg tcttgaatag gcagaccttg aatttctgaa gtctcagacc caaaagtggc  90420
agctgtcact tccactgaca tatcactgat ggaaacttaa tcatgtgatc ataccaaact  90480
gctagggatg ctgggaaatg tagttttgtt gggaactcca tgacttggct aaaattccat  90540
tactgtagaa gatggtgggg gatgggggag tggtggacat ccagtggttg ctaccatatt  90600
tattgaatca aattgtcaaa caggacctat ctgataaggg gttcttttcc agaattaact  90660
gaagtattaa atcaggggca aaggcatgtc acctcatctt tctctcccta tattggcttt  90720
ctagggctgt tataacagag taacatgaac ttggcggctt aaaacaacag aaatttattt  90780
tctcttagtt ctggaggcta gaagcctaaa atcaaggtgt cagcagagcc accttgacaa  90840
ctgctctagg aaagaattct tccttgcctc ttctggtggc tcctggcaac ccttggtatt  90900
ctttgtctgg catccacttc aatctctgcc tccatcttca tttgcctttt ttctctgtgt  90960
gtctatgtcc tttcctcttc ttagaaggat accagtcatt gaatttaggg cttactctaa  91020
atccaggatg atctcacctc aagatcctta attagttaca tctgcaaaga gcttatttca  91080
aaacaagatt gcattctgag gtttcggtaa acacgaattt gggggaaata gtattcaact  91140
caattcactg ctttacttaa gaaaagagac catgaagtga gcctccttct gcttgagaga  91200
gagagcgagc ctttctgtgc aataggtcaa tgaatggatg cagctgaatt ccacataact  91260
ttataaaaat agatggccag cccatggggt ttgctgaccc ctgcccaaaa attccaaagt  91320
caacagcagt ctctttttta atcatttctc tattttttaa tttattttta tttttatgtt  91380
gagatagagt cccgctctgt cgcccaggct ggagtgtagt agtctcggct cactgcaacc  91440
tctaccttcc agatacaagt gattctcctg cctcagtctc ctgagtggct aggagtacag  91500
gtgtccgcca ccatacccag ctaatttttg tatttttaat agaaacaggg tttcaccatg  91560
ttggccaggc tggtctcgaa ctcctgacct caagtggtcc acccacctcg gcctcccaaa  91620
gtgctgggat tacaggcatg agccaccatg cccggccagg attttcttca ttttaacagc  91680
attcttactt gtcccacatc cattctatcc tgggtctaat tagataacaa aatctacaga  91740
tcttgtttaa ctgacattgt cctgggggat actttttatc ttttgagaca aggtctcact  91800
ctgttaccca ggctggagtg cagtggcctg ataacagctc actgcagcct cgaccacctg  91860
ggttcaagcg atcctcccac ctcagcctcc agagtagctg gaaccacaga tgcatgccac  91920
cacacctggc taatttttaa atttcttgta gaggtggggt ctccctatgt taccaaaggc  91980
tggtctcaaa ctcctgggct caaaagagcc tcccacctta acctcccaaa gtgctgggat  92040
tacagatatg agccactgtt tccagccttg gaaatatagt ctaagaactg agtcaatagg  92100
cgattttgtc attgtgtgga catcatgtag agaacttaac acaaacctag atggtataaa  92160
```

```
ctactgcaca cctcagttat ggggcatacc ctattgcacc taggctgcaa acctgcacag  92220
caggttactg tcttgaatac tgtaggcagt tgtaacacaa tggtaagtat ttgtgtatct  92280
aaacatatct aggccgggca cggtggctca cgcctgtaat tccagatcac ctgaggtcag  92340
gagttcgagc ccagcctggc caacatggcg aaactccttc tttactgaaa aatgcaaaaa  92400
ttagccaggt gtggtggcag gcacctgtaa tcccagctat tcgggaggct gaggcaggag  92460
aatcgcttga acctgggagg tggaggttgc agtgagctga gatcatgcca ctgcactcca  92520
gcctgggtga cagagcaaaa ctccatctca aaaaaataaa aaataaaaaa catatctaaa  92580
cagaaaaggt acagtaaaaa tacagttata accatatggg accaccattg tataggcagt  92640
ccgctgttga tcaaaacata tcaaaacatc gttatgtagc acatgactgt accataaacc  92700
acacggcttc aaacaaggga aatgtattct ctcactgttt tggaggccat aggtctgaaa  92760
tcgaggtgtc accagggtcc ctccaaagga tccgggggag gatccttcca ttggatttgg  92820
agttgcttca ctccagtctc tgcctcagtg gtgacagggc gttctcctct tccctctcaa  92880
agttccctct tctgctgtgt cataaggata catatgactg catttaggcc ccactcagaa  92940
aatccaggaa taaactcttg ccctcatatt cttaactaaa tcgtacctgc ataccttatt  93000
ttttctaaat aaggtagcat tccagggatt aggacatcaa cataacttct ggagggttca  93060
ctgttcaacc cactacagcc agaatgcgct ttgaattcag gttctgacat ctgggactgc  93120
ctcccacgta cacacaccac taccttgtac tgaatgcctg aagggttctg cccccacctc  93180
cactccccca aatatttgct gtggacctga gaaagctgac ttcatggaag cttcattcca  93240
ttgttctaag gacttttcat acattaacaa atgtcttctc tctatgggga aaaccacaga  93300
gaaatcaaga cagagtgggg ttaagtaact cacctgagga ggaacagtaa gtggcagagc  93360
caggattcaa accaacatgg ttttgcacag ttttgacatc atttgcaaca caaatattgt  93420
cacagatacc tttttgagca tctactgtgc taaccgccag gaaggaaaag aacatggggc  93480
cgggagagct cttgacaggg gacagggctg gccatggagg tctgtgtctt ggtggaagat  93540
gctatggttc tctttttttt tttttttttt tgagatggag tcttgctctg tcacccaggc  93600
tggagtgcag tagtgcaatc ttagctcaca gcaacctcca cctcccgggt tcaagcgatt  93660
ctcctgcctc agcctcccaa atatctggga ttataggcac acaccaccac gcccagctaa  93720
tttttgtatt tttagtagag atggggtttc accatgtggg ccaggctggt ctcgatctcc  93780
tgaccttgtt gtgatccacc cgcctcggtc tcccaaagtg ctgggattac aggcatgagc  93840
caccacactg ggcaactatg gttctctttt aactccttgt gctgaaatta ttgcagaagc  93900
ccaggccagt tcatccccag aaagtgaggc ataaacaggc agagctctac agaaacagag  93960
aatccacgac tggtttgatg gaggctgcct cactacctac agaatgggct ctgggtggat  94020
tgttctatct ggggagccag cccacccacc agtctcagcc cttggcgact ctttcctgct  94080
gtcacagcag ctggacattc agaaaccgaa acatgacagc cttccctccc tgttcctgcc  94140
cagtggagtg gaaacccctc gggacccaca taccgagcgt gcacagcagc acagagttgc  94200
acagttaaca cagcgcttct tctccagccc tccggatgca agctgacaga ttggcagctg  94260
gctgacttcc aaggtccagt gagttcttgg cagtcgcttt ctgacctgga cgagtggctg  94320
ccacctcctg gaacatcagg ctgcccccct ggggagaggg tgacggtctc tctggaaaga  94380
ctgtgagctt tgaggtggtc atcaaaagcc attcttggaa acattctttg agctgtaccg  94440
tgcaattcgg tcaccaattg cacgtatttg gatattaata tccgtatgtg gatattaaat  94500
```

```
tggttttggg ttttgttttg ttttgattgt ggcaaaatat acacaacaat cctcctgcct  94560
cagcctccca agtagctaca ggcatgcacc accataccca gctaattttt ggatttttta  94620
aatttgtttg tttgtttttg ttttttgaga tggagtgtag cactgttgcc tgggctggag  94680
tgcagtggcg cgatctcagc tcactgccac ctccgcctcc tggattcaag tgattctctt  94740
gcctcagcct cctgagtagc tgggattaca ggcgcccgcc aacacgccca gctaattttt  94800
tgtattttta gtagagatga ggttttacca tgtcggccag gcttgtctcg aactcctgac  94860
cttgtgatcc acccgcctca gcctcccaaa gtgctgggat tacaggtgtg agccaccgcg  94920
cccggccgat ttttgtagtt ttagtagaga cagggtttca ccatgttggc taggctggtc  94980
ccgaattcct gatctcaggt gatccaccgc ctcggcctcc cgaagtgcta ggattacagg  95040
catgagccac cgcacacagc ctaaatgctg tgcctcacgc ctgtaatccc aacactttgg  95100
taagctgagg ccagaggatt gcttgagccc aggagtttga gaccagcctg ggcaacatag  95160
gaagacccca tctctataaa aaataaaaat aaattagcca ggcgtggtgg tgcaggcctg  95220
tggtcccagc tactcgggag gatgaggcag gaggatcgct tgagcccaag aggtcaaggc  95280
tgcagtgagc tgtgattgtg ccactgcact ccagcatggg tgaaagagca agaccttgtc  95340
tcaaaaaaaa ttaagcgaaa tttaaaattc tgtttctcac tcacacaggc tgcacttcaa  95400
gtgcttaatc atcccttgtg ggtggtggct atcatattgg acagcatgga tagagaatat  95460
ttttatcagc gtaggaagct tcatcagaga ggaccgctca gaggcctgtg ggaccagca   95520
cagtgcagta gaagacacag gccagctggt gagagactgg tcttctgatc ccagatctgt  95580
ccctcacttg ctaggtgacc ttggacagct ccctcagtcc ctctggagtt ttctcttcat  95640
tgttaaatca ggaaattggc ctcagtgaat tctgaggccc catctacttt tttttttttt  95700
tttttttttt tttttttaat tgagacagag tctcgctctg ttgaccaggc tggagtgcag  95760
tggcatgatc ttggctcact gtaacctccg cctcccaggt tcaagcaatt ctctgcctca  95820
tcctccccag tagctgggac tacaggcgtg caccaccatg cctgggtaat ttttgtgttt  95880
tcagtagaga ccgggttttg ccatgttggc caggctggtc tcaaactccc aaccttgagt  95940
gatcctcccg cctcggcctc ccaaagtgct gggattacag gtgtgagcca ccacgcctgg  96000
cctcatctag ttctaaatgt tatgacccac tcagctctga agacaaggga ggaacatcct  96060
ctcagtctag ctctgacatg cagaagcctc tcaccctgtc ccccaggtca taaaggcagg  96120
cgtgttgtga agagcacaga atgggctgag aaaaatatgc agggattgcg tctatctccc  96180
ttccttccgc acgtttcctt gtcggcacca cctgcctcta ttccgcgccg cacacacacc  96240
cgccttctct ctgtctcgga ggaagacagg atcttccatc ccccaaatcc tgccctgatt  96300
cctactctga agcctctgcc ctgactcctt taagctccct gggaatacag cccatctcct  96360
atgccctcct catcccagta gttcctacct tccccaaaat cgctttggga aagtccccca  96420
atgagtaacc agctgtccta catgggcatc tcagaacttc tcttctgttg ttgttgttgt  96480
ttgttttgct tttgttttga gacaggatct ctctttttca cccaggctcg agtgcagagg  96540
tgtgatctca gctcactgta gccttgacct cccaggctca ggcgatcctc ccccctcagc  96600
ctctggaata gctgggacta caggcacacg ccaccacacc cgggcaaatt ttttttagga  96660
cttttggtag aaatggagtt tcgccgtgtt gcccaggctg gtctctaact cctgggctca  96720
agcgatccgc ccactttggt ctctcaaagt gctgggacta cagacatgag ccaccacacc  96780
cggcagagct tctatttctt gagtgtgttc tcagccatgc taagacattt tctcttctca  96840
gcctgatgat gcttttggct tgtgtttctt tgtttttaat taccccttcc cagtcgctgt  96900
```

```
catgggatca tgagggtctt ctgtccatct agatgacacc tttcttgtgc cacgtgtctc  96960
caacattccc tggtttttaa acccttattg ctttcaagat actatccaag ctccttaatg  97020
tggcacattg tccttcgctg ctatctgcct gctttttttt tgagacagag cctcgctcta  97080
ttgcctaggc tggagtgcag tggcgcaatc acagcttact ctgcagcctc gacttcttgg  97140
gctcaagcaa tcctcctgcc tcagccttct gagtagctgg gaccacaggc atgcaccatc  97200
atgcttggct aatttatttt tatttatttt tatagagaag gagtctccct atgttgccca  97260
ggctggtctc aaactcccgg actcaaagtt cattgcagtt tcaatttttt ccttggctca  97320
aggatcctcc cacttcagcc tcctgagtag ctgggactac agacgggcac caacacacct  97380
ggctaatttt tgtatttttt gtagagatgg ggtcccacta tgttgcccag gcttctatct  97440
gcttttatct caccttccac tcttccatcc ttcctttctt ttcttttatt tcctttccct  97500
tcccttgcct tccttttctt tctttctttc tttctttctt tctttctttc tttctttctt  97560
tctttttctt tctttctttc ttgacagagt ctggctctgt cacccagact gaagtgcaat  97620
ggcaagatct tagctcactg caacctccac ctcctgggtt caagcaattc tcctgtctca  97680
gcctcccgag tagctgagat tacaggtacc tggcaccaca cccggcaatt tttttttttt  97740
ttttagtaga gacggggttt cgctatgttg gccgggctgg tcttgaactc ctgacctcag  97800
gtgatcctcc cacctcagcc tcccaaagtg ttgggattaa caggtgtgag ccactgtgcc  97860
tggccttttt tttttttttt ttttttttta agacaggacc ttgctctgtc actcaggcca  97920
gagtgcagtg gcactataat cactttctgc agccgtgacc tcctgggctc aagggatcct  97980
cttgccttgg cctccctagt agctgggact acaggcatgt gccaccacac tggctaattt  98040
ttaaaacttt ttgtaggccg ggcacggtgg ctcacacctg taatcccagc actttgggag  98100
gccaaggcgg gcggatcacg aggtcaggag attgagacca tcctggctaa cacagtgaaa  98160
ccccatctct actgaaaata caaaaaatta gccaggtatg gtggcgggcg cctgtagtcc  98220
cagctactcg ggaggctgag gcaggagaat ggtgtgaacc tgggaggcgg agcttgcagt  98280
gagctgagat cacgccactg cactccagcc tgggcgacag agcgcgagac accatctaaa  98340
aaaaaaacaa aaaaaaaaaa caaaaaactt tttgtagaga tggattcttg ctaggttgcc  98400
caggctggtc tcaagcttct aggctcaagc agtcctcttg cctgtgcctc ccaaagcctt  98460
gggattacag gcgtgagccc ccacacctgg tcctaaccca ctttctgaac ttccaaccac  98520
accattttgt cctaatattt aagtcacacc ataacatgtc ccacttcaga aatgcctacc  98580
aaagtagtct tcaaatcttt ttaaatcagt ggaccctttc taccaaacaa atgttatttt  98640
ttaaatattt attttagagt aatttagact tttagaaagg ttgtagctgg gcgcagtggc  98700
taacgcctgt aatcccagca ctttgggagg ccgagacagg tagatcacct gaggttgggc  98760
gtttgagacc agcctgggca acatggtgaa accccgtctc tactgaaaat acgaaattag  98820
tcaggtatgg tggcacgcgc ctgtagtctc agctactcgg gaggctgagg caggagaatt  98880
gcttgaaccc aggaggcgga ggttgcagtg agctgagatc gcgccactgc actccagcct  98940
gggtgacaga gtgagactcc atctcaaaaa aaaaaaagaa aagaaaaaaa agaaaggtta  99000
taaatatatt ataaagagtt cccacatacc cttcacccag tttctcctgt tgtttgtatc  99060
ttatattatc accatatgct tgtcaatgct aaggaattgc tgggtgcaga gtggcacatg  99120
gctgcagtcc cagatactca ggaggccaag gcaggaggat atcgcttgag cccaggagtt  99180
caagtctagc ctgggcaaca cagtgagacc tcttttctgc aaaagaaaac aaataaaaca  99240
```

```
tctaaaaaag aatacactgg aggcggcgtg gaaacaagga tctcatttgg gagttgtctg  99300
caatgttctg agcaagcagt aacggaggcc tcaagtcagg gctgtggtca tggaggtggg  99360
gaggggtggt tggtttcact atctgtgttg acttaatttt agatttgcag actcaactga  99420
gtatgaactt taagagaaag agagaggcca ggcacggtgg gtcacacctg taatcccagc  99480
actttaggag gccaagtggg gaaggccgct tgagcccagg agtttgacac cagcctgggc  99540
aacatagtga gacccctgtc tctacaaaaa aaaattttta aattagccag gcagggtgat  99600
gtgtccctgt aatcccagct actcaggaca gtgaagcagg aggatcattt gagcccagaa  99660
agttgaggct gtagtgagct gtagttgcac cattgtgctt cagcctggga gacaaagtga  99720
gaccctgtct caaaaaggag aatggggaga gagagagaga gagagaagga gaaagagaga  99780
gaaagagaga gagggaagtc aaggagaacc ccacattttt tgacatggtg tattagtctc  99840
ttctcacact gctaataaag acatacctga gactgggtaa tttataaagg aaagaggttt  99900
aatgcactca cagttccaca tggctgggga ggcctcacaa ccatggcaga aggcaaagga  99960
gaagtaaagg catgtcttac atggcagcag gcaagagagc ttgtgccatt tataaaacca 100020
tcagatctca tgagacttat tcactaccac aagaacagta tgggggaaac tgcccccatg 100080
attcagttat ctccacctgg cgccgccctt gacacgtggg gattattaca attcaagttg 100140
agatttgggt gggaacacag ccaaacccta tcacatgggc aagtgaaagg atgggtttgc 100200
catcaaataa aatggggaag gagactgact aggtgggcag attaggaact cagctttcta 100260
tgaagtgcct actgatggat agagatattg tgttggccat ctattaggtt ggtgcaaaag 100320
taattgcggt tttgccatta aaagtaatgg caaaggaaat aacctttgca ccagcctaat 100380
aggaattgga gtctaaaatt caaaaaaggt aagtcagagc tggagatcca aaggcaggag 100440
tcagcctcct gtggaggcta tttaaggaac tgaataaggg catagatgca ggagagcacc 100500
caggactgag cccagggctt actctccatc attaaagagg ttggggaaga tgaggaggag 100560
ccagcagaga agactgaatt ggagcaaatc agaagaatgt gggtgctggc tgtcatgcaa 100620
ggaaagtgct aagccatttc aagtatgagg gaatgatcaa tgatgtccac tgatgctgat 100680
gtgttgactc aaatgaaaaa tgagaatcaa ccattggatg tagtggcatg gagatctttc 100740
gtgacctgag ccagagctgc ttaggtgaag aggtgaaggc aagaggctac tggaaggatt 100800
actactagct cttttaaaga gttctgctgt gaagggtaga ggaagagaga tggggcatgt 100860
gttagctggt gggggaagtg gatttcagag gtttgtttcc cttaaaaaaa aaaaaaaaaa 100920
gaaaaaagaa taaagaaaaa aaaaaggcca ggcacaatga ctcacacctg taatcccagc 100980
attttgggag gctgagacct cgggaatttg agactagcct ggacaacata gtgagacccc 101040
atctctacaa aaaaaatttt tttttaatta gctgggcatg gtggtgcatg cctgtggtcc 101100
tagctacttg ggaggctgag gtgagaggat ctcttgagcc tgggaggtcg aggctgcagt 101160
gagctatgat cacaccactg cactccaggc tggacaacag agcaagaccc tgtctcaaaa 101220
aaaaaagatg ggagacctaa cagcagattt tatgctgata ggaataacct attaggggag 101280
aaaaacatga ggatgctgga ggaagaagag tgtcaggagg acatctcttg gtggacgaga 101340
ggggatggca tttggtgtac aggtggaagg tttcacttta gatgacagca cacacagtta 101400
tctatagaaa caggagaaaa tgcactatat gggcatacat gctgggaggt agagagtaaa 101460
taatagtggt ggttgcttgt ggaaattctc ttctaatgtt tttatatttt tatggtttat 101520
caaggacaat ttatattttt acagtttact gcaaacaaca agttctaatt tattcaataa 101580
ttatttgtgg gtagaccgag tgcagtggtg catgcctgta atcctagcac tttgggaagc 101640
```

caaggtggga ggattgcttg aactcctgat tcacttctga gcttgaatca ggagttcgag 101700
atcagcctaa gcaacatggc aaaacactgt ctctacacaa aatacaaaaa ctagccaggt 101760
atagtggcat gcacgtagtc ccagctattc gggaggctaa aacgggagga tcatttgagc 101820
cctgaaggtg gaggttgcag tgagccaaga gcgagccact gcactccagc ctgggtgata 101880
gaataagacc ctgcctcaaa aagaaattct tattcttctt cttcttatta ttatttgagg 101940
agacatttac tttgtaccag gcgctgtgct agatgctgga gatacagaca tcaacaatga 102000
caaggctaag tgcctggcgt atttgtactt tgagtctaat aaaagacatc acacagacac 102060
acaacacaca cacacacaca cacaggattg tcaaaggatc aaccatttca catgtcaaga 102120
tcaggaatga tattggtcta ctactgcctt accatatctc ctaccatgac ctcatcttcc 102180
tcttgccaga ttttaagtct ttatacctca actcccagaa ctctcttcgc ctcacaccct 102240
atcacaatgt catccgtacc ccacggccaa tactccatca ttcgggaaag caaagttcca 102300
aagcgtcaag attgtatcaa tggacctgtc tctatggcaa cagtcctgaa tgagccaagc 102360
aaggtaaccc tggagatggc gtgaatgaga aagtggcctg ttgccacgga gacgtgctga 102420
atgggaaggc ccccacgagc caggctatgt cacgaagccg aaacagtcag catgaagtcg 102480
gtatgtctat tttcaactcg gaattacaaa aatacatttt aatagagctc atgacccatc 102540
tccttcctcg tccctgcctc ccaccccact cttcagcctt catcctacaa cacaatcgag 102600
cctcaccagg aacccttcaa acccctcaag gacaccttac tgttccttca gtacacagtc 102660
cccttcctgg gctgaggtgg tattcctttg accaactact gtctcccctt tgggaccaac 102720
agtattctca aaagccatga gcttatggga agaacattaa ctacattctt tggggcaaga 102780
acagttgctc acctgtgaac cagctcagct tgcatctgtg agaatgattg caatgggtag 102840
accagttctc catcaaagaa tggccctagc accccacaca cagtggtata atctgatcat 102900
gctggtgtat tgaacatata atgttagtgc cacatgaaag gaatttgtaa aaggacttag 102960
tgcctagaaa ggtacctttg aagatcttgg aatctctgaa acttacccag gttccttata 103020
ccctgctcaa agtattcctc catttatttc ttcattcatt agttcttttg tttcaccaca 103080
tatatatttt tgaaacgggg tctcactctg ttgcccaggc tagagtgcag tggcaagatc 103140
gtggctcact gcagcctcaa cctccccatc tcaagcagtc ctcccacctc agcttcctga 103200
gtagctggga caccacaggt acaagccacc acgccaggct aattcttgta atttttgtag 103260
agacggggtt ttgccatgtt gcccagtgta ttcgtttgtt ctcacattgc tataaagaac 103320
tacctgagac tgagtagttt ataaagaaaa gaggtttaat tgactcacgg ctccacaggc 103380
tgtgcggaag gcatggctga ggaggccaca ggaaacttgc aatcatggcg gaaaatgaag 103440
gggaaacaag cacatcttca catggtggca ggagagagag agtgaggggg ggagtgctac 103500
aaaaccaggt ctcacgagaa ctcactcact gtcatgagaa aagcaagggg gaaatctgct 103560
cccaggatcc aatcacctcc taccaggtcc ctccccccaac attggggatt acaattcaac 103620
atgagatctg ggtggggaca cagagccaaa ccatatcacc caggctggtc tctaactcct 103680
gagctcaagc aatctgcctg ccttggcctc ccaaagtgct aggattacag acgtgaacca 103740
tatttattaa gcattgttac agcaaagaga agcattgttg cagcataaca attggaagac 103800
tccattgatg gacgtctcca tcaacaagaa ctgtcggata aactatggta cacccatccc 103860
ttagcgtgtt atgaagtcat tacaaaaaga agaagcagat ctctgagtgt caataagagc 103920
tagtacttat agggtgtcta ctgtatacaa gtgctgttag aaagtgagta ttaactcatt 103980
taattcttgt aacaagcctg tgaggtggat tctttcatat ccccatttta cagagaagga 104040
aataggaatc tctatatcca agatatgtta tcaggtgaca aaagcagttt ttgaatggtg 104100
ccgccatttt ctcgtaagag caaatctgga agattccatg agaaattaat aattgtgttt 104160
gcctctgtag cggcaccctg aaagatttgg aagtaggtgt ggaaaggaaa cttactttct 104220
tgtgtctttc tgaattttgt actgtctacg cgttttgtct ttcacaaaac caaacagaaa 104280
atgaccattt ggtgcatttt gtgtgtcagg cattcttcta gtctagagaa gcacaggaga 104340
gcaaaatatt ttactgacga gaaaaatgag gcatggagaa gttaagtgac ttgcccaggt 104400
agcagagctg ggattccaca tcatagggtt tatacaggaa acaggtaaac agagctgtgc 104460
ttgtgtgtgg gtatgtgtgt acacatgcat acatgtgtgc atgtgtgtgt gtgtttgtgt 104520
gtgtgtgaat gtgcttgtgt gttgggagag ggaaatggca agagaagaac ctacagaagg 104580
tcagcaggaa ccaacccatg ttttgaggag tttggacttt atcctgaagg cacaagggag 104640
ccatggaagg atttagacaa ggggtggttg tgcttagctt tttatttaga aggatgactc 104700
tggctgaagg gtgatggccc agaatacagg tatatgtgaa ggactcctcc tgccctagta 104760
ggaggatgcc cacccaccct ctctgcccag tgcagtatca aagggcaaat tgggtacaga 104820
gaattctcac caagctgggt agaatccact ctgatgctgg ggagtggaca ctgaatgcac 104880
cagcctctcc tcctgctcaa tccctgaatt gaagctgttc cactaatgtt agggatcaga 104940
ttcccttcat atatatatat atatatatat atatatatat atatatatat atataatttt 105000 tttttgaga cagagtctcc ctctgtcacc caggctgaag cccattgtcg cgatcttggc 105060
tcactgcaac ctccacctcc caggttcaag caactcttgt tcctcagact cccaagtagc 105120
tgcgattaca ggcacccgcc accacacctg gctaattcta tatttttagt agagacaggg 105180
attcacctat gttggccagg ctggtcttga gctcctgggc tcaagtgatc agtctgcctc 105240
agcctcccaa agtgctagta ttacaggcat gagccaccat gcccgtcctt tttatattac 105300 cttttttat agagatgtgg tttcactatg ttgaccaggc aggtcttaaa ctcctggcct 105360
caagcgatcc tccctcctca gcctcccaaa atgctaggat tacaggtgtg agccactgca 105420
tctgtccaga ctctgttctc cataaagctg gcatatggaa agagggaaga ccatccaggc 105480
aatatcgaag tcccattggt gctgatgtgg ctgctgagac cacatgaatg gatgcattct 105540
gactctgcca cctctcagct atgtgaccct gggccagtca gcaagtccct ctataactca 105600
gttttctcat ctgtaaaatg gcgtcaacag tagccaaccc cagcaaatac tgtgaaatat 105660
acagaacatc attataatgg tgaggatgat agagatgcta tgttatcaga atacctgggc 105720
ttgaaccagc tccccttctt gcaagctgtg tgacttggag ctgatgccca aacctctgtg 105780
ggcctcattt gtttcatctg ttcaatgggg ataataacac tcttacttca tacagttatg 105840
gaggatttat tgaaataatt gacatacagc tcttagaaca gtatccggct ccttgtaagc 105900
gctcaagaaa tattacagac tgttgataat aatgcaatac tactaccaat aatatggcca 105960
ggagcaatgg ctcacacctg taatcccagc actttaggag gcagaagcag gctgattgct 106020
tgagcacggg agttcgaggc cagcctgggt aacataggga gactctgtct ttacaaaaaa 106080
taaaaataaa aatacaaata attagccagg tatggtggtg catacctgta gttccagcta 106140
cttgggaggc tgaggtggga ggattgcttg agcccaggaa gttgaggcta cagtgagctg 106200
tgatcacacc actgcactcc agccagggca acagagtgag accctatctc aaaaataata 106260
ataatggccg ggcgcgctgg ctcatacctg taatcccagc actttgggag gccaaggcgg 106320
gcagatcact tgaggtcagg agtttgagac cagcctggcc aacatggtga aaccccatct 106380
actaaaaaca caaaaattag ccgggtgtgg tggcggggtg cctgtaatcc cagccactca 106440
ggaggctgag gcaggagaat cgcttgaacc cgggaggtgg aagttgcagt gagccgagat 106500
cacaccactg cactccagcc taggtgacac agtgagactc catctcaaat aataatatga 106560
gtaataataa taatatcatt tttatcatca ttcttactaa cagtctctca ctccttgccc 106620
tgcagttttg cctgttttct tggaataaca ctcttccaca cctttcccct cagggatggt 106680
tcacgtttag catcatgacc cacccctggg gattagttag ctcatttctg gaaagcactt 106740
tggagctgta ggtgctttgc aggctggaaa catcacggga cttgtaccat atttaagcaa 106800
tgccagatta ttctgcctgg cagggggagg acacagagga tacggccctg gtatcttttc 106860
tccctgccta cctcagcttt gctctgaacc attttctgtc ctgttcaggg cagcctgggc 106920
cacttgccac ttccagcttt ctcgggagag gatgccttcc tgatggcacg cctcttaaca 106980
cacacctggt gctgttgttg aaaaagcaac aattgactcc agcgccagca ctgagaggct 107040
tgtccttaaa attagcagga gctgttggaa ggtcgctgtt agctcttttg actggaacac 107100
actgttcccc aggtggcatg aggctgaata cagtgcaggg attggctctg ctctcaggtg 107160
gcctgctcca cgctcctgag ctccgggtgg aagctgtgac cattatttcc ttaacagaaa 107220
catatatagc agcattaact atgaacctta ttactgtgtg tgtgtgtgtg tatatgtgta 107280
tatatatata tgcacatatg tgcatatgtg tgcctatgaa cctgttctga gcactttaca 107340
aatgtcaatg tattttatcc tcccaacaac ccattttata aataagactt gaggcacaga 107400
gaggttacgt tactgcccca agatcacaca gctggagagt ggtgaggcca agatttgaac 107460
atatgtacca ttgtaccata tgtaccaact tttttttct ttttgggatg cattcttgct 107520
ctgtcaccca ggctggagag cagtggcatg accacggctc attacaacct caacctccag 107580
gttcaagcta tcctcccacc tcagcctctc aagtagctag gaccacaggt gcataccacc 107640
atgcccagct aatttaaagt tttttttgt ttgtttgttt gtttgtttgc agagatgggg 107700
tctccttata ttacccaggc tggtctagaa ctcctaggtt caagcaatcc ccccacctcg 107760
gccttccaac atgctgggat tacaggcatg agccactgca cccaggtcct ccctccttat 107820
aaaggtcgcc aagcacaatc ttgtgagcct ggccctatcc acacccatac gcaacatggt 107880
gtgtattttt caaacaaaaa ctgaatgaac acctctggtt tgggttcccc tcacacttgt 107940
cccgggtttg ttgactctgt gttgtgggcc tagacaaagc agtgtctgga gctcctagac 108000
ccagggacca gacagtctgg gttcaaatcc tggctcttcc acttctgcct gagtgctctc 108060
tctgaacctg tctttcttta tctataaaat ggagataatt tttttaaact catcacttgg 108120
tcaaactgct ttgagcatgc aaatgagttc atatgtataa acctcttaga atgtcccagg 108180
caaagaacaa cacttcactc agatcaacat ttatttagca tctactgtgt acccatgact 108240
attctaggtg atgaggagac cctctggttc ttatgaggta gtgaggtggg ggagggtgag 108300
aaccctaaac attaacgatg gtgtgttcgc aggtgggaaa atcagtaaag tcgggtaaag 108360
ggaatttggg agtgctgtgc tcaagtcctg gccctgccac tttctggggt gcaagataca 108420
gcattgaata gggtggtcag ggtaggcctt attgggaaag tgatatttga gcagacgatc 108480
tagatgtcgg cacatattgc tactgtttga tggtactaat atgagtttga gtttcacttg 108540
caagtatata tatatatata tatatatata tatatatata tatatatgtg tgtgtgtgtg 108600
tgtatatata tatgtgtata tatatgtata tatatgtgtg tatatatgta tatatatatg 108660
tgtgtatata tgtatatata tgtatatata tgtatatata tgtgtgtata tatatgtgta 108720
tatatatgta tatatatata tgaaatttgg tccatttatt tatgctgatc aattaattga 108780
tgttgaaatt ataattgaat gttttattaa taaacagata cccacatact attttttcag 108840
aaattgttag gttttggggt tttctttaga ttttgattat ttttatttgc ttaattttct 108900
tttttctttt ttttaatttt atttttccat aagttattgg ggtacaggtg gtatttggtt 108960
gcatgagtaa gttcttcagt ggagatttgt gagaacctgg tgcacccatc acccgggcag 109020
tatacactgc accatatttg ttgtctgtta tccagtgctc acctcctact cttcccccca 109080
agtctctaaa gtccattgta ccattatttt actcacccac attctttggc ctgagatgct 109140
gagtggtcat gactcccaga tcccttcttg tttctgtatc aaagatcttt actaagatcc 109200
tggcctaggg aacctattcc ctttcctcat ccccaatggg agaaggggct tcttccccag 109260
cttatttgcc aactcatagg aaaggtatga aggagaggac tgtagttgtc ttgaagctgg 109320
tcagatgttg aagagatgat aatatttgct gatcaagaga gacaaagcaa tgctggaaga 109380
agaggctgtg ttagttaaca ccagctgcaa taaccaataa aaccaaaaat ctctggctta 109440
agagtatgca tgagtgagaa atcaacttct aaagtacaac tggtggccgg atgtggtggc 109500
ttatgcctgt aattctagca ctttgggagg ctgtggtggg agggtcgctt gaccccagta 109560
gtttaacgcc aacctgggca acacagtgag acaccatctc tactaaaaat aaaaaaataat 109620 aaagtgaaac tggtgagggg tgcaatgagg tggagtggtg ggtgactcaa atatggctcg 109680
actccatgca gtcactcagg gatccaggct gttggaggct ctccctgctt aaacatgtgg 109740
cttccaaggt tgttctaaga gcctacattg agacagcagc tggggaaaag ggaaagtgga 109800
gtgggaggta cttatgaggg ttcctggaag tggtgaacaa cacttctgcc tgcattctat 109860
tgggtggaat ttagtcatgt ggcccaggct agctgcatgg gaggctggga aatgtagtct 109920
ctgattaggc tgccatttcc cagtcccact tgtgaatctt tagtgggaag ctcaccatgt 109980
ttgcaccagg gattcagtct acctcccact catgcctcaa ctatgtatca ggcactgtcg 110040
taagtacttt acatatcagc ctacctaatg caaacaacta ctcagtgggt gctttattgg 110100
tcacatgtat tagtgagaac atggaaaccc agagccgtta aatatcttgc ccaaggtcac 110160
acagctagga agtggcagag ttggaatttg aatccaggaa atctggctgc agagccccac 110220
gcttagtata aattcattgt agtttagaaa gaggcagaag gaccctaaaa ttggcataat 110280
ccattttttg gtccctaagg aactgactga attgactact tgtaaaagtg agtcctggac 110340
aggcaacagt ggctcaggtc tgtaattcca ggactttggg aggctgaggc gggcagatca 110400
cctgaggtca ggatttcaag accagcctgg ccaacatggc aaaaccctgt ctctaaaaaa 110460
atagaaaaat tagctgggtg tggcggtggg tgcctgtaat tccagctact caggaggctg 110520
aggcaggaga atcgtttgaa cctgggaggt ggaggttgca gtgagcaaag atcacgccac 110580
tttactccaa cttgaatgac agagcaagac tctgcctcag gaccgccatg gccccctggg 110640
ttctaggtca gagtttctcc gccacagcac tgatgacttt gggggctgca ttattagctc 110700
caaaatggga gctatcctgt gcactgcctc aacttacttg atgccagtag cgcccgcgcc 110760
ccagttgtga gaaccaaaaa tgtctccaca cattgccaaa tgtcccctgg gaggtgaaat 110820
cacccctggt tgagagtcac tgttctagat tgttaaatat tatcttacac tctagcacaa 110880
gtccaaggca aactgactta gaaattacca accttgcaaa aaatagaaga tttcttaaag 110940
tcagtgagca tgatggtggc aagctgctga aatcacaccc ccagacatta gcagatggga 111000
tctggacagt attcatctag ttaaaaattg acaaggactg ggacactgca ggctcttcaa 111060
aagagaatca tttgaataac aaggggtcaa gacaggggta attggtgaaa gcccctgctc 111120

```
ataatttgaa aatataaata ggcatcatga aaattcatcc tgcaaaagtc aaaagtcgaa 111180
tgtgcagtgt tatacatgat cagttgattt gggaggggaa attgcatgca cacacatgag 111240
agcttgcaca cccacacaca cacacctgtt caagtgtgtg tgccagtgct cagtgaggac 111300
catctcccca acctgtctga tcatcttgct ttggggtgac cctatgggtg aggcagaaat 111360
tcttggatca tagttttcta atgaatatta taattgttaa cttctgatgg gtgctgactt 111420
tttcatcttt gcaacactgc gtaggtattt ttactctccc cattttacag atgagacaac 111480
tgaggctcag aaagattgat tagctctaca cgaagccagg atccaggctt agcctggctc 111540
caggaatcat gttttgagtt acgtagcttc cctgattctg agggacctcc ccacttctga 111600
aatcttctac tgttactccc catggccctt tcctattgac cggaggcacc ccagctcctc 111660
actcgtccct tatcttatga aacatgacca tgatgtctga attcaaagga gagcctgggc 111720
tttgtgggga aaacgaagca gaaaaagaaa ggtggaggtt ggtggttgtt tttggcatgg 111780
tgaggagcct gtcgttgctt gaggaaagca agaaaggaga ttgctggggc ttggatccat 111840
ctctgggtgc ctgtgggtct gtctgtaaaa atgagaactg gtcgtgctca ttagaggatt 111900
tgaccgttag gccttgggat agcgatttgg gaactttttt ctgctaagac aaagaataat 111960
atggttcagg ttcattttgc tcctgctttc ccaagcccta catctcttct gggctttttt 112020
tttttccttt ttctctcctt cttcttcttc ttcttcttct tcttctcatt tttggatctg 112080
gacttctgct gactcatctc tctgagcaag gaaggaggga ggaagtcaga attgctcatt 112140
aaccgttttc tttagtgact cagctgtgat tcacatttta attaatggag gagaaaaacc 112200
tgatcagtcc taaggcatct gcccaatcac gcataactcc aggctggtga taataataat 112260
acttgaaaaa agtggggtgt cctgaattaa actatggctc attccccaca ttagtcttga 112320
ggactccacc aggccctcta agttccaggt ctcaatgggg ctccctgaac cagagcagct 112380
agtccaagcc ccgagcagca tttctgcaga gttagtctga ggtcaggaca agaaacagag 112440
gctcaagccc tcctgggatc gcaggaggat catgggaatg taatattgtt tcctgagctg 112500
gtctttggct ataatcccag gctcaagcct ggcctccctc ccctcggggc ctgaaatttg 112560
tcagagccta ttgcaggggc agcttctgtg ctttttgttt gcccagagaa tgagaaaagt 112620
ccagataatc atgaccgcta cttcctgagc acttactatg catcaggtgg tgtgctcagc 112680
acttctcatg aatgatcacg ttgaatcctc actctgtcca caaaaagaaa gagcttttat 112740
ataattctcc aacctcccta tgaggaaact gaggcttggc aattgcccaa tgtagacaat 112800
tagtaaataa tcaggcagga tataaaccca accctttccc acctgggagc cagagcttgc 112860
atctactata cttctctgct ttccagtcag ctgcaaagaa aaattggaag ctgatagctc 112920
attcaacaaa cacttattga acccttccac ctgctcagcc ctgttctaga caccagagat 112980
ccatcagtga accaaagagg caaatccatg gtctcatgaa actgacaatt tacctgccca 113040
agtgtattag ttactgttta taagttccta ttaagtgtat tagatatgct tgcagctgta 113100
acaaagaatc ccaacatgca taagggctca aaacaataaa aatttcgttc ttgcacagat 113160
aaagttcaaa aggtgtattc tttttttttt tttcttttgc gacggagttt tgctcttatc 113220
ctccaggcat gagtgcaatg gcccagtctc ggctcactgc aacctccacc tcctgggttc 113280
aagcattctc ctgactcagc ctccccagta gctggaatta caggtgcccg ccaccacacc 113340
tggctaattt tttgtatttt tagtataggt ggggtttcac catgttggtc aggctggtct 113400
taaactcctg acctcaggtg acccacctgc ctcggcctcc caaagtgctg ggattacagc 113460
```

cgtgagccac cgtgcctggc caaaaaaaaa atgtattctt aaacagcagg cacctctcct 113520
ctaagcagta agtcaggggc ccaggcttgt tccatattgt agctcctcat cttcaaccca 113580
tggcttccaa agtctccatg cttcttgata tcaagccaca gaagggaaaa gagcatgaga 113640
agggcacagg agaaatgttt ctgggacaga cccagaagta gtccatatga cttccatcta 113700
cctcccactg gctagagctt acatggcggc acccacttgc agagctggga aatggagtct 113760
aactgagcat ccaggaagga gagacagaca tgagtctttg cgtgggtcct cactgagaat 113820
caagctccac attttgatcg atgtcaccag agcgtacatg gcggcgccca cttgcagagc 113880
tgggaaacgg agtctaactg agcatccagg aaggagagac agacatcagt ctctgcgtgg 113940
gtcctcactg agaatcaagc ttcacatttt gatctgtgtc acctccttgc aagccctacc 114000
ttaggacaat tttaagggac attcctatct tcttccaccc ttaggacagt tttaagggac 114060
actcctgagt tcttccaccc acctcctctg tttcttgggc ttccagctct caggatttgc 114120
ctttgcctta caatggggtg aagcaagaat ctggaagaat gtctctcccc acaatttgaa 114180
gtcttatttg aaaaaaagca gtagagcatc cctccctctt gaggtaggga aatctagaat 114240
caaatcctgc ttctccagac tttgacctca gaaactgggg ggacttcaag gtcttcaggt 114300
gggcagcttt catgaaccat tcattcctcc cacctcatac caatcagggt cctaacagga 114360
aaaagaatta acttctagat ggttcaaaag aagaccatgc catgaagaga ctccttaaag 114420
agataggaac aggtgagaga aatagataac ggctgtttga ggtcctcaga gagaagccat 114480
cgcgagccct acatttcctg gaacccagtg gaggcagagc tgtgcagaag ggactactgt 114540
cagaaccagg gagggagcag ggaagcaata ttccaatctc tttccctccc ctcatcttct 114600
gccagcgctt cccctcagcc aaaccaaacc ggaaacggag caaagcattc tgggagttgt 114660
agtcttcaag ggtccgcctc gagggcacag agcccgctgg agcattgacc tagagggcac 114720
acagggaatg actagtttgc accatcatgt gacggactgc acgccctcga ttatgtaatc 114780
cactctataa ttcaactgca gagctgcatg gtacagcagg atagccacta gccacacgag 114840
gctatttaaa tataaatgta cattcattaa aatttaacca aatgaaaatt ttagccactg 114900
agccccattt caaatgctca ttagccacac gtggctcttg gctaccatat tggacagatc 114960
agaatagaac atttccatca tcccagaaag ttctaggggc cggcgcagct gtggtgtaac 115020
ctgagcccat gcatgttatg gaatggagaa gagagaaaac agcacaagag gcagttttga 115080
agggagacag agagctgtgg atcagtaggg aggagactct ctaggcaaag gagcagttga 115140
gaagcaagaa agttgagtga gctgctttgc tgcgatggag gcttccctca cggggaagag 115200
tagagtcaga aagctttagt tcaagttcag ctctgaaatg aaccaatgag tgttctgaca 115260
agacacctgg ccttccggaa ccttggtttt gtagtggcca agggcttgac cctctgaagg 115320
ttcactgaaa aaaatcaact cacaaggcat attaattgga gaaaaggcag gcagatttat 115380
ttaatgtgtt tgcacgagag ccttcagaat gaagacccaa agctgcaggg gaaattgtcc 115440
gttttttaag cttaggttca acaaagtatg gacagcggtg tagaaatatg attgaacaaa 115500
aagtgtacaa tgtaaatgct aatagactga gtggggaaac ccaaaaaggg ctgtcttgat 115560
tctccttggt ctctctgagc atgcatttct tccgggtatg ggacaagacc ctctctggaa 115620
tggagggggg gctctcttgg ttctccttgg tctctctcag catgcattcc ttccgggtat 115680
ggggcaggac cctctctgga ataagggggc tgtcttgatt cttcttggtc tctcagagca 115740
tgcattcctt ctgggtatgg ggcaggaccc tctctggaat gggatcctta taacctacgg 115800
tcaaataacg taagttagat aatttctttt tttttttttt cttttttttg agacagagtc 115860
tgattctgtt gcccaggcta gagtacagtg gcacaatctc ggctcactgc agcctctgcc 115920
ttctgggttc aaatgattct cctgcctcag cctcccaagt agctgggact acaggtaagc 115980
accaccatgc ccagctaatt tttgtatttt ttagtagaga cagggtttca ccatgttggc 116040
caggctggtc tcaaactgct gacctcaagt gatccaccac ctgggcctcc caaagtcctg 116100
ggatttgtaa tcccagcatg agccactgtg cccagccaga tcatttcttt ttctttttct 116160
ttttcttttc ttttttttt tttttttgag atggagtctc actctgttgc ccaggctgga 116220
gtgctgtggt gcaaactcag ctcactgcag cctctgcctc ctgggttcaa gcaattctcc 116280
tgcctcagcc ttccaagtag ctgggactag aggtgcgcgc caccatgccc agctaatttt 116340
tgtattttta gtagagacag tgttttgcca tgttggccag gctggtctta aactcctgac 116400
ctcaagtgat ccacccacgt cggcctccca aagtcccggg atttgtaatc ccagcatgag 116460
ctaccacagc tggccagata attttttat aactagtttt tacaaagaaa ggtggaggga 116520
aagttagagt aacattttta ggtgttaggg ctgactttgg ggaaaagagg tctggtttct 116580
acgacccgcc ttagggaaga gggattctag tttttgtggc tagccccagg ggagaatggg 116640
actaagagat agaagggcag gagaaggtca gagaaaaact tttgcttctg tggctgcttc 116700
ggagaacttc attttggggt attgttttct gagccccaac agtttgctta tcagtgaagt 116760
gggtataggc gcccacctcc cacagtgacg atgctgtgaa cagggctttg gaagagtaga 116820
actatgaaat atttgttgtt gccttgtggg gaaatggtcg ttaaagccaa aattgttcaa 116880
gagaagaagc aggaagagtt cctttctttc ctgcaggtat cctcttaagc tgagtcttca 116940
gaatcccctg acaacgttta atcaacactt tattaaattc accccaaccc tgcttcaaac 117000
cttcacctgg tcctcgagat cttccaactg tttcttgatg aagttagcag gcaattgtat 117060
ggcgggatca tcatctcatg ttttgttttg ttttttcct ttttaccctc tgactttgag 117120
aaatccttgt ccttttactt ttccaaacct gagagcattg cagagaagtt agaattgagc 117180
aggacatggg cttaagaccc agcccagcca tgtgctagct gtgtgaactc gaagcagtga 117240
ccccacctct ctgacctgga aagtagaggg aatgatagga cccaccaccg ccacacttgt 117300
agggtcatca tggggattga ataaaataat gcataagact tggcccacag caagcactca 117360
agaaatgtta gctacttcct aaatatattt ttaacctttt attgaatata acatacatac 117420
agaaaagcac atgtatcata caagtagagc ttgagtgatt ttcaaaaact gagcccagtc 117480
atgtaaccag cgcctagttc aagaaacaga acatagccga gtgaggctga ggcaggagaa 117540
tcacttgaat ctgggaggca gaggttgcag tgagcagaga tcatgctatc gctccccagc 117600
gtgggcaatg ggggcggagg ggaagagaga gagagagaga gagagagaga ggaaggaggg 117660
agggaaggaa ggaaggaagg agggagggag ggagggaagg gaaggaaggg gagagagaga 117720
aaaggaaaga aaagaggaag acagaaagag agagagaaag gtaaagaaag aaaaggaaag 117780
aaagagaaag aaagaaaaga ggaagacaga gaaagaaaga gaaagctaaa gaaagaaaaa 117840
aaggaaggaa ggaaaatagg gagggaagag gaggaggaag aagaagaaga aggggggag 117900 ggagggaaca gctgcagctt cgaggaagga aggagggagg gaaggaagga aggaaaggaa 117960
ggaaggaaaa aaaaacagca ccaacgttta gaaacccccct tgtgcctctg aggtcaccag 118020
taactccatc ctgacttcaa acagtctaga ttagttttgc ttgtttttga actttaagca 118080
catggggtca tacagcatgc atgcattgac ttctttccct tgacgttgta tgtgtgagat 118140
tcatctgtgc tgttgctgtt catttgttct catcgctgtg tgtgctgaac cacctgttca 118200

-continued

```
tttactctac taatggtggg cagtttggtg ctttctactt tggggctatt ccagagaaag 118260
ctactttgaa cacactcaga tatgtctgtg ggtgaccact cttcatattt ctatgggaga 118320
tattcctagg accggaacat ctgagtcaga gggaggaatt ggtttagctt tggtaggaac 118380
tgcctaacaa ttggccgggc acagtggctc atgcctgtaa tcccagcact ttgggaggct 118440
gaggggggca aatcacttga gctcaggagt tcgagaccag cctggccaat gtggcaaaac 118500
ccctggccaa catggcaaaa ccccgtctcc gcaaaaaaat acaaagatta gccgagcatg 118560
gtggcgtgtg cctgtaatct cagctactca ggaaactgag gcaggagaat tgcttgaacc 118620
tgggaggcag aggttgcagt gagcagagat tgcactactg tactccagcc tgggtggcag 118680
aatacatgaa actccatctc aaaaagaaga aaggaaggaa ggaagggaag gaaggaaagg 118740
aaactgccca acagttttcc caagtgtttg ggatggaagg aaggaaggaa ggaaggaaaa 118800
gaaactgcct aacagttttc ccaagtggtt ggaccagtta aaactcccac cacctgtgaa 118860
tgagagtttg tttttatttt gctcctggag tgcctctcct gtagcaggtt cccactgaat 118920
gtctgggaat tcaaatgtaa tgcacttgtt catttcctca agagcttcac tccatcaatt 118980
ggattcatcc attggctctc ccatctccac tgacactatg ttctcacctc tatttggaag 119040
acatcctgcc tccacctgcc caagtcacat tatcttctca ttccagcctc tcaaggagag 119100
ttttctcttt caccacctcc tctagccctg gtgattggca aggtctcgca acagtaccct 119160
tcaaaacact catgactgtg aatgcactgg ccttcactaa gtttcccatt cttctctttc 119220
tttcttttt cttttctttt cttttttttt gaacagagtt tcactcttgt tgaccaggct 119280
cgagtgcagt ggcacaaaca cagctcactg tagcctcaac ctcctgagct caaggtatcg 119340
tcctgcctca gcctccttag tagctgggac cacagacatg caacgttgtg cccagctgat 119400
tttcttttt ttcttttttt tttttttttt gagacatggt ctcaccctgt caaccaagtg 119460
cagtagcatg atcacagctc actgcagcct tgacctcccg ggctcatgcg attctcccac 119520
ctcagcctcc cgagtagctg gggctacagg cacaagccac catgcctggc taatttttgt 119580
acttcttgta gagaccaggt ttcaccatgt tgcccaggct ggtcttgaac tcttgggctc 119640
aagcagtcct cctgcctcag cctcccaaaa tgctgggatt acaggtgtga gccagcacgc 119700
ccggccatgg ctaatttctt catttttggt aaagacaggt ctcactttgt tgcctaggct 119760
ggtcttgaac tcctggactc aagcaatcct cctgtctcag cctcccaaag tgctaggact 119820
accgatgtga gccaccgcac ccggcaattt cccctcttg acttctccag agctctcatc 119880
cctctcgagc tcctgtctct tctagaatca cttacctcac caccttatgg ggtttttgcc 119940
tctgttccta ctcctcttta tttaagaaaa cactgtactt taagagggct tcagaaacca 120000
cccgaaatag aaacatgtcc ttttgttcaa tcctttactt taaaagacaa ataaaatgaa 120060
gaattgctct ccatgtagaa ggttaaggag cttgggagga ccttctgtga gtggggagaa 120120
ctttacatta aaggaaaaaa aatgctggag aatagctgtg aacccaggaa gggagaagga 120180
cttcctccac tgaacttgta aagcacaaac tctaaggcaa aaaaagacat gattacatga 120240
aaactaagat atttgttcaa ataaagatgc aattggggcc aggtgcggtg gctcacgcct 120300
gtaatcccag cactttggga ggccgaggca ggcgaatcac gaggtcagga gatcgagacc 120360
atcttggtca acatggtgaa accccatctc tactaaaata caaaaaatta gccaggaatg 120420
gtgtcacgtg cctgtaatcc cagctacttg ggaggcttag gcaggggaat tgcttgaacc 120480
agggaggtgg aggttgcagt gagctgaaat cacgccactg cactccagtc tagcgacaaa 120540
gcaagactcc gtccaaaaaa aaaagatgca atagcaggtg gttcgggaac caaaccttac 120600
```

```
atccagatgc tggttgtccc atttcctgtg aatccttggg tgagttatca acctctctga 120660
gcctcagttt cctcgtcaat aaaatggaga aaatagtatc tacctatgga attgttgtga 120720
gttttgaatg agttaatatt tataaatcat ttagaatagg aattagcaca tggtaaatag 120780
tggatagaat cataaaaaaa aaattgatca ggggttaact tctaactgct gtttgttata 120840
gaggtcccta gcactgtgtg gtcattttaa atttagatga tttagaatta aatgaaattt 120900
aaaactcagt tcttcattca cactagccac attttaagtg ctcaaaaccc acaggtgact 120960
agtggctacc atatttggca gcacagattg agaacagatt tatcatccag aaagttctgt 121020
cagacagtgt tgatcaaggc tacatgaggg tctgggtgca gtggctcaca cctgtaatcc 121080
cagtgctttg gaaggccaag gtgggaggat cactggaggc caggggtttg agaccagcct 121140
gggaaacaga gagacctcat ctctaccaac attttaagaa ttagccaggc aaagtgttgc 121200
atgcctgtag tcccagctac tcaggaggct gagacaggat tgcttgagcc caggaatttg 121260
aggctgcagt gaactatgag cgcaccgctg cactccagtc tgggtgacag agtgagacct 121320
gtctctaaac ataaaaaata aaaatgtagg tggggcatag tggctcccgc ctgtaatccc 121380
agcactttgg gaagccgaga tggcagattt gtgaggtcag gagatcgaga ccaccctggc 121440
taacatggta aaaccgcgtc cgtactaaaa ataaaaaaaa attagccagg catggtggcg 121500
catgcctgta gtcccagcta ctcgagaggc tgaggcagga gaattgcttg aacctgggaa 121560
gcagaggttg cagtgagctg agattgcgcc actgcactcc ggcctgggcg acagagcgag 121620
actctgtctc aaaataaata aataaataaa taataataaa gtaaaaataa aaatgcaaag 121680
actacctgag ggaatgtctg caagtcaacc agaataacac agcaacccca ataggaaaac 121740
aggccgaaaa tgtgaacagg cggatcaggg aagtgaagtc tgaaaagcta atcagcctat 121800
gacatggtac tcaaagtcat ttgtaaccag aaagatggaa atgaaagcag tatctctgta 121860
cacctttaat attggggaaa aaatatgtga ataagccaag ggtttccagc gatgcgggca 121920
cagaggaaag tcttgcacca ctcaaagggg tgtggcccag ggaggccact ctggagacat 121980
atcggtagta ctcagtccag tgaggtccag caccatcagc gcttatgtcc ccaggcatcc 122040
atcccaggga cattcttacc aggtctgtta ggggcaggta cgagaatgct tactccagca 122100
ccatctatat aaggggagct gaaggccacc tggtgtccct cctggagacc aggaggcggc 122160
atgtgacagc ggcacccatg gagcaccaga atgagtgaga gctccagacc gcatatccga 122220
cagatactac gggatggggc ttttagaaat atggttgttg ccgggcacgg tggctcatgc 122280
gtgtcatccc agcactctgg caggccaagg cgggtggatc acctgaggtc aggagttcga 122340
gaccagcctg gccaacatgg tgaaaccctg tctctattaa agatacaaaa attagctgga 122400
cgtggtggcg ggtgcctgta atcccaacta ctcgggaggc tgaggcaaga gaatcgcttg 122460
aacccaggag gcagaggttg cagtgagccg acatcgtgcc actgcactcc agcctgggtg 122520
acaagagcaa aactctgtct caaaaaattt aaaaaaacaa aaataaaaat atggttctgg 122580
gtgaaaacag gaaacaacag aatgtgtcta acttcatcct gcttatgtca gttaaaaata 122640
gacacactca aaatatcgca cgtgtttttg cgagaatgca ctcctataag gccaaattaa 122700
acattctctc agttgtctct gggagggaga agaatgaaag tagggtatag agagatatag 122760
gggaattaat gcatgaatga atgaaggtat aaacaagaga caggcgtcat acagaccaaa 122820
ggtaaagata tcccgtaacc tgaggagagc aaagaacttg actctgcatt tgaagattca 122880
gaaaatgaat ttcagaaata gttttctcgc cagggggtgg ctcacgcctg taaccccacc 122940
```

actttgcgag ggcgaggcag gtggatcact taaggtcagg agttcgagac cagcctggcc 123000
aacatgatga aaccctgtct ctactaaaaa tacaaaaatt agccaggcat ggtggcatgt 123060
gcctgtaatc ccagctactc aggaggctga ggcaggaaaa tcacttgaac ccgggaggca 123120
gaggttgcat tgagctgaga tcacaccatt gcactccagc ctgggtgaca gagcaagact 123180
ttgtctcaaa aaaaaaaaaa aaaaaaaaaa aaaaagaaga ggaagaaatc gttttttcaa 123240
gaaggggaaa gctgggtgat ttaagaatga acttgaagag gatcactcag tcctcaacct 123300
aggagtggca agaatataga ctgtatggga agtggttctg ctccttggta cccatcttag 123360
aaatatttgg cctgagtctg taagaggcag gtactttatc taacctgagg ttagggggcc 123420
actacatccc catcccctcc cctgctttct aaccatgcta acatcttctc actctcctgt 123480
ctcctctcct tctcactccc ctaatctgcc tattcacatt ttgggcctgt tttcctattg 123540
gggttgctgt gttattctca ctgatttgca gacattcctc tgtgtcatct ttttaatttt 123600
gttttaattt ttagaggcag gatgtcattc tgttgcactg gctgtagtga cgtagctcac 123660
tgcagcctca aactcttggg ctcaaactcc tgtcctctgc ctccacttct caactggtaa 123720
cctcacttct cttcatgagg tctctccagc cccagggcct ttgcacatgt tcccctctct 123780
tctgagtggc atatggtagt tgctcctctg taaatattta ttgacatcct gacttccaac 123840
cagcagagaa ttgacctcct tcccatgctc aggctagtga aggcatgagt ttggctgagg 123900
tcccagtggg gaaggtgagt ggggtggcag agttaaccag gagcagcatg gtagaatggg 123960
taaaaccaga cgtagcacgc aggcaccaca tgttagctgg acaagtagtt taaccccatg 124020
ggtctcaatt tccccatcaa tgaaagggag aatagaacaa gtccctggta agcagcataa 124080
aatgagctct cagaatgtaa agtaacaagc acacaacctg gaagagaata catttagtga 124140
atattggctc ctttaatcag caggttctga tatgacttag ctacaattaa gaaaataaaa 124200
atggaggccg ggcgcagtgg ctcatgcctg taatcccagc actttgggag gccaagacgg 124260
gtggggtgga tcacctgagg tcaggagttt gagaacaggc tggccaacat ggtgaacccc 124320
atctctacta aaaatacaaa aattagccag gcgtggtggc gcacgcctgt agtcccagct 124380
actcgggagg ctgaggcagg agaaacattt gaacccagga ggtggaagtt gcagtgagcc 124440
cagattgcac cactgaactc cagcctgggc gacagagtga gatttgtctc aaaaacaaaa 124500
gaagtctgga ggccaggagg ttggttgcag ggttggttcc ttggctcaac aatgtctcca 124560
aagagtcctt ccatctttcc actctaacat cgtcactgta aggacttttt ttaacattta 124620
ccactcacag ccccaagacg actgcgtcag ttctttcttt ttttccttca gacagagtcc 124680
cgctctgtcg cccaggctgg agtgcagtgg catgatctcg gctcactgca acctctgcct 124740
cctgggttca agcgattctc ctgtctcagc ctcccgagta gctgggatta caggtgcctg 124800
ccactgcatc cggctaattt tttgtatttt ttttagtaga gatagggttt caccatattg 124860
gtcaggctgg tctcaaactc ctgacctcag gtgatgcacc tgcctcggcc tcccaaaggg 124920
ctgggattac aggcgtgagc cactgtgccc ggccgatgac tgcctcagtt ctaaggtact 124980
tacccagcca tccacgtaga cagacacaaa agcatccggc caaagaagag ggagaggaag 125040
ggctgtctct taccatgtga ctcatctcac ggggaaaaaa tccttttcca gaagcaccca 125100
gcagattttt cacccagatc ctgttaggcc tacgaatggg tcatgtgaca agtgctctta 125160
ttgcaaggaa tcttgggaaa aagagactat taggcatttt ctgcctcttt gatgggaggt 125220
gggctctgcc agtaaggcgg gtagtggtgg tggctcttgg atggacaact gtgtcttcca 125280
ttcttcttct tctttttttt tttttttaa gagacaaggt ctcactctgt tgcccaggca 125340
gaaatgcagt ggcacaatca cagctcactg ctgcctcgac ctgccaggct caggtgatcc 125400
gcccacctta gcctcacgag cagctggagg agtgtaccac catggccggc taatttttat 125460 atttttgta gagatggggt ctctttatgt tgcccaggct ggtcttgaac tcctgagctc 125520
aaacaatcct cctgcctcag cctcccaaag tgctgggatt acaggcataa gccaccacgc 125580
ctggactctc ttctttaaat actgagcctt ccacctcttc tagaatatac tctgttaatt 125640
atcaaccaca cttttctaca tttttgcttc attattcatt cagtaaacat ttattgagtg 125700
cctactgtat gccaggcaca gctttaggtg ctggagatgc tatgaacaaa acagatgaaa 125760
atttctaaaa aataaaataa aaaataaaaa taaattttgc aaagccaggc acagtggctt 125820
aggcctatag ttccacctac tcaggagtcc aaggcagtag gatctcatga gactgggagt 125880
ttgagtccag cctgggcagc atactaggac tctgtctcta aaaaagaaaa gaaggccggg 125940
cgcagtggct cacgcctgta atcccagcac tttgggaggc cgaggcaggt gaatcgcaag 126000
gtcaggagtt tgagatcagc ctgaccaaca tggtgaaacc ccgtctctac taaaaatgta 126060
aaaattagcc aggcatggtg gcaagtgcct gtaatcccag ctacttggga ggctgaggca 126120
ggagaatcgc ttgaacctgg gaagcggagg atgcaataag ccgagatcgt gccactgcac 126180
tccagcctgg gcaacagaat gagaccctgt ctcaaaaaaa aaaaaaaaaa gaaagaaaga 126240
atagaaaata tctgccctac ggggatggac atgctagaac atcaaagtcc aatggaactt 126300
tctgcactga tgaagtatgt atgtatgcac cagccacatg tggcttggga gcacttaaaa 126360
cgtgactggt acaagcgaat ttttcattta atttaaatga atttaaatct gtatttaaat 126420
agccatgtgt ggctagtggt tactttattg ggcggtgcag ctctctaaag gccaagagat 126480
acatcatcaa cttctctccc ttgacccata ttcagttctc tcccaccctg aaaatctcct 126540
ctcctaccca ggctcacatt tccagttctt ctcctcttgt tctccctcaa ccatcagccc 126600
ccgcaagact gacgtgaccc tgatgccgta tgaaatgcat tcttcatcct ttactcttac 126660
tcacctctgt gcggccctgg agaccagtga cctctccttt ctcaaaatac tttatttctg 126720
tgtgtttttg ttgttgctat tgtttttggg gggttttctt gagatggagt ttcactctca 126780
tcacctaggc tggagtgcag tggtgcgatc tcagcttact gcaacctctg cctcccaggt 126840
tcaagcgatt ctcctgcctc agcctcccaa gtagctggga ttacaggctc ccgccaccac 126900
ggctggctaa ttttcttgta tttttggtag agacggagtt ttgccatgtt ggccaggctg 126960
atctcgaact cctaacctca ggggatccac ctgcctcggc ctttcaaagt gctgagatta 127020
caggcatgag ccaccgcacc cagcctcaaa atgcttttga acttgactgt caggtatgcc 127080
attctccaca ccagtctcct cccatgtctg tgtcttctcc ctctccactg gggacccttg 127140
gctttttcca cttcactcat ctaccctggg ttatctggtc ttccataacc ctgtcctctg 127200
ccacacctca cttattcacc caccacaata tttattgagt actcactagg ccatgaaaga 127260
tgctatacaa aaaaagcccc tgtcctcgtg gagctgacat tctagaagaa agcatgaata 127320
ataaatacga cttaataaac agtacggcca ggcatggtgg ctcacgccta tcatccaaac 127380
actaagagac caagatgaga ggatcacttg aatccaggag tttgagacca ccttgggaaa 127440
cgtactggga ccctgtctct acaaaaaaaa tattaaaaat tagctggata gggtaatgca 127500
tgcctgtagt tccagctact tgggaggaca aggtggaagg attgcttgag cctgagaggt 127560
caagtccgca gtgagctgtg actgtgcact gcacgccagc ctgggtgaca gagtgagatc 127620
ctgtcttaaa aataaataaa taaacaaaca aacaaacaat ataattccag agagtgaaga 127680
ggcaggatct ctttagctag gaagttgagg gatgttctct ctgagaaggc agaatctgag 127740
tttcaacctg aagaattcga agaggccagc taggcaaaag atgagagttg aaggaatggg 127800
gacggcagag gagacagcca atatagtaat tctcaataaa gcagaaagtg agcttttcct 127860
gctggcagaa cagaaaggaa gtcggagtgg ccagggtgtt gtgggacaag gtggtcagca 127920
ggagtcacat cacgcaaggt catgtggtca tggtagactt taaattttac tccaagcctg 127980
atggaagcca ttggaagatt ttaactaagg agtgacggaa aactggcatc tcaaactcaa 128040
catgtctaca acccagttct tgatctttga aaccttcttc ctccatcttc cccatctcca 128100
ttgacagcaa cttcatcctt cagttagctc aggccaaaac cctggagtca cccttgatac 128160
ctctctcctg ctccacactc agtctttcca ttggaagccc taggggctgc catattgttc 128220
tccatagcac ttcacaccgt ctgacatact atatcttttc ccactattgc tttgtccttg 128280
gtagcatctt taggcactct ctgaatatct ggcacatagt acgtgctcac taaatccttg 128340
ttgaataaat gaatgaacat cactccgtgg tcctttcaga accagagcca ttcttctctt 128400
tcttcaccac cgttgcccct caccccgccc aactagtcac aggagttgaa ggatgacaca 128460
gtagagaact gggattctgg agtcctgtgg ctggtctggg gttcgagttc ttactcagtg 128520
gtaggaacct ccatgtggga ttaacttatc tggtctttag tttcctcctc tgtaaaatgg 128580
gcctcaaact gccaaccgct gggatgcagg gaggatttga tgagcccagg caggctccct 128640
ggagcacagc aatcaatggc agctatatat aaaccggggc ctcttttgta ctcccactgc 128700
ctttgtccta gttccagccc tcattacacc agcctgctct tgcggctccc tcctaacttc 128760
tgctccatca ccaccaatct gtcctttcag ctgtcaggct tgtcttctga acgccaaccc 128820
taatcacatc ccttcctgct ccaaaacctt acatgactct cactgtccac aggacaagac 128880
ccagcctcta gttgacagcc tccactgtcc agcttaccca acctctcccc taccacatac 128940
cctgagtgga gccttctgcc tccatagggc tttcttagcc agagaagcct cccttatctt 129000
cctgttctcc tcctaattcc ttcttatcct tccagggagg aggctgtgag gtaatgcatc 129060
ttgggagcca gctgggattg cacagggtgg tgagattatc tgcatttccg aggcttgaac 129120
aagttaaggc aatgggaaag gtcacacaat gagaaaatgc agggccagga tttaacccgt 129180
ctgagatgtt ctgactgtgc tatgctgcct ccccggacat gagctctgcg ataatgctgt 129240
ccccaggctg taatcattcc ctctttcatc cctgcctcct ctatccctgg ggtcagaggg 129300
acttgtagtt gaatctctca ctcactcatt ggtgtggtct ctccctaaag cagggtggag 129360
tttgtcttag cgttatcact gcatccagca caacctccct ggtccaggct tatcagcgtt 129420
caactgcgtc aatgcagttg cctcctcctc aatctcccag cttccggcct tgccccctag 129480
agagatcata ttttaataca agtcagatta catccctcct cccctcagaa ccctccatgg 129540
ctcacacctt actcagagaa aaagccaaag tcctctccac aacccacaaa gccctgcacc 129600
atccatcacc tcactgcctt cgtcccctca caccctcccc cttgctcgct ctgcttcagc 129660
cacaccaact catctctgtt tctcaaatac accaggcatg gcctagctat taaatgcacg 129720
gtccagcctg gtgcatttga agaacacgga tgaattggtg tggctggaac agagtgagtg 129780
agggggagag cgggaggagg acctttgcac cagctggacc tttgcaccgg ctgttccatt 129840
tgcctagagt tttccctgac atattcatat ggctcactct cttgcttccc ttgctttctc 129900
ccagtcttta ttcaaatgtc tatttctctg cacttgtgct gtttgataca gtcaccgctg 129960
gccacatgtg gcctttgagc acttcagttg aaacacatga aagtgtagaa tattgaccag 130020
attccaagga aaaccatgtg caaaatatct tttatctctt aagatacagg gtctcgctct 130080

```
gtcttccagc ctggaatgca gtggcacgat cacagctcac tgcagcctca aaatcccaaa 130140
ctcaagtggt cctcccacca acagcctccc gagtagctgg gattacaggc acacaccaca 130200
atgccccgcc catttttta attgttatta ttttttttaa tagcgacaag gtcttgccat 130260
gttgctcagg ctggtctgga actcctggcc tcaagcgatc ctcctgcctc agcctcccga 130320
gtagctgaga ttacaggcag gagcttttgt gcccagcagg tctacgatct tcttagaatg 130380
cttcaggctg ggcatagtgg ctcatgcctc aaataccagc actttgggag gccaaagcag 130440
gcagattgct tgagctcagg agttcgagac cagcctgggc aatatggtaa aaccctgtct 130500
ctccaaaaaa aatacaaaaa ttagctgggc ttggtggctc ccacctgtag tcccagctac 130560
ttaggaggct gaggaaggaa gatcacctga gcccaggagg cggaggttgc agtgagccaa 130620
gattgagcca ctgcactcca gcctagacaa cagggagacc ctgtctcaaa ataaataaat 130680
aaataaataa ataaataaat aaataaataa acaaacaaac aaacaaacca ataaatgaat 130740
tttacctgtt tctttttact tttttaatgt ggctactagc aaattttaat tttttttttt 130800
tttttttttt tttttgagac agagtcacgc tctgtcaccc aggctggagt gcagtggtgt 130860
gatcttggct cactgcaacc tccacctcat gggttcaagc agttcgcctg cctctgcctc 130920
tgagtagctg ggattacaga tgcccaccgc cacgcccagc taattttttg catttttagt 130980
agagatggag tttcgccatg ttggccaggc tggtctcgaa ctcctggcct caagtgatct 131040
gcctgcgtcg gcctcccaaa gtgctgggat tacaggcatg agccaccgcg cctggctata 131100
aaatttcata agtagctctt aatagatttc tcctgggcag tgctggtcta aacacttttt 131160
tttttttttt ttttttttga gacggcatct tgctctgtca ccaggctgga gtgcagtggc 131220
gcgatctctg ctcactgcat cctctgtcac ccgggttcaa gctattctcc tgccttagcc 131280
tcccaagtag ctgggactac agacacccgc caccacgccc agctaatttt tgtattttta 131340
gtagagacgg gttttcacca tattggccag gctggtctcg aactcctgac cttgtgatcc 131400
gccagccttg gcctcccaaa gtgctgggat tacaggcatg agccaccgca cctggctata 131460
aaatttcata agtagctctt aatagatttc tcctgggcag tgctggtcta aacacttttt 131520
tttttttttt ttttttttga gacggcatct tgctctgtca ccaggctgga gtgcagtggc 131580
gcgatctctg ctcactgcat cctctgtcac ccgggttcaa gctattctcc tgccttagcc 131640
tcccaagtag ctgggactac agacacccgc caccacgccc agctaatttt tgtattttta 131700
gtagagacgg gttttcacca tattggccag gctggtctcg aactcctgac cttgtgatcc 131760
gccagccttg gcctcccaaa gtgttgggat tacaggtgtg agccaccgcg cccggccctg 131820
taacactttt aacactgaac tgtttgcctt ccaggtggta aagagcaggt gcctttactg 131880
atagaaatgt caccactccc ttcatcccgc cagccccatg tcactgacgc gtcctttccc 131940
cttgctctgt ggtaactttc tcctaagcac tcatcgccct aacatctgtc atacaggtat 132000
acctcagaga cactgctggt ttggttccag gtcgccataa caaagcgaat attgcaataa 132060
agggagtcgt gcctttttttg gtttcccagt gcacataaaa gttatgctta cactatagtc 132120
tgttaagtgc atgatagcat tatgtctaaa aaaaaatgta catacettaa ttttaaaatc 132180
catcaaggct gagcacagtg gcttgtaatc ccaacacttt gggaggccaa ggcaggagga 132240
ttgcttgagc ccagggattt gaaaccaggc aacaaagtga gaccccgttt ctacaaaaaa 132300
attcttttta aaaatagctg ggtatggtga cgcatgcctg tggtcccagc tacatgagag 132360
gctgaggtgg gaggctcact tgagcctgag agattgagac tgcagtgagc tgtgatcaca 132420
```

ccactgcact ctagcctggg ggacagagtg agaccgtatc tctcaacaaa aattaaaaaa 132480
aaaaaaaaaa aaggctgggc acagtggctc atgcctgtaa tcccaacagt ttgtgaggcc 132540
aaggtgggtg gatcacttga ggtcaggagt tcaaaaccag cccagccaac atggtgaaac 132600
cccgtctcta tgaaaaatac aaaaaaatag ccgggtgtgg tggtgcacac ctataagccc 132660
agctactcgg gaggctgagg cacgagaatt gcttgaacct gggaggcggg ggggagattg 132720
cagtgagccg agattgcact gctgcactcc agcctgggtg acagactgag actctgtctc 132780
aaaaaataaa taaataaata aataaataaa taaatgtttt attactaaaa aagttaacaa 132840
tcatctgagc cttcagtgag tcctcatctt gctggtgaag ggtcactggc tcagtgttga 132900
tgggtgctga ctgatcgtgg gggtggttgc tgaagattgg ggtgcctgtg acattttctt 132960
aaaataagac aagaaagttt tccgcatcca tcgactcttc ctttcacgaa agatttctct 133020
agcatgagat gcttgttgac agcaatttta cccacagtag aactttttttc aaaattggag 133080 tcagttcttt caaaccctgc cactgctttg tcaactaagt ttatgtcata ttctaaatct 133140
catgttgtca ttttaacagt gttcacagaa ttttcaccag gagtagaatc catctcaaga 133200
aatcactttc tttgctcttc cataacaagt aacgcctcat gcattgaagt ttgatcatga 133260
ggctgcagca attcagtcac atcttcaggc tccacttcta actctagttc tcttgctagt 133320
tccatcactt ctgcagtgtc ttcctccagt gaagtcttga actcctcaaa gtcatccatg 133380
aggatcggaa ttgacttcct caaaattcct attaatgttg atattttgac ctgttcccac 133440
gaatcacaaa tgttcttttt gttgtttgtt tgttgtggat tgttttttta tttttaattg 133500
agttgaggtc tcactatgtt gcccagactg gtcttgaact cttggcctca agtgatcctc 133560
ctgccttgat ctccctaagt gctgggatta caggcatgag ccactggaac agccacaaat 133620
gttcctaatg gtatctagaa tggtgaatgc ttttcagaaa gttttcaatt tcctttgccc 133680
agatgcatca aaggaattta tctatggcag ctatagcctt atgaaatgta tcccttaaat 133740
cataagactt gaaatagaga attacttctt gatccatggg ctacagaatg aatgttgtgg 133800
ctgggcatgg tggctcacac ctgtaatccc agcactttgg gaggctgagg caggtgggta 133860
acttgaggtc aggagttcaa gaccagcctg gtcaatatgg tgaaacccca tcactactaa 133920
aaatacaaaa attagctggg catggtggcg tatgactgta atcccagcca cttgggaggc 133980
tgaggcagga gaattgcttg aaccctcttg aagacagagg ttgcagtgag ccaagatcac 134040
accactgcag cgacagagtg agactctgtc tcaaaaaaaa aaaaaaatgt tgtgttagaa 134100
gtcataaaaa caacattcat cttcttgtac atgcccatta gaggtcctgg ataaccagtg 134160
cattgtcagc agtaatattt tgaaagaaat cttttttctg gctgggtaca gtggctcgca 134220
cctgtaatcc caccactttg ggaggccgag gcgtgtggat cacctgaggt cgggagttca 134280
agaccagcct ggccaacatg gtgaaacccc aactctacta aaaatacaaa aaaattagcc 134340
aggcatggta gcaggtgcct gtaatcccag ctaccctgga ggctgaggca ggagaatcgc 134400
ttgaacctgg gagtcagagg ttgcagtgag ctgaggtcgt gccattgcac tccagcctgg 134460
gcaacaagag tgcgacttca tctaaaatac atatatatat ataacatgtt atatgtaata 134520
taaattatat atataacata tatgtaatat aaattatata tcacatataa catatatcat 134580
gtgttatata tatcacatat aacatatgtg ttatatatca catataacat gtgttatata 134640
tcacacataa catatattat gtgtatatat gtcacatata ttatgtgtta tatatgtcac 134700
atataacata ttgtgttata tatatcatat ataacatata ttatgtgtag tgtatcatat 134760
gtaacatata ttatgtgtag tgtatcatat ataacatata ttatgtgtag tgtatcatat 134820
ataacatatg tgtagtgtgt tatatataac atatattatg tgttatatat ctcatatgtt 134880
atatataaca tatattatgt gttatatatt atatatatat ttttttctga gtagatctca 134940
acagtgggct taaaatatca gttatccatg ctataaacag acgggctgtc attcagtctt 135000
cattgttcca tttatagagc acaggcagag tagattcagc ataattctta agaccttagg 135060
actttaggaa tggtaagtga gcattggttt caacttaaag tcaccaggag cactagctcc 135120
taacaagaga gtcagcctgt cctttgaagc tttgaagcca ggcattgact tctcctctct 135180
agctatgaaa gtcctagatg gcaacttctt ccaatagggc atttcatcta cattaaaaat 135240
ctattattca gtgttgccag cttcattaat aatctcagct agatcttctg gataacttac 135300
tgcagcttct ccatcagcac ttatcacttc accttgcact tttatattat ggggacacct 135360
tctttcctta aacctcatga accaagatct tctagcttca gatttttctt ctgcacttcc 135420
ccacctctct cagtcttgct gtgggcttgc tgtggattag gctttggctt aagggaatgt 135480
tgtggctggt ttgatcttct atccagacca ctaaaacttt ctccatgtca gcaagaagcc 135540
tgtcttactt tcttatcatt catgtgttta ctagagtagc ccttttaatt tccttcagta 135600
atttttcctt tgcattcaca acttggctaa cctctagctt atggcctttt gtttgtttgt 135660
ttgttttgtt tttgagacag ggtctcactc cgttgcccag gctggagtgc agtggtgcaa 135720
tcaccgctca ctgcagcctt gacttcctgg gaccaagtga tcctcccacc tcagcctcct 135780
aagtagctga gaccacaggt gtgcaccacc acacccagct aatttttttta ttttctgtag 135840 agatagggtc tccctatttt gcccaagcta gtctcaaact cctaggctca agccatcctc 135900
tcacctcagc ctcccaaaat gctcggatta caggcatgag ccaccatccc tggccctatc 135960
tcagcttttg acacgccttc ctcactgtgt ttaatcattt ctagctttta atttaaagtg 136020
agagacgtgc aactcttctt ttcacttgag cacttaaagg ccattgtaca gttatacact 136080
gacctaattt caatattgtt atgtctcggg gaataggaag gcccaaggaa agcgggagag 136140
atggggaaat ggccagttgg tagagcagtc agaacacaca caatatttat cgatcaagtt 136200
tgccatcttc tatggatgtg gttcgtggca cccccaaaca atgactatag tcacatcaaa 136260
gatcactgat cacagaccac cataacagat gtaataatta tgtaaaagtt tgaaataccg 136320
taagaattac cagagtgtga cacagagacg caaagtgagc acacgctgtt ggaaaaaaaa 136380
tggccctgat agacctcctt gacacagggt tgccacaaat cttcaatttg taagaaacac 136440
aatatctaca aattgcaata aagcaaagca caatgaaatg aagtcttcct cggccggtgt 136500
ggtggctcac gtccataatc ccagcacttt gggaggccaa ggcaagagga tcccttgagc 136560
ccaggagttg gaggccagcc tgggcaacac agggagactc catctctaga acaaaacaaa 136620
acaaagcctg cttatattta ttgggtttac tctcagtctc ccccacacag agatagggcc 136680
tggcttgtta ttagtgctca gttgatgttt gtgaagtgaa atactaagga cttaaccact 136740
gcctgttctt tgctgttcat gccctgacag cttttatgtg ccagcacaga agaaaacaag 136800
gtgcaagaag agaatagtga tctctaagtc agaatttgag gaacccaaat tagtaccaga 136860
aagctgggag gagaagagaa aaataaagta aatcaaatta aaagttgaat gggccaagtg 136920
cagtagctca tacctataat cccagcactt tgggaggctg aggtgagagg atcacttgag 136980
gccaggagtt ctagaccagc ctgggcaata tagcaagacc ccatctctac aaaaaaaatt 137040
ttttaatttt ctgaatatgt tgttgtacac ctgtagtccc agctgcttag gaggcagagg 137100
tgggaggatc gcttgagccc aggaggttga ggctgcagtg agctgttgtt gcaccactat 137160
actcaagcct gggtgacaga ataagtccct gtctccaaaa ataaaaataa ataaattcat 137220
tttttgtaaa gttgtatgtc atggcccctg cctactctgg cttcatgact tgctgcttga 137280
acctcaccat ccaaatccca gtggtgacac catgtcattt cttgaatttg ccaagccctc 137340
tttcagtccc aagctctctg tcatggccac tctcagcctg gaaagttctt tccccactgg 137400
ccagatttct ccccctcatc tatgggaact tgacttgaag tagggggtat cccaggccct 137460
ggactagtta acacgacctg ctgtgtgccc ctcaaagcca ttgtcttcct agctgagaag 137520
gcatcacacc tgcaacagat tcactcattg tgtgcatgtt tttcttaacc acttctcttc 137580
tgcatcagct ccatggggca gggatagtct catatgtcac tctacccagc acataggata 137640
cgctcagacg cccacttgtg gatggtggaa aaggtcagcc caacctaata tgcccatctc 137700
tcctctaggg gtaatcttga gaaaaaaagt tgggaacttg ctttgtgtta gtttaggatg 137760
acccagaata gatcctgaaa caagaattta gggcaatcct tgtgcaagta gttcatctga 137820
gaggtgaccc cagaagggtt ggagaaggag aggggaggtg gggcaaggaa gggtgagttg 137880
tcctgtaggc aactgagctc cgtcctactg ggagcccacg tggaactcac ctcttaagtg 137940
atccagaatg aagggtgagg gagctgcggt attgatccac caactcccag caatctttgg 138000
ttgagggctg ctcccttaaa gttcattccc tgggcctgcc ccagatttgg agacagccct 138060
aaggcaagag gtacagatac cagttggcca cagactgaag tgttaagacc caagcccctg 138120
gataaaactg aaaaatcaag ccagatgtgg tggttcccac ctgtaatccc agctactcag 138180
taggctaagg caggaggatt gcttgagccc aggagttcaa tgctgtagcg agctatgatt 138240
gcaccactgc attccagcct gggcatcaga gcaagacccc atgtctaaaa taaaaataaa 138300
ctgaaaaatc cccaagttat ttgctgtgac caaccttcca ttaaccacag accctctggt 138360
attcagcatt tcttgtccat tatatgaagt tctgatgaca gtctctttta ttgtattgtg 138420
ccttgaccac gcactgtaca tcacttagct ctgaaatgga catgttcagg aaacagggcc 138480
aggtgggacc ctgtgtttca acagcaatac ttttacaaat gaggtctcat gacagggtct 138540
tgctcggagg gtttctatgg aagcctcatc ccacctactg ctatcatcct tactaacttg 138600
catttacaaa agggactctt tttgaccaga ggcttggggt ctgtagctgc cttctagcca 138660
gctgatgctg gctggtccac acaagcagga tcacacccat ttttttgttt tcttatttat 138720
ttctgaatag gttagcatac cggtaacctg tgtgcctggc attgtgctga ccactttttg 138780
tcaacttact gaatcctcac aacccttgga ggtattgata ctattgttat ccaggttata 138840
caaaaggggg aaactgaggc acagagcagg gatgtccctt gcccaaggtt acccaactgg 138900
aaagtggcag atctgggatc tgaacccatg caggctgggc tcttaacact gaactacttt 138960
cctgccattt gttaaagagc cacaaaccag gccaggcacc atggctcacg cctgtaatcc 139020
cagcactttg ggaggccgag gcgggtggat cacctgaggt caggagttca agaccagcct 139080
ggccaacatg gtgaaaccct gtctctacaa aaatacaaaa aaaagtaccc gggcatgatg 139140
gcgggtgcgt agtaatccca gctactcggg aggctgaggc aggagaatcc cttgaacccg 139200
ggaggcagag gttgcagtga gctgagatca caccattgga gatcgcactc cagcctgggc 139260
aacagagtga gactctgtct caaaaaaata aaataaaata aaataaagag ccacaaaccc 139320
cgaaaggtct gccattcccc cagggcccca ggccacccca caatctattg tcattgtagg 139380
ttgtgaaata tactgaatgt caccccaacc ttgagccatg gggaagattc catttctctc 139440
attgcaacat ttgtgcaaca tgaaccatct gttgggggtc ttcgtaaatc accttttatc 139500
ccgtgaggca ggtactgtta agaccatttt acaggtgaca aaactgaggc cagtggtgtc 139560

```
gagtcacctg cctgtggtca cccaaccaat acaggacagc ttggaatccc aagcaccccc 139620
gccctgctgt ctgaccccca aaacccaccc tctgttctcc attctggctt ctttctttca 139680
gcatcttggc gacagttggg acggagtttg acctacggac gctgagggca gttcgagtgc 139740
tgcggccgct caagctggtg tctggaatcc caagtgcgtg agtttccgac cctgacaagg 139800
ggtttgctca cgggccccag gagccctcag tttcccctat gcagagcatc tcaggaggcc 139860
acatcctgcc accagcctgt gtgagggcag tctcttcttt gggactccct atagggaacc 139920
ccctaggaat atgactgtag ctccccatga gctcctgaaa gcaaactagg agccacaccc 139980
atttattgag cacctactgt ctatcgggag ccatgctaag caccacgtgt gatctcattc 140040
agtactcaca gccctatgaa gttgatagga ctgatgtctc tattttatgg agggggaaac 140100
tgaggctcag agtggctgaa acattggagc agggttttgt ggctgagaag tggcagaact 140160
aggagtgagc aagtgtgact ccaagcctgg gccgtaccac tggtggcaat gaccattccc 140220
atttaatgag tgcctgctgc gtgcagggca ctacagaagg actttacatg aattacctta 140280
tttcatcctc acagtcaccc agcgaacacc cattttacag atgagacggt tgaggcttaa 140340
ggaggttaaa ttactcacct gaattcttag agtggacagt aatgagctct aaaattcata 140400
ctcattcctt gctgctttct cattctccac agatacatct agtccccgtt taagggtggc 140460
tgccatatgc agggtcaaga ttaagtgtag gttgagccaa aaaaaaatgt aaaaagcaaa 140520
aataaaacag ggctgtcctt tttctatctt cttgtcttgg ttaataataa taatttagcc 140580
aggcatggtg gctcatgcct gtaattccag cactttggga ggatcacttg aggccacaag 140640
ttcgagacca gcctgggcaa cattgtgagg aacaccaccc ccaccccccc gccaatatct 140700
acaaattttt tttttttttt tagaaattag ccaggttgac tgggcacagt ggctcacacc 140760
tggaatccca gcactttggg agaccgaagc gggcagatag agcgagctca ggagttttaa 140820
gaccagcctg ggcaacatgg cgaaaccctg tctcaaaaaa aaaaaaaaat tagcaggcat 140880
gatggtgcac acctgtagtc ccagctactt aaaaggctga ggcaggagga tctgagccca 140940
ggaggtcaag gctgcagtga gctgtgatag caccactgca ctccagcctg gacaacagag 141000
tgagaccttg tctcaaaaaa acagacaaca aaaagtttaa aaacaaacaa tttataggct 141060
gggtgcagtg gctcatgcct ataatcctag cactttggga ggccaaggtg gatgggtgga 141120
tcacctgagg tcaggagttc gagacctgcc tggccaaaat ggggaaaccc cgtctctact 141180
aaaaatacaa aacttagccg ggcgtggtgg cgggcatcta taatcccagc tactcgggag 141240
gctgaggcag gagaatcact tgaacccggg gggcggaggt tgcagtgagc tgaaatcacg 141300
ccactgcact ccagcctgga tgaaagagtg aaactccgtc tcaaaaaaag aaaaaaaaaa 141360
attaaaaagc acttactatg tgccagacat tattctaagt atttccattt ttttaaagtc 141420
ctttatcctc ccaacaagcc tgtgaagtag tctcttttat tatcaccatt ttacatttta 141480
ttggcttcgt tcttccggtt cattgctacc caggtttaaa gagtaagatt tcccagagga 141540
tcaccagcag gatctttttg tagaaagaag acacttctat ccaaggtctc tgcaagatcc 141600
cagcagatgc ctgcatcata ttaaattaag ggccatccca aatctaatag tcaaaagagc 141660
caggtgcagt ggctcacacc tgtaatccca gcactttggg aggccaaggc aggacgattg 141720
cctgaggcta ggagttcaac accagcctgg gcaacaaagt gtgaccctgt ctcaaaaaat 141780
atatgtatat tataatagca gtagtaacaa gagtctctgt ttaatgacca cctatgactt 141840
accaggtact tcactgtgtg tgaactctct catctaatcg tatgagggag gtactattgc 141900
```

agtccccatt tacagatgga gaagctgagg tttggaattc actagtaagt ggatgactag 141960
gtcaggttcc cttgaagcgg atacttaggt gggtgttcag atgcacctgc tttattgggg 142020
gacggctctt gggagagaca gcaggagatc agcagggtgg ggctggggaa tggatagagc 142080
agggacgcaa tttcagctgg agtgtgtgtg acaccagagt tgtcctccaa tgcatggcaa 142140
ggatgccggc cttttgtact tctatagtca gtcactgtgg atgggaggta gagacgcagt 142200
agctcccagg tgagatagct tttgatcacc aagggcaatt ctactaagaa gagaggcagc 142260
tgggaggcat tagcaaccaa catccatagc agctggaggg cgggtacacc agaaagaaaa 142320
tgggatcttg gccagacacc aagagtatcc agcaccttaa ccactgcacc acactgcatc 142380
tgttagcacc cacattacat tttttttttt tttttttttt tttgagacgg agtctcgctc 142440
tgtcgcccag gctggagtgc agtggcgaga tctcggctca ctgcaagctc cgcctcccgg 142500
gttcacgcca ttctcctgcc tcagcctccc gagtagctgg gactacaggc gcccgctacc 142560
acgcccggct aatttttgt atttttagta gagacggggt ttcaccgtgt tagccaggat 142620
ggtctcgatc tcctgacctc gtgatccgcc cgcctcggcc tcccaaagtg ctgggattac 142680
aggcgtgagc caccgcgccc ggccagcacc cacattacat ttttaagccc ttggagtggc 142740
atggcccctc gagctatcct gacagcttcc ctctcttact gtggtctcca cccatcaaga 142800
gccatgggaa gttcctgcaa tcaagaagca aagcctcagg ctatatgttt gaaccttcat 142860
tttgatcata gactttccta gtagatacca tagtggttac aaacatagga tgttgtcatc 142920
gttcagacct gagttaatag cctcaagaaa aaaatggtag tggaaccagg tatggtgaag 142980
tgtgcctgta gtcccaccta ctcgggaggc tgaggcagga ggctcgcttg tgcccaggag 143040
gtcaaggctg cagtgagccg tgatcatgcc actgtattcc agcctgggtg acagagcaag 143100
cccatctcaa aaaaaaaaaa aagccaatga taggcagaga aatactaact aaggctcttg 143160
ctctgtcgcc aggctggagt gcagtggtgc aatcacagct cagtacagcc tcaacctccc 143220
cagactcaag caatcctacc atctcagcct cccaaatagc tgggactcca ggcacacagc 143280
accatgccca gttaattttt ttgtattttg tagagacagg gtttcaccac gctgctcagg 143340
ctggtctcaa actcctgagt tcaagtgatc cacccgcctc agcctcccaa agtgctggga 143400
ttacaggtgt gagccaccac gcttggccag ctattattat tattaacatt cttcgagtct 143460
tacaacagtg gaacttttag tgcaggatgc gaatttcagt attaacccct tcctctccca 143520
aaaggatttg aagcccagag taattcagcc gccatgaatg aaccatttgt tagatgagag 143580
gctactggag gctgagcttg gtaggataag agcttgcatg gggtccctga ttgatgacaa 143640
tacccccaga tttaggtctt cagatgccca gttgggtgtg tcttctgttc cactgtgtcc 143700
cttcggggac tgttccctgc cttctttctt tttgagatgg aatctcgcac tttcacccag 143760
gctggagtgc aatggcgtga tctcagctca ctgcaagctc cacctcccgg gttcacacca 143820
ttctcctgcc tcagcctccc gagtagccag gactacaggt gcccgccacc acgcccagct 143880
aatttttttg tatttttagt agagacgggg tttcaccata ttagccagga tggtctcgat 143940
ctcctgacct cgtgatctgc ccgcctcggc ctcccaaagt gctgggatta caggcgtgag 144000
ccaccacacc tggccccctg ccttcttatt caccaccatc tttctgaatt gggttgctca 144060
gaacagagaa agcaacatca gcacatgggc aaacatgggg cttcatttca gatggacctg 144120
ggttcaaatc ctagttctgc cttttttttt tttttttttt ttttttgaga cagagtcttg 144180
ctctgtcacc cagactggag tacagtggcg tcatcttggc tcactgcaac ctctgcctcc 144240
caagttcaag caattctcct tcctcagcct cccaagtagc tgggattaca ggcgctggcc 144300
accatgccca gataattttt tgtattttta gtagagatgg ggtttcacca tgttggccag 144360
acttgtcttg aactcctgac ctcgttaatc cgctggcctc ggcttcccaa agtgctggga 144420
ttagaggcgt gaaccgccgc cgcgccctgc ctagttctgc catttctcat gcattctctg 144480
ggtgaatcac agcatctctg ttagccttgc ttcccacttc tgtaaaatga gagtgacttt 144540
acatgtatgg ccacctcagg ggcttgtcac tagaagccag tgaaataatg ttgagtctgg 144600
ttccttgggg ttgaaattgg gaccgccaac cgctttccta cccagagcag caactagcct 144660
atatggcggc cttttatgaa tgaggaaaag acaccgcctc ttggcagaaa aaaaaaatta 144720
agaaaatggc tccctcttct gggtgcaagt tgcccaacac ccaggaatat ggctccaaaa 144780
gcaatggact cccacccctt tcttgcccaa aagatcatca aatggaacag catgtcaaat 144840
acctttatta agtactttaa agttggctgg gctctgtggc tcatgcctgt aatcccagaa 144900
ctttgggagg cagaggctgg aagatcgctt gaggtcagga gttcgagacc agcctggata 144960
acatagtgag accctgtctc tataaaatat atatatagat ttatttgaga cagcgtcttg 145020
ctctgccact caggctgggg cgcagtggca caatcatagc tcactgcagc cttaacgatc 145080
ctcctgcctc agtccctaga gtagctagga ctacaggcat gcaccatcat gcctggctaa 145140
ttaaaataaa taaataaata aatactttaa agttaaaagt gctttttaaa aaataataag 145200
gccaggcgtg gagactcacg tctgtaatcc cagaactttg gaagaccgag gcgggtggat 145260
cacgaggtca ggagatcgag accatcctgg ctaacacggt gaaaccctgt ctccactaaa 145320
aatatgaaaa attagctggg cctactcggg aggctgaggc aggagaatgg cgtaaacctg 145380
ggaggcggag cttgcagtga gccgagatgg caccactgca ctccagcctg ggcgatataa 145440
caagactctg tctcaaaaaa aataaataaa ataaataata ataataatag gggccaggta 145500
tggtggctca cacctataat cctagcactt taggaggctg aggagtttga gtccttggag 145560
accaggggtt tcaggccagc ctgggcaaca tagcaagacc ccatctctac aaacaagttt 145620
taaaacttag ccaggcatgg tggtgcatgc ctgtagtcct agctattgca gggactgagg 145680
caggaggatc acctgagccc aggaggttga ggctgcagtg agctgtgatt gtgccactgc 145740
actccagcct gggcagcagt gcaaaaccct gtctcaaagg aaaaaaaaaa cctaggaagt 145800
gttgttccca tgataaggat cagcctccgt gtggtgcttc cttcaccatt gcccaatccc 145860
caggctcctg ggtgcttaat attccctcag gaacacacct gctttgtctg ggagagacct 145920
gggcgtcttg gtggcggggt ttgggggtac ttgctcatgg gcttatgggg cctctctctg 145980
tgtcccccca ggtttacaag tcgtcctgaa gtcgatcatg aaggcgatga tccctttgct 146040
gcagatcggc ctcctcctat tttttgcaat ccttattttt gcaatcatag ggttagaatt 146100
ttatatggga aaatttcata ccacctgctt tgaagagggg acaggtaggt ccacggagca 146160
tgatgcatct ttccagtttt ctccttcagg gacaagctct tgggaggatt aggcaggggt 146220
gtgcttcttt ctcctggcag ctgggaggac cgtctccttc agagagcact acaggagagg 146280
cagtgagtga aatagcctct gagatcttag ctgttgaaag gggtggggtt ccacagaagg 146340
tgacccagca gagaaagagt ttatttggga atgatcccag gaagcaccat cgggggaatg 146400
aggaagtgag cagagaaaga agggatcttt taaagagtgt gctatcaagc gggttaccac 146460
ttaaaactgg gactggatcc ccctgggcac ctctgggaga cagcaaagaa cacacaactc 146520
agctggtcac ggtggctcac gcctgtaatc ccagcacttt ggggggccaa ggcgggtgga 146580
tcacctgaga tcaggagtca gagaccatcc tggccaacat ggtgaaaccc catctgtact 146640
aaaaaataca aaaattagct gggtgtggtg gcaggcacct gtagtcccaa ttactcagga 146700
ggctgaggca ggagaatcac ttgaacccgg gaggcagaag ttgcagtgag ccaagatcac 146760
accactgcac tccagcctgg cgaaagagtg agactccatc tcaaataaat aaataaataa 146820
aaatataaat aaaaaaagaa cacacacctc agagccgtcc cagccaaggg gcaagggagc 146880
tggggtattt atacactggc ttctttttga cattggtgag gactgctcct agagtgggaa 146940
ttaatgcctg gcacatctgg ctgagtggaa caggtattct gggtgctttc agacctcgac 147000
cagtcctgac ttctaaagca agcaagaagt ggggagagtt gggccagaaa agggttattg 147060
cctcaatgca ttgtgagtgg taccttgtgg aaggtgagag acagagaaga ttccaggcac 147120
aggtgccatg ctaaacgata gttctcattt attataggaa cccatggatt tattttgttc 147180
tctgccctga gtgctgggtg agagtactgg atgagtcctc ctggtctccc ccaaccccca 147240
ggatgtacca gagatacccc aattgggagt cctggcacca accaatcaga acctagcact 147300
cagcagcatt ctgcccctcc ctgactatgc ccacattaac ccttcagtgg ctgggtctgg 147360
gggtagggtg agccccggaa aagccaggca gcgcagagac actctcccag ggctcagctc 147420
tgaaccagca gtgtggaagc agtgtgtcca ccacgatcca cactcaggaa ccaaatagcc 147480
cttggatacg ttttcagtta aatctttgcc atccaaactc tagctgcttg ctctctaaag 147540
ctccagaatg aaatggaatc aagtaggaag ggatgccttc agtatttcag tatttggacc 147600
actggccatc tgggtgcaga cagactgaat agcagttctg gttctgatga tttgggtcaa 147660
gggagctgtg aattgaagga gtggatagaa ggaatcaaga agcccaaagg ggaacccagg 147720
tgggcagaga aagaggtttc aggcccctta tttgggaaag gcagccacag aagaagattc 147780
tgtctgggag tggatttcca cccaccctct ccacccagtg acccccaagt ggatccgcag 147840
aggcagcccc tgagccctcc ctccccactc ctccccacgg ggagggaaaa cccactgggg 147900
aaggtttatt tgcaatggtt ggaggtttgg gtttttttgt gggttttggt ttgttggttt 147960
tttttttcct ctttttctct tgctcctcct gtctctttct ctcctgggct tgtgaagttt 148020
gctcaatatg gaatgtccta attatttctt tccccgatga agaaggtgtt aattgaggca 148080
gagctatttc tgctcctggc ctcgtcaccc aggcggaaat gcgagagaga gagagagaga 148140
gagagagaat gaatatgggg cagggcctct tggaaaaatc agccgtgagc agagaaacca 148200
ggactcctgg atcctaggtt tctgtgaagt tttattttat gtttttctac cctagactag 148260
ctaaaggaga agaggccatg gggttggctt gggtccgagt ggggttttga ggggacagat 148320
gtgggtggtg ccaccagagg ggaggaagcc tcgatttagg agaaagactg aaaagctagc 148380
tcacgattaa aaatataaga cgtgtgagta agagacagat atatacagac acccaggcag 148440
tgggttaatt ttaaaatgta tttataaccg aattcctcag acactctgga cgcttgtttt 148500
tctagaagca acgctcagag tgtttcgtgt cggtggttgg ggggttgagg gggattgcaa 148560
agctgctaaa gatagacccg ttttcagtag cattcctcag tgtcgggagc ccagttcctg 148620
tgtgcccagc accgtgccaa tcgcttagaa ggaagcaaag ataaagtgga aggcttcctg 148680
ctttctaaga gcttccaaaa tagttagagg aaacaagacc cctcatttgc agccattttt 148740
aacagtgaag gctaatgtgt gattataccc acgcccccct aaatatgaaa attcagtagc 148800
tattgtatgc ctgaaagggg ccaggtgcag tggctcacac ctgtaatccc agcactttga 148860
gaggctgagg tgggagtatc ccttgaggcc gttagtttga gaccagccta ggcaacatag 148920
ccagaccctg tctctgctaa aataaaaatt taaaaattgg ccgggtgcag tggctcacgc 148980
ctgtaatccc agcactttgg gaggccgagg caggcggatc aaaaggtcag gagttcaaga 149040
ccagcctggc caacatagtg aaaccccgtc tctactaaaa atacaaaaaa aataaattag 149100
ccgggcatgg tggcgtgtgc ctgtagtacc acatacttga gaggctgagg caggagaatc 149160
acttgaacct gggacataga ggttacagtg agccgagatc acgctactgc actccagctt 149220
gggcaacaga gtgagatttt gtctcaaaat aaaaaaattt aaaaattagc catgagtggt 149280
ggtacatgcc tatagtccta gctactcagg aggctgagga agaaggatca cttgagccca 149340
ggaattggag gctgcaaggc tgcagtaagc tatgatggtg cccgcactcc agcctgggtg 149400
acaaagtgag accctgtctc aaaaaaaaaa aaaaaaagag agagaggaag gaaagaagga 149460
aggaagggag ggagggaggg actggggctg tgttaactgg gctacacaaa gaggctacat 149520
ggagggtggg aattgagcca gacttggaca tggcgtggag acagagaaga ttccaggcac 149580
aggtgccatg ctaaacgata gttctcattt attataggaa cccatggatt tattttgttc 149640
tctgccctga gccttatgtt taaaagattt ttgccttcca acctgtattt atcaaataat 149700
agttcatgta ccaagtccag cataagtgag gaaggcgttt ccaacaactt aagttcatgg 149760
cgaggctaga cttggagttt ctattcagcc agagcttgaa aggccaacaa gattcattca 149820
ttcagcattg gtttatttcc ctctgctgtg tgctcagtca agggagcaga gaattggtgc 149880
tgcgaagtct gtagcacata cattgagaga tatttttgtt gagtaggaag cttgagttta 149940
cacacactca gctgtttgtt ttcttgtccg acaatgccac ggtcgtcttt gaaaaccttc 150000
aaaagcatcg ctcacagaat aaggtcctct cagacccgct gtgctggtaa aatgaggaca 150060
ctcccagatg tgagctttcc tgcctcccta ccccatcaat accttaagat ttggactgac 150120
ctttagcgtt cagcctgact gccacctccc caggaagctg tctttggttt ccagcaaaag 150180
gggtgtctgt tggcacgttt ctctctcctt gtggcatttt cacagcctgc ctcctgctat 150240
ttggggagaa agctcagctc ctgttcctta cccttaggca agggtaggaa ctgtgtgtac 150300
tggtgtccct cacccccaga acagctccct gagcccagta catcccaaga agaaaaaaat 150360
cagcaaggct tataggagaa taacacaatg cgcttgacaa atttgtccta atggatgtcg 150420
gaagaaggct gcacttacca gctacaccat gcacacggca catttactaa aactgactat 150480
attatggacc ataaagtttg tctcaacaga ggtcaaaaag ctgaaaaaaa tacaaataca 150540
aaacatattt tctgaccgta atgcaattaa gctggaaatc agtaacaaaa agagaactct 150600
aaaagtgttt gcagattaac agacatgcct ctcatttatg gatgaaatga tatgatgtct 150660
gagctttgct ttaaaaatat tctaggctgg gtgcagtggc tcacgcctgt aatcccagca 150720
ctttggaggc cgaggcgggc ggatcacttg aggtcaggag ttcgagacca gcctggccaa 150780
catggtgaaa ccccatctcc actaaaaata caaagattat ccaggtgtgg tggtggccac 150840
ctataatccc agctacttgg gagcctgagg caggagaatc ccttgaacct gggagtcgga 150900
gattgtagtg aggtgagatc atgccattgc actccagcct gggtgacaga atgagactcc 150960
gtctcaaaaa aaaaaaaaaa aaaaaattct agtggcaagg caaagtgttt ggaggggata 151020
cagaggaata gatgaaacaa aatttgccag aagtaaatag gtaagtgtct aaattggtga 151080
taggtacatg gtgaatcatt atattgtttt atacttctct ctcgctctct ctctcccccc 151140
gttctctccc tgtcttcctc tcccctctgt cttcatatat atatatatat atatacacac 151200
acacacacac agacacctaa taagtttttt taaaaaacaa atacatctaa attacccata 151260
ggtcaaagaa gaaataataa tggaaattag aaaatatttt acttgaacaa taatgataat 151320
gcatgacaaa atgttgagat gcaggtaaag ccacacttaa aggcaattta tagccttaaa 151380

```
ggcagttaat ccatccatct caaaagttta ggaaaagaat agaaaaaaaa aaaaaactca 151440
tggaaaacat aaagagaaaa gtagtaaagc tcagagaaga aattaatcaa tagaaaacca 151500
ataatagacc cccaaagcca aacattgatc tctttgaaga ctgatcacgt ttgtcccaaa 151560
agttattcgt tccaacagca ttatagagtc actggtccct atttctcaga gctggttttc 151620
cctgctcctt cccctgactt ttctcccctt cccttttgta gatgacattc agggtgagtc 151680
tccggctcca tgtgggacag aagagcccgc ccgcacctgc cccaatggga ccaaatgtca 151740
gccctactgg gaagggccca acaacgggat cactcagttc gacaacatcc tgtttgcagt 151800
gctgactgtt ttccagtgca taaccatgga agggtggact gatctcctct acaatgtaag 151860
tgatgctggg acagtgtgtg tggacaatca gagtctcagg gaggtggcct cctgggacca 151920
gtgagactcc aaggctgcaa tggagggacc ctgagctggg aaaggcagcc caaggacaac 151980
acagccccac tgaagctggc ctgaggctca ggcttttgaa gattacaggg gctcatgagc 152040
agaactctaa ctatagggca tagaagtctg gagggccccc agatgcaaca tcatttttca 152100
ttgtgcaagt gtttagatat aattttagat ttttgaatac ggaaaggtta tgtgatccaa 152160
aaaccaacac agataaaaga tagagtaata tctttggacg taggcgaggg gtccctgccc 152220
tgaggctcac ccagtccttc tccagccata ccactccccg tgggatgaga agttcctgga 152280
gccaagggga tgtgtctacc aagagcttgt gccccacttt gtaggccatg ttttaagtta 152340
ccaggatcct ggaattccct gcccatggcc agattccatg aacttgcgtg caattctcat 152400
atggatctgt tcgtaaccca actgagggcc aaggacatcc gaggggtggc tgttaacaca 152460
aatgtggcca gagcttggat gtacaagctg gaatgcccac acatatgtgt ggagcccctc 152520
tggcaggaca gagccatgac taagaagaga aagggacagg acagggctgg ctctccccac 152580
accttgaccc agtgcagata tccggattct aaattccacc ctgaccttcc aaagtgtaaa 152640
ggaaggtata tttgcaaagt agaagcacac agcatgtttt atttagttac cttttcaata 152700
tttccccgta gtatgtggtc tgcttttgta ctcttgccct agatcttaaa aatgttaggg 152760
atgtttctgg aaagatgtat ccctgccccc acttgcatgc tacttcctct tcccacaata 152820
tgcaacccct ttagttcctc agaatatcct tccaatgttt atttatgcaa ttataattat 152880
aagcataatc gaatctatgt cctccccccct ctttcttatc ccaaggagta gcattctata 152940
catgctgttc aattctgtga tttttgtttt ctcataacca cacgttctag agatctttcc 153000
actgcaggac atggacagtc tcttcacggg tgcacactag tatgcccagc taatttttgt 153060
agagacaggg ttcttccgtg ttgcccaggc aggtctggaa ctcctgggct caagcaatcc 153120
tcccgcctct gcctcccaaa gtgctgggat tacaggcgtg agccaccacg cctggccttc 153180
tttattcttt tgcacagctg catagcattc tattgtgtgg ctgcccatag ttttatttgt 153240
ttgccattaa gagaaatgct tgactggctt cctgtccact gacatggaac atgatgctgc 153300
tctgccagga gcatgttgca cgtacctctt catacttttg cagatatagc taggggggttg 153360
gagggtctcc attcccagaa gtgggattgc aggatcaaag actaaatgca tttataattt 153420
tatttttggg gaagattttt gttttgtttt tttggagaca aggtctccct ctgtcgtcca 153480
ggctggagcg cagtggtgta atcatagctc actgcagcct taaactcctg ggctcaggtg 153540
atcctcccac cccagcctcc tgagtagctg ggaccacagg cacacaccac catacctagc 153600
taatttttaa gaacaatttt atagagatgg ggtctcacta tgtttcccag gctgctctca 153660
gactcctggc ctcaagcaat cctcctgcct cagcctccca aagtgctagg attacaggtg 153720
tgagccactg cacccagcct aaatgcattt ataattttga tagatattta ggtgtgcaag 153780
```

```
ttttaaaccc cactctgtcc tcaccacagt tcaccttccc tcacctacta tgcaggtaag 153840
cagtccccag gcaggtcact tgtcagcagc tggagtgggg cagagccaag gattcaggat 153900
caaacacaag gatgccacaa ctgtagtgac cccatagagc accctggggc tgctccatac 153960
acacagctct gttgaccagt ggaggtctcc tcttcacctg ccctaagggc tgaaattacc 154020
attgaagttt aggccagcgg ttggcctgac ccgggagcaa tacctggctt cctcctcctg 154080
tacatagaga agctgaactt tcctcttggt cctagtgtat gttccttaac aacccattta 154140
tgcctagtgt tccattattg gaatgctaat cctgtgggag ttatttacat cctgctgctc 154200
aaggtcatca ctaaggtcgg atttttcaca cacacaaaaa ttgcaacctc cggcataaat 154260
gggttaagga atttccccac ttgtgggtgg agggagattt gcaaaaactc atccttgtaa 154320
tcctgatcaa caaaggcccg ttttagttgg gagtaggcag caaaaggagc cacatgaaca 154380
gttgcgcctg tcacgcactg cacaagaatg tcattcatat catagacaac atacgatttc 154440
tactgttatc ctgataattt attgacagaa aaaaggatgt ggggaaggga catggtgttc 154500
taatttgcat gaaaacctcg tctgagtgta gcatctctgg gaacatgcag cagatccgag 154560
ctcaggccct ctcttggccg tcacctgcaa acagcttgga caaagggtca gcccaattgg 154620
ccaaaactca ctggggaatt tttgtgggtt ctaggttttt actttgcaag gctggtgtga 154680
gaggaggttc cagcaggaaa tgaaccctcc tgagagggaa agagactggg aaatggagaa 154740
ggctgggaac tcagggagag aatgggagtg gggaatggga gctgaaaaaa attgtgagca 154800
taaaaaaggg atatgtcaca gggttggatg accagagaaa gcgtctgggg gttcagatta 154860
agatgctggg ggcgtgccca gtggtgggac aggaagcatg aatttccaga gggctcggtt 154920
ataaacatca ttgtccaatg ggtgtttccc ttggaagcct ctaagcttag agctaagcca 154980
cctctgggga cacaaactga gtggttaaga gcagagactc aggtgtcagc ctgtctgggt 155040
tccttccgac tcttccactt ccttgctgtg cagccttcgg caaggtgctt ggcctctctg 155100
tgccactatt tccacatgtg caaaacgaag agaagcatag tcccacctca caaggcacga 155160
ggactaagta aggtggattc gcatgaagtg tttagaactg atcctggccc ggggtgacct 155220
ccgtgtaagt caaattcccc accctgcatg gtgttccttt tagaaatgtg catgaatttt 155280
tcattagaac agctccagca gtgcctgagg aagtggagtg aggtgtgaga ggtcttactt 155340
tattcccctc gctggccctg ctattaacca ctaactcaga gtagctttct agcactttcc 155400
acacatttac atcccaccct cgtcctttgg ttagcagccc atgcaatgat ttggccttaa 155460
tgtgaaccta gaacacagct tctcgcccag ggatgatttc tgcccccagg ggacacttgg 155520
cagtggctgc agacattttt ggttgtcaca actggatggg aagaaggagg atgctattgg 155580
catcaagtgg gtaaaggcca cggatgctac tcaacattct acaatgcaca gcatccccca 155640
cctctgcccc accatagaga atgatccagg cccaaatgtc agtaaggttt ctgtcaggaa 155700
accctgggtc agaagaccaa ggttccttga ggacggggat gccttatact gcaatcagct 155760
gtcactctct gcctctctct ggggctgctg tgatcacctg gcctgcatgg acaaccccta 155820
ggagcagccc ccatccagtg cctggagaag tcagtggata aataccccag ctccctccct 155880
gtcgggcgtt ttgctctgcc ctgcatctct ccagtgggat caggctctgg ttgcccgcag 155940
ggttaacctg gtcacgtaca caccccttcac ttgccacctt cccttccctg tctggtattt 156000
cctgggatga acttttagat ttatttcctg ggctgctat aatgaagcac cacagactga 156060
gtagcttaaa acaacaggaa tttatggtct gacagttctg gaagccagaa gtccaacccc 156120
```

aagatgttag cagagctgac aacacgcccc tcaaaagcct ccgggggagg atccttcttt 156180
gcttcttcct ggcttttgct ggtttcccac aatctttggg attccttggc ttctagagcc 156240
ttcattctcc attccagtct tctgtcatct aatagcatcc tcccagcccg ggcacagtgg 156300
ctcacgcctg taatcccagc actttgggag gccgaggcag gcagatcact tgaggtcagg 156360
agtttgagac cagcctggcc aacatggtga aaccccatct ctactaaaga tacaaaaatt 156420
agccaggcgt ggtgggcggg tgcctgtaat cccagccact tgggaggctg aggcaggaga 156480
atcacttgaa cccgggagat ggaggttgca gtgagccaag atcatgccac tgcactccag 156540
cctgggtgac agaatgagac tccgtctcaa aaaaaaaaaa aaaaaaaaaa agaaaaagaa 156600
aagcatcctc ccttcgtgtg tctgtgtgtg ttctcctctt cttagaagga catcagttgt 156660
attggatcag aacctaccct actccagtcc aacctaattt taactaatta cgtctgcaat 156720
taccctattt ccaaataaga tcacattctg aggtaccagg gggttaggac ttaaacattt 156780
ttgtgtgtgt agcaggagga cgtaattcca tttataactc ctcctaaata aaacgacttg 156840
catgtgaact cttgtctggg gcttcccaaa gtgagataac ccctctctct acccctaaaa 156900
caacgagtag cgtctgtcaa tgccagggtg caggggctaa ggtgcccatc tttgagtttc 156960
tgctgaggag gacacagctg ctacgttgga gcactcttgg gttctgcctt cgtgcccagc 157020
catctccctt gggctagccc tgccctgggt ctatcctaga atgagcctcg atctgtttgg 157080
ccataggcaa gcagagtgtc tggaaatctt tgtcctccat gactggtgct ggagccgaag 157140
ccagtgggtg tggccttgcc agccaactcc atttacccag ctctgaacaa gctagtagtt 157200
gagatcaacg gagagtccag acagtcgctc caagcatctt ggaatccatg gacacaggtg 157260
taccgcagag gcttcccacc tgggtaggca gccctttgta agatcctggc accacattta 157320
ttctcttaac atcctttcag ttatccagta atcatttatt gagcacctac tgtgtgccag 157380
gcaatgatta ggtgattgga gacactgcaa cgaagaagac agactaaaat ctccaccctg 157440
gtaggagaga cagatgcaaa tggtaaacat gataaataat caatcaccca gaaagcagga 157500
gacactaagc aaatgtgtat gtactatggg aagcccaata ggaacgaaag ctacacaaga 157560
gaacaagtga tgggtggttc cttagtctag gtcaggcaat cagggagggc ttctcagagg 157620
aggtgatgtt tgagcagaga aggagggagc caggcagatg ttttggaaac agcattctca 157680
gcatggagaa cagtggcagc tcacctacag gatgtgtttg attcccttcc agattttgta 157740
ttcgtttctt gtttttctcc cttggcttcc tggtttaaat gccttttgaa gaaatctaag 157800
ctcaactaat cagcgatgct gttgaaggtt tatatcagga tatgcatccc agagttattt 157860
acaaaattag aacaaaactg gaagcaattg aaagcctgac aataggagat cagttaaata 157920
ccgtatggtc cttccgtatg atggcatatt atgtcatcat taaaaatcgt ctgctgggag 157980
aatattaagg atacagggga aaggctcacc atataatgat gagtgggggt gctgggcgca 158040
gtggttcatg cctgtaattc cagcaatttg ggagtctgag atgggtggat cacttgagcc 158100
caagagtttg aggccagcct gggcaacaca gtgaaaccca atctctacaa aaaaaaaaaa 158160
acaaaaatac aaaaatcagc caggcatagt ggcgtacatc tgtagtccca gctactcagg 158220
aggctgagac aggaggatag gatcacttga gccctggagt cagaggtggc aataagccgt 158280
gatcacgcca ctgcactcca gcctgggcaa cagagtgaaa ccctgtcaaa aaacaaaaca 158340
aaaaaaatga tgagtgggag aaacaagttt ttaaacaggg atcaaggagg ccaggcatgg 158400
tggctcacac ctataatccc agcactttgg gaggccaagg caggcagatc acctgaggtc 158460
aggagtttga gaccagcctg gccaacatgg cgaaacctca tctctactaa aaatacaaaa 158520
attagccagg catggtggcg ggcgcctgta atcccagcta cttgggaggc tgaggcagga 158580
aaatcgattg agcccaggag gtggaggttg cagtgagctg tgatcatgcc actgcactcc 158640
agcctgggca acagagcgaa agctgcacga gagaagaagt gatgcatggt tccctagtct 158700
aggtcagcca atcagggagg gttcctaaga ggaggtgatg tttgagcaga gaaggaggaa 158760
gccaggcaga tgttttggaa acagcattcc cagcatggag aacagtggca gctcaccctg 158820
tctagaaaag aagaaatgat aagaggggaa aatgagtttt taaaaaggaa tcaaggggag 158880
gtaaacctta tgatctcaaa ggtacaaata tgaaaatata agtaaagaaa aactggagga 158940
cactgtacca agctgacctt cgggtggtgg gatttgggaa tcttgatatt ctcaatactt 159000
ctttgtatct tcaaatttct ctatgatgat cacagtttac tttttttttt tttttttgag 159060
atggagtctc actctgttgc ccaggctgga gtgcagtggt gcgatcttgg ctcacttggc 159120
tcacctctgg ggttcaagca attctcctac ctcttcctcc caagtagctg ggactatagg 159180
catgcaccag catggtcagc taattttttg tatttttagt aaaaatgggg tttcatcatg 159240
ttggccaggc tggtctcgaa ctcgtaagtt caagtgatcc accaacctca gcctcccaaa 159300
ttggcttgag ccaattaaac ttgtcttgct aaatggttag cggggagaaa gaagaaggtc 159360
tcgggtcatt cctagaccag gaggcaggga gaaagggagg agaatgaacc tttcttaggc 159420
aaacagtgtc ctaggtgtcc ttatcttaca taatctgtcg agagagtcac actaaaataa 159480
atcattgatt gattgattga tacatcaata ataaatggcc agccttggtg gctcacatct 159540
gtaatcccag ctacttagga agctgaggtg ggaggattgt ttgagacaag gagttcaaga 159600
ccagcctggg aaacacagca agactcatct taaaaaaatt ttttttttta attagccaga 159660
tgcggtggct cacgcctgta atcccagcac tttgggaggc cgaggcgggt ggatcacgag 159720
gtcaggaatt cgagaccagc ctggccaaca gggtgaaacc ccgtctctac taaaaataca 159780
aaaattagcc aggcgtggtg gcacacgcct gtagtcccag ctacgcagga ggctgaggca 159840
gaagaatcat atgaacctgg gaaacagagg ttgcagtgag ctgagatcac gccattacac 159900
tccagcctgg gcaacaagag caaaactaca tctcaaaaaa aatgtttttt aattagccgg 159960
gtgtggtggt ccatgtctgt agttccagct acttgggagg ctgaggcagg aggattgctt 160020
gagcccagca gttcaaggct gcagtgagct atgatcccgc cactgcactc cagcctgggc 160080
aacagcaaga ccccatctct taaataaaca cataagtaaa taaatgatca tttttatttt 160140
attattaaat acacaagata aatgaaaaac aggcaaatct ttcttacaaa agaattccat 160200
ttaaagtatg taaacttcac tccccactgc cccaggaggt ggagactaat ctcccctact 160260
ttgagagtgg gctggattta gtgactcatt tccgaagaat agagtaggta aaggggaaaa 160320
tagaagtttt atagcggagg aacagataga taccacttta accaaatgat gaagattagt 160380
atcccccagg gatgtggata ttatgtaacc cttgatttta tgcctatata gcgttcttcc 160440
caaaaactcc taatcccagt tttttggggt tttgctctgt cttctaagct ggagtgcgat 160500
gatgcaatca tagctcactg cagctcaaac tcctggtctc aagcgatcct cccacctcaa 160560
cctcctgaat agctagggct gtaagcacat accatcatgc ccagctaatt gtattttttt 160620
ggtagagaca tgttctcaca cattgcccac gctgtcctcg agctactggc ctctagtgat 160680
cctcccaccc cagcctccag agtcactggg attataggca tgagccactg tgaccagccc 160740
agaatttttt tttaaggagt tgtgatgtcg tttaagagat gtgattcttc ataacacatc 160800
aacaacaagt cccagcgatg ggttggataa gtcttgggat ttcatgggag tattaagctt 160860

```
aaaagacttt gcatgatatc tgtgaactat atgtgatttc tgttggtaat gggggtcact 160920
gattctgcgg tttgccacct ccaatcatca tggaagaaaa tgttccactt ccagtgaaag 160980
taagaggaag taaaggggta attattttct atctaaattc acgaactcct tgaattctgt 161040
ccacagaccc ctaagtgttt cctccccaag gtgaaactga gagaatcttg ccagtgcctt 161100
ccgcagtcac tgtggctaga aaacccctca gaagaggtga tagtttagca ggtaactgga 161160
gttctcacca tccgtgtctg gctcagcccc catcacaacc agttacccag cccaaaatgt 161220
cagtagtact gaggttgaga ggctctgctc taggaggcca ggcctctcag aggaaggagg 161280
attggggtac tggctgggcc tcaagatgaa cctacccccct aagagctttg ggatggcgtg 161340
agtttctgtc catacccaag gactacaaat gcaggtttac tggaaattct gtgccaaaag 161400
tgaggtccaa ctcacttcta actgctacaa aacaaacctc catcaacata gcccatctct 161460
gttcttgacc tggaagctcc aaggtatcca catggctccc atgcccacta gacgggcctc 161520
ttccctggac cttcctgggc cagagaaggc tctgggtagc cttgtggaat caagatgggt 161580
gatcagccac ttcctctgtg ccaccctgtt ttggctactt ccctaggcat cagcctggga 161640
ttccttgatg gtaaaaatat aaaactctct gagctagggc ctttaatatc cccattttac 161700
agatgaagaa actgagtccc agagctgtgc acagcgattg agagtcagaa ttcagctctg 161760
tctcactcag tgtcaacatc ctcagattct gccatttata gcctcccaca gcaaatagga 161820
ttgagggctg cttctctgag ctcaagggga tagaatgggg aaccccatga gtactgcaac 161880
aaaactgttt gctggagaca agagctggtg gctctgtgtt gttctagtga caggtggcct 161940
catttcacag ggacccccctc accctatgtg ccccatgtgg ctcagaaaag ccagaaattg 162000
tctccactct cacaggggaa ggtccctgac cccctctttg ccagctgggc caaggcaaat 162060
tggggtcact tcatggggta caggacctac cctctcttgg ttgcccccaa ggaggggatg 162120
tggaggggct ggggacctgg caggaccagg gtgtcttgag ttaatttggg gctgccttta 162180
gccgagggct tctgtgtgcc tggcatcagc tttacattgt gtcttgatcc gtaaaacagc 162240
cctgtgagga aagatatttt taaccccatc ttccagatga ggaaacggag gcccacaggg 162300
tgacgtgacc tgccaaggtc ccctagccaa gagtgacaaa gccagggttc acacacagct 162360
ctggacacaa ttcatcaccc ttcatccgtc tctctctgac tctttctttt tccctctctc 162420
tctttgtctc tctttttttt tttttttttt tttgagacag cgtctcactc tgtcacccag 162480
gctagagtgc agtggcgcaa tctcggctca ctacaacctc catctcctgg gttcaagcga 162540
ttcttgtgcc tcaacctccc aagtagctgg gattacaggt gcgtgccacc acacccagct 162600
aattttgggg ggttttgttt tgttttgaga tggagtcttg ctctgtcgcc aggctggagt 162660
acagtggcgt gatctcggct cactgcagcc tctgactccc aggttcaagt gattcccctg 162720
cctcagcctc ctgagtagct gggactacag gcatgcacca acacgcccag ctaatttttt 162780
gtattttagt aaagacgggg tttcaccatg ttggccagga tggtctcgat ctcctgagct 162840
catgattcgc ccgccttggc ctcccaaagt gccgggatta caggcgtgag ccactgtgcc 162900
tgccaatttt ttgtattttt aacagagact gggtttcaac atgttggccg ggctggtctc 162960
gagctcctga cctcaagtga tctgcctgcc ttggcctccc aaagtgctgg tattacaggc 163020
atgagccacc atgcccagcc tttgtctctt ttattcttgt gttctctctc tctcttcctt 163080
ctctttctcc acctccttct ccttctctcc cttctcctca cccttctttg tgcttttctc 163140
tgtgagtttc tcttcttctc tatttctctc ctttggtgaa tgtcaattag aaaagcagaa 163200
aaactgcgtt taatttgtga tcataaatgc atgtccctgg ccaggcgtgg tggctcacgc 163260
```

```
ctggaatccc agccctttga gaagctgagg caggaagatt gcttgagacc gggagttcaa 163320
aaccagcctg gtcaaaaagc aagaccccat ctttaaaaaa gaaaaataat taattagctg 163380
ggcatggtgg tgtgtacctg tagtcccagc tactcgggag gctgaggaag gaggattgcc 163440
tgagcccaag ggtttgaagc tgcaccgagc tgtgattaca cccctgcact ccagcctggg 163500
tgacagaacc agaccctgtc tcaaaaaaaa cctaataatt aaaaataaat aaataaataa 163560
atgcgtgtcc cctggccagt ggttgctaat gtttggaatc acctttgacc catgcccttt 163620
ttcattcata gatgtttgtc ttgaccaaaa tcaaagcatt agactttgga ctataaatca 163680
ctggttcatt caacaaccat cattgaatgc ctactgtatg cagacactct tctggacaca 163740
gaggagttga cgtgttggtg gggaaagcca gtgatcagtt gggataaaaa gggcagacag 163800
cagacattaa atagtttagg ctttgtgggc cagatggtct ccatcgcaac gactcaatct 163860
gctcctgtag cgtgaaagta acgacagata aagcgcgtaa gtgaatgagc atggctgtgg 163920
gccaattaaa cgttaaccta taaaaacagg tggctggccc gcgggctgta gtttgtggat 163980
cactgcctta gagatagtgt tagagggtgg tgagaggtcc gggatagaat aaaacagtag 164040
agagtttgtg cattgtcaag atgagaggtt gcagttcttc ttatacaccc cgaatggccg 164100
ggcaccgtgg ccattatgat ctataattct aacactttgg gaggctgagg caggaggatc 164160
ccttgagccc tagagtttaa gaccagccta ggcacatagt gagaccccat ctctacaaaa 164220
aaaaaaattt aaaaattagc tggacatggt ggagcatgcc tgtaggccca gctacttgag 164280
aggctgagat gggaggactg cttgagcctg ggaggttggg gctgcagtga gccgatcatg 164340
ccactgcact ccagcccgga tgacagagca agaactgtct caaaaaaaaa aaacaaaaaa 164400
acaaaaaaaa cagacctgaa ggaacaaatc atatgaatgc attaaagtat cacatgtatc 164460
caaaaaatat atacatctat cagcctggca cggtggctca tgcctgtaat cctagcacat 164520
tgggaggcca aggcaggcag attgcctgag ctcaggagtg caagaccacc ctaggctaca 164580
tggtgaaacc ccgtctctac taaaatacaa aaaattagct gggcatggtg gcaggcgcct 164640
gtagtcccag ctacttggga ggctgaggca caagaattgc ttgaacccag gagacagagg 164700
ttacagttag ccgagatcgt gccactgcac tccagcctgg acaacagagc aagactctgt 164760
ctcaaaaaaa aaaaaaaaaa aaaaaaaaaa aaaatatata tatatatata tatatatata 164820
tatatatata tatatatata tataatcaat taaaaatttt ccttaataaa taaacatttc 164880
tctccttctc tcccttggtg aatgtcaatt aataaagcaa caaaactatg tttagttagt 164940
gatcattaat gtatgtccct ggctgggtgt gatggctcac acttgtaatc ccagcacttt 165000
gggaggctga ggcaggagag gatagtttga ggccagcaat tgcttgaggc tttttgaaag 165060
acatgaagga gatgaaggga gccatggaga tatctcaggg aacagcagcc gaggtagatg 165120
gaacagccag tgcaaaggtc ctgaggcagg atgttcctgg catttgtgag gacatgtagc 165180
tgcccagatg tccagtgggg agtgagtgag gatgaaggaa ggagctgatg aaggaagatg 165240
ataaaatact tcatggatca gccaggcatg gtggctcccg cctgtaatcc cagcactttg 165300
ggaggccaag gcgggtggat cacaaggtca agagttccag accagcctgg ccaacatggc 165360
gaaaccccgt ctctactaaa aatacaaaaa aagttagcca ggcgtggtca tgcacgcgtg 165420
tactctcagc tacttgggag actgagactc gagaatcgct tgaacccagg agatggaggt 165480
tgcagtgagt tgagatcacc ccactgcact ccagcctagg tgacagagcg agactctgtc 165540
tcaaaaaaaa aaaaaaaaaa aaaaagactt cgtgaacaga cagcctatat aatttatgat 165600
```

ccaaaccagg acagttttga gagtgaaagg ggaaaaagag cactgaaaaa ataattagca 165660
ggcctggcat gatctataac gggtataaag tgggacacac agcctctctc acggtcactg 165720
tcagacttca gctttttcac actcaaatcc acccccatgt ttatcccata tactggagaa 165780
acgggtgttc tcctgagctg agttttgggg ttttttcctt ttgttttgtt ttgtttttgt 165840 tttttaaca tcctgtatac tttttctcaa tgaaccatgc tcaaaaaaat tagaggaaaa 165900
taaaccataa aacagaaggc actgaaggat tttgctggga ctcagccatt agtttgtttg 165960
atgagtattt atggagcgct ttctaagcac caggcaccac cagcgatact gggatgaatc 166020
agtaacatcc ctcacccttg aagctctctt gggcccattg ttatttactt aaaatactat 166080
gcaagtacgg agaaggggtg aagtgggaaa aaatcagttg gttgtaaagg ccagaatgac 166140
gggtctagtc ccacccatgc catctgcacc ctgtgtgatc caggcacatc atgttgcctc 166200
tctcagcttc agtttctcca tccaccaggc acagagatgg cgggaatcga ggaagatgtg 166260
gggagtattt catcagccca aaaagacttg gctaatgcga ccataattct gccttctgcc 166320
tctcctttcc cagaaaaata gcttaatcat ttggatttgg gataaacaca tttcctgtgt 166380
ttattattta aatgatccac caagctgggc atggtggctc acccctgtaa tcccaactct 166440
ttgggaggct gaggagggcg gattgcttga gcccaggagt tcaagaccag cctggccaac 166500
atggcgaaac cccatcttta ctaaaaaaat acaaaaaaat tagctgagcg tggtggtgcg 166560
tgcctgtaat cccagctact tgggaggccg aggcacaaga atcacttgaa cctgggaggc 166620
agaggttgca gtgagcctag atcgtgccat cacactccag tctgggcgac agagtgagat 166680
tctgtcccta aataaataaa taaataaata aataaataaa taaaataaat gatccaccaa 166740
caggaacccc aggaacattt gtattgacta tgcaactaat gcttagtgag cacctactat 166800
gtccctggtg ctgatctgga cactgggatt tagacaggaa aaatctctac cctggaggag 166860
ctgatgatca agatgacaat cttgaaatgc ataagttgac aagatgattc agacagtgga 166920
acgtgctggg aagagaatga gatgtctggc tgagctgcag gaaggggcaa gtccttttga 166980
ttgagaggtc caagaaggct tctctgatgg gggcacaatg gatctaaggt tgagtgataa 167040
gaagaaattg gccaagccaa gacctaaagg cagagttgct ccaggcatag gttcagagaa 167100
tggaaataat tggctgattg tgatcttgaa cttgaccttt cttttcttct gctaactttg 167160
ggtttggttt gttcttgctt ttctggctcc ttgaggtacg tgttgggttc ttaatttgta 167220
attttttttt ttttttttg cttttttgag acagagtctc actgtggtgc ccaggctgga 167280
gtacagcagc atgatcttga ctcactgcaa cctctgcctc ctaggctcaa gtgaacctcc 167340
cacttcagca tccccagtag ctgggactac tggtgcacag caccacaccc agctaatttt 167400
tttattttta ttttttagag atggggtctc actgtgttgc ccaggctggt ctcaaacccc 167460
tagctcaagc gatcctcctg ccttagcccc ccaaagtgct gggatgagag gcgtgagcca 167520
ccacatctgg cctctgtttt ttgtgatgta ggtatttgat gctataaact tccctcttag 167580
ttgcttcttg gccctttagc taaggtcaag tgtaaacttc cctcagcact gcttctgctg 167640
catctcacag gtgttggtgt gttgtgtctc tattttcatt catttccaaa attttttaag 167700
tctccatctt aatttctgca ttgacccaat ggttgttcag gagcatgttg cgtaatatcc 167760
atatatttgc atcatttctg aaattcttct tggtattgat ttctagtttt atcccacggt 167820
agtctgagaa gatgcttgac agaattccag tattttaaaa tttgttgaga gttgttttgt 167880
ggcctaacat gtggtctgtc ttggagaatg tccatgtgct gatgagaaga atgtatgttc 167940
tccatcagac atgcaagaga cagacacttt ctcacctgcc tcatgggatc cataaaagag 168000
tcaatcagaa gttggcattt aagaaagacc agaaggaggc tgggtgcagt ggctcatgcc 168060
tgtaatccca gcactttggg aggctgaagt gggtggatca cctgaggtca ggagttcaag 168120
accagcctga ccaacaaggt gaaatcttgt ctctatttta aaaaatacaa aaattagcta 168180
ggtgtggtgg cgggcacctg taatcccagc tactctggag gctgaggcag agaatcactt 168240
ggacccagga ggtggaggtt gcagtgagct gagatcacac cattgcactc cagcctgggc 168300
aacagagcaa gaccccatct caaaaaaaaa aagaaagaaa aaaaagaaag aaagaccaga 168360
aagaggtgaa ggagcaagct acagagatat caaactgtat caatctggct gggcgtggtg 168420
gctcatgcct gaaatcccag cactttggga ggctgaagca ggaggatcac ttgagcccag 168480
gagttcgaga ccagcctggg caacagagac cccctctcta caaaatataa aaatttaatt 168540
aaaaagatgt attggtcagg gcagccaagt tatgctgcag taacaaacat ccccaaagcc 168600
tccatgactt ttgacaacag atgtatttcc tgctcatgct acatgtccag tgcaggttgg 168660
cagtggggaa gaagggggct ctgttcagtg cagtcacttg agacctagct aatcacctag 168720
aacattgcca cttgctattc cagaaggaaa aaaggaatgc tagaaggtcc cacactgaaa 168780
gttcaatgct ctggctccaa aatgacagct atttccactc actcctcatt ggccagcact 168840
tagcatgtgg tcctcagcca accccaaagg gactcaggaa ggaccatccc accatattgc 168900
tggaaatatt tgatggcagc attaatgggg aacagtgttc caggcagtgg aagtctttga 168960
gcccttggaa gaaagacaag gcgatctcta gagcacatcc ttcccaatat taatgaattt 169020
aacaaatgag caagccatcc tcccccactc tccttcccga attcagactt gtgcatatcc 169080
ctcccttaac ttgaactgcc aaagaagaga tgagaaccag gagaagagat ctgtgacccc 169140
atctttgctg atgaactacc acagaacagc catggcatct ccagtccttg tgcttgtaaa 169200
atgtactttt cattttgctc ctgaacgaaa tccacccacc cccaccccca aaccagggaa 169260
agctcatctc ctaatccaaa actgcaccca gccttccacc accttcttcc ctgggaattg 169320
ttgattccag agtatggaat tgaataattg gatgagtttg gaagagaaaa agtgtctcta 169380
aaatcaggca gcagaagccc actccccaga gaggatggtg cagatgagag ttcaggaggg 169440
agcttggctt ggggttgacg atctgagcta tgcagggaac ttggacacac ctctcaatca 169500
gtcattcaac agacaccact tattgagcac cgactgtgtg ccagatgttg tcctaggggg 169560
ctgggaatac aggaatacag cagggaacaa aaaggacaaa gcccctccct cttgtcgaat 169620
ggacattcca gccaggaaga cgagagaaca agagaaataa gtaaagtata taggcggtga 169680
aatgcaaatg ggaaaaaaga aacaatgggg accagaaatg aggggtgcaa ttgtaaaggg 169740
ccatcagggg aggcctccct cagaaggtgg catttgagta aaaaacctga aggaggtgag 169800
gggaaaccat gtagcaatct caggaaagag cattccaggc agggagggac agcctgtgca 169860
agggccgagg taggactgtg cttggcgtgg ttgagaaact gcaaggaagc caggtggctg 169920
gaaccgaatg agcgagggaa aaggggagga gataaaagca aggagatggg agggttggag 169980
gccccctctg ccattcagta actgagtaac ttcatttatt tcctgtagct tgaaccacaa 170040
agaaccacaa atagagtagc tgaaaacaac agaaatttat ttattctctc gcagttcagg 170100
aggccaggag tccacagacc atcaaggtca gctgggccac agaccatcaa gatgtcagct 170160
gggccatggt gcctcctgag acttggtctg aaatcccttc ttgcctccct cctagcttct 170220
ggtggtttgc caacagtgct tggtggtcct tgtcttgtag acgtatcacc ctgatcccgc 170280
cttcatctcc atttcacatg gccttctccc tctgtgcaag gttgtctctg tgcccaggtt 170340
tctccttttc ttattattta cttatttgtt tgtttgtttc tttattttag acacagggtc 170400
ttgctctgtc tcccaggctg gagtgcagtg gtgcgatcat agctcactac agcctcaaac 170460
tcctggcctc aagcaatcct cctacctcag cctcctgagt agctgggact gcagatgtga 170520
gccactgtgc tctgcccaga tgtcctcttt ttataaggaa acccgtcatt taggatgagg 170580
ttccacccta atgacctgat cttaacttga ttccatctgc aaagacccta tttccaattc 170640
ataggtacca gggattagga cttcttcaat gcatcttttt ggagagaccc actgcaaccc 170700
acaacagaac tgtgggcatg taacttgacc tctcggccag gcgtgatggc tcacacctgt 170760
aatcccagca ctttgggagg ccgaggtgag tggatcgcct gaggtcggga gttcgagacc 170820
agcctggcca acatggtcaa accccgcctc tactaaaaat agaaaaatta gctgggcatg 170880
gtagcaagca cctgtaatcc caactacttg ggagggtgag gcaggagaat tgcttgaacc 170940
caggatgtag aggttgcagt gagccaagat agtgccattg cactccagcc tgggtgacag 171000
agtgagactc catctcaaaa aaaaaaaaaa aaaaaataga cctctctgtg cctcagcttt 171060
ctcacccggg aggatgggga taattatata cccactcctg ggttcatgga gaggattaaa 171120
tgagctcaaa cagtccaagc ctccacgtgt gtctgttgtg gtgctgggta gcatgtcctg 171180
tggccagagg ttcccaagct tgtcgaggac ccaggcaagg gcagattcgg gtcttgttgg 171240
cagcacctga gatggacggg ctgccttggt atggaagggc ctcggctgtt tttccctttc 171300
agtcctgtcc ctctccccca tcctccaccc tgtccctgtc atctgagcct gctcctcgtg 171360
atggctcaga gtctccctac tggcggccgg tgcagagttt cgttccctgg gctatattta 171420
gccctgagaa atgggaacga gaaccctcag ccgccaaagt gatggagaga ggagcacaaa 171480
gccagtgctg ccttctgtcc agcaatgttc cgctgactcg gttctttctt ccagaacctt 171540
ccagaagcaa agcattggca tttctgagct cgttaaaaca aggatgtggg ctggtggctg 171600
gcacattcat tgtccccaga acctgtctgt gtccatgatt aaagctgact ttgttagttt 171660
tattttcagt gctttttttt ttttttaatc catggcaaaa cacacatgac ataaaattta 171720
ccatcctaat atttttttta actttgtaac atttttttaat tgacaagtaa ttgtacttat 171780
tcatggggta catagtgacg tttcaatgca tataatgcgt agtgctcaga tcagggtaat 171840
tagcatatcc atcttctcag acctttattg tttctttctg ttaggaacat tcaagctcct 171900
ccttctagct atttgaaacc attaatatat tgttgtcatc ctaaccattt ttaaggatac 171960
agtttcgtga aattaagtat aatacattca cattgttgtg caactgtcac caccatccat 172020
ctcccaaact tttccatctt ccaaatgtaa ctctgtcccc actaaacgcg aactccctgt 172080
tccccctccc ccagcccttg gcacccacca tgctactttc tgtttttata aatctgacga 172140
ctctagggac ctcctataaa tggaatcata caggattttc ccttttatga ctggtttatt 172200
tcacatagca taatgccctc aaggttcacc catgttgcag cacgtatcag cattttcttt 172260
ctttttaagg taaagttgac tattaaaaaa aaacttctgc cgggctcagt ggctcacgcc 172320
tgtaattaca gcactttggg aggccaaggc aggcagatca ggaggtgagg agttcaagac 172380
cagcctgacc aacatggtga aaccccatct ctactaaaaa tacaaaaatt agccaggcat 172440
ggtggcgggc gcctgtaatc ccaactactc aggaggctga ggcaagagaa ttgcttgaac 172500
ccgggaggca gaggttgcag tgagctgaga tcatgccact gcactccagc ctcggcaaca 172560
gagtaagact ccgtctcaaa aaaaaacaac tttttaagaa ttgaagtaga ataaacatac 172620
agaaaaatcc gcggattata agtgaagagc ttgattaatt gtcacaaact aaacacatcc 172680
atgtaaccag cacacaaatg aggaaacaga aacttctcag ccccagaagc ccccctcata 172740
tcctgttcct agtcactacc tccccgcaag ggtaccccta ccaggacttt gagcatcatt 172800
caccagttta gcctgttttg tattttgcat aaatgaagtc tggcttcttt tgcttgacgt 172860 taactttttta agatctcatg tgacctgtgg cattgttcat tgcatgtatc ctctctctcc 172920
tattgataac agtgtggatt gtttgcaatt tggagctatg atgaatacca ttgctatgaa 172980
tgttcttgtg tgtgctttct gttgtgtaat tattcagaat tactatttcg gaattactat 173040
ctaattgtag tgatcttgga tcagtaacta tccaagaatt actgggtgtt ggcaaaggta 173100
catacagtta tacactgcac aatggcattt tggtcaacaa cagatcaaat atgtaacagt 173160
ggtcccataa tggaccgaat acataacagt gattatcata cagtattttt actatagctt 173220
ttctgttttt agattctttt ttttttgaga cgaagtctcg ctctgttgcc caggctggag 173280
tgcagtggtg tgatctccgc tcactgcaag ctccgccttc tgggttcacg ccattctcct 173340
gcctcagcct cccaggtagc tacaggcgcc cgtcaccagg cccggctaat tttttttgta 173400
tttttagtag agacggggtt tcaccatgtt agccaggatg gcctcgatct cctgacctca 173460
tgatctgccc gcctcggcct cccaaagtgc tgggattgca ggcgtgagcc accgcacccg 173520
gcctgttttt agatattttt agatacacta tagagttaca attgcctaca gtattccata 173580
gaataacatg ctgtatgggt ttgtagccta ggagcaatag gcgagaccat gcagcctagg 173640
tgtgtagtag gctataccat ctaggtttgt gtaagtacac tccatgatgt ttgcacaaca 173700
aaatgaccta gtgacacatt tttcagaatg tatgcccatt gttaagcatg acttaatttt 173760
agcatagaaa ctctcaacca atttttcaag tagttgtacc atgtgttatg ggttttattg 173820
tctcacccca aaattcatat gttgaagtcc taaccccag tacctcagaa tgtgacctta 173880
tttggaaata gattcattgc acatgtaaag gttttgccat tggcaaaact gccgttattt 173940
ttgcaccaac catagcagtt aagatgagat cattagggtg ggtcctaatc taatacgatg 174000
gtgtccatat aaaaagggga gattttggca cagagacagg cacactcaca ggaagaatgc 174060
catgtttaaa caaaggcaga gctcaggatg atgcctctac aagccaagaa tcagcaaaga 174120
ttgccagcaa accgccagaa gctaggagag aggcataaaa cagattctgt ctcacagctc 174180
tcagaaggaa ccagcccttc tgacaccttg agcttggatt tttggcctct ataactgtaa 174240
gacaataaat ctttgttgtt taagccacct aggttgtggt tccttgttac agcagccaca 174300
ggagatgaat acagcatggt gccctcccat tggcagatta tgagggttcc agttgctcca 174360
cagcttcaca gacacctggt agtaatgacc tcatcttaac ttctttctca ttttagcctt 174420
tcttccaggc agcagcagtg tcatacatgc ttttaaaggt gggcttttaa agccacactt 174480
gagagccctg cattctgcag gtgtcacagg gtgatcaact attcaaaggc taccccctgcc 174540 ctgacagctg gaggcaaggc ttcccagcac agaggttaag cccatggact ctggggccag 174600
gtggttagtg caaatcccat gtccactagt gaataactct gtgatcttgg gctgatgatt 174660
ttgtctttct aagcctcagt ttcctcaata gtaacatggg cattataaca tagaggcatc 174720
atgaggatta aatgactaag tgagctaaca tacataatgt gcttaggaag gtgccagcac 174780
accataaata ctctgtaagt gctggctttt atcattcttt tctctctctc tctctctctc 174840
tctctctctc tctctctctc tctctccctc tctctctctg tctctctttc tctctccacc 174900
ccccaacctc ctctccttga ttttcttccc ctcatcttac ttccttcttg ctatagtgtt 174960
ctattttctg tttcagagag tattctattt gtggactttt ttcctcttga aaattgagct 175020
gaaacttctg agaatttttt gtgattggca ttaaggctgc agggaatgga gcagggagac 175080

-continued

```
acttgaggaa agggctcatg gaccatctgt ctggcttggt gatttcacca ggccatcaga 175140
ctctgtggtc atgcatctcc tctaagggga gtctatgact gtgttgggag aagagaagga 175200
accagggatt aattaatcca tttcaatagg ttttgtgttt tgtttggttt actttttcct 175260
tctccttctg gactgtggtc tgggaagtcc tcttgtgttt cttactccat tcccaggtca 175320
attatgttat gtgaggagaa cataattaag agagagcttt accctttgga tgttttcttc 175380
agaaaacgtt cctccatttc cccctctggg atgccagagc cccagaactc cacaagccaa 175440
gaacatttaa gacagagcca caagagaacc gagcttcccc ttccctcacc tgtcaggttc 175500
tatctgagtc ccagtcaact ctcacctgct ttccctcctc acaccctaca gagcaacgat 175560
gcctcaggga acacttggaa ctggttgtac ttcatccccc tcatcatcat cggctccttt 175620
tttatgctga accttgtgct gggtgtgctg tcagggtaag tttctgctac tccccacccc 175680
atcccactca ctcctctttg ctaacttctt tccaagtaga ggccattgaa gctttgtttt 175740
cattcactag acagagaaaa ggcttcttcc cttgtttggg ttaccagact gttattagca 175800
agccatgcac aggtgcagag gttgtgtact gctaggggta cccagtgaga gggttcatat 175860
gggctttact ttctttacat ttttttaaa aaccaatagt ttgggtttac ttctccccca 175920
ttttccaaat ataaaatcat agcatatgct ctaacggtgt attttcctga cccatattgt 175980
cctctatccc caagattttt ttggcttaat cataaatggg cttcattttt cttaccataa 176040
gaagtctggg cacttgtatg gtggctctat ggcaccatca gcaaccccag attcttccag 176100
ctttccattc tgacatcttt accagaggct tccaatctcg tggatacctc atggtcttaa 176160
gatggctgcc tcacgccctc cggatggcca cttcatgttc caaacaggaa aaggaagaag 176220
ggaaacagga agaggtggga cctatggcag agaagccaac ctgctgcaga aatctttcat 176280
tcatggctta ttggtctaac ttaaaagagg gctgaaataa ttattagcca aaagtatgaa 176340
gagaatgaga atgaggtatg cagccagtgg tggttggcat ggcatggttt tatcctttcg 176400
gttttttct tttttattgt ttttttttga gacggtgtct agctttatta cccagactgg 176460
agtgtagggg gcgatcatag ctcactgtaa cctagaactc ctaggcacaa gcgatcctcc 176520
tgcctcagcc tcctgagtag ctaaggcaac aagtgtatgc caccatgccc agctacattt 176580
tttatttttc atagagatgg ggcccactgt gttgtccagg ctggtctcaa attcctggcc 176640
ttaaatgata ctcccatctc agcctcacaa agtgctggga ttacagacat gagccactgt 176700
gcctggcctt tttctttacc taggcacagt tgtcgggaaa tgtgtgaagc tggcagaagc 176760
acccatcact ataatatccc agtcttttcc cagaagtcct gactcctcct gttgaaaact 176820
cctgacctcc agggacttct gaatccccaa acacacacac acacacaaac acacacacac 176880
acacacacac acacacacaa acacacacac aaacgtttcc taacattttc aaaacagcca 176940
tactctggct tttctatgct tctccaggga gtttgccaaa gaaagggaac gggtggagaa 177000
ccggcgggct tttctgaagc tgaggcggca acaacagatt gaacgtgagc tcaatgggta 177060
catggagtgg atctcaaaag caggtgaggc cctttcatcc tggggcccag ggatggagat 177120
cccaggccac ggagtacaaa gagagtcatg cagtttggag aaggctaagc tgggagggtt 177180
atgatgggag gagaaagaga acctgaattg gtagtcccaa attttatcaa caagaatcca 177240
gagtctgata tgaagaagtc taagatgaag ccaggatctg acatcacgta acttgaattc 177300
tgaaatcaga cgctggttta catcccggcc ctgccacttt ttacccatgc accacacatc 177360
cctgtacctc cgtttcctca gctgttacat ggaggcgatg gtagtgccta agtcatagta 177420
ctattggagt atttagtaaa ataatctcag ctgagtcact tggggagaga agtgcctgat 177480
```

```
acacggtagg cacatattta tttgttcagc catttaacaa acatttaggg agcacctgct 177540
gtgtgccagg cactgatcta agcactgagg atatgggagt aaacaataca caccaaatcc 177600
ctgccctcag agctctgata ttctaatgag agagataaag caaacaaata catgtcatgt 177660
tgggaactcc caaattcaga gaaggaagat aaaacagact aggaagataa aacagagtag 177720
gaagttggcc gggcgcggtg gctcacgcct gtaatcccag cactttggga ggctaaggcg 177780
ggcagatttc ctgaggtcag gcattcgaga ccagcctggc caacatggtg aaaccctgtc 177840
tctactaaaa atacaaaaat tagccaggca tggtggcgca cgcctgtaat cccagctact 177900
cgggaggctg aggcaggaga attgcttgaa cccaggaggc agaggttaca gtgagctgag 177960
gtcgcaccac tgcactccag cctgggcaac agagtgagac tctgtgtcag agaaaaaaaa 178020
aagagtagga agttagaggc agggtggtca gggaaggctt ctctaaggaa gtaccctctg 178080
agcagagaga cctgaaggac gtgaagaagg aagctgtggg gatgtcaagg gaaggggcat 178140
tccaggcaga gacagcaagt gcaaaggccc tgagctagga acgtatttga gacacagcaa 178200
ggaagccagt gcagctgaaa cagagtgaga ggtggggaca gctggaggag aggaagacag 178260
gaaggtgatg gagatcagat caagcagggg cttataggct gtggtgtgga cattggtttt 178320
tattttgcgc gaggtgggga gaatgttggc tattgctact gttgcggagg tggggcttga 178380
agtcacaaac cacccagcag catgtttttt ggtcggttga gctgtcacca tcagtcagca 178440
gagaatgggg gtggccgggc agacccttct tcctggtcca agggagaact catcctccaa 178500
atgcaggagc ttaactctgt gctcttcctc ttcagaagag gtgatcctcg ccgaggatga 178560
aactgacggg gagcagaggc atccctttga tggtaactgc tctaaaccca cctcaggggt 178620
gggtcccagg ggagaaggga gaagctgtgg tggggagtcg ggggagagca ggtgactggt 178680
tctaaggatc ttgcagaggg tagacgttcc tcttggagga attttaggac ttccatgcag 178740
agtttcccta ttctggcctc cacttttttg ttttaaccat ggacctggtt ttttctgctt 178800
tgtgccttgg tttttctcat ctgcaaaatg ggtatgatat aaacaatacc ctagctcacg 178860
agattgtttc tcagaatgat attcgttatg gcaaatagaa cacctgggat agtgcctggc 178920
atggggtcag cacgtttctg tttgctaaat aagtaataat tccaccaata atccagttta 178980
ctgtgaacgg ctgctgtctc ccatgttaga aacttaacga gacagaacca tgactttctt 179040
tcttttcttt ttttttaat tgagacagag tctcgctctg tcacccaggc tggagtgcag 179100
tcacacgatc tcacctcact gcaacctctg gctcccaggt tcaagcaatt ctctgcctca 179160
gcctcatgag aagctgagat tacaagcatg agccaccatg cctggctaat ttttatattg 179220
ttgatagaga tggggtttcg ccatgttggc cgggctggtc ttgaactcct tgcctcaaat 179280
gatctgcaca ccttggcctc ccaaaatgct gggagtgtag atgtcaattc atggtcccct 179340
ggaaacctga atatgaaagg agggaccatt aaaaaggtgt ccaaaagccc aacctcccca 179400
gcatagctgg gagtcagggg acagactgta agagtcactg tgtatccaac ctgaggcttc 179460
atgaaagtaa agtttcctag aatttagaga tagggttgga tgcggtctgt ctgtggctca 179520
catctgtaat cccaacactt tgggaggcca agacaggagg aacacttgag cctgggagtt 179580
caagaccagc ctgggcaaca taatgaggtt ccgtctctac aaaaaataaa cttagccaga 179640
tgtgggggca cacgcaccta tggtcccagc tactcaggag gctgaggtgg gaggatcact 179700
tgagcccaag aggtcgaggt tgcagtgggc accactccac tccagcctgg gtgacagagt 179760
gagaccctgt ttcaaaagaa aaaaaaagaa tttagagata ggccagaata atatgtctgc 179820
```

aatataataa taacagcaat aagaaaaata atagtactcc ctgaaaaatg caacttcttg 179880
cttgagattt atcttctcat actttagaaa actggttaga caggggctgg gcgtggtggc 179940
tcatgcctgt aatcccagca ctttgggagg ccaaggcggg tggatcactt gaggccagga 180000
gttcaagacc ggcctggcca tcatggcgaa accccatctc tactaaaaat acaaaaatta 180060
gctaggtgtc atggcacacg cctgtaatcc cagctactca ggaggctaaa ctacgagaat 180120
tgcttgaacc tgggagacgg aagttgcggt gagccgagat cacaccactg cactccagcc 180180
taggcgacag agcaagactc tgtctcaaaa aaaagaaaga aagctggtta gacagggtga 180240
tgacttttga ttaaaaatct gagagatttg agggaaataa aagaactggc actgcgtccc 180300
agaaggttat aaaatgaatt ttattatctt agttggggag gggagattac ctaactcccc 180360
taaatgagtt aggtaatcta actcatttag ggtacctaaa tctttttatt ggaagtctac 180420
acctgaactt gtctgctgtg gagcccctgg ggtgtatagc ttgaatatgg gggcagaatc 180480
ccaaaattgc agcctgccta gcgagtatgc tacaggtcaa ggggtggact gttttcataa 180540
gaaagtgagg tttcttagaa tttaaaaata gaggctgagt ggggcggctc acgcctgtaa 180600
tcctagcact tttggaggcc aaggcaggca aatcacttga ggtcaagagt ttgaccagcc 180660
tggccaacat ggcaaaaccc catctctact aataatacaa aaattagcca ggcgtggtgg 180720
tgcatgcctg tagtctcagc tactcaggag gctgagggag gagaatcgct tgaactcagg 180780
aggcagaggt tgcagtaagc caagatcaca ccactctctg ggtgacagag caagattctg 180840
tctcaaaata aataaacaaa taaataaata aaccagaagg aaaatagtgg ctgagggccc 180900
agacctggag tcggactgaa cccgacttga ttcttgtctt taccccttta agcaaagtga 180960
tagtgccacc ttgaacctca gtttacacat ctgaaaaatg ggtatactat tagttcccgt 181020
gagaacagtt gccgtgagag ttaaatccaa ggacacactg tgtccatatg gtctgtgttg 181080
caaaaagggt aacgtctttt tctcttgcca tgtttccatt gttggagctc tgcggagaac 181140
caccataaag aaaagcaaga cagatttgct caaccccgaa gaggctgagg atcagctggc 181200
tgatatagcc tctgtgggtg agtcccttcc tctgccacct atcagttgtt catcacctat 181260
cgcccaagag acatggtggg gtgggggcag agggcttgca aaccgtgctg cctggatttg 181320
ggtctcagct ccaccctttc ccacctgtgc gtgtgtcctg ggcagattac atcattatgg 181380
gaataacatc cgtgcctagc ttctcattat tttgtgggaa ttcaactaaa tgatccccat 181440
gaagcatggc aaaccagcac ctggcaggga cgaagctccc agtcaagttg gtgaatgttt 181500
gtgactcatt cgggaagtat tcatgggga cctgcttata ttaggtgctt ggttgcaaac 181560
aagacaaggc agtcacgagg ctgagctggg aggatcactt gagcctggga agtggaggct 181620
gcaataagcc attattgtgt tactgcactc cagcctgggc acagaaaaaa aaaaaaagac 181680
acaaactgag ccaggcacag tggctcacgc ctgtaatccc aacactttgg gaagctgaga 181740
tgagcggatc acctgatgtc gggagttcga gaccagcctg gccaacatgg tgaaaccctg 181800
gctctactaa aaatacgaaa aaaattagcc tgtagttcca gctactctgg aggctgaggc 181860
gggagcatca cttgaacctg ggaagcagag gttgcagtga gctgagatct catcactgcc 181920
ctccagcctg ggcaacagag caagatcctg tctcaaaaaa aaaaaaaaaa aaaagacaca 181980
aaccaaatcc ctacctacat ggagctcaca gtccagtgca ggaaatagaa attaaacaga 182040
gaattacaca aataaacctg taatggtaat ggcacttcag ggagaggctc tgggcttagc 182100
ttgctctaga aggatgggga gcagtcaggg aaggctacct ggaggaagtg acggttaagc 182160
tgggaactga aggatgggta ggagatcact gtggtggtga tagcagaagg aacagtgtga 182220
gaggcagggc tcagaccttt gccaccacaa gggccagagt tcgagggagg agggaacatt 182280
tattctttcc cttctcactc ctctgtccta ttgattcatt ggctgtgatg atgttgattt 182340
tgaccttcta aagtgagaat gtattgttat tgttgttgtt gttctttaat gggtttttgt 182400
ttttaatgga aggaagagca tccaggcaga ggaaataaga ctggaataag attgagggga 182460
gaaggaattt aggctgcttg ggaaactgtg tggccgcagt ttagaggaag aaaggatggc 182520
aagagaaaga ggaagggagg aagagaagga gggagagaag tgaaggaagg agggaagtta 182580
gtacatccat gtgtttctga tccatagttt ctgatccact atttcgtatt ccccttttat 182640
cgctcgcccc tagtttataa ccttattgct gagtttaggc ataatttcca ttgcgatcac 182700
atatctcgta gggtggatac actatggttt gtttagccat agctctatta tagggtgttt 182760
gagttgtttc caataatttc tcttacgaag aacactgctg tgcacattta cgtacaatga 182820
ctccccccac cctttgggcg tatttccttg gggataatta taggatcaaa gatattaaca 182880
gcttttcaac tcattattca aagagccatt ctgagtttca aaaacatgga acccatttat 182940
aaacctgcca agtatgcata tgttcatgga ttccccaccc aggccatcga atattaccaa 183000
tttaatttcc tttcccagtt aagtgggttt gtaatgaaac cttaaagctt gttttcattt 183060
gcatttttaa tttccagcca aaacacgctt ttctttgtaa tggagaactc attctgcttc 183120
cactcgtgtg tgcatctgtt taatttcctg taagcaaatg tcaagaattg gagcgctcag 183180
taggtgtctt gagtatttga tcaattatgt ctgtctcacg tgttacgtta cctccattgt 183240
ttaaaatctg ttttatgacg aggtacagtg gttcacgcct gtaatcccac tgctttggga 183300
ggccagtgca ggaggatctc ctaagatcag ccgttcaaga ccagcctggg caacataaca 183360
aggctccatc tctgaaaaac aaaatgttga aaaacttagc caggcattat ggcacacacc 183420
tatagtccca tctatttagg aagctaaggc aggaggattt cttgaaccca ggaattcaag 183480
gttgcagtga gctatgattg tgccactgca ctgcaacgtg ggcaacagag tgagaacctg 183540
tctcttaaaa aaataaaata acatacattc ttaaaaatct actttgctgg ccgggcgcgg 183600
tggctcacgc ctgtaatccc agcactttgg gaggctgagg cgggtagatc gcttaaggtc 183660
aggagtagga gaccagcctg gccaacatgg tgaaaccgtg tctgtactaa aaattcaaca 183720
attagctggg tgtggtggcg tgagcctgta atcccagcta ctcaggaggc tgaggcacaa 183780
aatcacttga acccgggagg cggaggctgc agtgagctga gatggcgcca ttgccctcca 183840
gcctgggcat caagagtgaa actccatcaa aaaaataaaa aatctgcata tacatatata 183900
tgtatatata tttttaattt ttttaatttt tttttttttt tctgagatgg agtcttgctc 183960
tagcacccag gctggagagc aatggtgcca tctcggctca ctgcagcctc cgcctctgtt 184020
aacaaggcag gtgacattgc agctttctaa acagacccaa aacccaggcc agtggcttgt 184080
tctttcatag ccacgtttgc tacaggcaaa tccaccaaaa cccacctcat cagcctgatt 184140
actcaaaaag acaaagaaag gagcccccaa tctagccagt ggttttctag accaccccaa 184200
aagagatctc tggaattcca ggattctggc aaggaatcac atttagcttt atttatttat 184260
gtaaagaatg caacaataca ggctgggtgt ggtggctcac gcctgtaatc ccaacatttt 184320
gggaagctga ggtgggagga tcgtttgagg tcaggagttt cagaccagcc taggcaacat 184380
agtgagaccc tgtctctatc aaatattagc tgggcattgt ggcacacgcc agtagtccca 184440
gctactcgtg aggctgaggt ggatcacctg agcccaggag gtcaaggctg cggtgagcca 184500
cagcatgccc ctgcactcca gcctgcgtga cagagacttc atctcaaaaa aaaaaacaaa 184560
aaaaagtaat aatacagtaa tgcatatttc aaagtaaggt gggagctatg tggtatttgc 184620
gttcacgttc acattatacc acagtatgca cagtcctttt tttttttttt ttgagacagt 184680
gtcttgctct gatgttcagg ctggagtgca gtggtgcagg catagctcac tgcagcctca 184740
aacccctgga ctcaagtgat cctcccacct cagcctccca agtagctggg actataggtg 184800
tacactgcta cactcagcta agttttttat attttttact agagatggga tctcaatatg 184860
ttgcctaggc tggtctcaaa ctcctggcct caaacaatcc tcctacctcc acctcccaaa 184920
gcagtgggat tacaggcgtg agccaccaca cctggcccac atgcagtctt atataattgg 184980
tgattctact gcgctgttga atcagttgat aaacgcacta taaagcaggt tcattcctaa 185040
ttgatgaact tactgctgaa ataaggaact tgaatcattt acatgaaaag ttgagccatg 185100
ttgctgaaag gatatcaatt tttttttctt ttttttcttt tttttgaga tggagtctta 185160 ctctgtcgcc caggtgggag tgcagtggtg cgatctcggc tcactgcaac ctccaccttc 185220
caggttcaag cgattctccc acctcagcct ccaagtagct gggactacag gtgcacacca 185280
ccacgccctg ccaatttttg tactgttagt agagatgggg tttcaccatg ttggccaggc 185340
tggtctcaaa ctcctgacct caagtgatct gcccacctca gcctccgaaa gtgctgggat 185400
tacaggtgtt agccaccgcg cctgacagga tatcaaattt catttagact gcaggaatac 185460
gttcaagaga tctattttgt acagcctggc gactgtatta ataacaatgt attatatact 185520
tgaaaattgc tcagagagta ggttttaagc attctcaccg tgagaaaagt gataagcata 185580
tgtaataatg catatgttaa ctagctcaac tgagccactc catagtgtat acatatggtc 185640
aaaatatcat gttatgcact ataaatagat acagcctgta tctgtcaatt taaaataaat 185700
gaataataac tttaaaaaga aaaataacag tatggctggg cacggtggct cacacctgta 185760
atcccagcac tttgggatgc caagacaggc ttgaggccag gagtttgaga ccagcctggc 185820
caacatggcg aaactttgtc tctaataaat atacaaaaat cggctgggca tggaggcggg 185880
cgcctgtaat cccaactact tgggaggcag aggcatcact taacctggga gatggaggtt 185940
gcagtgagcc aagatctgca ctccagcctg ggtgatagag tgagccttta tttatttctg 186000
taaagaatgc aataatacag gcctggtgcg gtggctcatg cctataatcc caatgttttg 186060
gaaggccaag gtgagaggat catttgaggc tacaggcgca tgccacagtg cccagctaat 186120
acttgataga gacacggtct cgctatgttg cccaggctgg tctcaaaacc ctggcttcaa 186180
atgagcctcc caccttggcc tcccagagtg ttgtgattac aggtgtgaga cactgtacct 186240
ggcctgtatt aaaaaaaaaa aaaagaagaa gaagaagaag aggaggaaag aagaagaagg 186300
aagaaggaag aagaagaaga ggaggaggag gaggaatggg aaggggaagg ggaagaagaa 186360
gaggaggaag gggaagggga agaagaagag gaggaggaag gggaagggga agaggaagaa 186420
gaagaggaag aagaagacga agaagaagca caatgataaa taagtaaaat gtggagcata 186480
tgaaaacaaa acaaaaaaaa gttgatccat tatgaatgga agctgccatt gtaactctgc 186540
ttttttagga aaaccagacc ccatttagat gattttattt gtttttaaag gcaggttctt 186600
gctctgtcac tcaggctgga gtgcagtgat atgatcatag ctctctgcag cctggagctc 186660
ctgggctcag gcgatcctcc cagcttagcc tcccaagtag ctgggactac aggcaccacc 186720
acacccagct aatttgttgt tgttgttgat gttgttgttg agatggggtc tggctatgtt 186780
gcccaggctg gtctcaaact cctggcctca agtgatcctc ctgccctggc ttcccaaagt 186840
tctgggatta caggcatgat tttttattaa tttatttgca gctgacaaat ggtaattgtg 186900
tatgtttatg gagtgcagtg tgatgtttta atctatgtat acatcataga atgattcagt 186960
catgctaatt aacacatcca tcgcctcacc acctcaccgt tttttgtgtg tggggaaggc 187020
attaaaaatc tcttagcaat tttgaaatat gcaacacatt actatttatt aataatgcaa 187080
tataaataca caataatgta ttaatgcatc actaaatgcg atgcaatgca atgcaatgca 187140
atagatcact aaaacttact cctccagtct aactgcaact tatacccttt gatcaacatc 187200
ttctccttct caatccctcc tcctcccctg cagcctccag gaaccacctt cctgctcttt 187260
ctatgagatc aatttttttt agttttaagc tcccacatgt gagatcatac tgtaattgtc 187320
tttctgtgcc agcttatttt actcagtata atgtcctcca gttctgtccc tgttgtcaca 187380
cattacagaa tttctttctt ttagggctgt atagtattct atttgtatac ataccacatt 187440
ttctttatcc attcatccat tgtgggacac ttagtttgct tccatatttt ggctattgtg 187500
aataatgctg aagtgaacgt gggagtgcag atgttctgaa aagacttaaa tgtcagacct 187560
gaaatggtaa agatgctcca agaaaacata aggagaaagc tccatggcat tggtctcggg 187620
aatgattttt tggacaggac ctcaaaagca caggcaacag aagccaaaat ggacaaatgg 187680
gatcgtatca aactaaaaaa tttgtgcaca gcaaaggaag cgttcagcag aggaaagaga 187740
caacctaagg aatgtgagaa aacgtttgca aacaatacat ctgataagga gctaatatcc 187800
aaaatatata aggaactcaa acaactcaac agcaagaaaa caacccaatt aaaaatgggc 187860
aaagacagct actcgggagg ctaagatgtg acgatccctt gagcccggga ggaggaggtt 187920
gcagtgagct gacattgcat cactgcactc caccctgggc gacagaagga gaccgagacc 187980
ctgtctcaaa ataaaaaata aaaatgtgca aaggatctga acatacatat cccaaaagaa 188040
aagacataca agtggccaac aggtatatga ataaaatgct gaacatcact catcatcagg 188100
gaaatgcaaa tcaaaaccac cattagctat cacctcacac ctgttagagt agctattatc 188160
tttttgtttg tttgtttgtt ttttgttttt tgttttgttt ttgagaggga gtctcactct 188220
gtcacccaag ctggagcgca gtgttgtgat ctcagctcac tgcaacctct gcctcctggg 188280
ttcaagggat tctcctgcct cagcctcccg agtaactgaa attacaggca cacgccacca 188340
tgcccagcta acttttgtat ttagtttcac tatgttggtc aggctggtct tgaattcctg 188400
acctcaaatg atctgccctc cttggcctcc caaagtgctg ggattacagg tgtgagacac 188460
tgtgcccagc ctagagtagc tattatcaaa aagacaaatg aggtttgttg aagttctaac 188520
ccctggtacc tgcaaatgtg gccttacatg aaaatagggt ctttgcaggt ggtaatcaag 188580
ttaagatgag atcaaactta attagggtgg gtcctaaatc caatgactgc tgtctttata 188640
agaggagaag caggctgacc aacatggtga aaccccatct ctactaaaaa tacaaaaatt 188700
agctgggtgc agtagtgcac acctgtagtc ccagctactc aggaggctga ggcaggagaa 188760
ttgcttaaac ccaggaggtg gaggttgcag tgagcagacg tcatgccact gcactccagc 188820
ctgggtgaca gagtgagact ccatcttaca agaaaaaaaa aaaagacaaa tcataacaag 188880
tgctggcaag gatgtgggga aacggggatc catttacatc attttaataa cacaggctct 188940
atatgggtgg tattgagttc ccagagttgc cattacaaaa tgtcacaaac ccagtggctt 189000
aaaacaacag aaatttcttc tctcacagtt ctagaggcca gaagtccaaa ctgaaatcaa 189060
ggtgtcagca gagccaccac gttccctcag aaggttttag gggagaatct gttccatggt 189120
attttcttag tttctggtgc tgccagcgat acttggtgtt cctcagttca tagatgcata 189180
attccagtct ctgcctctgt tgtcatatgg tcttctttct gtgtttctgt atgcgatttc 189240
tttttttttt tttttttct gagacaagtc tcactccatc acccaggctg gagtgcaatg 189300

```
gcacgatcac agctcactac aaccccaacc tcacaggctc atgccgtcct cccacctcag 189360
cctcccgagt agctgggatt acaggcgtgt gccaccatgc ccggctaatt tttgtatttt 189420
tagtagatac ggggtttcac catgttggcc aggctggtct cgaactcctg accttacgat 189480
ctgcccatct cggcctccca aagtgttggg attacgggca cgagcccacc gcacctggcc 189540
ctaattactt tatttttttg taaatttttt tttgtaaatt tcatgtagcc tgagcataca 189600
gtgtttataa tatatacagg agtgtacaat aatatcctag gccttcacat tcactcacca 189660
ctcaactcac tccctcacca agagcaactt ccagtcctgc aagctccatt catgccaagt 189720
accctatgca gctgaaccac cttttctctt ttatactgtg tttttactgt accttttcta 189780
tgtttagata tgttcagaca cacaaatact atgatgttac agttgcctac agtattaagt 189840
acagtaacat gctgggcagg tttgtagccg aggagctaca aaccacgtag cctgggtgtg 189900
gagtaggcta caacatctag gtttatgtaa gttcacttta agatgctcac acaaggacaa 189960
aattgcctaa caatgcattt ctcagaacac gtctccctca ttaagccaca catggctgta 190020
ttacaattta catataattt taagcgtata taaattgcca gaaatcacca gatgaatcct 190080
tggcggtgac ataccccttc ccccaccata gaacattgca gactggcccg gacgcccagt 190140
atctcatgcc tgtaatgcca gcactttggg aggctgcagc gggcagatca cttgaggtta 190200
ggagttcgag accagcctga ccaacatggc aaaacaccat ctttactaaa aatacaaaaa 190260
ttattcggac gtggtagtgg gcacctgtag ttccagctac ttgggaggct gaggcaggag 190320
agtcacttga acttgggagg cagaggttgc aatgagccaa gatcgtgcca ctgcactcca 190380
gcccgggtga cagaatgaga ctctatctca aaaaaaaaag aaaaaaaaaa aaaaaggaaa 190440
agaacatttc agactggtac cagttacacc ggctcttgat cccttgaatg tggctgaccc 190500
tgaactagga tgtacttcat aataacacgt ccggctggga atacttagta caaaagaaag 190560
agtataaaat atcttttgaa tccaccttga tattgattcc atgttgaaat ggtaatattt 190620
tggatgtatt gggttgaata aaacatctca tgaaagtgat ttttaaaaat ctagaaattg 190680
tctgcaatta taattccaga ccacagagaa aaacgagaga caggaatgta tagaaaaagg 190740
gaacgtggga caaagtgagt atgaaattca actaacagaa gtgacagtgc ctagcatggg 190800
gtccagcact tagtaggtgt tcaattaata ttcatttccc tctcccttac cagtgaaggg 190860
tatgcctgtc gtggggaatg tgtcttcagg ctgagtgatc aggaaggact ttctcaatgg 190920
ctggcacgtg aacctagtca tgatttcagc tcttgaggtt gtactagaag atttatatcc 190980
aataatcgta aggtaccact tagcatcacg ctaagatgta ttaattcatt tatgcctttg 191040
gatggccctt tgaggtagga agtgtggttg tctccagttt accaaggtgg cttgcccaag 191100
gtcatctgct ggttggtgat taagccaggt tttcagtgtg gctccagcag gagtgggggc 191160
tggggacctt ctacctgctg tggtttctct ctctctctct ctctctctct ctctctctct 191220
ctcgatctgt ggaacatccc ccctgtcccc caaggtccca agggtcttat ttcttttggc 191280
caagcccttt ggagacctgc agatctggac acatctttga gagtttcagg aactagggcc 191340
agaaatgctg ggcagggtca tgaggagctg ccactggggt tgagaaggtg atggacatga 191400
ggggaagggt ctttgcagaa aggagaggcg tccctgtaag caggtcacag ccactgggcc 191460
tggccaactg cagccgagtg gaatgtgccc ctgccccatg accatatgcc ccaggtgtgc 191520
aatgtggcgg cccagagcac acactctgaa ccatcttgac acatcttcac tggttactag 191580
acccccctca gcctgtttcc ttggctgtaa aatggggatg acgctggtcc ctacttccta 191640
gggctctgag caggagtaag tagcttgtcg tataaaacat gttccctgca gtgcctggtg 191700
```

```
cctgctaaat gttccataaa cgtcagctgt tattttcatt caggggaagc tgaaatccat 191760
attttcatgg aaaatctccc agtttttaaa tgtggaccaa taatttcagc tttcacaaac 191820
ccagtatgag tcggtatggc ccctagggtg ccaactcaaa atctctgttg agaattttgc 191880
tgataggaag tggcctcctt ggaggtgttt gctgtgtcct gtgtctggca agtggggtgg 191940
ttttgataaa cgtgctggat ggatgtatgg gtgaatggat aaatggagga atgaatggag 192000
aaacaaatga gcaaatgaat aatgaatgga tggatgaatg gatgagcgaa tggatggatg 192060
aatggatgag caaatgaatg atgtacacac aaaggaatgg ataaatgatg aatgtgctaa 192120
tgaatttaag aatgatgaaa gaatgaatga ataaatgaac aaatggatgg atgaaagaat 192180
gaatgaatgt actaatgaat gaatcaatca atgaagaacc atttaaaaat gaatgcaact 192240
gagggtttat aagaaaaggt atcttaagcc tgggcatggt aattcatgct ggaatcccaa 192300
tgcttaggga cgctgaggcg ggaggatcgc ttgaacccag gagttcaaga ccagcctggg 192360
caacacaggg agacctcatt gctaccaaaa acaaaattgt tttaattaag cgggcatggt 192420
ggtacgtgcc tgtagtcata gctacttggg aggctgaggt gggaggatcg cttgaaccca 192480
ggagttcaag gctgcagtga gctaggatca agccactgca ttccagcctg ggcaacaaag 192540
caagatcctg tctcaaaaaa aaaaaaaaaa gatgtatttt agaaggtaaa ttcaatctgt 192600
ccaaaactga gctctgacct tcccctaaac ctgtgcccat tcagtggatg agagctccat 192660
cccttaaggg gttcaccaat tcatccattc ctttgtatgt acatcattca ttcaccttgg 192720
ctcatccctc tctcttacat ccacaccgtt ccatcagcaa atgttgaatc tgtcttaaat 192780
gattcatccc aaatcctccc cgcttaacta ccacccaact ccagccccca tccatcatca 192840
tcatcacttg cctggatggg ttcagtcacc tccagcctgg tctcccagct cccgtcctca 192900
cctctcactg tctactctcc cactcggcag ccagagggtg cctgtgaaca cccaaatcag 192960
gttccatccc tcctctactc agaaccctcc acggctcccc cctcactcag ggtaaaagcc 193020
aaagtcctcc ttgtggtcca ccaggccatg catgatctgc ctgtcacctc cctgccttca 193080
ccaccttcct cttttcccct caaccactcc actccagcca cactgacttc cttgtgctct 193140
tccccaaaaa tgtcgggcag acacattcat gcttcaggac cttaaatttg ctgtttcctc 193200
tacctaagat actaaagtga caagtcaaca cactcacctt gaccatgcaa tttaatgttg 193260
cagcctaccc tgtggactct ccaagggctc ccagtccctc tgtgatgctt tactttttct 193320
cttaaaaaaa aaattgttat ttaaaagaac ttgtctcgct gtgttgccca ggctggtgtc 193380
aaactcctgg cctcatacag tcctcccatt ccagcttccc aaagtactgg gattagaggc 193440
atgtgccact gcacccatcc caactttttt tttcccatag cacttttcat tttccatccc 193500
actgttaatt tacttattac gtccactgtc tgtctcctcc ccttagaggg tcagaccccg 193560
gaagtccagg ctctgttgcc taatgtatcc tgagcccctg gaacagagcc tggcacaaaa 193620
taggtactca ataaatgcat aagagcaaaa ctatatgtag gcagaggaca cacccagctt 193680
attcctcagt gatcacttct aaagttaaat gtccatggaa aacagtctca tccacatctc 193740
tttctggagg ccttccaagc gtgctccatg cagctctgtt gcctgcccct gcatcaggga 193800
atggaggctc tgctttatcc tgccctgtgg tgtgactccc agaggcatca gatgtggctg 193860
ggagtgggag acatggaaaa ttggctcctg caacagagaa ctatcagcct tcccatcaat 193920
tggttacttc taattctgtt atttttcagg ggcactgtct tctcataagc tccatctatg 193980
caaaactaag cccatgggtc atgatggttc cctcaggcca gaggcttgct ggagagacta 194040
```

-continued atggatcccc tggctaaaat ctgtgcttgg gctgcacatt ggttaatttc ttctgaagga 194100
acagcctgag cctgacattc tccatctttt ccctggcagg ttctcccttc gcccgagcca 194160
gcattaaaag tgccaagctg gagaactcga cctttttca caaaaaggag aggaggatgc 194220
gtttctacat ccgccgcatg gtcaaaactc aggccttcta ctggactgta ctcagtttgg 194280
tagctctcaa cacgctgtgt gttgctattg ttcactacaa ccagcccgag tggctctccg 194340
acttcctttg tgagtatcac ccagccccac ccctgccaac tccctgatcc ctccctcaca 194400
cccttttcc acttctcttt ctctggtagt atgtgtatct tctttggtcc tcattgaatc 194460
tgccctttcc tttagccatt tctataactg tcactggggc caatgttact gttgctatga 194520
caatggaacc catctccctt agacctgaga gctggaagct ggaattcaga ccaacaaatg 194580
ctcctgtgat tcctttctaa gagagaggga cagaggggtg ctggtgaagg ggatgttgga 194640
agagagacag agaaagacgg agctcataag atagacagat agaaacagaa acatacatgt 194700
attaataatt tttatgtaca tctctggaaa tgttcataac ttatggttaa gagaggatgc 194760
cttagaaata aggagtggct tatatgttgc cctcattttc tctacttatt tctgactcta 194820
cttctctctt ctttcaaacc ttctgcttct ttcctgttag gttggtgcaa aattaattgc 194880
gtttttgcc tttttttttt tttttttaa ccacagttac ttttgcacca acctaatact 194940
tcctcccctg ccctttttgg cttccttatt cattcataga acatcccctc cagtatctgc 195000
gagagcgttt tgctccctca aggtacaagg cccactaagg ctttgccctc tgggcctatt 195060
cccagattct atgtgagtta gcatgagata gtatcaaaat tgagggccaa gtgagggtga 195120
ggaaaagcag caaaagatgg ggagatgtct gagcaggatt taaaaagtaa agagctcgag 195180
gaatcaacaa gagcagcgac tggggccagg catggtggct cacacctgta atcccagcat 195240
tttgggaggc tgaggtgggt ggatcacttg aggccaggag ttcaagacca gcctggccaa 195300
tatggtgaaa ccctgtcttt acaaaaaata caaaaattag ccagatgtga tggtgcacac 195360
ctgtaatccc agctactcag gaggctgagg cactagaact gcttgaatcc aggaggcaga 195420
ggttgcagtg agccaagatc atgccactgc actccagcct gagcaacaga gagagtgtct 195480
gtctcaaaaa ataaagtaaa ataaaataaa ataaaataaa gagtagtgat tgggcagtga 195540
ggggggcagg tggatgccct ggctttggct cacaggcccc aagtaaggac ttctcaaaac 195600
gtcttttgcc tactggctgt ctaatttatt cactgacctt ctgacctggt tcagaattga 195660
cttaggacag caagaagaga cagtctagtc tttgacctag aaaggcccgt gagcctagtc 195720
caggccattg tcttcttata accctccttg ttcccagtca cgttggctga ccccccagga 195780
cacccctcag gaaccagttc tccttcccag ggccctgacc tagtttcaaa cttagtaatt 195840
gtttttagtc cctctggagt ctcttataaa tgaggactct acttcgtgtt ttaacttcct 195900
ctaatactct atttttaatc tcctatattc tctctactaa tcatcttgta cagtctgtcc 195960
tggttcagga acaagggact gagacttcct gcctgggtcc tcagtgtcta taaaggtcct 196020
ttactcattc ccactttccc tttgagaaaa ctgagacaca gagaggttaa gtagattgcc 196080
caggatcaca cattagcttg gcatgatggc gggcgcctgt aatcccagct acttgggagg 196140
ctgaggcagg agaatcgctt gaacctggga ggcagaggtt gcagtgagcc cagatcatgc 196200
cactgcactc tagcctgggc aacagagcta gacgccatct caaaaaaaaa aaaaaaaaaa 196260
aaaagataca cattaatttc agagatgtca aaatataaac aaaaatgtat atcttggcat 196320
cagtgaagtg tagttgtttc tctggatctc agactccaca tctatgtggt agaaaccgga 196380
tttgatggtc ctgaaagttc ttccagatgc aacaatgcta aggataagta attctttcaa 196440

```
gtcttgtgca tcacctgcta tcatgtttcc atggtaactg aggaacaaga tctcagaaac 196500
tcttcagtcc tcccagagtt acttctggtg ggtctaggaa tgtgtcagat gttacaaaca 196560
gacttcctct gctgatattt tggtcctagg aaccctagag ttcccctcag acactaagat 196620
ctccttagcg tcctataaat aaggagaaat tttggtgata aatactgtga aggactttga 196680
cggtcagttc aaaacacctc ttaaaagcat gacatagcaa acacccttgg caaatatctt 196740
agttcatttg tactgctata acaaattacc cgagactggg taatttgata agaacagaaa 196800
tttattttct cacagttctg gaggctggga agcccaagat caaggcattg gcaggtttcc 196860
ctgtctggcg aaagctactc tctgcttcca agattgcacc ttgaacactg tatcctctgg 196920
aagggaggaa cactgggtcc ttacatggca gaaggtggag gagcaagagg gacaaacttc 196980
ctctgtcaac ctcttttata agggcaccta atcccattca tgagagctct accgtaatga 197040
cttaatcacc tcctgaaggc cccacctctt aatactgtta cattggcaat taagtttcaa 197100
cgtgaatttt ggaggggaca caaacattta aaccatcaca accaccaaac acaattagct 197160
ttgtggcctt aattagctat atgaaattca tggaagttag tttcagtcct ctgtctcttt 197220
cctttctgta tgctttctgc tcctcagaaa ccctcctcat ctctcctttc tatccattaa 197280
gtacccacgc ccttcctaac tcctcatctt cctaccctac caagaaagcc ctctcagaaa 197340
aggatctgat gtcagccatt tatttgctgg agcaaatgca tatccatgtt ttacccctcc 197400
ctgaggcatt tgcaatttta tgcttgctca tcaaagaaca aaaggctttg tcttactcaa 197460
gactttttag gtcactcaca acacaggatt tctaggggac ataagacaag ttttctgagt 197520
taggagaaaa gccatacctt aggtgggttg cctgtgtcgc tccaactaag tacttaactt 197580
caggattaca aataggatat cattatgatt tctatttcct tttatccttt ggagctcagt 197640
cacgtagaag tagattaaat ataattgtta gatcacagca ccctggcatt atggggccgt 197700
tatggtccat tgttattatg tgaattattc agttaattag tttatttttt aaatgtgata 197760
aacacccagg aacccaccag tcaacacaaa agtccttggc aataatctat atccgatcct 197820
tctcatcgaa ccagggcaaa aactacaaga tggagaccca ctgatatttt tctcattcct 197880
tttaaaatcg gcctaaggtt ggttagcttg ttggttggag ggtagggcat aattgttgct 197940
ttttttttt ttttttttt ttagacaagg tcttgctctg tcacccaggc tacagtaggg 198000
tggcccaatc ttggctcact gcaacctcca cctcccaggt ttaagtgatt ctcatgcctc 198060
agcctcccaa gtagctgggt ttacaggcat gtgtcaccac actggctaat ttttgtattt 198120
ttagtagagg cggggtttgc catgttagcc aggctggtct caaactcctg acctcagttg 198180
atctgaccgc ctaggcctcc caaagtgctg ggattacaga cgtgagccac catgcccagc 198240
cagctcttcc tttttaacag aggggaaact gaggcccatg ggaaggacac cttggacagg 198300
gcgtggccac agtgggtcat gtatataatc ccagcacttt gggaggctgt gctgggagga 198360
tcacttgagg ccaggagttc aagaccagcc agggcaacat agtgagaccc ccatctccac 198420
ataaaaattt taaaaagaaa aaagataagt cagaagttgg gtgtggtgac acatgcctgt 198480
agttctagca tgttggaggc caaatcaggg aaactgtttg aggccaggag tttgaaacca 198540
gcctaacagc atagcaagac ctcatctcta caaaaaataa aaagtttaaa aatgataata 198600
aaaggaaagt cagagccacc tggaacccct accctcagca agcctaacct cctctctgtt 198660
tcctccttct cccttctaga ctatgcagaa ttcattttct taggactctt tatgtccgaa 198720
atgtttataa aaatgtacgg gcttgggacg cggccttact tccactcttc cttcaactgc 198780
```

```
tttgactgtg gggtaagtgc tcttgtttct aagagttcat ttctccagct cttgcctgga 198840
atgacagata cctggacaca ttaaagggag aaaggtaaag tcacccctga atatgagaga 198900
ctcagatgga tgcagaagga atgagaaaac aatcccaaac actggcaagg atacagtgta 198960
cccagaaccc tcaaccaccg ccagtgggag gaaaacgtat agaccccctt tggaaagcta 199020
agtgggggac ataagacaag ttttccaagt tgggagaaaa gccatgcctt aggtgggttg 199080
cctgtgtcgc tccaactaag tacccaactt caggattaca aacaggacat caatatgatt 199140
tctatttctt cttttccttt gtagctcagt catgtggagg tagatgaagt ataattgtta 199200
gattacaaca ccctggcatt atggagccat tatggtcctt tgttattttg tgaattactc 199260
agttaattaa tttattttt aaatgtgatt aacacccagt aacccactag tccacacaaa 199320
acctaagtcc tggagaataa tctacgtcca atccttctca tcgaaccagg gcaaaaacta 199380
caagatggag atatgaccca gcattccatt gctaggaatt catcctagaa aatctcaccc 199440
agatacctag gagacacagg ccagaatgtc cctgcagctg gaagtgaaat taaggttgtt 199500
cgcaaataag tggagaatgc ctggcccagg gcagccctaa tcatttacca tagtcctgtt 199560
ggtctcagaa aggcttaata atttatttat ttttttttat tttttgtttt tattttttgt 199620
ttttgagatg gagtctcgtt ctgtcaccca ggctggagtg cggtggcgcc atctcggctc 199680
actgcaagct ccgcctccca ggttcactcc attctcctgc ctcagcctcc cgagtagctg 199740
ggactacagg tgcccgccat catacctggc taatttttg tatttttagt agagatgggg 199800
tttcaccgtg ttagccagga tggtcttgat ctcctgacct cgtgatccac ccgccttggc 199860
ctcccaaagt gctgggatta caggcgtgag ccaccacacc cagccagctt aataatttat 199920
aataactgaa tgttgtactg ttttctgcca ttatagaaaa ttatgttgtt ggagaaaaca 199980
aaatacatac aaacaagcaa accttcccta cataaatgac ccaagtagtt aaagaataaa 200040
accaatttct ttccattaaa aagaaaagaa agccgggtgt gatgcctcat gcctatagcc 200100
tcagctattc aggaggctga ggcagcagaa ttgcttgagc ccaggagttg aaaaccagcc 200160
caggcaacat agcaagaccc tgtctctaca aaaattaata ataattagcc aggtgtggtg 200220
gtgcacacct gtagccccag ctactcagaa ggctaaggtg ggaggattgc ttgagcccag 200280
cagtttgagg ctgcagtgag ctatgatcac accactgccc tccagcctgg acaagagagt 200340
gagaccccat ctctaagaaa taaaagtagg ccaggcacag tggctcacac ctataatccc 200400
agcactttga gaggcggagg caggtggatc acctgaagtc aggagttcaa gaccagcctg 200460
gccaacatgg cgaaaccccg tctatactaa aaaaatacaa aaattagcca ggcgtcgtgg 200520
cacatgcctg taatcccagc tacttgggag gctgaggaag gagaatcact tgaactgggg 200580
aggcagaggt tgcagtaagc tgagattgca ccactgcact ccagcctggg tgacagaatg 200640
agactccgtc tcaaaaaaaa aaaaagaaaa attttaaaat gtcctgagca accttgtttg 200700
taatagttcc aagtctcaat atccgtgtat ccctttgctg tagaacagat aaatattttg 200760
tggcatatct atataatgaa atactctgtg acaatcaaag tccaccaaca gcagccacat 200820
gcccaacaac aggaatgaat ctcacccatg taacatggca cagaaggagg caggagctag 200880
caacgtaagt ccatacagtt catgcaaagt tcaagtggac aaaattaaac tctctctctc 200940
tctctacata tatatatata tatatatata ttttttttt ttttttttt ttttttttt 201000
ttttttgaga cagagtctca ctctattgcc caggctggag tgcagtggcg caatcttggc 201060
tcactacaac ctccacctcc cgggttcaag ccattctccc gcctcagcct cccaagtagc 201120
tgggattaga ggcatgcacc accaccccg gctaattttg tattttttgt agagaccggg 201180
```

attcagcaat ttgcccaggc tggtctcgaa atcctgatct caggtgatcc acctgccctg 201240
gcctcccaaa gtgctgggat tacaagcgtg agccaccacg ccccgcctta aactgtattt 201300
tttaaggatg atacttgaat acgttaaaaa ggcgaggacc ttgaaaacac aacgctcggt 201360
aaaagaaacc aaacacaaaa ggtcaagtat tgcataattc catttgtatg aaatgtccag 201420
agcaggcaaa tccatagaga cagaaagtag attagtggtt gctagggtct gggtgaggga 201480
gagtggggag taactgctca tggggacagg gcctcctttg ggggtgatga aaatgttttg 201540
gaacttgata gaggtgatag ttgcagaata ttgtgcatgt acctaaaggc actgaattgt 201600
gtaattcaaa gtgtgaattt tatgttatgt gaatttcacc tcagtttttt ttaaggtaag 201660
aaaatggtta ttacaaaatt caggatggta gttatatcac agtgtctctg gaaacttcca 201720
gggtatccac atgtcccttt ttattttatt ttattttta ttttatttga gatagggtct 201780
tgctctgttg cccaggctag agtgcagtgg caggatcatg accctctcct gtctcaaatt 201840
cctaggctca agctatcctc cctcctcagc ctcctaagta gctgggacta taggcacatg 201900
ccaccatgct tgactaattt ttttttttt tgtaaagtca gggtttccct gtgttaccca 201960
ggctggtctt gaactcctgg gctcaagtga tctgcccacc tcggcctccc aaagttccag 202020
aattacaggc atgagccact gccctagcct tctcctaatt gttgacatag gtagtagttg 202080
catgacattc actttgtaat tatgtgtttc aggaattctc aggcctgtgg gagctcttaa 202140
taaataaaaa agaggccagg tgtggtggct cacgcctgta atcccagcac tttgggaggc 202200
cgaggcaggc ggatcacgag gtcaggagtt cgagactagc ctggccaaca cagtgaaacc 202260
ccgtctctac taaaaataca aaaaattagc cgggcgtggt ggcgggtgcc tgtaatccca 202320
gttacttggg aggctgaggc aggagaatcg cttgaacctg ggaggcggag gttgcagtaa 202380
gctgagatcg cgccactgca caccagcctg ggtgataaga gcaagactcc atctcaaaat 202440
aaatgaataa ataaaaataa ataaataaat aagaggccgg gtgcagtggc tcaatgcttt 202500
ggaaagtgga ggccaacagt tggagagacc aaagcaggag gatggcttca gcccagaagt 202560
ttgaggccag cctgggcaat actagcgaga cactatctct ataaaaatgt tttaaaatta 202620
gccagatgtg gtggggcaca cctgtaatcc cagctactca agaggctgag gtgggaggat 202680
cacttaagcc caggaggaca gtgctgcagt gagctatgat tgcgccactg cactccagcc 202740
tgggtgacac agtgagaccc ggtctctata gataaatgaa tggatgaatg agggggtcaa 202800
ggatcctcac ccggcttcca tttggaggga ggagtttggt tgagttcttg caaggttggt 202860
acctaggaaa tgcttgccag ttctggagcc cagacactgt ccctggacat gagaccaggt 202920
tctctgccct aggttatcat tgggagcatc ttcgaggtca tctgggctgt cataaaacct 202980
ggcacatcct ttggaatcag cgtgttacga gccctcaggt tattgcgtat tttcaaagtc 203040
acaaagtaag tctttggggt tcctggacat ttgtacaggg ggtggggatg ggggacatgg 203100
tggggccgcc tccagaaagt tgggaaagtg agcctcgtgt ttcgagggct gactccgggg 203160
ccctgcctcc cccgcctggc ctgagtcctc gcctggcctc tgtcggcagg tactgggcat 203220
ctctcagaaa cctggtcgtc tctctcctca actccatgaa gtccatcatc agcctgttgt 203280
ttctcctttt cctgttcatt gtcgtcttcg ccccttttggg aatgcaactc ttcggcggcc 203340
agtaagtcct tcacaggaat tccaactcct ggttccctgg ggtcaggctc agggaacaca 203400
cagtcccctc caccgtgcag gctgccttcc tcgtagccca gacacccatt gcggtcaccc 203460
aaatgggcag ggccctgggt accactcagg gtttcctggg gacagagatg atggagacgt 203520

```
tcgtttcctt ggagatgaga tactgagcca caccctcaga gcaccccggg tggggccaac 203580
gtgaaatgtc tgtgtcctcc ctgcaggttt aatttcgatg aagggactcc tcccaccaac 203640
ttcgatactt ttccagcagc aataatgacg gtgtttcagg tacagcctcc acctggcccc 203700
acgggccaac acctctcagt gtcacagatg aaagtgcctg ctccacatcc aaggggcttc 203760
cctgaactcc tccttctcta cctggccttt tcacaccact ttgaaacaca gattttatgg 203820
ttatcattat tcaattatgg tgaggccaac agatcaggag atgaatgtca ttggaaagat 203880
agtttgtggc tgggcacggt ggctcacacc cataatccca gcactttggc caggtacggt 203940
ggctcacacc tgtaatccca acgctttggg aagcccaggt gggcggatca cttgagatca 204000
ggaattcgag accagcctgg ccaacatggt gaaaccccat ctctactaaa aatacaaaaa 204060
ttagccgggc gtggtagcac atgcctgtaa tcccagctac tcgggagatg aggcacaaga 204120
attgcttgaa cctgggaggc agaggttgca gtgagccaag atcgcgccac tgcactccag 204180
cctgggcaac agagtgagac tccatctcaa aaaagaaaaa gaaaaaaaaa accactttgg 204240
gaggtcaaga tgggaggact acttgaggcc aggagtttga gacaagtctg ggcaacatag 204300
tgagactccg tctctgcaaa aaaataataa taataattag ctgggcatgg tgatacatac 204360
ctcctagcta ctagggcagc tgaagtggaa ggattgcttg agcccaggag gttgaggctg 204420
cagtaagcta caatcacacc actatactcc agcctgggcg agagagcaaa gccctgtctc 204480
aaaaacgaaa agaaagtttg ttatactcac agatcctcag agaaggagca caccatgcag 204540
gaccaagcag agaagcaaca gggtcaagca ggaagagaag gaaaatgtgg gcaagaggct 204600
tgattgtggt ttccatggga cggaatgggt gaggcagagt aaacagctcg agactggcta 204660
gtttggatca tttcagtggg ctctggggca gaggagctgt tcctacttgt ctaggacctg 204720
gccttggggt gattagggca ggtggatagt gctgggaaga taaaggaggt ggttgggata 204780
tgggctggtt gggatattgt ttggtttgct tttaaaaagc ctgctcaggg ctaaattgtt 204840
tactacctct agggactggc tagtgctgga ccgggcagtc cctccagagt cagcaagacc 204900
ccagatgcat cagaataaag aaaataaaat gcgtggccag gccaatgagg tggttcatgc 204960
ctgtaatctc agcactttgg gagaccaagg cgggaggatt gcttgagccc aggagttcaa 205020
ggctgccgtg agctccagcc tgcaccacag agcaaggccc tgtctcttaa aaaaaaggca 205080
gagaaaaaaa atggctaata cacccatcaa atctgaagat accttggtct catattccag 205140
ggtgatcaac ccaaagcaac ttctgcaccc atgtgggcgc attccctgag gcttgggact 205200
ggcccagccg ggaccttcag agcatctttg gtggattctt tctctttgag ggactgagag 205260
tgtatagaaa atgtgacttc actctctcct tctcctgggg aggtagtttc taaatgagac 205320
cccaagacag ggagttgaag aggaaacctt ccatgaaggg aagttctgag cccccacata 205380
agcgattttt tttttttttt tgagatggag tctcgctctg ttgcccaggc tggagtgcga 205440
cggcacgttc ttggctcact acaacctctg cctcctgggt tcaagcgatt ctcctgcctc 205500
agcctcccga gtagctgaga ctacaggtgc atactaccat gcctggctaa tttttgtatt 205560
tttagtagag acagggtttc actatgttgg ccaggctggt ctcgaactcc tggcctcgtg 205620
atctgcctgc ctcggcctcc caaagtgctg ggattacagg catgagccac cacacctggc 205680
ccataagcga ttattaatag cactgatcgc tagtcatgta tctttagctc agaggttctc 205740
acccaaggac aagtctgtcc tccaaggaca tgtagcaatg tctgcaagca ttgttggttg 205800
tcacagctag ggagagggtg ctactggcat ctggtgggtg gagactagga atgctgctca 205860
atatcctaca atgcacagga cagccccaaa tagaataatc tggccccaaa tatcagcagt 205920
```

```
gctgaggctt agaaaccctg ttttagcaga ttcatgtttt tggagttctt taacatttac 205980
tttatcctca tggggatatg gatagaagga aggaagttgg atcttttttta aaggagcatg 206040
taggtgctgt ttgaatatcc ccttggttct ttcagtatgc atcagcacaa cttgcgtctg 206100
tcaacaccta atcctttgcc ttggtctttc tctggtcccc tgctctgccc ccaaggaact 206160
gcagtccagc agtactgtga attttttgtg ccacacctta aaaggagcag ccgttggtgg 206220
ataaataccc cagctccctc accctcaggt gggatgaccc ctagagctcc ccagcaagac 206280
caagccccgg ttacctacag tggaaactcg cttgatcaca tactgtttac gttccacccct 206340
cttttccctt ttctcacttc tcctctcccc tactggtgct tcctgagatc acctcccaga 206400
caaaccactt gcacccgaac ccttgttcca gggtctgcct caggcagggg gaccccaaac 206460
gtgtccttgt gctacatttg tgctatccac gtagtagctt gtttaatcat caccatgacc 206520
acatgaggaa cacaggtaaa tattaaaatc ctgtcttagt ctgctcaggc agccataaca 206580
aaataccaca cactgggtgg cttatacagg aaacatttat tctctcatag ttctggaggc 206640
cgggaagtcc aagatcaaag tgttagcagg gttagttagt tcctggtgag ggccctcttc 206700
ctagcttgca gatagccacc ttcttgctgt gtcctcatat gtcaaagaga gagagagaga 206760
gttgtgatgt ttcttcctgt tcttttttttt tttttttttt tgagacaaaa atctcaaaaa 206820
aaaatctatt ttttttttag gcaaatcaca tttttttgtc acccagcctg gagtgcagtg 206880
gcacaatcat agctcactgc agcctcaaac tcctaggttc aaacgatcct cccacctcag 206940
ccccttgagt agctgggact acagatgggc accagctaat ttttttaaat tttttgtaaa 207000
gatggggtct tgctatattg cccaggctaa tcttgaactc ctgggctcaa gtgatcctcc 207060
caccttggcc tcccaaagtg ctgggattac aggcatgagc catggcatgc ggtctcttcc 207120
tgttcttata agggcactaa taccatcatg aagtccccca tgacctcatc taaccctagt 207180
tacctcttaa aggccccatc tccaaatacc atcccatcat aggttagggc ttcaactcat 207240
gaatttggag gcgggcacaa tttagtccat aacaaatccc cttaatcaca tcaagtaaga 207300
cagagttaca ggagggtctg tgactcctcc agggtcccat tttcctagaa gccaggctaa 207360
gagccccacg acgcaggaac ggccctttct actcgcaaac aaagagaaaa gccaaggaga 207420
agccaacacg gagtctggct ctgcaaaccg ggcaggattg ttaaagacct cctgggctcg 207480
gggatggggt gggcggattc cggctccaca gctgcatctc caaggggccc gtggctgaga 207540
ggggggttgg ctgtgtgttt cttcctcccc tttcagatcc tgacgggcga agactggaac 207600
gaggtcatgt acgacgggat caagtctcag gggggcgtgc agggcggcat ggtgttctcc 207660
atctatttca ttgtactgac gctctttggg aactgtatcc ttcatggaga gagagaaggg 207720
gacaggcctg gacctctggc agaggagagg ttgcaggggc tcaagggagg gtactgagag 207780
acccagatac ccagggccca agtggtgtcc caccagtggt tgcttttcct gactcagaca 207840
tttgcagaca ccctcctgaa tgtgttcttg gccatcgctg tggacaatct ggccaacgcc 207900
caggagctca ccaaggtgga ggcggtggga gaatgtttct ctggcaaagt taccacctgc 207960
ccatggcaga tcaggacggg ggtgggggtg ggggtggggg tgggggtggg ggcatgggaa 208020
cagggttaga acttttgccg gggatgcacc atgcaaagag aaggcgcctc tccccccact 208080
cccagaaaca gactgtccct catcaagcaa attctacagc caagagggtg ggaaggggga 208140
aggcagtgag gtcgctgcag gaaacggatg gcaaactcaa ccaaaaggcc gtttacaggg 208200
agtaagcagg gtttccaagg aatggtgtag cccccaggct agtggatggg agagggagtg 208260
```

ctgttatggg gacccagtca gagctggggc caaggaaaaa gggctgccac cagccctggg 208320
accttagaga acccagaacc atggcaaggc acagatggag tggccaataa atgtccccac 208380
cttctctctt cctctggctt cccgctggag cctcccctta gccaaacgca gcatgttaag 208440
agctagcctc cgtccagcct aagcctctcc ccaaggaccc tattaagtta agattacatg 208500
taacaggtac agggtcttcc tctcagccct ggggtctccc tcagcattgc agccccacct 208560
ccagtgcctc gaggtattca ggacatgttt gtgaaattga accaaaccaa gcagacgttg 208620
ccaacgctcc atctgccggc cctggcagga gggagagaga gtttcccggc cccagctccc 208680
agtggaggga agcggaagtc tctgccatcc caagcacacg gccacaagcc tggccactgt 208740
ggagctggct ggcatggctg agccgagggc tgatccagcc atgagctcat ccaagttcca 208800
agagtccatc cttaggggct ggtgcaggag ggtagcagaa ggggagggag aaaggccagt 208860
tcgtttatct cctgggaggt gtggacattc ctctccagat ccacattctt tctttcattg 208920
atcctacaag catttcttgg tcatttaata cgtgttttta atcctattca gtcctcatgg 208980
aaaccttagg agccaagttc tctgagcccc attttacaga tttcatcatt cagtaagcac 209040
ttaatgagca cctactgtgt gaccaaggcc ctggtctagg acttagggat taagcagtga 209100
acaaaaaaag gcaaaaatcc ctgcctccgt ggagcaggga ttcaagaggg gagacagaca 209160
agaaacaaga taaatttgta aacatacgta gcttgtcagt tggtgataaa cacaacagag 209220
aaaaattcag tagggaaagt cagggagagt tggaatttta gatgagatgt gtgtcgcaca 209280
gagaggttga gagacttgcc caaggccaca cagcagtaag ttgtggagct gggatttgaa 209340
cccaggccgt ctgggtctgc agcttgtgct cttaactgct gtgtaccagt tgcttgaatt 209400
tgggcatgtt ttatgctcac ttgggaacct gtgggaaatg cagattccag ggcccagcac 209460
tggttctata gattatttgg ggagcctgag gatctgcatt ttaggtgttt ctgaggcaga 209520
tggtccagag acctagctct gaaaaatgct gggaatggtg ccaggagggg tgggggtggc 209580
cctatgagag cagggtggcc agccagatcc catctccatg ttgtctctga cagtgtcctg 209640
atctgaccat ttccaaggtg gtaaggttgc tccccgttcc agtgattcgg agcacagcgg 209700
gagagctgcc tgcaatggca tgacttttct tatgggcggg ttcatttctg gccatttctt 209760
tctcgttgcc ttttctttgc tttttctttg ttggcttttc tgttttacga atgaggccct 209820
gcatgaaggc tgaagaagga tttaaagtcc aaaaacgtct ttttctgtat gtatttttaa 209880
aacctcttcc cccattctcc tcctctctga acctaaccac cagtgagcag cagcaccctg 209940
ggcagttggc tgtagcccaa gtgccctgct ctcctctccc caccgccttc ctgtcatggg 210000
ggctgggaat ataaattcct ctcctcattc tccttctggg ggctgttgac agtgcatggc 210060
aggggccatc ggatgccagg ctcttctgtg tgtgagggta gttggtgttt tttgaaagtt 210120
ggttcagaga gttcacatgg ctcagaaagc ctagtgagag gaaaatcttt gcactgcttt 210180
ccagctcatt aagacaggat gcaggggcca ggcatggtgg cacatgcctg gaatcccagc 210240
actttgggag gccgaaatgg gaggatcatt tgaggccaga agttcaagac cagcctgggc 210300
aacatagtga gaccctgtct ctacaaaaaa aaaaaaaaaa ttaaatgtat acaggcatag 210360
tggcatgcac ctgtagtccc agttgcttgg gaggctgagg tgggaggatt gcttgagccc 210420
aggagttcaa ggttacagtg agctatgatt gtgccactgc actccaggct gggcaaccaa 210480
gggagactct gtctctgaaa acaaacaaaa gaaaaaaaaa taggctgcag gaaagtcttc 210540
attgtaggaa gagaagggac atttttattt tttgttatct ggctgtgtgt taaaataggc 210600
ttcataatga gttagatgtc aaacttatac acagagggga tagcaataca cttaaccaat 210660
agcaggtacc cattccaatt ggggagcctt ggttctgatt ggtcgaaata tttcaaatgt 210720
tgcccctggt cagcaacagg gtcagaagtg agtccccaag gcctagttca tgttttgtga 210780
acaaagattc cacgtgcctt ttaggacgag caagaggaag aagaagcagc gaaccagaaa 210840
cttgccctac agaaagccaa ggaggtggca gaagtgagtc ctctgtccgc ggccaacatg 210900
tctatagctg tgtaagtgcc cctaatccct gggatgctac cctggctcct gaacgtccac 210960
actatcccag gcacagattt gggaagcagt gggggtggtc cttgacagaa ctgagcttta 211020
ggaagagaca cttcttgtcc ttccacccac tttcactcaa taaatatttg gttagcagct 211080
gttatgtacc cagcactgtt ctaacttctg gggatacagc attaacaagg aggaaaaaaa 211140
aaatcccacc tgtgtgtagc cattctagca agggaaggag tcaataaatt agataaataa 211200
gtaaattata tattgtgtta gaaggcgatg gaactacaga gaaagtaggg gagggaaata 211260
gcaaatgctg ggagtgaaga gagttgtgat tttaaacgaa gttgtcaggg aaggcatcac 211320
ctagaatagg ggtccccagt cccggggctg tggactggta ccaggccgag gcctattagg 211380
aacggggctg cacagcagga ggtgaacagt gagcaagcaa gcattaccgc ctgagctcca 211440
cctgccgtca gatcagcagg cagcattaga ttctcatagg aacacaaaca ctattgtgaa 211500
cggtgcatct gagggatcta ggttgcgtgc tccttttaag aatcgaatgc ctgatgatct 211560
caggtgaaac agtttcatcc caaaaccacc ccccacacct aggtctgtgg aaaaactgtc 211620
ttccacaaaa ctggcccctg gtgccaaaaa ggttggggac tgctcaccta gaaggttaca 211680
tggcctgaag gaggtgaggg aggagccact ggggggcctg gggaagggca tcccaggcag 211740
agggaacagc ataggcaatg gccctgaggc aggaacatgc ctgatgtgaa ggaggcctgt 211800
gtgactagaa tcgaatagta agtgtgagga ggtgaaggca aggaggtgac aagcagatta 211860
cacagggcct tctgggtcag gggggaggac ttgggctttt gcccctagcc aggtgggagc 211920
catggagggt tcttgagcag aggaggctgg gacctgactc agatgctcac agactcctag 211980
cattcagtgg ggagtagagg gtggagagca ggagtgggag gctgagatgt gggttggttc 212040
gcctgggtca tccatccaag ctacagtgcc tagcaatgct ctaagtcctg tgaccatgcc 212100
actgcaggaa agagcaacag aagaatcaaa agccagccaa gtccgtgtgg gagcagcgga 212160
ccagtgagat gcgaaagcag aacttgctgg ccagccggga ggccctgtat aacgaaatgg 212220
acccggacga gcgctggaag gctgcctaca cgcggcacct gcggccagac atgaagacgc 212280
acttggaccg gccgctggtg gtggacccgc aggagaaccg caacaacaac accaacaaga 212340
gccgggcggc cgagcccacc gtggaccagc gcctcggcca gcagcgcgcc gaggacttcc 212400
tcaggaaaca ggcccgctac cacgatcggg cccgggaccc cagcggctcg gcgggcctgg 212460
acgcacggag gccctgggcg ggaagccagg aggccgagct gagccgggag ggaccctacg 212520
gccgcgagtc ggaccaccac gcccgggagg gcagcctgga gcaacccggg ttctgggagg 212580
gcgaggccga gcgaggcaag gccggggacc cccaccggag gcacgtgcac cggcaggggg 212640
gcagcaggga gagccgcagc gggtccccgc gcacgggcgc ggacggggag catcgacgtc 212700
atcgcgcgca ccgcaggccc ggggaggagg gtccggagga caaggcggag cggagggcgc 212760
ggcaccgcga gggcagccgg ccggcccggg gcggcgaggg cgagggcgag ggccccgacg 212820
ggggcgagcg caggagaagg caccggcatg gcgctccagc cacgtacgag ggggacgcgc 212880
ggagggagga caaggagcgg aggcatcgga ggaggaagta agtggaggtg acctcgaatc 212940
cgcagaatga cggtaacatt aataatgaca acagccaaag tagcacgtgc tgtgtatttg 213000

```
tttataaaaa tatattataa aatgctgtat ttggccaggc gcagtggctc acgcctgtaa 213060
tcccagcact ttgggaggcc gaggcggatg gatcacgagg tcaggagttc aagaccagcc 213120
tggccaagat ggtgaaaccc cacctctaat aaaaatacaa aaattagccg ggcacggtgg 213180
caggcgcctg tagccccagc tactcaggag gctgaggcag gagaatcgcc tgaaaacagg 213240
gggcggaggt tgcaatgagc cgagatcaca ccaccgcact ccagcctggg cgacagagtg 213300
agactctgtc tcaaaaaaaa aaaaaaagtg ctgtatttgg ccaggagcag tggctcatgc 213360
ctgtaatccc agcactttga gaggccgagg cgggcggatc acttgaggtc aggagttgga 213420
gaacaggctg gccaacatag tgaaaccccg tctctactaa aaatacaaaa attagtggtg 213480
gtgcccacct gtattcccac tactcaggag gctgaggcgg gagaatcagt tgaacctggg 213540
aggtggaggt aggttgcagt gagctgagat cgtgccatca cactccagcc tgggcaacag 213600
agcaagactc tgtctcaaaa aaaaaaaaat gctgtatgtt tttgtttttt tgacacaggg 213660
tctcgcctgt tgcccaggct ggagtgcagt ggcagtcata gctcagtgca gcctctacct 213720
cccgggctca agccatccgc ctcagcctca caagtagctg ggaccacaga catgtgccac 213780
atgcctggct aatttttgta gagacagtgt tttgtagaga cagggtttca ctgtgtttcc 213840
caggctggtc tcaaactcct gaactcaagc attccgcctg ccttagcctc cctaaagtgc 213900
tgggactaca gggttgagcc accacactca gcctaatttt tttaccttta gtagaaatga 213960
ggcctggctc tgttgcccag gctggtcccc aactcctggc ctcaagcaat catcccacct 214020
cagtctccca aagtgttcgg attagaggct tcacagatgg ggaaactgag agattgagtg 214080
agctcctcaa ggtcattcct ctaaccagtg tccttgaacc caggctctct ggcaccagag 214140
gccttgagca tttcagggaa actattaaga gaagccccac tgtcgtccag aattatatag 214200
tcttctgtgt tcttgctgtg tgacttttgc aaagtgactt catatctctg ggcctcacac 214260
aatggaaata gtgggatcta attgggtcat tgccaggatt gaatgaggta atgtatgcaa 214320
agggcctgga agagcagctg acacataata agtgctcggt aaatttagag catttttggc 214380
cattttcagc caactctatt tacctaatgc tattctttgg aagtttgaaa agccactctg 214440
ttgggaggcc aaggtgggag gatcacttga taccaggagt tggagaccag tctgggcaat 214500
agaggcagac cccatctcta taaaatataa aaaattaaac agatgtggtg gcatgcacct 214560
gcagtcccaa ctacttggga ggctgaggca ggagggtcac tggagcccag gatgtctagg 214620
ctatgatgag ctatgattgc accactgcac ttcagcctgg gcgacagagc aaggctttgt 214680
ctcaaaaaat aaaataaaaa ataaagaaaa agaaaaggca ctttgggccg ttagaattga 214740
agggagagca gagtttcaaa gctttggatg cagcgggatg tggtggctca tgcctgtagt 214800
cccagcactt tgggaggcca aggtgggagg atccacttga gccccggagt tcaagaccag 214860
cctgcgcaac atagtgagac ctcacctttt aaaaataaat aaaaatgtta gaaagctttt 214920
gaggcatctt ccaggccagc aacttatcca ttcagaacca gcatcctctt tttcataacg 214980
acattttgta atactttcta gcagatgcta tagtgattct gcatataggg actcaacaac 215040
ttacccatta aaatagacat cgtagacatt gtcctattac aaattaacct gctcttagtc 215100
ctcttttata ttaccatcag ggcataatat tgattttttt aatgatgggt ttaagtgatc 215160
ctgttgtatg acatatgagg taggccagca cttctcaaaa tctaatgtgt atgtgaatcc 215220
ccagggatct tgttaaaaca caaattgtaa ttccgtaggg ctaaggactc agtggagcct 215280
gagattctgc atttgcaacg agctcccaga tgaggctgat actactggtc cagggaccac 215340
attttgagta atgagactct ggaggacata gtgaagtaat tctgatatgt acaccataca 215400
```

caaaatcacc atgaagtgac aggcacaaat gatggctaac tctgggttgt gtggacaatt 215460
caaaccacat gaggggagtt gccagcagtg tcaagatgtt ccacaatgtt gaacacctct 215520
tggcaaagtt ccatatacaa aagagtctag tctttcttcc atttatttaa tagttgcatt 215580
gcaggaaaat gcaatgtata ttaaaaacat acaaaaaata tgttgtgttc ttatgtaaaa 215640
gagttaggtt taaactaaaa gcacaggatc aggtgcagtg gctcccacct gtaatcccag 215700
tgcattggga ggctgaggaa ggagaatcgc ttgaggccag gagttcgaga ccaacctggg 215760
cgacataagg agacctcgat ctctacaaaa gaagtttttt aattagccag gtgtggcggc 215820
aggtgcctgt agttctagct acttggaagg ctgaagcagg aggattgctt gagcccagga 215880
gttcaagatt acagtgagct atgattatgc cattgcattc caacctgggc aacagaacaa 215940
gtccttgtct caaaaaaaaa aaaaagaaag aaagaaagaa aaaacccaaa caaacaagca 216000
aactaaaagc acaggtaatt acaagcaaga tttttcacct ctttgaggga cattagaaag 216060
tcatgaagag gaaaagataa gtctttccca tatgggactg tcatgtacat ggtagggtat 216120
ttagtataac tgcctaccat tctctaagtg cctgcagtgc ccctcaatca ttatgttatt 216180
aggtttccac gtagttctac aacagttttc tgaaaaccat tgttctaggt cattctttcg 216240
cttcaatctt ctcctatggg tttatgcatt cattcagtta gtatttacta agtgcctact 216300
atattctaag ctcatgctgt gagttcagtc acacaactgc aagtgaagtg gtctgagaca 216360
ttctgagaaa tacgaccaag aaactgctcc cagggtctca gggcaggttt ccagaggagc 216420
aatctgagaa gggagtagag tgtttcagtc taacaacagc atgtgcaaag gccctggggt 216480
ggaccagaag gaggccagtt tgcaggacat gactagtgac gagaaagtga caaagaaatt 216540
gaaggtgcat tgatgagact ctggggctgt cagtcactca ggggaatgag agatcaaaac 216600
gggagtttag gtggaataaa gtgtttacca cagcactctc tgtatagtaa agaccaatga 216660
agagccaggt acaggccagt gtgatggttc acgcctgtaa tcccagcact ttgggaggca 216720
gagacaggtg gatcacctga ggtcaggggt tcagaaccag cttggccaac atggcaaaac 216780
cctgtctcta ctaaaaatac aaaaaattag ccaggcgtgg tggtggacgc ctataatccc 216840
agctactcag gaggctgagg cacaagaatt gtcctgcgag gcagaggtta cagtgagctg 216900
agatcacacc actgcactcc agcctgggca acagaacaag actctgtctc aaaaaaaaaa 216960
aaaaaaaaaa aaagccaggt acagtggtat gcacctgtaa tcccagctac tcaggaggct 217020
gaggcaaagg attgcttgag cccaggagtt cgagaccagc ctgagcattt agagaatggg 217080
aggccagtat actaaatacc ctaccatgta caagacagtc tcatatggaa aagaattatc 217140
ctttcctctt catgactttc tagtgctcct cacacaggtg aaaaatcttg cttataatta 217200
tctgtgcctt tagtttgttg gtttatttag ggttttgttt gttttttttt ttttttgag 217260 gcagggtctt gctctgttgc ccaggttgga ttgcagtagc attgctcatt ttagagatga 217320
gcaagacctc atgtctaaaa aaaaaagaaa gaccaatgat tattaattac tcttgctatt 217380
attactaata ttactgttat tatcagcctt attaacagat ctactgttat tgaaggaggc 217440
agagtgacag ggacaaaatg tctctcccta acaatatgcc aggaagagtt tttgaaagac 217500
aacagtaaac attggaaact acaagagcag caaagcctgg ttgtgaaagg caaggacttt 217560
ggggcaggca gtcacattcc tgccctatca cttccaggct gtgtgacttt cagaatttca 217620
ctcctctctg ggcctccatt tcctcatcta taaaatgaag ataagaatag tagctacctc 217680
cttctctggg tataagattt aactgagccg ggcgcggtgg ctcatgcctg taatcccagc 217740

```
actttgggag gccgaggtga gcggatcaca aggtcatgag ttcaagacca tcctggctaa 217800
tatggtgaaa ccccatctct actaaaaata ccaaaaaaaa aaaaaattag ccgggcgtag 217860
gtggtgcacg cctgtagtcc cagctactcg ggaggctgag gtaggagaat ggtgtaaaac 217920
ccgggaggcg gagcttgcag tgagccgaga tcgcaccact gcactccagc cggggagaca 217980
gagcgagact ccatctcaaa aaaaaaaaaa aaaaaaaaaa agatttaact gagttagtac 218040
gtgtaaaatg ctttgagtgg ttcctggctt ataccaagag ctcaataaat gttagcaatt 218100
ttttgtagca ttttggggtc tcactatgtt gcccaggctg gtgtcaaact cctggcctca 218160
agaaattctc ccactttggc ctcccaaagt gctggattta cagacatgag acaccatgcc 218220
tggccatgtt agctattatt aatatgaata ttattaagta ctcaatgaat gctattttta 218280
gcagtaatag taagcactca ggaagtgtca gctaatactg ttagtaatac tctcatcaat 218340
aaacataaaa agcaataagg acccagcttg cccaaatccc acagatggtt cctgctccct 218400
ctcttcttca gaggaagaaa ctatctcccc actttcaccc ccatagcctc agctggccag 218460
acccccattc tgaaccaggg gagtactgct aattccatta ttaatagaca catcaaacaa 218520
tctggccggg agagacatta ttcatttggc tgataaagag gttctaaggc tctttggaaa 218580
taaaagttca tgaagattca tgcactttaa gagaaaaaaa ttcaagatca gtcattcatc 218640
tgctttaaaa aaagtggcaa agataaaact ttatttgaga atataaaata ataaaaagac 218700
attttcgttc tctgttgtga caaagccagt ggccttcgga ggtctgcctt gtacattttt 218760
cctcttcttc agtcattcct tgaggctttt tgcaaacgta ccctgtgttt ttcattctcc 218820
agcatattga taattttttt tttttgagac atggtctcgc tttgtcatcc aggccccgga 218880
gtacagtggt acaatcatgg ctcactgcag ccttgacttc ctgagctcag gtgattctcc 218940
cacctcagcc tcccgagcag ctgggactac aggtgtgcat gaccatgcct agctaatctt 219000
ttgtattttt tgtagacaca gggttttgcc acattgccaa ggctggtctc caactcctgg 219060
gttcaagcga tcctcccacc tcagcctccc aaagtgctgg gattacagga gcgagctacc 219120
ttgccaggcc gatcatattt ttttcctttt tattcacttt gtcttctcct cattcctacc 219180
ttcatctgtc tttcagtggc tcactccagt gaaaagtgga ctgacgcaca ttctatttca 219240
tataattcaa tggctgctgg ccccagatcc cccataccag gtggccgagc ccagtggccc 219300
tgcagggtgg acaaaatgag ggtggaactt tcccagactg tcagtaaaaa tctatggagg 219360
acagagcttc tgcctctccc ttgcaaccag gcagtgcctt ctcccaggcc tatctgcttg 219420
caaagggaac ttttgccaag acctgctcca ctctagaatt cttatctctg ctgttcgcat 219480
cctaattcca cctgcatctg tcaccatgac aacctgctcc ccaaaaggaa caggaagaga 219540
gatgctggac ttttgagctc cacagtttat cctgcatggg ggtagggagt ggttaattac 219600
ttagcactct aattcttacg gtacccccaa tgggcccaag ttggtttttt taaaaaaaaa 219660
cagtcttgct ctgttaccca ggctggagtg cagtggcaca atcatagctc actgtagcct 219720
caaactcctg gactcaaatg atcttcccac ctcagcctcc caagtaactg gaacaacagt 219780
ctcgtgcaac tacgcccagc taattttttt tttttttttt ttttttttaga gatggggtct 219840
cactatgttc cccagactga tctcaaactc ctgggctcaa gcgatcttcc ttcctcagcc 219900
tcccaaagtg ctaggattac aggcgtaagc cactgtacca agctgcccca ttaaagcttt 219960
gaacaccaga gagcccagct cagctgtttt ccagctgggt aactctgggt aactttgcct 220020
ctctgaacct cagtctcctc ctgtgtgaaa tggggctgat cactataccc atctcggatg 220080
gtggtagttg cagggattaa atgagttaat acgtgaggtc cttaggacag ggggtgggga 220140
```

cacgagataa gcaataaaca ggaactgctg ttattatcac ccccacataa tccgatctca 220200
gggtctgagt gtgccccagg caaggtgtcc acagccctct gcagaaggat gcccaagtga 220260
tcagctggca caagaacgcc acgcacagca ggtgttatgc aactggccac ctattccagg 220320
cagaggatgc cagatcccca gggagaaggg ggtaggggtg cagcttcaaa gttttctgcc 220380
ccttttgagt tctccttgga gacactttgg aaatgaaacc tcccggaaat tgatattagg 220440
cctctgcagg ctgagcttgt taaaatttcc caacaaacag agccaacaga cgctctacaa 220500
ggaagcaaaa acaagacaaa acacattggc agaccctttt ccatctgctc ttggtagatg 220560
gtattcctct aagaaaatgc cgccacgagt ttctccatgg cttcttgagc tggtggccaa 220620
aggatttagg ttctctttga aattataact taactgggcc tgctttatgg cagggatatc 220680
actctctgaa atgtgtatat atatgtgtat gtatatatat acacatatat acacatatac 220740
atacacaggg ccaggcgtgg tggctcacac ctgtaatccc agcactttgg gcggccaagg 220800
caggtggatc tcttgagccc caggagttca ataccagcct gaacaacata gtgagaccct 220860
gtctctacaa aaattaataa aaataaccag gcatggcagt gtgtgcctgc aatcccagct 220920
acccagggtg ggaagatcgc ttgagcccag gagttaaaag ttgcagtgag ctatggtcat 220980
accactgcac ttcagcctgg gcaacagagc aagaccctgt ctcttaaaaa tatattatta 221040
ttattataca cacacagaca cacacagaca cacacacaca ttacagatga tgagaaaata 221100
ctctcagcca ggttttcatg atacacaact tctcaaaaag catcacaagc aggttagaat 221160
tagggatttc tttgtggact gtccaagatg ttgaggaaat attggtttag aatttacctc 221220
atttaggcca gaaatggtgg ctcacgcctg taatcctaac actttgggag gccaaggcca 221280
atggatctct tgaagccagg agttttagcc tggccaacat ggcaaaatcc tgtctctact 221340
aaaactacag aaaaaaaaaa aaaaattagc cgggtgtggt ggcacaggcc tgtagtccca 221400
gctactctgg aggctgaggc aggagaatca cttgaacctg ggaggcagag gttgcagtga 221460
gccgagatcg tgcattacac ttcagcctgg gtgacagagc aagactccat ctcaaaaaat 221520
aagatagata agataaatat atataatata tatgttatat atataatata gaaactacag 221580
aacaagtgat ctttgtatgt ttccagaata taacagcggg acaggcatag gatagacgtt 221640
cccattgcaa aagggagaaa ttggaaggga taaagaggtc accagtccta agcaagtgct 221700
aaatccagca agacaaatcc cattaggttt caaggcctga gaataatcct cggtgactct 221760
cagctcatta acatacttag ttctcagagc cagactcaat gaggttacgg cccgcatgtt 221820
atgggtcagg aactgaggct aagtaactca ctggagatta tgtggtaaag aaggtccagg 221880
atcattgctt cagtctccag gatatgggga aggttctact cctgttatcc caaattttaa 221940
aatgtgggaa ctaaggctca gagaggttaa gcaaatcaca cagggttgca cagctagtga 222000
tgttgctgag atttccctgt gtgtagtggc tcatgcctat aatcccagca ttttgggagg 222060
ctgaggcaag agggtcgctt gatcccagga gtttgagacc agcctgggca atatagtgag 222120
acctcatctc tacaaaaaga aaaattaaaa agttagccag gcgtggtggc aggcacctga 222180
agtcccagct actgggaagg ctgaggtggg aggattgcct gagcctggga ggtggcgatt 222240
acagtgagct gagatcgcgc cactgcacta caacctgggc gacagagtga gaccctgtct 222300
caaaaaaaaa aaaaaaaaaa gacattgccg agattcaaac ccaggtcagc ctgtcttctg 222360
aaatgtccct ctatgaccca ctcacaaaac tgagaaggca gaaagttgct tggacctgtc 222420
tatttcccct gtgcagtctc agagaaacag tggaactgcc tcggtttctc cttccgggaa 222480
gtattcatag aagcatccca cttacctact ttggtctgaa aataaattag cttgtctctc 222540
ttccacttac taaaaacacc gtgggttttt gcaagttaaa atgcaaaaat aaaatgagga 222600
gaatggtgct ggtagtttag ccagtgggaa gccctctggg gaaagccagc cttttattta 222660
ttacttattt atttatttat tctttctaga tagatttatg ggaaaccagg gctgtgttgt 222720
ccaggggtct gtagtccaga aggcatcaga tgggctacta agtgagtctt tgtccacctg 222780
tagatggcaa gaggcagggc ccaggtgtcc atggcttgga gaggcagggg ttgatgggag 222840
gtttgaggct gtgggatctc tcctggggcc tcagtatcct catctggata atggggacat 222900
tctggccagg cacggtggct ctatatatcc agcacttagg gaggcctata atcccagcac 222960
tttgggaggc tgaggtgggt ggatcactgt aggccacgag ttcaagcagc ctgggcaaca 223020
tggcgaagcc ctgtctctac tgaaaataga aaaactagct gggtattgtg gtgcacgctg 223080
gtaatcccag ctattcggga ggctgaggca cgaggatcac ttgaatccac gaggcagagg 223140
ttgcagtgag ccaagatcct gccactgcac tccagcctgg gcaacagagt gaggctctgt 223200
ctcagttaaa aaaaaaaaga aaaaagaaaa agaaagaaag aaaaagaaaa tgggggtatt 223260
catttatcat ttgacagtaa gtttacccag cattgactgt gtgagaggcc ctgtactagg 223320
cagtgaaaac tcagctaaga ataagaaagt taaaaacaag ctgggcattg tggtttacgc 223380
ctgtaatccc aacattttag gaggccgagg aggaagaatc acttgaggcc aggagtttga 223440
gaccaccctg ggcaacatag tgagacgcca gtctctacaa aaaattgtaa aattagccag 223500
acatggtggc gtgagcctgt agcctcagct acctggaggc tgagatggga ggatcactgg 223560
agcccagaag ttcaaggctg cagtaagcta tgatcctgcc actgctctcc agcctgggca 223620
acagagtaag accctgtctg aaaaaaaaaa aaaaaaagag gccaggtgca gtggctcaca 223680
cctgtaatct cagcactttg ggaggctgag gtgggtggat cacttgaggt caggaattcg 223740
agaccagcct ggccaaaatg gtgaaacccc atctctactg aaatacaaaa aattagccgg 223800
tcgtagtggt gggcacctgt aatcccagct actcaggagg ctgaggcaag agaatcgctt 223860
gaacctggga gccagaggtt gcagtgagcc gagatcacgc cactgtacga cagagcaaga 223920
aaaaagaaag aaagaaagaa aagaaataag atgatgggga gttgtggaaa cctgtccatg 223980
ggcacgtgaa ggtcttgacc tctgaccaag aagtgaacag gctcctctca attccaggca 224040
ctgcagggat ctgggacatg acttctccat gaccaaactg taccctttcc ttttcttttt 224100
tgtttttttg gtgacagggt ctcactctgt cacccagact ggagtgcagt ggggcgatca 224160
cggctcactg cagcctcaac ctcccaggct caagcaatcc tcccacttcg gcctcccaag 224220
tagctagaac tacaggcaca cagcgccacg cccgtcaatt tacacatttt ttgtagaaat 224280
agggtctcac tatgttgccc aagctggtct tgaactcctg gccttaagca atcctcctgc 224340
ctccgcttcc caaagtgctg ggattacagg cgtgagccac tgcgcccagc ccaaattgta 224400
ctcttgaaag atggaatctt agctaggatc ctgaactgtt gccttttatc ctaaatcagt 224460
tgttggttct ttttcattca cttgccttcc tcagagagaa ccagggctcc ggggtccctg 224520
tgtcgggccc caacctgtca accacccggc caatccagca ggacctgggc cgccaagacc 224580
cacccctggc agaggatatt gacaacatga agaacaacaa gctggccacc gcggagtcgg 224640
ccgctcccca cggcagcctt ggccacgccg gcctgcccca gagcccagcc aagatgggaa 224700
acagcaccga ccccggcccc atgctggcca tccctgccat ggccaccaac ccccagaacg 224760
ccgccagccg ccggacgccc aacaacccgg ggaacccatc caatcccggc ccccccaaga 224820
cccccgagaa tagccttatc gtcaccaacc ccagcggcac ccagaccaat tcagctaaga 224880

```
ctgccaggaa acccgaccac accacagtgg acatcccccc agcctgccca cccccccctca 224940
accacaccgt cgtacaaggt gagaccctct gctctcacat cactgggcag gggacctggc 225000
gtccctggag ccagaggctc tgctgagtga ccctggactg tgaccccatc tctctggcct 225060
cagtctcctc ccctggaaaa tgggcatagg cgtagtttcc taccccacag ggctgtggag 225120
ggttcagtga gataatttgt gcacagtgcc tggcacgggg ttgtgttcag tcgggttagc 225180
aatatcttct acgtccttcc ttcccaaggg gagccaggaa gccaccccat ttgaggagca 225240
atagggtcct ctgatggaag cttgaggggg tcagatgatt gattctctcg gcccagcact 225300
gtccaaaaga aatgtaacac aggccacatg caaatgtcag tttaaactct ctagtcgcca 225360
cattaaaaaa ggggccagat gtactggctc atgcctgtaa tcccagtact tcaggaggcc 225420
gaggtagagt gagccaagat ggcacctctg tactgcagcc tgggtgacaa agcgagactg 225480
tctcaaaaaa aaaaaaaaaa aaaaaaaatg gtgaactgct gggtggatta tgtcttaagt 225540
tcatctagtg tcagttctat gtgagagatt ttcatgagtt tgctggataa aggctttcca 225600
tggtcctgag acctaagatc ctaaggtctt gtcactgtgc ccattttata gatgtaggga 225660
ctgaggctca gagaggctca gcctgcccgt gggcacataa gcaggctggg ctgcagaatg 225720
gaagctccag aggctgatgg ctcctccccc tgagtcaaga gaggggtgct aatgggggca 225780
tgccatgcag tttatgggag gtctcagtat ttctatctgt tcagtgggtc tcttggcact 225840
ctccctacct gcctgcaagt gagggtgtga aggtccaacg aggatagggg caggtctgtg 225900
ttaatatccc atgagggccc caccgcactc aaggctatag agtggttgag agcaggctct 225960
cgggggccag gccgcctggg ttccaaatgc cagctctgcc acttcctgct gtgtgacctt 226020
agacaagtca ctttacttct ctgtgcctca atttcctcat ctgtaaacag gagatcagaa 226080
tatatcaacc tcagggctat acaagggttc agtgatgtca taagatgcct ggtatataca 226140
gcaggcactt tagaaatgtc agccgcttct tgcctgccct gggagtacac aggagttccc 226200
agagacttgt gggaaattgt ggagggagcc ctgtgttggt tcttgtccca acagtgaaca 226260
aaaacgccaa cccagaccca ctgccaaaaa aagaggaaga gaagaaggag gaggaggaag 226320
acgaccgtgg ggaagacggc cctaagccaa tgcctcccta tagctccatg ttcatcctgt 226380
ccacgaccaa cccgtgagta tggcccccag caagggcagg gggggcctgg ggctcccacc 226440
agggtggcgg aagtcaggcc agatagaggg caatgagtga gtgttgacca ccatgagtcc 226500
agggatacct ttgaacaagt tgaaaatgga tgctccttcc gtaagtcagg taagatgatt 226560
tgtcacaata tactttgttg gaagagaccc ctgtcctgcc atccactaga aaatcattgt 226620
tatttatgac aataaataaa caaatttgtc ataaataaac aaataaattt gtcctaaaca 226680
acaaataaat ttgtcataaa taaacaaatc ttcactgtga tgtaagaggc accccccttag 226740
aaatggctgc cttgtgcagt acacagcctg aacaactgca cgtggcagcc ctaggacctg 226800
aactctgttt ctaacctaga ctctgtaagg gtttagattc tgggcggata gtgtctgagt 226860
tccatggcct tctgtcttgg gcatctttga aatggataga ctatttaggg gagaaattta 226920
tcccatgaat gtcgtagtgg ctcggaggtt gttttagaat tgaatgtctc ccagggatat 226980
ttcttgaaag cctgaccgct caaaatgctt cttgacaatg aaggatcatg tcagataaga 227040
tgggggagaa gctgctttct ataatctgcc tcttggcaac tcaccctggg tagtaataaa 227100
taaaagtacc tttaaagtac ttttttattt agttgactta tcgattttac taaggaaaca 227160
cttatgtggt atctactcag tgccaggcac tgttctgagt gccttaaaat tttttttaat 227220
```

ttctctgagg ttgttactat gcttagctcc atttgacaga tgaaaaaact gaggtccaga 227280
gacgtgaatt cacctgccca aggtcacaca gcaagccagt gggagagctg gagtttgagc 227340
ccagacactg gctctagcct ccttgttctt aaccactcag ctctgctgcc attcacacaa 227400
ccttatgaac tatttattat tggctccact tattaagagg ttaactggca catcccattg 227460
gcacattcaa ggctctgata aggcctgcaa ttcataattt caataactaa ctttttggag 227520
cccctatcat gagccaggca taaattaagt cttgggtctc atgattttgt gaagtaagca 227580
ctagtattac ggctatttta cagatgaggg caccaaggca cagaggggac aagtaacttg 227640
cccaaggtca cacagctaat ttttaaaaag aaagaaagaa atctacttaa cccatagatt 227700
cacaatattg tttggccctg ggacatttaa tatcgaaaag cctttttatc tcctacagaa 227760
ttaaggaccg tatttcttca acctagcttg ggatcaaga tacttcaaga gggtcgtttg 227820
ggagtgatag gaactttgct aaacagggca tgtgaatgtc ttctctcacc gaggtcccct 227880
ctgccttctt ggggttccag gacccagaga gggcccccac ctggaggagt ttaatagttt 227940
gttgtgtagg aggccttggg ggttggagat ctcagtagtg gtaggtaaca tgagattatg 228000
gaagaaaagg gtttgtgagc ctgtggtctg agtggacctc tgcacgccca tctgtctcca 228060
acagccttcg ccgcctgtgc cattacatcc tgaacctgcg ctactttgag atgtgcatcc 228120
tcatggtcat tgccatgagc agcatcgccc tggccgccga ggaccctgtg cagcccaacg 228180
cacctcggaa caacgtgagt cccacagagc acaccccttc ctagcctggc tgctctgcct 228240
caggccactt tctcctgcat ccaaaatgct cataggtagg gtgggatgtt ggggtcaccc 228300
ctaggcatag cccttatggc tgctggttga gaggggaagc tctgattcct tggggatgct 228360
cttgggagca agacattcct tgaggcagtt tctctgtgag cctggtgggg tggaggtggc 228420
ccagagtgac tggggctgaa aattgctgga ttctctaatg gaggcgtgag actagcagga 228480
tatggatgtt gcacattctc tacatggaat aggggggtta ctggggcagg ggcggtgctc 228540
agaggtggtc ccctccgcag tagacatttc cctttgtaca cgaagctttg aaagaaacaa 228600
ctatttggct cagaaacaca gcctaagctt ttggttttta tgaaagcaag cccctttgcg 228660
gatggtgggt ctgttgacaa cccctgttaa ttgagcactt gctgtgtccc aggaagaaac 228720
tcagcatgca gtatctcatt taatcctcac aatgcgcccc cccaaccccc cgcccaggca 228780
tccccatttg acagatggga aaactgaggc tcaggggaat gagagagtgg taagtggcct 228840
gtccagggtc acacagcaga attccaactc tgcatccccc aaagctccca ctgcttcccc 228900
caactgtctg catttactaa tcacctactg tatgctacgg atgggtgtgc atagcccctt 228960
tgagtcctga caagcaggaa tgagtgcatg cttgtggttg agatggggaa accgaggcac 229020
caacaggcaa gggcgtgcct cagtcatggg ctgcgggcag aggcttgacc ccagggcctg 229080
gtagagggtg gactggtggc tcctgtttcc ctccccagct ccctccccca acccttccct 229140
cccaacccag agccaaaaaa gtgtgttttc tgctggtcca aggctctgct gccctggcta 229200
agtaggttag gacccaggca aagctggcga gccccatccc tcaagcccgc ccacagctta 229260
ccatgcactt tcccttcctt cccaggcctg gcaggccccc ctggggacct gatgggggag 229320
atggaaggaa ataattagaa cgcagctcct ggaggaagct agagccagtg ctcagcctcc 229380
tcacagtccg cttagttgct tcccgcagcc tggtttcccc caggggcctc caggagccag 229440
gcgtggggag gaggtgtccc tggaggggtc cacaaacccc ctgctgacgc gaggatgctg 229500
aagaaggcgt tgccttcggc agggagggca caggcatgga tgatccaggg ggcacggcag 229560
ctcccagggc tgaagggaat ctaggcagtg ctcagaccag gccccaggga ctgtttgcaa 229620
agagcgttca gctccccggc cccctccctc gtccatctcg cagtcgaaac ttctctacaa 229680
gaacactgtg gccccataac gttcacacca cgtaaccacc atccagggca agaaatagaa 229740
caaaaacgcc ccacgcggca tgtgcctcct cgatccccca cccccaccgc cttctttccc 229800
tctagagctg ctggggacac tgtctggaga catttttggt tgtcacgaca ggaggggga 229860 ggtgctcctg gcatctggtg ggtggaggcc agggatgttg ctcagcaccc gccgatgccc 229920
aggacagccc ccactctaga ggatgatcca gacccaaatg tccacagagc ccagcttgag 229980
aaaccctgcc ttaccggtaa ccacgacccc agcttctgga atgagcgttt ttggcttctc 230040
tctttttccc acctgcacag gcttttttt tttttttttt taagagacaa tgtctctctc 230100
tgtcgcccag gttggggtgc agtaacgtga tcatggctca ctgcagcctc aacgtcccgg 230160
gctcaagtga tcctcccacc tcagccccccc aggtagctag gaccacaggc atgcaccacc 230220
acacccagct aatttttaaa tgcttgtaga aacgggcctc gctatgttgc caggctggtc 230280
tcgaactctt gacctcaagc aatcctccct cctcagattc ccagagctct ggaattacag 230340
gcatgtaatt ccaattctta catgcctgta attggccaac actggccaat tcttaaaaac 230400
tgaatttatg tttgctcttc tgtaacattc aataaatgag acacttctat gcttcgcatt 230460
aaatgagtac atgttgcttt tgcaggattg atgggcattc tttttttttt tttttttttt 230520
gagatggagt cttgctctgt cacccaggct ggagtgcagt ggtgcaatct tggctcactg 230580
caacctccgc ctcccgggtt taagcgattc tcctgcctca gcctccagag tagctgggac 230640
tacaggcagg cgccaccaca cccggctaat ttttgtattt ttagtagaga cggggtttca 230700
cactatcagc cagactggtc tcaaactcct gacctcaagt gatccgcccg ccttggcctc 230760
ccaaagtgct gggattacag gcgtgagcca ccacgcccgg tcaatgagca ttctttatga 230820
tgctgttttg agatttactg tgtggcatgg gatgtgttat ccatcccctg ttgacagatg 230880
tttgggttgt ttctaagtgt gaatactgtc cccatgccac gcccctcaac atgtttcctg 230940
agtcacctgg acagtaattt ctccaggagg ccagatgcag tggctcacgc ctataatccc 231000
agcacttcga gaggccaagg tgggagcaat gcttgaggcc aggagttcaa gaccagcttg 231060
ggcaacatag tgagaccccc acctctacca aaaaaaaaaa aaattttttt tttttttaatt 231120 aaccgagcgt ggtggtgcac acctgtggtc ccagccactt gggaggctga ggtgggagga 231180
tcacttgggt ctggaaggtc aaggctgtag tgatccatgt tcataccact gcactccaac 231240
ctgggtgaca gagcgagacc ctgtctcaat aaataagaat tcctccaggg tataaaccaa 231300
aagcgaagtt tctagagcat ataatttgca agtggttggc ctcagtaaat gcagcttgaa 231360
tgtttattgg acaataaaca cagtgaccct ttgggaggcc aaggcgggtg gatcacctga 231420
ggtcaggagt ttgagaccag cctggccaac atggtgaaac cccgtctcta ccaaaaatac 231480
aaaaattatc tgggcgtggt aacacacaac tgtaatccca gctactcggg aggctgaagc 231540
acaagaatca cttgaaccca ggaggtggag gttgcagtga gccaagatgg cgtcactgca 231600
ctctagcctt ggcgacagag cgagaccctg tctccaaaat atatataaat aaataaaaat 231660
aaacacagtg ggccgggcac agtgggccgg gctcgcacct gtaatcccag cactttggga 231720
ggccaaggtg ggtagatcac gtgaggtcag gagttcgaga ccagactggc caatatggta 231780
aaacctggtc tctactaaaa atacaaaaat tagccgggcg tggtagcatg cgcctgtaat 231840
cccagacact tggaggctga ggcagaagaa ttgcttgaac ccgggaggca gaggttccag 231900
tgagccaaga ttgtgccact gcactccagc ctgggtgaca gagtgagaca ccatctcaaa 231960

```
aaaaaattaa aaaataaatg aacgcagtgg cccttgcacc agtagctcat gggaactcct 232020
gttcttccac atccttgtca acacttggta ctgtcgactg tttcatttgg ccgatctgct 232080
gggtgtggag tgagatctta ttggggttgt gcttggcatt tccctgtaat gaatgagatc 232140
aagcactttt ttggattaga ctgagccaca ggaaataaca ttttcaaata gatgaaaaag 232200
atctaagtat taggaatact tgaacctaat ttattggtct tttgatttcc tcttgcacag 232260
cttattaaga gctccagaat tagattcacc tgacccccac ggcctgccct ttcccagctc 232320
cctctcttcc ttctttcctt ccattcattc ctttagtaag tatttgataa gcaactacta 232380
tgtgccaggt actgagcgag ccagggagga ttgacagggt atgagatggt ccctgcactc 232440
ccagagccca caaaccacca ggcctttgac caggctgtgc ccactgcctc gtgcacctga 232500
aatactctcc caccaccatc ccctctgccc acccaggtct ttcaagccaa tccccttgca 232560
ccagcccctc cctccaggaa gtcacctcac cctgacccca ggcactctgg tctctgattc 232620
ctcttcaagc accacatata acaggaatat aagttataac cacacagatc acagagccca 232680
gctcctccag gacccagtac agccccaact gttgatgcat tcattcaaca aacatttctt 232740
gagcacctac tgtattcctg accctgtatt ataagctgga gacgccatgg tgacagacag 232800
acatccctgt ccttgtgggg ctgacatttg ggtgggggag atggacaatg agattatcag 232860
taactacaac aaatgttcag ggagtgataa gtggccgggg gtgtggtggg cagagggaag 232920
gagagacttc gtaaagagga tctcaagcac caggagatgg aatttaaaca gccggtcagg 232980
ggagtcctca ctgggaaagt gttatttgag ctaagtcata aaggaggaga aagacggaat 233040
caaatgggat gtgggggaaa gcattccaga gagacagaac agcctgtgca aaggccctga 233100
ggtggaagca tcttggggaa caaaaggaag tgagcaaggg agagaatgag aggaagtgag 233160
ggcagggagc tgaatggtca gatcgtgcag gggcttgagg gcctcgggga ggactttgac 233220
ttttatccct gaatgaggtg ggagccacgg aggattgtaa gcaggggaag gatgtgcctg 233280
acttctttgg tgttcacagc gccctctggt ggccatgttc agtaatgctc agcccttgca 233340
gcttctgggt ggatctgatt tttttttttt tttttttttt agacagtctc tgtctcccag 233400
gctggagtgc agtggcacga tctcggctca ctgcaacctc cgcctcccac gttcaagtga 233460
ctgtcacgcc ttggcctccc aagtagctgg aattacaggc acacgccacc atgcccagct 233520
aatttttttat atttttagta gacacggggt tttgccattt ggttaggctg gtctcgaact 233580
cctgacctca agtgatctgc ctgcctcagc ctcccaaagt gctgggatta caggctcgag 233640
ccaccgtgcc cagccggtgt ccaccccatg tctagcacca gccagacact gtgccggcgc 233700
accctcatct tcaggcctgg gtgacaccag aggtgtgcta tggtgtgtcc tggacagggg 233760
ctgggccaga ggacattgct cgtccaggca gaaacatcag gcctggggag gggcacagga 233820
aaaatcaacc taccctggca ggggcctggc cttgaagcag gaagagatgc cgtggcagga 233880
agttggcccc agtgtttaaa aaaaccacgt agcaactatt tctcgcccag gatgcccagg 233940
aaagcaaggg tactgggggga ttagatccat caccaagaag gatacagtca gccctgaact 234000
tctctggggc cgcttctaat ccactacagg gcttggggca aattttaaaa ggtacccttc 234060
ccgtgggtta gcgaactggc ctagtacagt gatttttttg ttaggatttg ctgccatctg 234120
ctggacaatt tcattcacaa catacaaatc tgcagtatga aaagagatgg gaggggccct 234180
tgtgcagtgc acgccctgcg caactgtata tagcagctgt gtttcctctt ctgggtagaa 234240
actctgctcc ccagtaggcg atcgttagtt ttaccggggc tctgctggaa caggccagtg 234300
atccactgct ctcttgcttt tatcccttac aggtgctgcg atactttgac tacgttttta 234360
```

caggcgtctt tacctttgag atggtgatca aggtgagtgc agattataag tgagaacaca 234420
cggtaatttt tttttttaag caagtgcagg gctgggcaca gtggatcatg cctgtaatcc 234480
cagcactttg ggaggctgag gcaggcagat cacttgagat caggaggttg aggccagcct 234540
ggccaacatg gtgaaacccc atctctacta aaaatacaaa aattagccgg gcatggtggc 234600
acatgtctgt aatcccagct actcgggagg ctgaggcagg agaatcactt gaaccctagg 234660
ctgcaatgag ccgatgtgga ggctgcagtg agccgagatc ttgccactgc attccagcct 234720
gggtgacaca gcgagactct gtcaaaaaaa aaaaaaaaaa aaagagctgg gattccagga 234780
gatcctgagc ctccaagaat gccccccttg agaggatgag tctcccagag gattagaaat 234840
gcctggtgtg tttgaagagc agcaaggaag ctggtgtggc tgggcggagt gagagaacag 234900
tggggaaacg aaggacagag agatgagtgg ggaggtgagg gggcaccttg tgccggggat 234960
cacagagagg gctcttcggc tcttactttg agtgaggtga gggccataga gtgttctgag 235020
cagaggaggg acttgatcca ggtgttcaca ggtgcccttt ggcatctgtg ggaagccaga 235080
ggacctgtga gcaggtgatc acactggtcc ccatgggcga tgacggggac aggatcaggc 235140
tggtgaccaa agaagaggtg agaagtggac agattcttgg aaggttctgg aaatagagcc 235200
agtgagtttt gctgatagag ccaccaatga gggatttggg acaaagaggc atcaaagagg 235260
atcccaaagt ttggatctaa gagccggcaa gccagagctg gcttccatca ggcaaagggg 235320
ggccgcctca tggggcaggg gctccccact cctccctgga gtcctctggc cactgcccat 235380
ccctgcaaga tgaggtggcc tcattggctt ccctgcctct ccccgagagg ctagagagtg 235440
ggtggcagca ccccagggtg gggatcaggt gggggttctg agcaccctct cttctccccc 235500
acagatgatt gacctggggc tcgtcctgca tcagggtgcc tacttccgtg acctctggaa 235560
tattctcgac ttcatagtgg tcagtggggc cctggtagcc tttgccttca cgtaagtctc 235620
ctcgcaaggg ttcctcttgc ctcttttccc ccaaccccca gcctgggcca cacatcggat 235680
tacaggacat gttctcaggg tctagggatg gggtgtgtgg gctccgggga cgtgggagat 235740
atcagcatgc caccaggaag agcttcgatg gctttttgca tgatgtccat ggaggaagaa 235800
ggagaaggga cccccccctcc tgccaacctt ctacctcctc acacagcaac gggcctcagc 235860
cacatcactg gccccttgct gtgcagcttc ctgtagacta gcctcgccgg aacatctcat 235920
ccccctacta ctccacaagc gccgcccaaa ccgctgtctc tttggaaagt ccctaaagag 235980
acaatcagga aacgaatgtg catgagaatt ctgacccccct ccctatgcct gaaggccccg 236040
tagttgtaga cctggtgact ccctttgtgt gtctttcact tctcctggca gtcctaggat 236100
tctctgccct ctgaaaggcc atgtgtcatc ctgcagctcc aagatggcgc cccagttgta 236160
ggcagccatt tcaggatggc acccaagctc ttagtagtca tcccaagatg gcatccaagt 236220
tctgggtggc cattccaaga tggcccctga gttctgagct atcattccaa gatggcctct 236280
gaatttgggg tggtcattct tagatggtcc ctgagttcca aggtgacctt caagttctgg 236340
gtagccattc caggatggtc cccaagctct gggtggctat tccaagatgg ccccaagttc 236400
taggcagcca ttgcaagatg gcccctgagt tccagggtgg cccccaagtt ctgggcaacc 236460
attccaaggt ggcatccaag ttctgggtgg ctattccaag atggcctctg atttctgggc 236520
taccatgcta agatggcctc tggattcttg gtggccattc ttacatggtc cctgagttcc 236580
aaggtggcct tcaagttctg ggtagccatt ccaagacggt ccccaagtct tggatggcta 236640
ctcgaaggtg acccccaagt tctgggcagc catctcaagg tggcacccta gttctgggta 236700

```
accattccaa aatggcaccc aagttctagg gcaaccattt caaaatggcc cccaagttct 236760
gggtgactat ttcaagatgg tacccaacag gtgagtggcc attagccctt agggccctga 236820
tagcagactt agcagtacat tcctgaagtt gtagacattt ggagcgggat gaaaaatatc 236880
taatcagtct ttaatcaaga aacaaatctt ggggaccctg gctgtgccca tcatggtgaa 236940
tgattccctg acaggttttg aaaggatctt gacacattca ctcccatcgt gagagaatca 237000
ggggcttcct cctgtgcctc tgcctctagg ctccctcctg agccaatctg gaggggccct 237060
tgaatggtct ccctcaccaa acaatgagga cttggtttgt caggagggcc aaaatagtgg 237120
cccatttcca gtagaagggc tgttaagtag gccacactta gattcttctc tgggaacaca 237180
atgaggtcaa gttgtgttag aacaaaaaat ctccagagtt tttggatgcc tcagagctgg 237240
agatgtatca tgaaggttgg gaggctgatt atacttcttt ctctttctct ttcactcctt 237300
cctcctcttt ctcctctctt tttgttcgtt tactcttttc tttttctctt ctcctctccc 237360
tccccacatc cttccctctc ctcaaagctt ttcagtgtct atttgactac tagagcaatg 237420
cacggtggct tacacctgca atcccagcac tttgggaggc tgagacaggc agattgcttg 237480
agcccaggag gccaagacca gcctgggtaa catagggaga ccccatctct aaaaaaaaaa 237540
aaaaacaatt agccaggcat ggtagtatgc ctgcactagc agctacacgg gaggctgagg 237600
tgggagaatt gcttgagccc aggaggttca aggctgcagt gagccgaaat cgcaccactg 237660
caccccagtc tggggaacac aggaagaact tgtctcaaaa aaataaaaag tttaaaaaat 237720
taaaaatcaa tgaatttgct atttagaata ttatgcttta tatggttact gaataatttt 237780
aatagtgatg agtacaaaaa aaacaggttt agcaagctgt tctgtaggtt aaaaagtaaa 237840
taaataaata attaattaaa caaaatacaa tgcacatcaa attaggggac aaagattgtg 237900
acgaataaga caaggagtcc atgtctttaa aatatgaaaa gcagttacaa atcaataaga 237960
aacactactt ctcaatggat aaatgggcaa aggacataaa cagaaatctg atagaatgct 238020
ggcaactagt aaaaatggag gtaaatcaac ccttggaatt cagagaaatg taaaataaaa 238080
acgagataca attcattccc tatcaagtta gcactgttcc cgccgcaccc ccacacacac 238140
acaaaaaatg attttttag ctaataaaca gcatatataa gaatgtatta taataggctg 238200
ggcacagtgg ctcacgcctg taaccctagc attttgggag gccaagggag ggggatcacc 238260
tgaggtcagc agttcgagac cagcctggcc gacatgacaa aaccctgtct ctactaaaaa 238320
atacaaaaat tagccaggca tggtggcgga tgcctgtaat cccagctact caggtgggta 238380
aggcaggaga attgcttgga cccaggagat ggagactgca gtgagccgag atcatgccac 238440
tgcactccag cctgggtgag aaagcaagat tttgtctcaa aaataaaaaa aggaatgtat 238500
tataataaaa tatacttttc tccccctcta tcacctattt aagcaggtcc ttcaagttgt 238560
caggtagaca tcatgctatg agaaaattta aatcctgaaa agccagaatg ttttaccacc 238620
ctcagcctgg aatgaatcct tctcctatgg aaataaccta cgggtttctc cacccctctc 238680
tgcctttcag ccccttccct ccctctcccc tccttttctt tctccctctt tctcttcctc 238740
ctttcccctc tcttccctct ctcttcttcc ctctctctgt ctctttctgt tcgtctttct 238800
ccttttaccc cctctcagtt tctatctttt tattttcctc tttctctctc tctctccctc 238860
tctttctctc tcactccctg cactgttgat gacctatgtc cttgggtgat gtgggcctcc 238920
cctggaccgt gtagcttgga gaaagctgac cctctgtcat cggtctggca acagggactt 238980
ggccccccta ccctgcattc tgatgaggaa tggtattcag acaaaggcag atcccaggac 239040
acaggaggac atgctcaggc agggaccccc gccccttcc tctggggcaa ggtctgctca 239100
```

```
gcagcctcca agattcctag ggctcaagag gtggcaggta gctcagggca ctagggcagg 239160
cagtggggtg aatatgtcac tcatatccac ctgtccacac acaatgctta ccttggccac 239220
ctgtgcccag gggaatgggt tttatcctgt gaatcctccc agtgaccacc actgagtgtg 239280
gcacagataa atggtaccaa gcccaagctg ttcaggtctc caatgtcact ttcctctcag 239340
acctctgttg tagctgacat actgtaatgc tgaggagggc cgggcacagt ggctcatgcc 239400
tgtaatccta gctctttcgg aggccaaggc agatggatca cctggggtca ggagttcaag 239460
accagcctgg gcaacatggt gaaaccccag gcaacatggt aaaaccctgt ctctactaaa 239520
aatacaaata ttagccaagc gtgatagcag gcgcctgtaa tctcagctac tcgggaggct 239580
gaggcagaag aattgcttga acctgggaag tggaggttgc agtgagccaa gattgcacca 239640
ctgcactcca gcctgggcaa cagagcaaga ctctgtctca aaaaaaaaaa aaaatgctga 239700
ggaggtgact gtcccacctc catcctccga gttgaccatc acaatttagg gaggggaatg 239760
acctacaaag gacccagaag caagcctttc aattgttgag cttttgccat tatgggccat 239820
cgtttacaac atgctgtttc taggttctct ggaggtaaaa ttagcctcct cttttaaaca 239880
aagctaatct gcaaaagcga accaaaaatt cttttccacc agagatcaat tagcagaatg 239940
agctgggtgc gatggctcac acctgtaatc ccagcacttg gggaggccga ggcaggtgga 240000
tcacttgagg tcaggggtcc aagaccagca tggccaacat ggtgaaaccc catctctact 240060
aaaaatacaa aaactagctg ggtgtggtgg ggagggcctg tagtcccagc tactcgggag 240120
ggtgaggcag gagaattgct tgaacccagg aggtgaaggt tgcagtgagc caagattgtg 240180
ccactgcact ccagcctggg tgacggagca agactccatc tcaaaaaaaa aaaaaaaaaa 240240
aaaaaacagc agaatgattc ttttggggag ttgacttttt ttttaatttc tgagttttct 240300
ttttaaatat caagttatac aagggcattc aaattggcct acaactcaca ggaatttggc 240360
agcctgtttg cagagtcaag cttttacatt gttctcatga aattggtaca ggcataaagc 240420
cacccttcac tcttgaaaat ccattttgaa tgttgttgtt ttaattctta tgcaagaaaa 240480
ggatctggat agggatttca ggccatcctg tcaaccctgg caggcttgta gatcatgcag 240540
gaactgggag gtgtgagatt ttgccagtag gatcctggca agtgcctggg actctcccag 240600
ggttttggaa gagccgacgg acatgagtcc aacagggagc atctttatat catggccgaa 240660
gggatgagag aggagaccct caaacctcac gcctaccaca ccctccccac cccactgtca 240720
agagtccatc tggtactgct gttcctcccc cagggcaggg ctgcaggccc agcacagctg 240780
gccaggtgcc ttgatcaagc cattcctgca cacctaagag ccaaactgct agaaaaccag 240840
aataggagct actgcttttt tccctaaaaa gttttggaat cttctccccg ttacaggttt 240900
ctggcctctt ttgcctgaga aggtctctca ccctatgagg actttgctta ttgtctttcc 240960
ttgttatcgg atagttggca cattggaagg agcatggatg ctctgaggtt ctcagcctga 241020
gcgctgaact ctccacccgc cccccacccc ccaccccagg gtcctctgct tatttccttt 241080
ctggtctttt aacttgcttt gtctgtcctc tgtgcatatc ccctcataga caaggctgag 241140
agccccacaa gtattagatt gaccttattg ttttaagaaa ttgtccctcc aggtctgttt 241200
gatttctctc tagatgtgca agtcctttag cctctctgtg cctcagtttt tcccatctag 241260
atgaggaaac tgcggcccag agggactgtg gagggaagta agtccgacaa gatcactgag 241320
gttgggttca gctgtcagat gctacccatc tcccagccct gaatacggag gctcacagtg 241380
agcagaatga tgctcagcag cctggccagc ctgggttctt tgaggcctgg cagggctgcg 241440
```

agatccaggg gaagggaata ggggaaggga gcataaggtt attcccttcc ttgttgaaag 241500
gaaccttgcc attctggcct gttggggtca aagcaaggat tcttccccca gtgctgtgat 241560
tgtggcctcg tctccgatat gggagaaaac tatccctgtg gtcccaccaa gggatgtatt 241620
gaagctcttc tgaagatgtc cacccctcct gcacctcacc caaatatctg tgtgtgtgtg 241680
tcctgctcaa ttcactgact gtgtcccttg tatccatgcg tctaccataa acaccccatt 241740
tcatgagcca tcacacgtgg tatcacgctc tgtgcccatg catcagggcg gccaactgac 241800
atttctcagc agctggcaga tcatgatcct gccctcaccg ccaagagtcc atctggcgcg 241860
gctgttcttc ccccaaaggc aggaccgcaa ctggcagagc gccttgatca agctgctcct 241920
gcatacccag gagccaaact gtcaggaagc caaagatgga gccctcaggc tgctatctct 241980
tgatcctcat cttcaaaaca gcccccaccc ctgaaggcat tatttttctt gtgtatgatg 242040
aaatggaaag aagattagag tgcgagatac ccacacctgg gtttgaatct tagtctgtct 242100
tcccagctgt gtgcctgccc ttgggcaggt cactcttttt ctctaggcct cagcttcctc 242160
atctggaaaa tggtcataat ggtgctgtct tcccataggc aaatgcagtg atgtccagaa 242220
gactcccata ttaaacctaa agtcagcaga ttaggcaaaa atcactgtca ttgaaaactc 242280
cctcaatcat ccgtaaagaa gctgggtgtg gtgtctctca cctgtagtcc cagctacttg 242340
ggaggctgag gtgggagaat cacttgagcc agggagttca aggctgcggt aagctatgat 242400
tgtgctactg cactccagcc tgggcgacag agcaagacca cgtctctaaa aatataaaat 242460
aaagccgggt gcggtggctt acgcctgtaa tcccagcact ttggaaggct gaggcagcct 242520
ggcaacagag tgagaatcca tcaaaaaaaa aaaaaaaaaa aaaaaaagta gaatctatat 242580
gattctacgt atgcaataat tcctagatac actgaatttg agaaccccaa gtcagactac 242640
aggaaaagga gatgaggggg tgtggaggag aatccacttg gaatatttgt agacatttaa 242700
accattctgt gttttaaaaa atatcacagc cgggcgcggt ggctcacacc tgtaatccta 242760
gcactttggg aggccaaggt gggcggatca cgaggtcaag agatggagac catcctggct 242820
aacacggtga aaccccatct ctactaaaaa tacaaaaaaa attagctggg cgtggtggtg 242880
ggcgcctgta gtcccagcac tcgggaggct gaggaaggag aatggcgtga acctgggagg 242940
cggagcttgc agtgagccga gatcttgcca ctgcactcca gcctgggcga cagagcgaga 243000
ctccgtttca aaaaaaaaaa aaaaaatcac taacttccag aggggtcgtg gatggaaaat 243060
tccatagagt ccgcttggcg acagggtttc cgccattctg atggcggtca agtctttcta 243120
acctggatct ccagtcattg ttgaaggcgc ctaatgagcc ccaagcctga ttccaatgaa 243180
tcacgagagg accagctgct aggtgctgat agctttcccc aggcccgcat ttgctcagag 243240
ggcttcagag ttgcttctaa ttccatccca agtcagaact ctttgctgac cccctccttc 243300
ataaagagca aagccaaggc catagctttt gttaatcaaa catcagaatt ccacagacct 243360
gagttggttg gttgtttgtt ttaagagaca gagtcttgcc caggatgcag tggctcacac 243420
ttgtaatccc agcgctctgg gaggcctagg caggaggatc acttgagccc aggagtttga 243480
gaccagcctg agcaacataa tgagaccccc gtctctacaa aaaatggaaa aatttgcctg 243540
tatttccagc tacttgggag gctaaggtgg gagaatcacc tgagccctgg aggttgaggc 243600
tacagtgagc caagatcccg ctactgcact gcagcctggg caacagaggg agaccctgcc 243660
tcaaaaaaaa aggagagaag gagagagaca gggtctccct atgttgtcca ggctggtctc 243720
gaacttctgg cctcaagcaa tcttcccaac tcgtcctccc aaggtgctgg gattatagct 243780
gtgagccacg gcacccagtc tgggcctgtt ttgcagatga ggataacgag aggcagagtc 243840

```
aggattcaaa cccaggtccc ctcaacttca aagctcacaa ccttttagac attctaaaac 243900
cttgcagctc cacaacgcct ggagaagagg ggtttctccg gctcttggca gtgactttcc 243960
gtggtgaatt cacctttggt aactgacagc tttgcagctg tcctgctacc tggaaatttg 244020
gctttcttag tgctttcttg ggcagtgcca ggtgcctgcc aagggcgggg gactgaatgg 244080
aggtgggggc ggcttccaga tggaaggatg gacatcggcc agcgccatga gcctgaggct 244140
cccccaactg ctgcccgggc gggactcggg ggtgctcagg ggtgcgtgtg tgtacgtgcg 244200
tgttctgtgt tcttttttct gaggccactt acgatctgtc tctccctccg atgccacatc 244260
accaggagca gtacacggta aagtctctct ctatctttct ctctctctct ctttctctct 244320
ctctctctct catattctgt ctctcgtgat ctgtcccctg gtgcagcctc gttagttctg 244380
ggcctgtttc tgtggccttg tgtccttgct gccgctgtcc tgtcgcttca aatgaccaga 244440
actcactccc tgcgaaggag gcatcccaaa gggtcttgcc aatgcctccg cccatgcccc 244500
accagttctt gcagagaaca gaaggggcag aggttcagtt tcaataggca agctgggtgg 244560
agcagttatc agaagcaatg aaagtgggcc agacacggtg gctcacgcct ctaatcccag 244620
cattttggga ggccgaggcg ggtagatcac ttgaggtcag gagtttcaga ccagcctggt 244680
caacatggtg aaaccccatc tctactaaaa atgcaaaaaa ttatctgggc ttggtggtgc 244740
acacctgtaa tcccagctac ataggaagct gaggcaggag aatcacttaa acctgggagg 244800
tggaggttgc agtgagctga gattgcacca ctgcactcca ccctgggtga cagagtgaga 244860
ctctgtctca aaaaaatata taaaataaat tgaacaataa aaaaataaaa tggccatgga 244920
atcgttttca gatgaggaga tgcagaatgc ccatggagac atgctcccaa ttgtcacttg 244980
tttgggacat caagatttta gccagttcca tgtgcaacct ggatgtacag ttccttgact 245040
ttttttctat caacatgtat tctaaagttc aatttcaaaa ggaaacttta gccaggtgca 245100
gtggtgcatg cctgcagtcc cagccatttg ggaggctgag actgaaggat cacttgagcc 245160
caggagttgg aggctgcggt gagctatgat cgtgccactg cactcccccc tgagattcca 245220
tctctttaat ttaaataaaa aaaaaggaaa ctatattatc cacttacaac cagcattgct 245280
aacctaagat aaatctgcaa ctgcaaaagt aaatgtaggc cagacatggt ggctcacacc 245340
tataatccca gcactttggg aggccgaggc aggtggatca cttgaggtcg ggagttcgag 245400
accagcctga ccaacatgga gaaaccccgt ctctactaaa aatacaaaat tagccggacg 245460
tgatggcaca tgcctgtaat cccagctact cgggaggctg aggcaaaaga atttcttgaa 245520
cccgggaggc agagactgct gtgagctgag atcacgccat tcactccagc ctgggtaaca 245580
agagagaaat gccatctcaa aaaaaaaaaa aaaaagtaaa tctaacagaa accagacaat 245640
gttgttgcct tcaagctggg ctctttgtta aaaggaaaat tactaagtgt tagggaggtg 245700
ttaaaggcct attagcatct acctgaggct tcctttctcg caaaagcaga gcgtctgaaa 245760
gatacgtgga aaagaaactt aaagtataat aaaaaagaaa gaaagaaaaa gaaatgatta 245820
tgcccctctg agatccaatt atttaatctg tgcccctgtt ctgcctaaaa ttatctcagt 245880
gactgtccaa cgtgtgtctc acacttgggg gcacagcctt gagatgataa tgatgatgtt 245940
agttttaaaa agaaaaaaaa aggttcagag ttctgaatcc tggagtatat ctctgcctag 246000
caggctaaaa tacaattatc gtctttgttc cctgaaaaat gaaaaaaatg gagtccttta 246060
aaaagcaaat ggtgtgaaga atgatgtttt tgcactggat actgagaccc atcgtgatgg 246120
gggtctctgg ggcagctctg ctcatgacct gggaggtcac tgtagggaga tgttttctag 246180
```

gtgacctccc cacccaaata ctccaaccgg aggcattcac gtgtcctgag accacacgcc 246240
aggcgcaggc taggggctag gacaagaatc aagattaaag gggaaatggc caggtgcggt 246300
ggctcatgcc tgtaatccca gcactttggg agtcaaggcc agtggattac ttgaggtcgg 246360
gagttcgaga ccagcctggc caacacggtg aaaccctgtc tctactgaaa atacaaaaat 246420
tagccaggtg tggtgactca tgcctgtagt cccagctatt cgggaggctg aggtgggaga 246480
atcacttgaa cccaggaggc agaggttgca gtaagccaag atcatgccac tgcactccag 246540
cctgggcaat agagcaagac tccatctcaa aaaaaaaaaa aaagattaaa gggaaaatga 246600
acacagagaa gagtagatta cactgtaagc ctttgaagag ttttctgtct aaaaccagag 246660
accgaagaaa caaacaaaga ttaactccga aatagcacat aggagctggc aggagccaga 246720
ggtaggcagt caggaaatgc tgtcggaggg agcaacaggt aatttgggct ttgaggaccg 246780
ggtagttctg tgactggaga agtggaggaa gggcatttct agcagcggga acagtatatg 246840
cataagcaga cagaggcaaa agaatgtggc tggggcttga gatatgtagc cataaatggg 246900
aatgcaaagg tgaaggtaag ttggactaga ttttcaagag cattgaatgc catgcccaga 246960
agtttgcact tgctcttctg agaattcacg tgctccagaa gaattctgag caagagaaag 247020
agtgacaagg tcattggctt tagccactgt gtgcataaaa catggaagaa aaggcaggga 247080
atgaggagca agttgggaga cgggtgaggg gggatggcac ccaggaatgg atggcgggat 247140
gttaaggaag gtgacccact ggggatgggg atggggatag agggcaggca gttgaccatg 247200
actctcaggt ttctggtgtg gacaactgga tgggtcatga gtgccatgaa ccacaagcta 247260
ttcatggtcc cactcaatac cctcctcttg gggggcctga gtcatggttg gccaagggtg 247320
tcatggcatc tctggggtct gcattgctaa gctcagttcc aacagacctt ggactgaact 247380
tctgtgcagt cctctctggc aaagatgggc tcagagaccc ttggagcaat gcagcagaga 247440
ccatggcagc agccacatca gcatctgaaa acagcggcac ccggttattt tccctccttc 247500
agactcaggg aatatggtgg gggaggggag atttggtata agggccactt taagtatctt 247560
ccagaatccc attggaaggg ggagaaaatc ccattttttt aagagcccac tgataccacc 247620
tttaaaaaga atacacaggg ggccaggcgc agtggctcac acctgtaatc ccaacacttt 247680
gggaggccaa ggtgggtgga tcacctgagg tcaggagttc aagaccagcc tggccaacat 247740
ggtgaagccc catctctact aaaaatacaa aagttagctg ggcatggtgg cacgcacctg 247800
tagtcccagc tacttggaga ggctgaggca agagaatcac ttgaacctgg gaggtggagg 247860
ttgcagtgag ccaagatcat accattgcac tccagcctgg gcaacaagag tgaaactcca 247920
tctcaaaaaa aaaaaagaat acatagggga ccactaaact cctagaccaa gggctttttt 247980
gaaaatagct gtgaccaggt gtagtggctc acacctgtaa tcccagcact ttgagagggt 248040
gaggagggca gattgcttga gctcaggagt ttgaaaccag cctgggcaac atggtgaaac 248100
ctcatctcta caaaaagaca aaacaattag ccaggcgcag tggcgtgtgc ctgtagtccc 248160
agctacttgg gaggctgagg tgggaggatg gctttagccc aggaggcgga ggttgcagtg 248220
agccgagatc gtgccactgc actccagcct tggtgacaga gccagaccct gtctcaaaaa 248280
agaaaaaaga aaagctgtgc agaaatgggg gtggggaatc agccaacccc cttgtgctgg 248340
gtctcaggga cacccaatac agctgctcag gcccagccag atggcaaagg gccctcaacc 248400
aaccctggga ccagaaccac aaaaagccac gtacttactg gctcccgagc ccaagcttaa 248460
caggtgaaat ggaccactct tcaccaggaa gggcagggct gtgccaagct caccccagac 248520
ttctaggcct gggagggtag ggtcccatgg agctgtgggc tgccccctac ccaacctgac 248580
ctctgcttcc tctcttccct tcttcccacc taaacattcc tccacagtgg caatagcaaa 248640
ggaaaagaca tcaacacgat taaatccctc cgagtcctcc gggtgctacg acctcttaaa 248700
accatcaagc ggctgccaaa gctcaaggtg agattgggag atggtggggt gcggtggggg 248760
ggactgtcag ggttatcatg tacagctgag caggttgtac actgctcaag gacaacacat 248820
taaaggaggt gctgataaca tcctagccat cgtgtatgga tatttgtatt attacaactt 248880
cccagcagat ggcagtaaag tgagctgacc taaaataatc tgtgtattat ggcagttttt 248940
ctttagatga agtgtcttgg ggttaagatc ctttttccta attcgcatga aggcatcata 249000
tggatttaaa agggtataac cgtgatctgg gaagcaggaa ctagatttct tgttccataa 249060
aattttgact tttcatctac ctattctagg ctctagtatc tcccattcca aaatagcatg 249120
aaccagcatt tcccaaaagc ctgtcattca aaaacatata tatatattaa gggaaataaa 249180
atccagtcat tagagcaccc actttcactc tatgcttcac ctgggggtcc ccagtattat 249240
ctcttatgta atatgtttct ttaaatcaag tcacacccgt aatccctgca ttttgaaaga 249300
ccaaggcagg agtgttgctt gagcccagga gaatgagacc agcctgggca acatagttag 249360
actctgtctc tactaaaaat taaagacaga aaacagatac tgttatggaa atctaaccaa 249420
atatggctgc ctgcctaagg ctttgtgcat tgacaactgc tctttcttgg ttaaagaggg 249480
aaaatgtcaa tggtaggtgt taacatggta gcaactaagt aaaaatttct ccttcactca 249540
aaaggattga gagagttgga aaggaagtaa ctttgttacc ttgtttttct gtgttgggct 249600
cctgtatcac ttaaaagcat ctctggtatc ccatctggga gttttagatc catagaatgc 249660
caggattgag tccaactcct ccaacgctta tttctgaaag ctggggggac cttaccctag 249720
tgacttgact tatgaccttg cctgtaaaat gggaatgatc atggcagtat tttggtatga 249780
tgggccactg gaggcagaag gttgggcagg tccccagccc ctcatgctct ctgtcaactc 249840
caccccacag gctgtgtttg actgtgtggt gaactcactt aaaaacgtct tcaacatcct 249900
catcgtctac atgctattca tgttcatctt cgccgtggtg gctgtgcagc tcttcaaggg 249960
gaaattcttc cactgcactg acgagtccaa agagtttgag aaagattgtc ggtgggtctc 250020
cactttccag cacattccca ttggaaccag caggtgggca ggggggaagt ggctagaggc 250080
attggccact tgggctcaga gactggagaa gtgatgagcc ttggaagtga ctcagttgca 250140
accagcttgg atcttgggta gaaagaaaac cggttttaga atttgagtca ccacccagag 250200
ccacagaatg agtcataagc aaattgattg acctttcagc caccgccttt gtcatgtgag 250260
ggatattaat acacatccac agttccttac ttgaaatcgt tacaggcaga tgtgtttcaa 250320
agttgagaat attttgagat tcccatgtgg gacatgacac cctcagctgg gtctaaggca 250380
gccctataat caaacacaat atttctgcca taaaatgtgt aactatttac atcaaatggg 250440
gtaaataaca agtataaaga gcttcatgtc caatcagatc aggtttcatt accaaataag 250500
ttaggtaaga ggccaggtgc agtggctcac acctgtaatt ccaacacttt gggaggctga 250560
ggtgggagga tcacttgagg ccaggagttg gagaccaggt tgggcaacat aatgagagcc 250620
catcctacaa aataaatttt aaaagttagc ggggcatggt agcacacacc tgtagtccca 250680
gctacccggg aggctgaggc gggaggattg tttaaacaca ggagttcaag gctgcaatgc 250740
actatgatgg taccactgca ctccagcctg cgtgacagag tgagaccctg cctctcaaaa 250800
atatatacat ataggccggg cgcagtggct catgcttata atctcagcac tttaggaggc 250860
cgaggcgggc ggatcatgag gtcaggagat cgagaccatc ctggctaaca cggtgaaacc 250920
ctgtctctac taaaaataca aaaacctagc tgggcatggt ggcagacgcc tgtagtccca 250980
gctacttggg aggctgagac aggagaatgg cgtgaacccg ggaggcggag cttgcagtga 251040
gcccagattg ggccactgta ctccagtctg ggcaacagag ccagactcca tctcaaacaa 251100
acaaacaaac aaacaacaac aacaaaaata tatatatata tatatgtata tatatatatg 251160
tacacgcaca cacacatatg tattatatgt gtgtgtgtat atatatgtat gtgtatatat 251220
agtgatattg ttaccagtgt aaagtggcat tttgcaacac atggtagcct gttgttatct 251280
tgatggctat ttattgaaat taggaggatg ccagatgtct ggataggagt ctggaactaa 251340
cccttgtttc ctgccttgaa aaggagtagc aacctccctt agcctgatga acctctaaat 251400
gtcccctatg tctctctgcc tcctcctaaa ctccctccac cccaccccca gcaagcctga 251460
ggctctcacc ctgaggacta gaagttatca cgttggaaga gggtgctgga ccctgggtca 251520
gctctcccac caggagtaag gttgtgccat cacccatgga tttatctcaa agtagatgca 251580
cacgtcatcc cctatgaagc acaggaacac atggtggcag gatggggagt cactgcttcc 251640
caagcagtct aggctggtgg accactcttc ctttccctcc ccctgtctct gataaccaaa 251700
gacaagtgca agacagcccc tctttcccat ttactaacag tccccactct ctgtggcaga 251760
ggcaaatacc tcctctacga gaagaatgag gtgaaggcgc gagaccggga gtggaagaag 251820
tatgaattcc attacgacaa tgtgctgtgg gctctgctga ccctcttcac cgtgtccacg 251880
ggagaaggct ggccacagta agtggcccga ctggaaatct atccaggagg agccctgggg 251940
agcaggagga taaagggcct gagagcttag caataagaaa ggtcttggag gccgggcatg 252000
gtggctcacg cctgtaatcc caacacttta ggaggccaag gcagatgtat cacttgaggc 252060
caggagtttg agatcagcct ggccatcatg gcaaaactcc atttctacta aaaatcccaa 252120
aaaaaaaaaa aaaaaaaaaa aaaaaaaagc tgccaggcat ggtggctcac acctgtggtc 252180
ccggctactc aggaggctga gacacgagaa tcacttgaac ccaggaggca gaggttgcag 252240
tgagccgaga ttgcaccact gcacttcatc ctgagtgaca gagcaagact atggcctccc 252300
cgccttcaaa aaaaaaaaaa agtgaggctg aatcatggac ttagtcttta tttaaaattt 252360
tgagccactt gtggtggctc atacctgtta tcccagctac tcaggaggct gaggtgggag 252420
gatcgcttga gcccaagagt tcaaggctgc agtgagctgt gattatgcca ttgtactcca 252480
gcctagacaa cagaaggaga cccctatccc tgaaaaaaaa aaagaagaag aaattgatat 252540
ttgttcatca tggacttttt gcattaattt tgattttta aaatattgga gcaaaagatt 252600
atcttgatta ctgagatttt cagtaccccc ttaatttgca cccaaaacaa atgcctccct 252660
ccctcacctc gtccaagtaa tggtctttct ctcagaggtc ttggaaatgc caggctggaa 252720
gcttggtaga ttccagcatg tgccctcagc atcctcacct ccctccctct ctcagcaaat 252780
atgccaacct gaacatgccc tactacccac tctcagacac atccagtact cacacatgtg 252840
ggaataatgc taacccacaa ggcacctttg agcaaagttt ttttaaacac ctttctcaac 252900
agacttcatt tccatctgtc tgaaaatcat cgcaatagac ttaaatgatt ttgttcaaac 252960
aaggcactga aggaccacct gccaaaaaat tgtcatcatg aatacacaaa tctatcatgc 253020
ctatcatgtg aaggtatcgc ttagacacag agcctttgag cagtgtgcaa cctgcactac 253080
tgtacagagc tgctgtgcac ttacccactc tcatatatat ccccattgta cctcctgagc 253140
acccagcacc acctgtgctc aaatacccac tctacatgca tacacccacc tctactccct 253200
ccattgccac aacctgtctt taaatcccaa cttggccact tataagtggg tggtcttcag 253260
cacgtccctt taaattgctg aacctcaagt tcctcatgtg caaagtggag ccagtaataa 253320

```
cctccctggg agggttgctg agccggtggg gatgaattgt tgaatattgt ttccagcaca 253380
cagcaagccc ttcatgcaca gcagtagaaa tgactgacat tggccaggcg tggtggctca 253440
cacctgtaat ctcaacagtt tgggagaccg aggcaggtgg atcacctgag gtcaggagtt 253500
caagaccagc ctggccaaca tggtgaaacc ccgtctctac taaaaataca aaaaaattag 253560
ccaggcttgg tggcgcatgt ctgtaatccc agctacttgg gaggctgagg caggagaatc 253620
atttgaaccc gggaggcgga ggttgtagtg acccaagatc acgccgttgc actccagcct 253680
gggcaacgag agcgaaactc catctcaaaa aattaaaatt aaaattaaga aataactgac 253740
attgttgtca gcctttcaaa aaacagcgac tacttaaatt tctttttcat ttccctctgt 253800
tcctgttctg ccatctcact tccaccctct ctccaccttc ctcatcaccc cttgggtccc 253860
tgtctctctc cttcctgccc cttccctctc cctgccccat tccttgcagg gtcctcaagc 253920
attcggtgga cgccaccttt gagaaccagg gccccagccc cgggtaccgc atggagatgt 253980
ccatttteta cgtcgtctac tttgtggtgt tccccttctt ctttgtcaat atctttgtgg 254040
ccttgatcat catcaccttc caggagcaag gggacaagat gatggaggaa tacagcctgg 254100
agaaaaatga ggtgccactt ccaattccat ctgtccttta aaaactgggg acacacacaa 254160
actttaaaac acacacaaca cccaggaacc cctttctagg ggtacctggg ggagggaaca 254220
gaagcattgt cccaaccgaa tccagtcttc agggcagccc ttcatggagt ttccagagga 254280
aacacatcat atagtgtatg tatcagtcag tttagactag gttatgccgc agtaacaagc 254340
aaccccagat ttcattgcca aatatccaca aagggactta ttttttgctc acactgcatg 254400
tcaacatcag ttgtggatct tgccatcttt attctggttc ccaggctggc agagcagcag 254460
agcagcctcc ctctgagatg ctccagatga aaaagagagt atgtcagact gaggttcagt 254520
tcttcaggct tgtgctcaaa aattacacat gtcacttctg ctcacatttc atcagccaaa 254580
gcaagtcaca catccattct gacatcagtg gagtgggcaa atacaatctc ccctagcgaa 254640
gggtggtgaa tatttatgaa tgaaaagcca agccaggtgt ggtggctcac acctgtaatc 254700
ccaacatttt gggaagctga ggcaggagga tcacttgagc tcaggagttt gagaccagcc 254760
tggccaacat agcaagaccc catctctact acaaatcaaa aaaattagcc aggcaggatg 254820
gtgcacacct ttagccccag taacatggga ggctgaggtg ggaggatgct tgagcttggg 254880
agttcgaggc tgcagtgagc tatcattatg ccactgcact acagcctggg caacagagca 254940
agaccctctc tcaaaaaaag aaaaggaaag aaaatccagt cccctgtcta ccagagagta 255000
tagacatgac tctttgcctc tctggcatca tccaagctaa atagaggacc tagaatatat 255060
cctctgctcc cttgaccctt aagacttaat aaccactatt cctccttctc tctccctcaa 255120
agagaaggag aagacgcagc aaagtattca gtaagaaaga atgggctggg cgcagtggct 255180
cacgcctgta atcttaacac tttaggaggc caaggcagga ggattgcttg agcccggaag 255240
ttcaagacca gcctgagcaa catagtgaga ccccatctct atgattaaaa aaaaaaagtt 255300
ttaattagct gggtgtggtg gtgcacgcct gtagtcccag ctactcagga ggctgaagcg 255360
ggaggatcac ttgagtccag gaggtcaagg ctgcagtgag ctgtgattgc actgcactcc 255420
agcctgggtg acaaagcaag cccgtgtcaa agaaaaaaaa aaaaaaagga aggagggagg 255480
gagggaggga aggaaggaaa tgagagagag aaagaaagga gggagggaag gaaggagata 255540
gggaagaagg aatgaagaag aaagaaaggg agcgaaggaa agaaggaaga agagagaaag 255600
gaaaggagaa aggggaaagg gtggaaggaa tgaagggaag gaaggaaaaa ggaaagtgaa 255660
```

ggagggaggg aggaaggaag gaaaggaggg agggaaggag ggagggaagg agggagggag 255720
ggaaggaggg agggagagaa ggagggaggg agggaaggaa ggagggagga aggaaggaag 255780
gagggaggga gcgagggagg gaggaagggg aagaaggatt aggcttcaat ttgatttggc 255840
acactcggta gctgtgtcac ctcaggcaag tggtttaacc tttctaagcc tctattttgg 255900
tgatctgcaa agtgaggcca ttgatagtac ccacttccca tgtttgtatt agccatgcaa 255960
taatggggaa atgtcagtgc aagttttggc agttggtgac atctcaagca actgtagctg 256020
ttgggataag aaagcaatgg tgagaaggaa gagagagccc aggaatcctg gctgggggca 256080
agagaggcag agactcaagc agaagcactt gagaaccgcg acgagttaga cagagggtgc 256140
ccggtgtaca gccaccttcc tcctgcctct gccgctctca ccactggcct ctctcccgca 256200
gagggcctgc attgatttcg ccatcagcgc caagccgctg acccgacaca tgccgcagaa 256260
caagcagagc ttccagtacc gcatgtggca gttcgtggtg tctccgcctt tcgagtacac 256320
gatcatggcc atgatcgccc tcaacaccat cgtgcttatg atgaaggtaa gtgccccaca 256380
ccagccccca gcactactta acccccacct cgttcctgcc tctaccctga taaaatgaaa 256440
ccatctgcag tttcccagac agaccacact ctggatcacc tctgagattt tgttcctgct 256500
gttccctcta cctgacacac tgttcccacc actcccccgg ccagcttctt cttcccagct 256560
gtacctgcag acctcttcct ccagaaagcc ttccctgacc acccaagact gcttgaggtg 256620
cccatcttag caggcatcct atctttatgt cgcctgccac aaaaatctgc gtcaggttgc 256680
atgacagtgt cccccaccca tttatgatga cctcagccct gaattcctag aggccaacaa 256740
ggatctggct cagacggaac aagaagctct ctataaatgt ttgattaatg aaatgagggg 256800
gctgggcgcg gtggctcatg cctgtaatcc cagaactttg ggaggccgag gcgggcggat 256860
cacctgaggt cacgagttcg agaccagcct gaccaacacg gagaaaccgc atctctacta 256920
aaaatacaaa attagccagg cgtggtggtg cgcatctgta atcccagcta ctcgggaggc 256980
tgaggcagga gaattgcttg aacccgggag gcggaggttg ccatgagccg agatagcgca 257040
attgcactct agcctgggca acaagagcaa gactccatct caaaaaaaaa aagaaaagaa 257100
aaagaaagaa atgagggaga aggggtaggt gaggacccta aaatccccag ggctaaggag 257160
cggcttccaa aaaaaaactc tgaaaacctt tcaccctgtg ctttggactc caaagcgtgg 257220
attcaagccc agctcttcca tttaattcat ttacctttgt acaagcaacc agtgactttc 257280
tggggactca gtttccctgt caataaaatg ggaatgataa taagagcaca tttgccccct 257340
ccagaggagg tgagaggatt gaatgagaaa gttcatgcaa ggaccttagc tccttctcgg 257400
cacttcaaaa acgatcaata gtggccgggc aaggtggctc acacctgtaa tcccagcact 257460
ttgggaggtc gaggcaggcg gatcacttga ggccaggtgt tcgggaccaa ctggccaaca 257520
tggtgaaatc ccgtctctac taaaaataca aaaattagct gggcgtggtg gcgcatgcct 257580
ataataccag ctgcgtgaga ggctgaggca tgagaatcgc ttgaacccag ggggcggaag 257640
ttgcagtgag ctgagatcac accactgcac tccagcctgg gtaacagagt gagactccgt 257700
ctcaaaaaaa ataaggaagc cggggacggt ggctcacgcc tgtaatccca gcactttggg 257760
aggccgagga gggcgatcac aaggttagga gatcaagacc atcctggcta acacggtgaa 257820
acgctgtctc tactaaaaat acaaaaagtt agctgggcat ggtggtgggc acctgtagtc 257880
ccagctactt gggaggctga ggcaggggaa tggcatgaac ccaggaggtg gagcttgcag 257940
tgagccgaga tcgcgccact gcactccagc ccgggtgaca gagtgagact cctcaaaaaa 258000
aaaaaaaaaa aaaaagtata attcagccaa gcacaatggc gtatgcctat agtcccgact 258060
atcaggaggc taaggtagga ttgtgagttc aagcccagcc tgggcaaaat aggaagaccc 258120
cgtctaccaa aaaaaaaaaa aaaaggttgg gggaggtttt tgtttttttg gatgtgaaaa 258180
gaagagccta gtccggcgga gagcggggct ttcctgaact gtgcctccta ccagtgaggt 258240
tgctcagacc ttgcctgggg ctggagtgtt gcctggagaa cagccatgaa gctgcctccc 258300
cacttcccac ttcccacccc tgctcgctga cccctgctac tcctgcttct ttcccctagt 258360
tctatggggc ttctgttgct tatgaaaatg ccctgcgggt gttcaacatc gtcttcacct 258420
ccctcttctc tctggaatgt gtgctgaaag tcatggcttt tgggattctg gtaagtacca 258480
ccttggggct acagctatgg gcttgggaga agcccaaggg ggaacaatgg gtcctggatg 258540
atggtctccc aacgtggccc caagaacccc aacctcaagg gtggcttcag tatcctgcca 258600
gtggccacag atcctactta ggcattcttg tgtttgccaa ggagtcccag ggagacccaa 258660
cctgtgagtg ttaccatatg gctgcttatg tatccagttc ctcaaaatga tgggagtcat 258720
catggctggg agtctttagc atccatttta gagataagaa aactgaaatc aggctgggcg 258780
aggtgtctca tggctgtaat tccagcactt tgggaggcca aggtgggcgg atcacctgag 258840
gtcgggagtt cgagaccagc ctgaccaaca tggagaaact ctgtctctac taaaaataca 258900
aaattagccg ggtgtggtgg cgcatgcctg taatcccagc tactcgggag gctgaggcag 258960
gagaatcgct tgaacctggg aggcagaggt tgtggtgagc cgagatcaca tcactgcact 259020
ccagcctggg caacaagagt gaaactctgt ctcaaaaaaa agaaagaaag aaagaaaact 259080
gaaatcaggc tgagcacagt ggctcatgcc tgtaatccta gcacttcagg aggccaaggc 259140
aggaggatcg cttgaagcta ggagttctca accagcctgg gcagcaaagc aagcccctgt 259200
ccctacaaaa aaaaaaaaaa ttttttttta attagccagg catggtaact cgtgcctgta 259260
gtgccagtta ctcaggaggc tgaggtggga agatattttg agcccaggag gtggaggttg 259320
cagtgagcta tgatcatgcc actgcacccc agcctgggca acagcaagac tccatcttta 259380
aaaaacaaac acagaggtca ggcacagtga ctcacacctg taatcccagc actttgggag 259440
gcagaggcag gcaaatcact tgagcctagg agttcgagac caccctggcc aacatggcaa 259500
aaccccatct ctactaaaac tacaaaaaat tagcctggcg tgcttgtggg tgcccatgat 259560
cccagctact caggaggctg aggcaggaga atcgcttgaa cccacaaagt ggaggttaca 259620
gtgagctgag atcacaccac tgcactccag cctgagcaac agagcaagtc tcaaaaaaat 259680
aataataata aaaataaata tgtctttatt tttcaccagc cactaactaa attttaacat 259740
ttccttccat cttaaaggga gataacaaac ccttagtatt agtattatca acccttaata 259800
ttatcaacat gacctgtgtc acttataaac atcagatatt ttcatactgc attataagag 259860
ctgcagatac cttaacattt aatttgcatt catcattgct ttaaaatgtt gcttgtgatt 259920
aaacctacag ctagaatttg ttactcagtg tttttttgtt gttgttctgt tttgttttgt 259980
ttgagacagt ctcgctgttg cccaggctgg agtgcagtgg cgcaatctcg gctcactgaa 260040
agctccaccc cctgggttca cgccattctc ctgcctcagc ctcccgagta gctgggacta 260100
caggtgcctg ccaccacacc tggctaattg tttgtatttt tagtagagat ggggtttcac 260160
catgttggcc aggatggtct tgatttcctg acctcatgat ccgcccgcct cggcctccca 260220
aagtgctggg attacaggcg ggagccaccg cacccggcct actcagtgtg ttaatggaga 260280
agtatattca ttgttagatc gccattttta aaactttttt tttttttttg agacacagtc 260340
ttgctctgtt gcccaagctg gagtaccgtg gcacaatctt ggctcactga aacctccacc 260400

```
tcctgggttc aagcgattct cccatctcag ccttctgagt agctgggact acagatgcac 260460
accagcatgc caggctaatt tttatatttt tagtagagac ggggtttcac catgttggcc 260520
aggctggtct cgaactcctg gcatcaagca atctgcctgc ttcagcctcc caaaatgctg 260580
ggattacagg catgagacac tgtgcctagc cttaaaaaat attttgatag ctattttatt 260640
acaaaaggta accttgaagc ccttgctatt ttgttatgca tttacaagcc tttatgcata 260700
aaataaaata gccagcacta ttctcacatg gccaaggttc atagcacaca cacaaaagta 260760
tagttggctg agtgcggtgg ctcacacctg taatcccaac actttgggag acagaggtgg 260820
gtggatcatg aggtcaagag atccagacca cccttgccaa catggtgaaa ccccatctct 260880
actaaaaagt acaaaaatta gctgggtgtg gtggcgcatg cctgtagtct cagctactcg 260940
ggaggctgag gcaggagaat catttgaacg tgggaggcgg aggttgcagt gagccgagat 261000
cttgccactg cactccagcc tgggtgacag agtgagactc catctcaata aataaataaa 261060
ttaaattaaa ttaaattaaa attatttttt aaaaaattgg gggctgagtg tgatggctca 261120
cacctgtaat cccggcagtt tgggagcttg aggagggcag atcccttgag gtcaggagtt 261180
caagaccagc ctggacaaca tggtgaaacc ccgtctctac taaaaataca aaaattagcc 261240
aggcatggtg gcgtgtgcct gtaatcccag ctactcgtga ggctgaggcc caagcatcgc 261300
ttgaacctgt gaggcggagg ttgcagtgag ccaagatggc accagtgcac tccagcctgg 261360
gtgacagagt gagactttgt ctcaaaaaaa aaaaaaaatt aaggtgaaga aggcttatac 261420
tagtgggctg ggacttgaag tgaagtgaat tcttgaaggt ccccagtgag tggccaaggt 261480
gggacttgaa ccaggacatc tgttctcttg accaccagct tagtccatcc ctttgaagag 261540
agtgacctac agtctgggtc tcagccaggg tctcaggaaa ccaggttccc accttggctc 261600
acggaggtgg ttaggggcat cagctttagc accagagttc agatcttgcc tcgtcctata 261660
taagctttgt cacctcccca tcattaaaag gagccatcct ccccctccac ctcagcagag 261720
ccctggtaaa cagcaaatgg actaacgtgc atctagaggg ttgaggatga agcctggcct 261780
ggcatgggca ctcaataaat gctaggggcc aggcacggtg gctgacacct gtaatcgcag 261840
cactttggga ggctgaggca ggtggatcgc ttgagcccag gagtctgaga ccaacctgga 261900
caacatagtg agattctgtc tctacaaaaa gtacaaaatt agcctggtgt ggtggcgtgc 261960
acctgcagtc ccatctactt aggaggctga ggtgagagga tggattcagc ccaggatgtc 262020
agggctgcag tgagtcgtga ttgagccgct gcaccccacc ctgggtgaca gagcaagacc 262080
ctgtatcaaa ataaataaat aaatgctagg aaagggatcc tactaatgga ccttttccct 262140
ccaaaacagt ggctttcatt tggtggagat gctacttatt agaagcactt gaggccaggt 262200
gtggtggctc atgcctgtag tcccagcact ttgggacttc tgccaaggca gaagaattgc 262260
ttgaacccag gcgtttcaga ccagcctggg caacatagca agacctcatc tctagaaaac 262320
attgaaaaat tagccagcat agtggcacat gactgttgtc ctaactactt aggcgaaggc 262380
aggaggatta cttgagctca ggagttcaag gctgcagtga gctgcgatca catcactgcc 262440
ctccagcctg agcaacaaca caagacccgg actctaaaaa tcaaaaaaga agcacttagg 262500
gaaatttctt aaaattaaat gataccctga gcaaacccct agatgttctg attcatttgg 262560
tttggtgagg tgggagggaa tcactgaatc tgtaatttat tattattttt ttttttttga 262620
gatggattct cactctgttg cccaggctgg agtgcagtgg tgcaatcttg gctcactgca 262680
acctctgctt cccgggttca agcaattgtc ctgcctcagc ctcccgacta gttgggatta 262740
caggcgccca ccatcacgcc cggctaattt ttgtattttt agcagagacg ggattcacc 262800
```

```
acgtcagcca ggttggtctc caactcctga cctcaggtga tccgcctgcc tcggcctccc 262860
aaagtgctgg gattataggc atgagccacc gtacctagcc tgcagttatt ttattctgag 262920
ttgatcttct gctggtgaag tgagtcttcc actggggcct ggagctgcat ctccctcacc 262980
ctgccaatcc tgcaagagcc agcactgagc ttcccctctg ctttctcttt tttttttttt 263040
tttttttttt tgagatggga tcttactctg ttgcccagcc tgttcttgaa ctcgtggcct 263100
caagcagttc tccctccttg gcctcccaaa gtgctggaat tataggcatg agccaccacg 263160
cctggtctcc cctttcagtt ttaaatgaag ccacaagttc cctgtataac atttgggaga 263220
tagaggggag ctctctagcc taggggttga ggtctgtgac caaacgccta taaagttgtc 263280
tttgtttgga ctcccccaga agcagagcct gagacaagga ttgagtgcaa ggaatttatc 263340
tgggatgcag ggcagtaagg gagagaggaa gtgacacagg gacagaaagg caaccaggaa 263400
agagtgtatt attaagccag ttcctgctgt gaacaaatgg ggctcagttt cagtggatac 263460
ctccaggagg caacagagag cacataccac agagtcatcc cacctcacag ggagggaatt 263520
ggagtattta tcctccagtg cccatcagac ataatcacag gccactccca ggggagctat 263580
taattcccta acacttgtgc agccacagag agaccctggg caaagtagtg tacctcaggt 263640
gtgtagttga gctatgggca gggccccagc aacacctgcc aaaatgccaa aagtgccagt 263700
gggacctgaa ttccttttta tttatttatt tatttattta tttattttta tttatttatt 263760
tttgacggag tctcgctctg tggcccaggc tggagtgcag tggtgcaatc tctgctcact 263820
gcaagctctg cctcccaggt tcacgccatt ctcctgcctc agcctccgga gtagctggga 263880
ctacaggcgc gcaccaccac gcctgcctga tttttgtgtg cgtgtatttt tagtagagat 263940
ggggattcac catgttatcc aggatggtct tgatctcctg acctcgtgat ccgcccacat 264000
cggcctccca aagtgctggg attgcaggcg tgagccaccg cgcccggccc cctgaattcc 264060
ttttttaggc agttgtgaaa caacaacatc ccatctgttg ggcacctact gtatattcca 264120
tgctcagcga cgcacattca ttgtctgatt gctgtgttac cactgccttc cagagaaggg 264180
cgcagaggcc ccaggcactt cgcctaggag ggaagcacag ctctaaggtc aggctccttc 264240
tctgtaaggt agaggggcta cttcagggtc acactgaccg ccccaacccc tgacctggcc 264300
tctgcttctg cgaagatgct gagaaggccc tgtgttttgt gttttgggtc ccactgaccc 264360
cagaggggag ggccatctct ttgacccaga ctcttggatc caaactgggg tgccacccat 264420
caccatgtca gtacccggtt gaggggagtc agagatagca ggagaccttg tgggacttga 264480
ggctgtgact gttctccaaa caatgtggag tatttccata ttttaacaaa agagaggcca 264540
ggcgtggtgg ctcacgcctg taatcccagc actttgggag gccgaggcgg atggatcaca 264600
acgtcaggag atcaagatca tcctggctaa catggtgaaa ccccgtctct actaaaaaat 264660
acaaaaaatt agccaggcgt ggtggtgggc gcctgtagtc ccagctactc aggagactga 264720
agcaggagaa tggtgtgaac ccgggaggca gagcttgtag tgagccgaga acgtgccact 264780
gcactccagc ctgggcgaca gagtgagact ctgtctcaaa aaaaaaaaac aaacagagag 264840
gttatgcttg tgtttcccct tgagccagca cccagcccag gaatgcagca gtcaggatag 264900
atcaagtgaa gctgcagtaa caaacagccc ccacatctca gtgacttaaa ttgatgggaa 264960
gggtttttta cattcagcag ggaagctgtt tgcctcatag ttacccaggg acccaggctc 265020
acagagtagc tgccattcaa aatgttactg gtcgccaagc ccagggttga gaggctagag 265080
agtccaacac tgaccagaaa gtgaccacac tgcttccaca cacagcacat cactgcacct 265140
```

agacacacat ggccccatct aaacacaagg ggaccaggaa gtgcgtgtgc ctgaaaggcc 265200
ccaaagcccc gtccagtgcc tgttctgcac cctgttactg tccgcctcca gatcaggaaa 265260
tggaggccca gagaggttaa gccacttgcc catagccaca cagctgtggt agcagagctg 265320
ggatttgaac ccagagtctc ctttctttgc gagtatgctg ccaacctagt ggggacctga 265380
acacagactg tgggctctct gaggcctggg ttcaaatcct ggctttacat ctctgtgctg 265440
ctagcctcag gcagatgagt ggcttggtta cctcctagaa aatgggtata cctgggagtg 265500
gtggctcacg cctataatcc caacactttg gaaggccaaa gtgagcagat cacttgaggt 265560
cagaagttcg agaccagcct gaccaacatg gtgaaacccc gtctctacta aaaatacaaa 265620
aattagctgg gtgtggtggc atgcacctgt ggtcctacct acttgggagg ctgaggcagg 265680
agaatcgctt gaacccagga ggcagaggtt acagtgagcc gagatcgtgc cactgcactc 265740
cagcctggat gactgagcga gactccatct caaaaaaaaa aaaaaaaaag agaaagaaag 265800
aaaaagaaaa tgggtgataa cccttccctc caggatcttc atgaggagct cagtgatgtc 265860
atttataaag cccctggggt ctcgggagcc ctcaaaaatg ctggagagac aggccacagc 265920
tctgaagagc agccccagcc ctgtggagct gaagcagggt ctggaggccc cctctggggc 265980
caggccaatc atgggaaggc ccccaggagt tcccagggag ggagactcag cacagatgat 266040
gtcgaacagc ctttaccgca gcccttcgaa caaccataac tgtcccgggc actccgctga 266100
tgggcaactg tgcctctaac atgcacccgg ccagcctagg gggccgggaa ccaagccctc 266160
tgttggcatc tctgtcttgt gggtccccat tctagaatta tttccgcgat gcctggaaca 266220
tcttcgactt tgtgactgtt ctgggcagca tcaccgatat cctcgtgact gagtttgggg 266280
taagtctccc tccagcttct ctctgggtga ctctgggctg gacgaggcag gcggcagggg 266340
gcgggggagc ggtcccagag gcagtgtgtc ccggaagcca tagctgcttg agccagcact 266400
tggccatgac cagagaggga gaactggggc cccggggaca agggcagccc ctcaggaggg 266460
cattgtgggg agatgggggt aaccaaagct tggctgtagg gccagcactg aggggtgggc 266520
tttcctgcat cctggcctag gaattaataa tgcagatgag tacactgagg gaactgagac 266580
actcaaaagc tctgaaagct gagccggctc ccaaacacca ccctatgtca ggagcccaga 266640
aagaatgggt ttcaagtcaa ttctgtttga accaaccctc tcctagttag tgggcaggag 266700
agagccacag ccctcaggcc agtgtgggga caccactccc agggccatag aggggtcccc 266760
agggtgtctt ccctcctcta gccccgggcc tgggagactc tcaacatggg agtctctgga 266820
cctctctgtg gtggccccac aggccacatt gcccttctcc ttttctggaa gactcagggc 266880
cccagaggtc ctgtcctaga ccctctcctt ggccatctgc caatgagccc aggcttgggg 266940
tccctcagga gattgggggg agggtagaag atccttgcag gggaagcaa tggtcaaaaa 267000 agggtgtcaa agccaagggt caagggtgat accaatgtca tcttactaac aataaaaata 267060
acaatagctc acgagaatcg cagccttgct gtgtgccagg gaactgtgcc aagtggttta 267120
cgtggattgg ctcagggtag aggtcttggt ctcagctcgt aagagaattc cctcggaggg 267180
ttcaactgaa ggcacccaaa tgcagacctc actggtggag gggaagggaa gggtacccac 267240
aagggtggca aggtgtccag cgaccaccca ccgtggggag ctgtcacctg cccaggtgct 267300
gaagtgggga gggaacctga gccggaggcc aggagaagcc accaagtggg agctgtcctg 267360
tcaatgtgga gagacagaga ccagggccca agcaggcaga gagcaatagg ggagaaacac 267420
cccaaccttt ctctcccctc atcccttatc tcctgccaga gcctcccatg gcccaaagta 267480
aaccggaagc aagctgaata tgatgctcag agcaggcagg gaagtcagga gaatagatct 267540
gggtgtggtc gggcctgagg aagagggtgt tgcctcattt cacagatggg aaaactgacc 267600
tcagctgggc acggtggctc atgcctgtaa tcccagcact ttgggaggcc gaagccggcg 267660
gatcacctga ggccaggagt tcaagaccag cctggccaac atggtgaaac cccatctcta 267720
ctgacaatac aaaaaaatta gccaggtgtg gtggtgcatg cctgtaatcc cagctactcg 267780
ggaggctgag gcaggaaaat tgcttgaacc cggaaggcgg aggttgcagt gagcgacggt 267840
cataccattg cactccagcc tgggtgacaa gagcgaaaac tccatctcaa aaaaaaaaag 267900
aaagaaagaa aactgatctt caatgcctgg ggaagtgaga gacactccca aggtcacaaa 267960
gccaggcctg ggtgactcct gagagtacac tgacagctcc tggggtgtcc cagtcagatc 268020
cccctacaga aaaggatctg tttgcctgct cttccgtcct agaaggccag gaggggctgg 268080
ggaactacac aaaagagggg gccattcttt gatatgtcct acggcacccg cacccaagtg 268140
atacacactt atttgccttc agctccagtg agccagaatt ttccccttcc cctcacccta 268200
tccctgaaac cttcctctag agggttcttg cccacatggg ggctctctcc actggggtgc 268260
ccccacctgg tcattctccc ctgtcctgag tttctagaga gggctggagc tccagctggc 268320
aatcaaaata tcttgccatc cggctacata caagacagcc ttgaaccaat gtccctttgg 268380
gtcaagaggt tagaaggatg gtccagctcc ccagaagggc aggtggggtg gaggaagtta 268440
gctgaaacct tcaatcacca gtaagagagc tgtagggaca gactccaaca gcctgttctc 268500
ctggctggca ggaagatggg gcatggggtg ttcatgggac atcaggaccc ttgcagtagc 268560
caaacagccc ccagccctcc ctaccagctg tttgatcttg gacaacttgc gctatctctt 268620
ctcatgtaga gtggggctaa ccattgcaac caacctcaga cacttgcaag actcacagtg 268680
atgcatgcac tcaaaagaca ttcattgagc acctactgtg tgcctggtgt gattataagt 268740
gctggagaca gaacgagaag gaggggtgcc aaacaaaaca gaccaagaat acagagtgtc 268800
tgctcccata gagctgacat tctaaggaga gagacgggaa ctttttacaa gtaaaagcat 268860
caacaggccg ggcatggtgg ctcacgcctg taatctcagc actttgggag accaaggcag 268920
gtggatcact tgaggtcagg agttcgagac cagcctggcc aacatggtga aactctgtcc 268980
ctactaaaaa tacaaaaatt agccgggcac ggtggcaggt gcctgtaatc ccagctactc 269040
aggaggctga ggcaagagaa tcacttgatt ctcaggaggc gagaggttgt agtaagccaa 269100
gattgtgcca ctgccctcca gcctgggcga cagagtgaaa ctctgtctca aaaagaaaag 269160
gaagaaaaag aaagaaagaa acgtgaagtg cttggcacag aacctgccag gaaaccagga 269220
gtttgaaaat ggtggttgtt aactattact gctgttgtta ttgttattgt gaatgggtgt 269280
gtagttttgt tagccagccc tgagttacag tcaatttgag ggaaagatag gggtgggtg 269340 tttgggtcct tctgggacaa ttaactccca acctggagta gggagaggca tgtcctggca 269400
ggcaaggagg tctcagttgc ccctttctgc ctcccaggta agcccactag ttctgaggcc 269460
agggcttggc caggctgaga caggaaatgc cagatgcttg ggcgggcagg tccctggggt 269520
ttagggggca gagggcatgc ggcagtacta accagtgctg tctcagctgc tgccccccaag 269580 tggctggggt gatgtgggtt tgccctgtgt gcaatggata atgactgtgt ttcttgtctt 269640
gtctcttttc atgcctgctc ttaaaactgt atattggcgc aacgccgtct gaaaaactca 269700
tccaatcaaa atgcactatg aaattcattt gttcatccat gacatggtct gtgtgttcat 269760
acaccaatga cttatctccc aacccaccgc caccaccacc cccactcccc gcccgggaac 269820
cgaaacccat tggtttttttg gcactggtta caaatcaacc taaaaaatgc tgaacacgcc 269880
tccccaactg cccccgcccg cccgctcccc ctcatcttca acatctgcat ctagaatccg 269940
gttggtctta cttctttctg aagtctaaat gccttacatt aactgtgaac gcatctcctc 270000
gcgtcggcat tgcatgccac accctgcctc tccaacgtgg gatgcctgac gctctcctca 270060
accctccgct ctcctctgtc tgtctgtcct cccgccccca gcccctgtgc ctcccacttc 270120
ctgtagactc tgtctctctg tttttatcgg gttctgaatg ggggttttct gtttggggtg 270180
gtttgcgtct tttgcagaga aagggatggg ttttcccagc gcagcacctc tctcttgccc 270240
catcccgcac acacatcccc tacactcaga gacaatagag gcaaatccac tcccagccac 270300
ctctcaccac tcctgtcccc cattcagctc catggacccc aggccccagg aaagctgcca 270360
actgtctcct cgcccctcca gctctctcca tcctgctgtc cccaatcctc catctcaagc 270420
ccacaagatc tttggccttg accagcagag acttgactct ccaagtctga taaaggagac 270480
ctgaaggcca ggcagtgtgc cggcaaagac tctcaggcag aggaactcag aagtgccaga 270540
cttggatctg gtagcttcat gtggggctgg cccactgagg ccctctcctg gagccttgaa 270600
ctgtacgtgc acacgcagtc acacagtcac tgcacacaga cactgcacac acagtcactg 270660
tgcacacact cagtcactgc gcacacactg tgcacacagt cactgcacac agacgctgca 270720
cgcagtcact gcagtcactg cacacagtca ctatgcacac acagtcactg cacacagaca 270780
ctgcacacac agtcactatc cacacacaca gtcactgcgc agacactgca cacacactgc 270840
acacacacaa tcactgcgca cacacagtca ctgcacgcag aaactggaca cacagtcact 270900
atgcacacac tgcacacacc actatgcaca cacactgtgc acagtcacta tgtacacaca 270960
ctggcactgc atgtagtcac tatggacaca cactgcacag tcactgtgca cacatacact 271020
gcacacactg tcactatgca aacacagtca ctgcacacag tcactatgca cacacactgc 271080
acacacagtc actgcacaca gagccactat gcatgcacac acagtctgca ttcacacatt 271140
gaacacacag tcgctataca cacacagtca ctgcacacac agtctatgca cccacacact 271200
gaacacacag tcactgcatg tacagacact gcacatagtc atgacctctt ctctttttct 271260
cactcattct ccaattctct ctctctctcg ctcttttttt tttttttttt tagacagagt 271320
ctcgctctgt cacccaggct ggcgtgcagt ggcacaatgt cagctaactg caacctctgc 271380
ctccccgttt caagcaatta tgatgcctca gcctcctgag tacctgggat tacaagcatg 271440
taccaccacg ccaggccact tcttgtattt ttagtagaga cagggtttca ccatgttggc 271500
caggctggtc tcgaactcct gacctcaagt gatgcacccg cctcagcctc ccaaagtgtt 271560
gggattacag gtgtgagcca ctacacctgg cctctaatcc tcattcactg ttcctgtctc 271620
tgtgtctctc acatacagtc atgcatgcat gcacgcatgc acacacacac acactggccc 271680
tctctgctac atctacccac cctgtacccc cactccagta catactgcac acatctctct 271740
ccctccccca cttctcagcc ccttgcacac cccttgttct gttaaatctc aactgcctct 271800
gcccctctcc tacccaccaa tgaggccctt agagggacgc cccaatggca tctttgccct 271860
ggaatcatcc cttccctgct ggcaatacac atgcattcac ccaccaaaca tttaatgagc 271920
ccctatttgg tgccacagat ggaattatgg gcagaagcag acaccattac tgtcccctct 271980
taccacatac agtcaggtgg gggaggcagg catcggtcaa ataacccctt gactccactt 272040
aaaattatac ctgcactgcg agctgaagga tgagcagcat taacaaggca gagagagatg 272100
cacagagcat tccaggccca ggacagcaca tgcaaaggcc ctgtggtggg acggaacctg 272160
tgaggggtca ggatctgcaa gcgagggaat gtggctgatg caaagacagc cgagaaaggc 272220
tggcctggag acagccgaag aaggcagaag gggacaggac ccggggctgg ggagggcggg 272280
gctatattgt ggaatatggg ctttctccta agcaccagga agggcctggg aggataggaa 272340
gcaggggagg cgcgactggt catgtgacta gacaagctcg ctctggttgc agggcaggga 272400
acagcttgac aggaggctgg gctggaggtg ggcaccagga atcgcagcaa gagatgacag 272460
tggaggagag agaacagtgg gagggttgtc ctctgcagga cccagggaaa gatcaggtct 272520
gaactgagat gaggtgcctg ggagcagtcg ggtctggctt aaaactggga gataggctga 272580
gcacggtgac tcaagcctct aatcccagca ctttgggagg ctgaggcagg aagatcacct 272640
gaggtcagga gttcgagacc agcctgacca acatggtgaa accccatctc tcctaaaaaa 272700
tacaaaaatt agccaggcgt ggtggcaggt gcctgtaatc ccagatcctc aggaggccga 272760
gacaggagaa tcacttaaac ctgggaggtg gaggttgcag tgagccgagg tcgtgccatt 272820
gcactccagc ctgggcaaca gagtgagact ctcttaaaaa aaaaatactg ggtgatagag 272880
gtgagcgagt gcaaggaaag gaccaggttg ggggaagaga ataggtgtgg gcatagcaag 272940
tttgaggtgc ctttaggaca tcccgaaata agtcagatag gcaggtgttg tgggggctgc 273000
agcttggagc tgaggtctac aagtagtagg acttttctgg agcccttagg tgggtggtct 273060
ccatatcctt ctgagcactt gaggaacatc tgagcacagc actggaaaag aaaagaccac 273120
aaggacgctg tcctcatgtc ttccaggggc tgtgtcccac ccccatcaca ttctagccag 273180
gaagttcagg ggaggtgttg aagagaggaa gctgcacctc ccaagccatg gattgaaatg 273240
tggaaggcag gaagagggaa cttgtcagaa gttctggggg cagtggaaag aattggtact 273300
gatgcaggaa gagatggagg gtggatgagg gcagactagt acccttcccc cactgcccca 273360
aacccttccc gtctccaccc ctacctgcct catgtgtctc ctcccccact tggctccaag 273420
aagggaagca tgttttctgc acgcatctcc ctgccagatc cctggctttt ttgcatggtt 273480
gcaagcttcc cctgctctcc tccaaacccc cctcctgagg ctgcttccag ggtccgcctg 273540
ccttcgcatg cctggccgag tccacatgtt atgatccgcc ccatgaaagg gatggcttgt 273600
actctggggt tgaacgggag ggggctgggg atacctgagc catcggcccc atccccaggt 273660
ggagctgggt ggccaggcag ggatgggggt cagggcagca gggcacagag agtgactctg 273720
ttagccaagc tgggtttggg gcttgttcga ggcactggag acattctcac agcacttgag 273780
cccagtgtgg tcagggtagg atcccccagc ccccttcccc atcctagagg cctaaggacg 273840
cactgatgtg tcccagagag catcctagac attgccatca aacccagagg cctcagaaat 273900
tccttgaact ccagtccttg cctctcagct cccaggccaa agccagcaca agacacagat 273960
ctggcagcca gaaagccctc tggaagccac caagtaggat gcccatgtca cccaaactag 274020
gacacttttg aaacaggagg gaggctgtga ctgtatggtc accctgtgcc atttgggggg 274080
tgaaggttag accaagttaa atcttgctac gtggcctgta gcaaatccta caaatcccat 274140
agaacaagtc tgattaagcc ccttccctta gtgtggagag accctctact cctcctgcct 274200
tcaccctgct gggtactggc cagcgaagga gggtttccat gtctgcctga ggctggggtc 274260
tcaaactcaa atgcctctgg gggccaggca gacaccagtc aaccaggaaa gcaagtgcca 274320
tttctaaaac gtgaggaccc tggaaaactg gagatcatgt ggcctgcttc cagggagcaa 274380
tcgcagcagg cctggggttg ccagaaagcc agattggtgg gcaaaatctc ttgattttta 274440
aacaatggca ataattttta attaaaaaca aggacaaatg aaaaaacact gctcgggccc 274500
aacaaaacag ttttattagc tagatttggc ccactcgtga cttcgagagt cccacccccc 274560
ccaccaaggt cccttgaagc cccacaatgg ccacttaact ctagctggtc tcctccctga 274620
ctctccaact ctctggcccc ctggttcttc tagcttgggt gggaggaggc agaggcagtg 274680
actagacagg gggtttttga gcagaggcag tggccaccca gggaggtcct gggggcaggg 274740
atggccccac ctcccggccc ccagcacccg cccccttggtg ggcccgggct gatttctgag 274800
ctcacccacc catgggagct gagtgcttcc tgcttcctgc aggcctggtc ccgtgctact 274860
ccacccagcc ccagaagctg agaagccatc cctgagaggg gggaaaaggg ccccaaatgc 274920
atcttctccg actcagcggg cagcgaggac tcaccctgca gccgaacagt cccagctccc 274980
tcccgtcctc cccattcccg ctcgccaagg gggtaagaaa agatgctctt ccgcttctcc 275040
caattggctc gagccgctgc tcctcttggc cgtggggtga ggtcagggcg ggcaggagcg 275100
ggtgggcagc tcggcagggc agggcagggc agggtgcccg gtgagtcccg tgacagatgc 275160
atttctggcc cggagcgtaa catgccctcg gaacccgcac atgtccacca ggcctgactg 275220
tgctggcgac ctccaccccc acccccgccc tggtgtttgt gcatcgtaca cgtatgatag 275280
attccgcaac ttgaccggct tgtgtccttt cgtctcagtg catttggttg ttgggagaaa 275340
caaaaaccat ctcgattttt ttcctgattg gatgattcgg atatattttc tttttcttgt 275400
tcttttgtta tttcttcccc atccccgttc ctttttcctc ctttcttttt cttttctttt 275460
ccccattgtg ggtggggctg gcagggaggg cttatgcttt tgagttgatg ccttttcctc 275520
cctcccaccc tctctctccc aacattattc ctttttcgag tttttcctct gcatcattgc 275580
attaatagtg ctttctctct ccctccttat ttggggtctg gcttgctttt ttcctgttgg 275640
ttggcttcat gtaggggcct ctgtgagtgg tgacagctct gagccttttg gggtgggtgg 275700
atggtcaccc ctcttcctcc atctccccag aataacttca tcaacctgag ctttctccgc 275760
ctcttccgag ctgcccggct catcaaactt ctccgtcagg gttacaccat ccgcattctt 275820
ctctggacct ttgtgcagtc cttcaaggtg agtcctcgtc cctgctgctg gcccagggct 275880
gagaagacag gtgaccctca tgctctggct gaatgtagaa gtcagattgg aagtgcctct 275940
gtgatgtagt cgtgcagaga atctgttatc tccaaggctg ttgtcaaact tcctgtccct 276000
ggtgtgtctt cagagctgta agggcctcat cctagagccc ccagagatgc ccaccagccc 276060
tggaaggact ctggcacgtg gcatatggcc acccaaccca gtggggcaga gcactgggac 276120
aagggaggaa gacagtgcgg ctgagggacc cccagcactc ttcttcattg cctttttttcc 276180
caccaggccc tgccttatgt ctgtctgctg atcgccatgc tcttcttcat ctatgccatc 276240
attgggatgc aggtgagtgt cgtgtcccta aggttcccag agcctcccaa ggagggcagc 276300
caccccttaga aaggggtggg tcagaggagc ctggttcaca gaagcagcca tggaggttga 276360
gctgggtttc ccagaagcca ctggaggaat ggcagcccct ggtcgtcacc ctccaattcc 276420
acaggtgttt ggtaacattg gcatcgacgt ggaggacgag gacagtgatg aagatgagtt 276480
ccaaatcact gagcacaata acttccggac cttcttccag gccctcatgc ttctcttccg 276540
gtgagaaggg gacctgctct gataattctg tttccgtggg gtggggtgcc tgccttcatc 276600
cttctgttcc catagaggat gtaccctcct cttccaatgc aagacgtgcc ctcctccttc 276660
tcttctggca ggggcgcgcc ctcacccttc ttttccggta gggggcgtgc ccttctcttc 276720
cggtagggga cgtgccggcc ttctcttccg atagggggcg tgccctcctc ctccttttct 276780
ggtgtggggg tggccagatg tgctcttatc cttcttttcc cgtgaggctg gaaatgggtg 276840
tcgtgggggg cccaggaatc ctagcagggc agaagcagag ggccctggga catagtcatc 276900
aaggtcattt tccaggcatt atctctgaat cttcctgacc accctgtgag gaagggattc 276960
ttggcagccc tatccgacaa ataagaaaac aggcttacag accgtgaggc ttgattcttt 277020

-continued

```
ggttcatcat cttggctgca cacaaaagtt ccttcactcg ttcagtgtag gtttttttggg 277080
ggggcttttt tttttttttt tttttttttt ggagatggag tctcgctctg ttccccaggc 277140
tggagtacag tggcgcgatc tcggctcact gcaagctccg cctcccgggt tcacgccatt 277200
ctcctgcctc agcctcccga gtagctggga ctacaggcgc ccgccaccac gcccagataa 277260
tttttttgta tttttagtag agtcggggtt tcaccatgtt agccaggatg gtctcgatct 277320
cctgacctcg tgatccgccc gcctcggcct cccaaagtgc tgggattaca ggcgtgagcc 277380
accgtgccca gccctttttt tttttttttt ttagatggag tctctctctg ttgcccaggc 277440
tggagtgcag tggcgccatc tcggctcact gcaagctcct cttgtggagg tgtattgagc 277500
acctacagca tgccaggcag ggctgaaaaa cgaggatgca ccaggaaata gagaaaagag 277560
acattttaag cactttggaa gctaacatcc ccatggggaa gacgaataat caggaaacaa 277620
attatagagg atgctggaaa aagataaaat tcaagaataa aggggaatag ggccaggtgc 277680
agtgactcgt gcctgtaatc ctagcatttt gggaggccga ggtgggagga tcgctttagc 277740
ccaggagttt gagaccagcc tgggcaacat agtgagaccc cgtctctaca aaaaaattgt 277800
ttttaattaa ctgggcatag tgccacacac ctgtagtccc agctacttgg gaggctgagg 277860
caggaggatt gctcgagccc aggagttcca ggctacagta agctatgatt gtgccactgc 277920
actccagcct cggcaacaga gcgagactct gtctctaaaa agaaaaatat atttttttaa 277980
tttttaaaaa aagttacaga ggtagatagt ggtgatagtt gcataataat gtgagcttac 278040
ttaatgctac tgaattgtac acttcaaaat ggttaaattg ataaacttca tgctgtgtgt 278100
attttgccac agtaaaaaat aataatgttt ttaatctaac aacaaaaaaa gaatagaggg 278160
ccggcaggtt atgcctctct gaaagtgtga catttgagag aaattggcaa gggagggagt 278220
cagtgggtat atggggaagg gcaggccaag ccgaggggac tgcctgtgta aaggccctga 278280
ggcaggagta tggctggcat gtttgaggac tgtgaggagc ccagcatacc tagaacagag 278340
tgatctaggg agaatatagt atgagatgac tgtcaccttc atggagggga gctttttttt 278400
ttttttaatc tgagacagag tttcggtctt gttgcccagg ctggagtgca gtggtgcgat 278460
ctcggctcgg cgcaacttct gcctcccagg ttcaagcagt tctcctgcct cagcctcccg 278520
agtagctgag attataggtg cccgtcacca cgcccagcta atttttgtat ttttagtaga 278580
gacggggttt tgccatgttg gtcaggccgt tctcaaactc ctgacctcag gtgatccacc 278640
cgcctcagcc acccaaagtg ctgggattac aggcatgagc cactgcaccc ggcctgaagg 278700
gagctttttt ttttttttgc tttttttttga gacagaatct ccctctttgt cacccaggct 278760
ggagtgcagt ggcgcgatct cagctcactg caacctccgc ctcctgggtt caagcgattt 278820
tcctgcctca gcctcccaag tagctgagac tacaggtgag cgccaccaca ccgagcaaat 278880
ttttggtatt tttagtagag atagggtttc accatgttag ccaggatggt ctcaatctcc 278940
tgacctcgtg atccacccac ctcagcctcc caaagtgctg ggattacagg tgtgagccac 279000
cgcgcccagc caagagggga gcttttaaag cataacagtg accagcctga gcaatgcagt 279060
gaaaccccat ctctacaaaa aaaaatagtt taaaaattag ccaggagtgg tggcgtgtgc 279120
ctgtagtccc cagctactca ggaggccgag gcgggaggat cacctgagcc tgggaagttg 279180
aggctgcagt gagcagtgat tgtgccacta cactccaacc tgggtaacag agcaagaccc 279240
tgtcaaaaaa aaaaaagaga gagagagaga aaagaaagga aaagaaagag agagagaagg 279300
aaaagaaaag aaaaaaacat atcagtgtcc tcaaatccca ccctagacca actgaatcca 279360
```

agtctgctgg ggtggggcac gggcattggt attttttcaa agctctctgt ggacttcagt 279420
gcacagccaa gaatgtgaat tcccttctct cagctcccag taaaaggagg tggtccacct 279480
ggggcttgcc tggccagctc cagagcccaa gtgctcaacg tgtgtgctcc acctcctggg 279540
gaggcgttgg tacccagtca gggctgggtg tccgagtctc tgatttctcc ctgtcctcag 279600
gagtgccacc ggggaagctt ggcacaacat catgctttcc tgcctcagcg ggaaaccgtg 279660
tgataagaac tctggcatcc tgactcgaga gtgtggcaat gaatttgctt atttttactt 279720
tgtttccttc atcttcctct gctcgtttct ggtgagtctg tggacactgt gagggccgtc 279780
tgggctccct aagcctggct tcctttcagg ggagtgggtt tctgtggaat gtggctgtgt 279840
cgaaggcttg ttccctccaa ggcttctctg aaccagcctg ggatcaggtg accctgagcg 279900
tctcaaactc agcactgttg acatttgggg gtggctgatt ctttggggtg gggccatcat 279960
gtgcactgca gtgtatggca gcatccctgt cctcccccca ccagatgctg gcagcacacg 280020
ccacccgttc ctcctgttgt gacaaccaaa aatgtctccg gacattgcca ggtgccccca 280080
gggggtgggg gtggggttgg gagtgggggc cagaattccc ccatttgaga ctcaatgaaa 280140
tatttcagct gggcgtagtg gccgatgcct gtaatcccaa cacttcggga ggctgaggtg 280200
ggagggtcac ttgagcccag gaatacaaga ccagcctgga cagcatggtg tgaaacccat 280260
ctctttaaaa aaaaaaaaaa aaattgaatt agctgcacac gtggtgctgt gcacctgcag 280320
tcccagctac tcaggaggct gaggtgggag gatcacttga gccttggagg tcgaggctgc 280380
agtgagccat gatcacacca ctgcacccca gccagggcga cagaatgaga tcctgtctca 280440
aaaacaaaca aaaacaaaca aaaaaaaaaa aaacattgcg agggaagaaa tacctcactt 280500
tggccttgtt gggggcagat gtgggaggat ttggggtcac agtggttctc ttggtgttgg 280560
tccctgtttc agaagcctcc cctccctctc actgactctg tttctttcca tcattcttgg 280620
tctttgtctc tctctctctt tttttttttt ctttgaaatg gagtctcact ctgttgccca 280680
ggctaaagtg cagtggcgag acctcagctc actgcagcct ccacctccca ggttcaaccg 280740
attcttcagc ttcaacctcc caagtagctg ggattacagg tgcacatgcc accacaccca 280800
gctaattttt gtatttttag tagagacagt gtttcaccat gttgaccagg ctggtctcaa 280860
actcctgacc tcaagtgatc tgtccacctc ggcctcccaa agtgctggga ttacaggcgt 280920
gatccaccgt gcccggccag tctttgtctc tttgtatctc tctctctcca tctctctctg 280980
tttctctctt cctcttcccc atctctccac ttgatctctc tctcactgga cctccttgtg 281040
tgagtgagca tcacctctcc attccccagt ctctttctgt ctctgtctca tttcctttcc 281100
ccatcttctc tctatccctc tctccatctg ggcctctgtg tacatgtctt tgggtctgtc 281160
tgtccgtctg tctgtctgta tccttctcac tcactcattc attccctcgg tctctgcccc 281220
cattctctct tggtccccgg ggtccccaca gatgctgaat ctctttgtcg ccgtcatcat 281280
ggacaacttt gagtacctca cccgagactc ctccatcctg ggccccccacc acctggatga 281340 gtacgtgcgt gtctgggccg agtatgaccc cgcagcttgg taagaagtca ccccgaatcc 281400
tccagccaca atactcacct ctccctggaa ctggaacacg ggctaggtca ggccccagac 281460
tctggagcac tgaactcctg gggtcctagc aggggtctca caggttcagt caggagagaa 281520
gatataagaa tcatcaccct tgcatacccc agattaaaca cgtagggtgc caaccctgcc 281580
caaaccctgg actttctggg aaatgaggga gggcgtcaac catgagatgt cctgaagagc 281640
cctctcctcc tacgagtctc tcctgtctct cactgtgaag tctccagatg gtgaggatgc 281700
attagccagg ctccagggag aaaaccaaca gcatcccagc ctcagttctc ttgagagtgt 281760 gggggaggagg gctggcctac ccttggcaga caggattggc agcaacatca gagtagcaga 281820
actcagctcc cactgggacc cgtgaacctg ggagtgagag gacatacagg ccaggggagg 281880
acgcagagcc tcaggggccc atgcatcttt gtggccacaa agggagtggg cgctcccatc 281940
tgggtagaca ccagaggggt ccctctccac tgacgggcaa tggtttcaga gggtgggttc 282000
caccttgtgc acgtgtattg agtgcccacc caacaccaag ccttgaagga cactcagagg 282060
ctttatctga atacctggaa cccaccagcc actaactgag gatttagttc aggctggtct 282120
tggggcctga agaagcatta ctggggggcc ctcagcagcc taagccccat cttcctctgg 282180
cctcagcacc agagaggagg ccgtcacgag gaaggtgggc aggaggtggt cttggctatt 282240
cccatagcct caaacaagta ctccatgaga ccgagaggct ggggagagcc gtgggtctgg 282300
ggctgggctt tggctggttc ctaactcttc ctcttttgat tttaggtcac agcaattgga 282360
tgctgtcccc aaggcctcta ttccacaagc cccccccac ccctgtagcc catgtagact 282420
gtggaggagg cagatgcaga gagagcccca ggggaggtgc cctgcagtcc cgaactcgac 282480
tgacatccta cacccctggg tctccccagt gtctgggaat gtactgggga ccttcacttg 282540
tccccagtct ctcccactcc ttcaagccag ggacacccca gcctcgggca tcatgacctc 282600
gctgtgtgcc cagggagccc gtgtgaaccc attgcctgca ctaacccct ttcttctcct 282660 ttcagcggtc ggattcatta taaggatatg tacagtttat tacgagtaat atctccccct 282720
ctcggcttag gcaagaaatg tcctcatagg gttgcttgca aggtttgact tccactaaaa 282780
cctgctagca tccatggaat gagtgtggct tggggttctt caatatatat atttcatata 282840
tatatatata tatatctctc tctctctcta aaaaaacaga gccatctctc tttcttgcat 282900
taaactagaa aactctctta gccaacagaa tgcagtcatg tagactcgat aaagcatgga 282960
acatatttcc tccttccctt cagccttcag ccatctttgc ttgctcttag ctgaagctgc 283020
ccatcctggg gtctccacgg caccccaaat cagatacatc ccctggggga ttgtaacttt 283080
gcatttctcc cccaaccatc acctccactc tctcccctc caccccctcac ctcccaaagc 283140 ccctagccct cctcccctcc ctggcactgg cccctgctcc ccacctaggc cccctcagag 283200
accagcctca gccaaaccag agaacgtgac ccaactgtag aaataacagt gatggccggg 283260
cgcagtggct catgcctgta atcccagcac tttgggaggc caaagcagga ggatcgcttg 283320
agcccaggag tttgagacca gcctgggcaa catagcaaga accccccttct ctataaaaaa 283380 ttagccaggc attgtggcgc atgcctgtag tcccagctac ttgggaggct gaggcagaag 283440
gattgcttga gcccaggagg tggaggctgc agtgagctat gatcacacca ctgcactcca 283500
acccaggcga cagagagaga ccctgtctct ttaaaaaaaa aaaaaaaaaa aaaaaaaggc 283560
aatgaacaaa agcatggctc tacgtcttcc aaagtgagaa ttctccctcc cctccgcatc 283620
cctccagaac tgtagctcag agcccacgct gaatctgact tttctctttt ctctctctct 283680
ccctgctccc gagcagtgaa gtaatctttt tttactgacc ttttcttcca tttttttttcc 283740 tcctcttttc cattgatttg aaatatctat tttatcattc tctgcatctt tctctctcta 283800 tttttcggc tcgtgtggat ttctttttc tttcttctgt ttctccccac ctctcttcct 283860
ttggttctct gttcccattc ccgttttgtt tttttgtttt tgtttttgtt tttttcattt 283920
tcggtgctgc caggggccgc atgccttacc tggacatgta tcagatgctg agacacatgt 283980
ctccgcccct gggtctgggg aagaagtgtc cggccagagt ggcttacaag gtagactacc 284040
cttgccgacc accgacgtcc aggcactggg tttttttttc ttcttcttct tcttttttt 284100 tagtgctgac cagaaacacc cggccgactc tctttttcca acgtttctct tctttttttgt 284160
ttttgattct tttttttctt ttctcgagtc aactgatcat gaccatccct tgattctaag 284220
cagcacactg tgtccgtcct ttctgatgag tgtcttcgtg ttttgagact ccattatggc 284280
cgacatgccg gggggagggg gaggggagcg cccaggtccc cttgcacctg gtctcccagg 284340
taccaaattg gaaacaaaca cgcttcttca gggagtcaaa acccatgctt cccacttctg 284400
cccacccaga gcggccccca tgcccaggct ggggcaggcg ccttgcagag aggggcttta 284460
gcccccgaaa gcaggcgagg tcccgggtcc ccgcccctgc cacgcacacc tgaagctgat 284520
ctctgaccta gggccttggg gattcgagac cttccaagga gcaccaagaa cctctcttcc 284580
cctcccttcc ttcccctgga gtttcgtccc cagcccccgt ccctaatccc cccaagacac 284640
cccaacatgc ctctccattg ttccagagtg ggcaggcggc cgcagctgga ccccctggacg 284700
gtggcacact gatgcaggcc atgcacgctg ccttggcggg gcctggggcg ggcaggcacc 284760
atggccgacg gggggtggtg catgctggct gagagagcga gcgtcctgcc gccaagcggc 284820
tggcccgggc cacccctcca gatccctgtc ctggaatctc ccttggtgcc caaggacaga 284880
tgctctgttc cctccattca tccacaagaa gttcagggat gacctttaaa gattctcccc 284940
acccaaaaag tattacccca tcatcctatt ctcccatcca ccttgatctt ccctgcgtcc 285000
ctatccatca atgctatttg tacctgcccc gtgttgccac ctcattcctt tccttcctct 285060
gtgcacccct cctcacctaa cctatatgtc tcccctcctt ctcaatcaaa gccggggaca 285120
aggttgtccc accagcatct cagacaatga gcctctcctg gcacctgtcg ctctgtgccc 285180
ctccctgccg cccccccccc cccccccggt tttcctcaag tcgcttctct cagtctctgc 285240
ttagatgaat gtgtgcgcat gtgcaagaga gggagggcga gcccttcctc tcctggtctt 285300
tgtgcaggac caccatgggt ccataagaca actttgtgca aatttgaaaa aggcaccctt 285360
tccacagaac atgcctgttg gaaaattgtt gcaatctacc aatgtggtga gaacaagaca 285420
cttttttttct atcacctggg aagctgttat atttaatata caaatcgggg gctgggcgtg 285480
gtggctcatg cctgtaatcc tagtgctttg ggaggctgag acgggaggat cacttgagcc 285540
cagttcgaga ctagcctggg caacatagcg agaccccatc tctacaaaaa gaaaaaatat 285600
tttaattaat aaataagtac ataaatctat catttccaag atgggagccc tttgtgcggt 285660
gtacaacctg cacaactgtg cacagtggcc cagtctatgt gtgtttctct atttcccacc 285720
tccttcccca ccctaccccc agtgtcccct ccagtgtcct gctctggatt taccataccc 285780
ctccccatct tcaactctgt gtttcctgcc cacttgtgtc tgaatcccca cccaagttgc 285840
cctcaccccc cttctctgtg ccacttcagc ctgggctggt gcacaccagc ccagcatcct 285900
ctcccatgcc accaagcatg gtggacagag cccctgcctg ggacatgggg aatcttttct 285960
tccctgggct ggaagggagt gcccctcacc ccttcccccct gccattgcac agagagccaa 286020
gatctggaca tgcccctgag atacacttcc cacggagcta tgaatgagtc tcgagattcc 286080
gtctgcatgc gcccctgtct gtgctgttct gtgtcacagc ctcgctgcat gcctgcgagg 286140
ggcctgcccc gtcagtgggg ggctgcctgc ctgctgcttc tcagaggaat gatgtggtct 286200
gtgcccatct gctctgtcct ggtctgggcc aagccaggga ttgggtgtgg ggagccagtg 286260
gcacccccca ccagcggctg tggtcctggc cccctcagcc ttggctgttg catgcactgc 286320
tcaaatccag cttgtgctct ttttctttgg ggtcagactg aaacggggcc atccagaaga 286380
actctggggc agggcggggg tggggcaagg gttgaggcaa accctggaaa tgccagctct 286440
caggtcaagc aggtggggga aaaaaggaga gggcagggga ccagaagtac aagagagcct 286500

```
tttgtgccct ccctgcgggc caccaagaga aactgagtac tgggacaggt aacctaagta 286560
agagacacct cagccgccac agctttcaga gttcttcctg ggactccctg ggtaggggcg 286620
ggcgcggctc acgggagacc caggagggat gcctgggaat gactgcgctt gccttgggtt 286680
ttctgtagcg gcttctgcgg atggacctgc ccgtcgcaga tgacaacacc gtccacttca 286740
attccaccct catggctctg atccgcacag ccctggacat caagattgcc aagggtaagg 286800
aagggacagg ggcgggcaca gacaggcgtg acagggtgga accggggatc tccctcccta 286860
ccccaaacta gaggatctgc tgtcaccacc cggatcttca ttcactcttc cattcattcg 286920
ttccacaggg tttttttgggg tttggggttt tggtgttttt tttttttttt ttttgagaca 286980
gagtcttgct ctgttgccca ggcagcagtg cggtgacatg atcgcaagtc actgcagcct 287040
tgacctccca ggctcaagtg atccttccac ctcagcctcc ccagtagctg ggactacagg 287100
cacacaccac catactcggc taattttttt tttttggtg tgacaatttc cctctgtcac 287160
ccaggctgaa gtgcagtggt gtgatcttgg ctcattgcta cctccgcctc ccgggttcaa 287220
gcgattctcc tgcctcagcc tcccaagtag ctgggattat aggtacccac cagcacaccc 287280
ggctaatttt ttatattttg ggtagagatg gggtttcacc atgttggcca ggctggtctc 287340
gaactcctga cctctggtct caaactcctg acctcaagtg atccacctgc ctcgacctct 287400
caaagtgctg gattacaggc gtgagccacc atgcccaacc taattttttta tattttttat 287460
agagatgggg tttcatcagg ttgcccaggc tggtctcaaa ctcctgggct caagcagtcc 287520
tcccaccttg gtctcccaaa atgctggtat tacaggcatg agccaccaca cccggcccat 287580
ttggcagata tttagtgcac tccttcaatg tgccagagac ccgtccaagc aggggaggac 287640
ccagcagctt acactttaga tggatgggga ggccgccact gaggaggtaa ggcagtgtct 287700
catggatccc tggggggaag gtgctccagg cagaaggact ggcaaaggcc ctgacagagg 287760
ggtgaacaca ggacacccgg ggcattgagc tgactcacct tctgagtgag ggcacgccac 287820
gcaggttcag agcagaggag gaacctgacc caactcacat ttgaacaggt tccctccggc 287880
cactgagggg atgggagacc gaaaggaggc cagtgtgggg gctgctgata tcatctgggt 287940
ggagacaggg cggcagctta gatctagggg taggctcgac gtggtggctc acgcctgtaa 288000
tctcagcact ttgggaggcc aaggtgggtg gattacttga ggtcaggatg accagcctgg 288060
ccaatgtggt gaaacccccg tctctactaa aaatacaaaa tttagccaga cgtggtggtg 288120
ggtactgtag tcccagctac tagggaggat gaggcagaag aatcgcttga acctgggagg 288180
cggaggttgc agtgagccga gatcacgcca ctgcactaca gcctgggtga cagagcaaga 288240
ctctgtctca aaaattaaat taaattaaat taactggaca tggtggcata tgcctgtggt 288300
cccagctact caggaggcag agatgagagt attgcttgaa gccaggagtt tgaggctgca 288360
gtgagtcatg atcgcaccac tgcactccag cctgggcgac agaacgagat cctagctcaa 288420
aacaacagaa agaaaaagaa aaaaacattt tttttaaagc tgagaagggg ctgggcgcag 288480
tggcttacgc ctgtaatccc agcactttgg gaggccaagg tgggtggatc acgaggtcag 288540
gagttcaaga ccagcctggc caacatggtg aaaccccatc tctaccaaaa atacaaaaag 288600
tagccgggtg tcatggtggg cgcctgtaac cccagctact ccggaggctg aggcaggaga 288660
atcacttgaa cctgggagac agaggttgca gtgagccaag atcgcgccac tgaactccag 288720
cctggatgac agagcaagac gctgtctcaa aaaaaaaaaa agctgaggcc gggcacgctg 288780
gctcacgcct gtaatagcag cactttggga ggccgaggcg ggcagatcat gaggtcaaga 288840
```

```
aatcgagacc atcctgggta acacggtgaa accccttctc tactaaaaat acaaaaaatt 288900
agctgggtgt ggtggcacgc acctgtagtc cctgctactc agaaggctga ggcaggagaa 288960
ttgcttgaac ccgagaggca gaggttgcag cgagccgagc ttgtgccact gcactccagc 289020
ctgggtgaca gagtgagact tcatctgaaa aaaaaaaaaa aaaaaagccg agaaggctgg 289080
acatggtggc tcacacctgt aatctcagca ttttgttgag gccaggcaca gtggttcacg 289140
cctgtaatct gagcacgctg ggaggccgag gtgggtggat catttgaggt caggagttcg 289200
agatcagcct ggccaacgtg gcaaaaccct gtctctacta aaaatacaaa aattagccgg 289260
gtgtcgtggc gtgtgcctgt aatcccagca ctttgggagg ctgaagcggg tggatcactt 289320
gaggtcagga gttcaagacc agcctggtca acatggcaaa accctgtctc tactaaaaat 289380
acaaaaatta gccaggtgtg gtggcgggta cctgtaatcc cagttactag ggaggctgag 289440
gcagaagaat cacttgaacc cgggaggcag agattgcagt gagccgagat cacatcactg 289500
cactttagcc tgggcgacag agcaagactc catctcaaaa ataaaaataa aaataaaaaa 289560
taccgagaaa ttcccccaaa gacctagctc agggctcact ctccatcatt agggggaaag 289620
aagaagagga ggccagggag gcgggcagag accagggcag tgtgggctcc tggaggcagc 289680
ttctatgttt aaaagggcgg cttcaggagg aaggggacca accgtgtcag gcactgccca 289740
gagaccaagg atgacaagga tcacaagtga ctggtcatca tggtcacttt gaccagtgca 289800
gctttggcgg aggggtcagg ggtcccctgt ctggagtgca tttcggaggc ccgaaagggg 289860
atgtgatgtg atttggcagc tgattaagga cagcagggca gagagacagg cgcacaattg 289920
ccagaagaaa cggggacctg aggctcacgc ctgtaatccc agcactttgg gaggctgagg 289980
aaggtggatc acttgaggcc aggaatttga gaccagcctg gccaacatgg cgaaacccca 290040
tctccactaa aaatacaaaa attagccagg catggtggtg cacacctata atcccaacaa 290100
cttgggaagc tgagcacaag aattacttga acctgggagg cagaggttgc agtgagccga 290160
gatcaaacca ttgcactcca gcctggggga cacagcaaga ctctgtctca aaaaaaaaaa 290220
aaaaaagaaa gaaagaaaga aaagaaaaaa caaatgggac cagaaaaaag gagtgggtgg 290280
gagaggagca ggtggatagt cccacacatg ggaaggtgct gagcccagct gaaaccacta 290340
gtaagtcagg aggagggaag actgagcctc gagacatatg tgccttccag ggtcttgagg 290400
gaaagaaggg aggaagagcc aaggccacgt ggcaagactc aaggaggaag tggcagggaa 290460
ggtgggggac tggaggggtg gaggacagat attgttaatg ccaggaacaa agtgaaggta 290520
aagagagcac aaggaagttg ggagcagtgg ctcacacctg taatcccagc actttgggaa 290580
gccaaggcag gaggatcact tgaggccagg agttcaagat cagcctggcc aacacagaga 290640
gaccccatct ctacagaaaa ttttaaaatt agccaggtgt ggtgatgtgc acctgtagtc 290700
ccaactactt gggaggctgg agtgggagga tcactgggga ctgggatgtc aaggctgcag 290760
tgagctatat gatgaccaca gacatagcag cttaagacac acctatttgt cagctcacag 290820
tcctgtaggt cagaagtcca aaaagctgga ctgggctgtc tgctgagggt ctcacgaggc 290880
tgaaatcaag gtgtcagcca agctgggctc ctctctggag gatctggggg agaatctact 290940
tccaggttca ttcaggtgtt ggcagaattg aagtccttgt ggctgtagga ctgaggtctt 291000
gttttatcac tggcttttta gctttttgct cctggaagtg catgtaatcc tccatgtgct 291060
ctcattctct ctgacttccc catctgccac ccagcagaga caatactgtg cttttcaagg 291120
gctcacctga ttggggcagg cctaccctga tcatctctgt attttgaggt cagctgactt 291180
gatatttttt ttttttcttg agacagaatt tcactcttgt tgccaaggct ggagtataat 291240
```

agtgtgatct cagttcactg caatctccgc ctcccaggtt caagcaattc tcctgcctca 291300
gcctcctgag tagctgagat tacaggtgcc caccaccacg cccagctaaa ttttttgta 291360 tttttagtag agatggggtt tcacaaggtt ggccaggctg gttttgaact cctgacctca 291420
ggtgatccac ccgcctcagc ctcccaaagt gctgggatta caggagtgag ccaccatgcc 291480
cagcattttc tttcttttt ttttttttt tgaaacggag tcttgttctg tcacccaggc 291540
tggagtgcag tggcgcaatc tcggctcact gcaacctcca tctcccgggt tcaagtgatt 291600
ctgcctcagc ctcccaagta ggtgggacta cagatgcgtg ccaccacgcc cggataattt 291660
tttgtatttt tagtagaaac ggggtttcac catgatagca ggatggtctc gatctcccaa 291720
cctcgtgatc tgcccacctc ggcctcccaa agtgctggga ttacaggcgt gagccaccgc 291780
accgggcctc cggtatttta attatatctg caaagtccct tcatagcctg ggcaatggtc 291840
cctagattag tgtttgaata aacagaatct tggcagaagg gcagcttttg aattctgcct 291900
accacagttc cttcgtttgt acaacgggtc taacaacacc cccactcttt gtatgtaatg 291960
ccatcgtaac tcagcttctg tggcactctg agaatctgtg ttcaggggtc ccaaaaccac 292020
ccacaggttc agtgattccc tggaagaact cagaactgag aaaagttttt atactcacag 292080
tttattacag tgaaagaata tagattaaaa tctgcaaagg gccgggcacg gtggctcacg 292140
cctgtaatcc cagcactttg ggagggcgag gtaggcagat cacttgaggt cacgagttca 292200
agaccagcct gaccaacatg gtgaaaccct gtctctacta aaaatacaaa aattagccag 292260
gcgtggtggc tggcgccagt aatcccagct acttggaagg ctaaggtagg agaatcactt 292320
gagcccagga ggcagaggtt gcagtgagcc gagatcccgc cacttcactc caggctggac 292380
agagtgagac tctattagaa aaaaaaaaaa aaaaaaaatc tgcaaagggc ctggcatggt 292440
ggcttacgcc tgtaatcctg gcactttggg agggcaaggc gggcagatca cttgaggtca 292500
caagtttgag accagcctgg ccaacatggc gaaaccccgt ctctaccaaa aatacaaaaa 292560
ttaggcatgg tgccagaccc ctgtaatccc aactactcag gaggctgagg caggagaatc 292620
gcttgaccct gggaggcaga ggttgcagtg agctgagact gtgccattgc actccagcct 292680
gtgtgacaag atcaaaactc tgtccaaaaa gaaaattagc caggtgtggt ggcatacacc 292740
tgtagtccca gctactccag aggctgaggc acaagaatcc tttcaaccca ggagatagag 292800
ctacattaag ccaagatcac gccactgcac tccagcctgg gcaacagagc aagactctgt 292860
ctcaaacaaa caaacaaatt ccaaaaacat aaaatgcgca aaggaagggc atctggggaa 292920
gggtccagga gacaccaggt gcgagcttcc agttgtctgc ctccagtgga gttgcacaga 292980
caacgcttaa ttctccctgc agtgtgtgac aacacgcacc gtgtactgcc aaccagggaa 293040
gctcacctga gccttggtgc cccagggttt ttattgaggg tttgtcatat aggcagggct 293100
gacgtagtta ctcagtctcc agtccctcca gaggtcaaac tgataccacg tggcccaaga 293160
ccccaacgat aaatcgcatt gttagaatga actgtatgga aaattatcca ggcgtggcgg 293220
cgggcggctg taatcccagc tactggggaa gctgaggcag gagaatcact tgaaactagg 293280
aggccgaggt tgcagtgagc caagatcgca ccattgcact ccagcctggg caatagagca 293340
aaaacaccat ctcaaaataa ataaataaat agaatgaact gtattggccg ggtacagtga 293400
ctcatgccta taatcccagc actttgggag gctgaggctg gaggatcgtt tgaggccagg 293460
agttcgagac cagcctaggc aacatagtga gaccctatct cttttttta aaaaaaaaaa 293520 aaaaaaaaaa aaagaatgaa ctatacagtg tggcccaagg ccccctgcta aataaagaca 293580
ctcttcaggc aggacatttc aaaggcttag agatcacctc ccaggagcaa gtcaatgggc 293640
cagtcctttc atcggaatgt gcagggtttg gacaacacta gcctactgag ctagtcctta 293700
ctgcttagca ccccagcttc tatgacacct actggattcc cttcctgagg gtttcaaaga 293760
ctcctggaga tgtctctgaa tttggctgtc acagttgtta cttgtacccc agatgccact 293820
cagttccctg aagacaatga tcccccagat ttctcagcca ggagcccctc cacctcttgt 293880
cctcagtggg tgccaggcct catcctggag ttccacagct gagccaggct ctcggggtta 293940
cggaaggtca agagggtgtg gggacaacaa tggaagagtg ataacagtgg cagccctttg 294000
agcagatgcg ggtctcagga gaacataacg cgctttcttt tcatagttca gctcactttc 294060
taagcacact gagcttcctt tccagcaggc taaggggctg caaagggggt acagattaac 294120
ctcattcttc agattctcaa aaatggtgtc accattcatt gctggagact gggagaaagg 294180
gggcaagtcc atctcattct ctctgtctct gtctctctct ctctcttccc tgtccatctg 294240
tttctctctc ccacccaccc ctctgttctc tctgcccaga agaatctcta ttttggtttt 294300
ggttttgttt gttttgtatt gttttgagac ggagtctcgt tctgtcgccc aggctggagt 294360
gcagtggcgc agtctcaact caccactgca gcctccacct cccaggttca agcgattctc 294420
atgcctcagc ctcccgagta gttgggatta caggcgcacg ccaccacgcc cagctaattt 294480
ttgcattttt actagagact ggtttcacca tgttgaccag gctggaccct atcctctttc 294540
aagcccccca ccccaggcat tgagggcaga gccaactacc tgcctgaacc aattagcata 294600
ttaaacgtaa acccagttag catatccaaa tagcagccca cagtgacatt ctgactgtca 294660
gaatgtggat tgcttgagcc caggagctca aggcttcggt gaacaaagat tgtgccacag 294720
cctgggcaac agagtaagtc cctgtcgatc gatagataga tgatagatag atagatagat 294780
agatagatag atagatagat agatagatag ataaattttt aaaaaaaata ataggccagg 294840
cacagtggct catgcctgta atcccagcac tttgggaggc cgaggcaggc agatcacctg 294900
aggtcaggag ttcgagacca gcctggccaa catggtgaaa ccctgtctct acaaaaatat 294960
aaaaatagcc aggcagatgt ctgtaatccc agctactcag gaggctgagg taggagaatc 295020
gcttgaactc tgaaggtgga ggttgcagtg agccgagatc atgccattgc actccagcct 295080
gagtgacaga gcgagactcc atctcaaaaa taataacaat aataaaaata ataataaatg 295140
ctctggcccc aaagtggcac attacatggt gcacacccca ttagcaagga ctcatcacat 295200
ggccctgcca accacaggag gaaccccccc atgtactcag gtaggagggc caggaaacac 295260
cgtcagagag ctttaatgac tcaccccatg actggggtga gggacgaggg actggctgca 295320
ggccaagggc atgtccgtgg cagtggagac ttgggaaagg ggaaaagacc tcctctgagc 295380
cacgcacagt ggctttcatc tgtaattcca gcactttggg aggctgaggt gggaggatct 295440
tgagcccagg aggtcgagac tgcagtgagc tatgtttgtg ccacggcact ctagcctggg 295500
cgacagagca aaaccctgtc tcaaaaatca aaataaaacc aaaaccaaaa cttcctctgt 295560
tggggatgct ccagggcgtc ccagccttga acagatgggt cactgcagta ataatcctat 295620
ggcagacact gtcccaaggc tgcacgcacg ttactttgat catcaaacaa ccaggtgata 295680
gccaggcatg gtggtgcgtg cctgtagtcc cagctactca ggaagctgaa gcgggagaat 295740
ctcttgaacc tgggaggcgg aggtaacagt gagtcgagat cacatgactg cacttcagcc 295800
tgggaacaga gagagactct gtcaaaaaaa aaaaaaaaac aggccagacg cggtggctca 295860
cgcatgtaat cgccagcact ttgggaggct gaggagggtg gatcacctga ggtcaggagt 295920
ttgagaccag cctggccaac atggtgaaac cccgtctcta ctaaaaatac aaaattagtt 295980
gggcgtggtg gtgcacacct gtaatcccag ctactcggga ggctgaggca ggagaatcgc 296040
ttgaacccag gaggcagagg ttgcagtgag ctgagattgc accattgcac tccagcctgg 296100
gcaacaagag tgaaactcca tctcaaaaaa aaaacaaaaa aaaaacaacc agccaggcgc 296160
ggtggcttac gcctgtaatc ccagcacttt gggaggccga ggcgtgtgga tcacccgagg 296220
ttaggagttc gagaccagct tgaccaacat ggtgaaactc cgtctctact aaaaatacaa 296280
aaaattagcc aggcatggtg gtgcatgtct gtaatcccag ctactcggga agctgagaca 296340
ggagaattgc ttgaacccag gagtcggagg ttgcagtgag ccaagctcgt gccactgcac 296400
tccagcctgg gcaacagagc aagactctgt ctaaaaaaaa aaaaaaaaca cacacacaca 296460
cacacaacaa ccaggtgagg caagtactct tgctatcatc tccatttcac agatggagaa 296520
actgagttac taagtggtag agtaacctaa gtcatgcagc cgataactgg gagacaagat 296580
tgggacccag gtcgcccagc tgttctccat gccgggctgt ctcctgcaca gctgctccat 296640
ggtcctggcc ccaccgaaaa ccagagccca caaggtcatt ccagcagcac tgcccagggc 296700
ctcctctggg ccaggccgtt ggggaactgg agaccccatg ggaccagaa agattggggt 296760
ctcgttctcg ggagcctatg gctttgcagc tgacccagag tccagctgac acccaggcag 296820
gcagtcaggg tctgtctaca cccccattgc aggaggagcc gacaaacagc agatggacgc 296880
tgagctgcgg aaggagatga tggcgatttg gcccaatctg tcccagaaga cgctagacct 296940
gctggtcaca cctcacaagt gtaagagctg agcccagccc tgggatccaa tccaccagga 297000
cagatggagg gggagggaaa ggggaggcct ggggagagtg ttggcctggg ctggtataca 297060
cagggaccca ggacaagggc cccaaagagg cctgcccttg gtgagctcac cgtgtgtgtg 297120
cccccagcca cggacctcac cgtggggaag atctacgcag ccatgatgat catggagtac 297180
taccggcaga gcaaggccaa gaagctgcag gccatgcgcg aggagcaggt gcgctgttcg 297240
ccgctctggg gacatctggg ctggggacag tggcttgcat gtcaccacgg gaaccaactg 297300
gaatatgagg gtggctgagc cccagggcag gtccctgaaa agtaggggct gtgcacagca 297360
gctcacacct gcaatctcag tgctttgaga ggccagggca gagggatcgt ttgagaccag 297420
gatgagacca ccctgggcaa cacagtgaga ctccatctct acaaaataaa acattagcca 297480
ggcatggtgg tgcacacctg tagtcccagc tatttaggag gccaagatgg gaggatcact 297540
tgaggccagg agtgggagac cagtctgggc aacatagaaa gacccatatc tctacaaaaa 297600
aaaaataaaa ttagctgcat gtggcgccat gcacctgtgg tcccagctac ttgggaggct 297660
gaggcaggag aatcacttga acctgggagg tggaggttgc agcaagccaa gatcaagcca 297720
ctgcactcca gcccgggtga taagagcagg actctatctc aaaaaaaaaa aaaaaaaaaa 297780
aaaaaaaagt tcttgccaag gacacatcat gtggattcat tcttcattca gctgctccac 297840
caacacttat tgagtattac tgtgtgcagg gcgctgttct cagtcctcgg ggatgcaccc 297900
atggggaaaa taggccagaa tccctgccct cagggagcag acattccaag tggggaaatg 297960
ccaatggtag caaatgactg aatcgtgcaa catccagcaa agagaaagaa agtgtcgtgg 298020
gggaaagtgg agaagaatcc agaagatagg agtatccagg ggaggagggg atgcggtggg 298080
aaatgggtag ttggggagcc tccctgagaa agtgacatgt gagcaaaggc ttgaaggaaa 298140
aggggagagg gagtgagcta agcaatacct ggaagggtgt tccaggcaga ggaaacagcc 298200
agtgcaaagg ctctgaggct ggaccgtgcc tgggttgttt gggtaacagc aaagaggcca 298260
gtgtggtgga aaagagcagg gaggagacaa gggcaaggag gtgacagggc agatccttca 298320
gggccatggg agctgcagga aggactctgg ctttttcccc aagcaagtgg gagccatgga 298380
gggttctaag caaaggaggg ataggacctg actcaagtgc tcatgggcgc cctctggtgg 298440
ctcttgtgga acagtggggt tgaaggtagg agcgggagac ctgggagaag gtgcctgcag 298500
tgagagatga ggacgtggga ccaggctggg gctatgactt gggtggagga gtgagaagtg 298560
gtccagttct gcgtggaatt ggaagggtct agatggatga gacctgagag agtgtgtgtg 298620
tgtgtgtgtg tgtatactgg ggatgtcgca atgccttctg ggtaccaccg tcccaccacc 298680
ccacccttgt ccacacactg ctctctgccc cattccccag gaccggacac ccctcatgtt 298740
ccagcgcatg gagcccccgt ccccaacgca ggaaggggga cctggccaga acgccctccc 298800
ctccacccag ctggacccag gaggagccct gtgagtgtca cccctgccag ggaggtggag 298860
tgtgggggtg ccgtggtccc cacgttctgg aagctgccca agcgcccact gctaccccgg 298920
cctctgtccc ccatgcagga tggctcacga aagcggcctc aaggagagcc cgtcctgggt 298980
gacccagcgt gcccaggaga tgttccagaa gacgggcaca tggagtccgg aacaaggccc 299040
ccctaccgac atgcccaaca gccagcctaa ctctcaggtg cctctgtccc ccaactcccc 299100
aatggctccc agggcccggg tggttcaggt ggaagggatc tgggcccccc acacacacac 299160
acctgcagct ccctccctct gcagacacca gggatctgga ggtcaggccc cagagctcat 299220
ctggctttgc catctgctcc gcagtccgtg gagatgcgag agatgggcag agatggctac 299280
tccgacagcg agcactacct ccccatggaa ggccagggcc gggctgcctc catgccccgc 299340
ctccctgcag agaaccaggt gagggctttc accactgccc tggggctgga cccctcactc 299400
tgcactgggt agggccaggc ccccccacaa gcagcccagt gcatcccctc cctgccggac 299460
tcaggcctgg gtagggactc cttcagtctc tgaagcagtc tgcaggcccc acccaccacc 299520
tggtcacacc tggagcacct gcagaccctc ctccctcaca gaggacagag aggaaagtgc 299580
tccccctggg gcagagggca gtggccactg caaaatggtc tctggctgcc ctggttggag 299640
gctgcagaca ggggaggttg tggaagattt gtgggtgcag cagggttcaa cagggccagc 299700
tgagacctgc cacgaagatc accccctacac aaacacacac acacatgctc aacatacatg 299760
cacacacatg tgcagctgtg cgcctactca gatgcttgca tacacacacg tgtgtgcacg 299820
tgggcatata cacactgcac atgtactcac acatgcacac atgtacgtgc acacgtgtct 299880
gcatatggga acttggcagg tcctaggata cagtagcaga gtctggggtg ggtctggggg 299940
cagctgggct cgtattttct gtctggtctc tgtgggagtc attggggggc acaggggtgt 300000
gtgcttgatg tgtgtctgtg tgtggccgct tcacccagct gccaggccca cctgcaggtg 300060
atcccgttgc cttggactca tgggacagag ggcccagagg catagctggc tgcccacccg 300120
gcctgaacag cgggggccca tgcacgcagc ccgcctctgg aggagaacag ggcatggctg 300180
tgagagcctg gcccgggtgc gtggcatgtg tggctgtggc gagctttccg tgtgccgtgt 300240
gtggcgtctg cacggggcag gaggctgtgc tgtgcctggc tggaccaggg tcacctgagg 300300
gcctggcctc tggctgctgg gaacgtgggt tggggagcac ccagcgtgca tgctgctgct 300360
ccctcaggac cgagctgctg ggccccagga gagggttggg acaagcccag ctgacggcca 300420
ccacatggaa gctttgagca tcggccggag ccaggggttg gggtgtgcat cgcatgaggc 300480
agagcccagg gccaggggct cgaggctgcg ccgtcctgtc tttcggtccc atgcctctgc 300540
catttgtctg tctgcatctc ctgtctgtct cctctgtacc catgggaata gaggacgccc 300600
agccccgggg gcctgggaca cccacccgcc aggactttaa cttttctttt cctccctgcc 300660
ttctccctcc gatttctctt gatgccagtg ccactcccct ccttggcttc ttctccatgc 300720
accacctcct cactctccct cttgcctttt atatttattt tcttctttct gttttttctg 300780
tgtgcaccat cccatggggc tgtgacagag gagaaggggc cggccacgtg ggaataacct 300840
cagtgtatgt accgcgcctg cccagcgccc agcagggctc cggccccctc ttcctcccca 300900
ccccccctcc agggagtccc gtcatctctc accgtccccg gaccccaccc tttctttggc 300960
aatcgcaccc tctcccctcc atggagccca atccttgtgt gtggtgtcct gtgtgtgccc 301020
ctcacccata agccctggtg ggcggggcca tccccatcct cacccctacc cccttttctt 301080
cagggccccc cacgccggag gacactggct ctccaagagc ctggcccact ctgcacctct 301140
ttctgggggg cttcttctcc tgacaccacc accaacccct ggtcctgcag ctcctacctg 301200
gagcagggcc accagcgctc agctgggctg gaccctggga ggcgggcgtc tgccccatct 301260
ccctccttcc ctcctctgcc tgctgcagag aaacctgtgt gtcagggctt gacccaggga 301320
tgaagcacca gggaaaagag tgggccccca gagcctccag tgcctgggta tcccccaccc 301380
ccacccagag ctccctagct tggcctcac cagaaggact cagacttgtg ggggcagcga 301440
gcacagcccc gttagccggg aggacccaaa gctgccatgc cgggcacctg gtcctgagcc 301500
cataggtcag ccagccacag tcggaggctt ctcaccctcc caggagagca agctggggca 301560
gggatgagtg cggcagtcca gggctcccag gtttgcaccc tggatgtgga gagggcttcc 301620
ctctggccag cctgagcctg cccaactgtg gctgggcccc caggactgga gagtgaggat 301680
cagatctttc tggtcagaac ccaggatggg ctcaaaagga gcagtcctgt ctctgaggga 301740
cagaggaatc ctcaggctcc accctcagag gcctggccac acccagagcc ctgattgatc 301800
agggggagcc aaggccccat ggcatcccct ggcccctgcc ccaggatggt cacaccgcag 301860
tcaccgaagg ccaccaccag gctgccacaa tggggcagga aggaccggga ccacttggtg 301920
ctagctgctg accccagccc accggcctgt cccctccccc agaccatctc agacaccagc 301980
cccatgaagc gttcagcctc cgtgctgggc cccaaggccc gacgcctgga cgattactcg 302040
ctggagcggg tcccgcccga ggagaaccag cggcaccacc agcggcgccg cgaccgcagc 302100
caccgcgcct ctgagcgctc cctgggccgc tacaccgatg tggacacagg tgggcagccc 302160
tgtggtgctc agggacaagc agaacagagg agaggagagg ggaggagaag gcagggcgga 302220
ggagacacta aggaagaaga aagggagagg cctccatgga gaggggacag agggggccag 302280
gcagcagctg caggaacctg ggtactaccc cctcccccca acccactgac ctgcctcggt 302340
tcaggggatc tctagggccc ccacaccttc caggtggcct cctgtgtgtg catctgcccc 302400
acctctccct cacgaccacc tgtgtgtctg tctgaccctc acccggccca ggcttgggga 302460
cagacctgag catgaccacc caatccgggg acctgccgtc gaaggagcgg gaccaggagc 302520
ggggccggcc caaggatcgg aagcatcgac agcaccacca ccaccaccac caccaccacc 302580
atcccccgcc ccccgacaag gaccgctatg cccaggaacg gccggaccac ggccgggcac 302640
gggctcggga ccagcgctgg tcccgctcgc ccagcgaggg ccgagagcac atggcgcacc 302700
ggcaggtggg tgcggctgca agtgacccca ggctgggctc ggccgggagg cggggaggag 302760
agaaggggat accccatcca acagccactc taggcaaagg tccccggatc ccggctgtga 302820
ccacctccca tcctgccccc aagccaccgg ggtgcccggc ggccggagcg gacacggatc 302880
cccaccacac cagctgccta tgctgtcccc ccagccccct tgcccacccg ccgccccctc 302940
cccgccgccc gcagctgctt gctcctcggt tgtggatcat atttgagttc tgggccgtgc 303000
cgcccgacct ttcactttcc tttaacccgg cttctgtttt tgtttcaatt atgatttctg 303060
tcctctggac gcctgtgagt aatttttgaa acttctgcta tttttaaccc cgaaacttac 303120
aaaactccat ttctcatttc tcttttcact ttgttgtgtt ggttttcgac tcctcccctc 303180
cctgtctcac tccccctcct cccctccctc ctccctgtgg ctgttgcttt tttccattca 303240
atgtcctgtg tccccccctct cctcctcctc ctcctcctcc ccctcccccct cctccctctc 303300 ctcccggccc ctctcccttc gctcccctct cttcctccca atcccgtgtc tcctttgatt 303360
ttgttgtatc ttttttttttg atttcctttg tttcaatttt cgtgtagggc agtagttccg 303420
taagtggaag cccagccccc tcaacatctg gtaccagcac tccgcggcgg ggccgccgcc 303480
agctccccca gaccccctcc accccccggc cacacgtgtc ctattcccct gtgatccgta 303540
aggccggcgg ctcggggccc ccgcagcagc agcagcagca gcagcagcag cagcagcagc 303600
aggcggtggc caggccgggc cgggcggcca ccagcggccc tcggaggtac ccaggcccca 303660
cggccgagcc tctggccgga gatcggccgc ccacgggggg ccacagcagc ggccgctcgc 303720
ccaggatgga gaggcgggtc ccaggcccgg cccggagcga gtcccccagg gcctgtcgac 303780
acggcggggc ccggtggccg gcatctggcc cgcacgtgtc cgaggggccc ccgggtcccc 303840
ggcaccatgg ctactaccgg ggctccgact acgacgaggc cgatggcccg ggcagcgggg 303900
gcggcgagga ggccatggcc ggggcctacg acgcgccacc ccccgtacga cacgcgtcct 303960
cgggcgccac cgggcgctcg cccaggactc cccgggcctc gggcccggcc tgcgcctcgc 304020
cttctcggca cggccggcga ctccccaacg gctactaccc ggcgcacgga ctggccaggc 304080
cccgcgggcc gggctccagg aagggcctgc acgaacccta cagcgagagt gacgatgatt 304140
ggtgctaagc ccgggcgagg tggcgcccgc ccggcccccc acgcacccca cgcacacacc 304200
ccacccgagg agccgcgcag aggccgcggg ggcccagcac agagggcccg ggagagggcc 304260
agccgggaga ccccagactc tggagaggcc agggctgggc cacaagggtg tcccgcagag 304320
accctcggcc aaaagagacc ctcctgggca gccacggcgc cccccaacca gccccgatcc 304380
ccccacccac gacaggggct ctcgggtggg aggcagggag cagacaaacc acacagccaa 304440
gggatttgaa ttaactcagc catttttgga gaactttggg gaacatgaaa aaaaaaaaaa 304500
aaaaaaaaaa aaaaaacatt tttaaaagaa aaaacgggga gaaaaaaata gcttctattg 304560
atgagtttta tcatctcaat tgaatctttc ctttccctga tgaagacagc tggtggccga 304620
gtgcggcaaa gaagccagaa ggaaccagaa tcccagtgcc ctacacccac caccagacac 304680
actcacaccc acacacgttc tcagacacac acaagagtgc ttgccggtta taccaaaccc 304740
tactattact gcctgcagaa atcaatttaa aaaaataata ataacaataa acaattttaa 304800
aaaggacaaa aaaattaatg attgagaaaa gaggcatttt tttctgacat ttggtcctgc 304860
ttgaaacaac aaaagaagaa gaaaaaccca ccatcaccac cgattccttt gcttcttttt 304920
tccttttttc ctaccttgtt tgaaaaccgt gggcttggga ctgtgaatta ttgcatgaca 304980
ttcaaaaaga aaaaaaaaat aaaaaaaagt tgaatcaaag ggcttttgga taggagtggt 305040
ctttgtccct tggctaggtg ctgcctgggt gggtctctct tggggaatca tacaaagagg 305100
cacttctttg ttagctccta gaagcactgt ttgaaagcga caaggaggcc gggcatcatg 305160
cacgcctgta atcccagcac tttgggaggc taaggcagat ggatcacttg aggtcaggag 305220
ttcgagacca gcccgaccaa catggcaaaa cctcatctct actaaaaata caaaaaaaat 305280
tagccatgcg tggttgcaca aactgtaatc ccagctactc cggaggctga ggcatgagaa 305340
tcacctgagc ctgagaggcg gaggttagca gtgagccaag atcccaccac tgcactccag 305400
cctgagtgac ggaatgagac tcttgtctca aaataaaaaa aaaaaaggca gggcgcggtg 305460

-continued

```
gctcacgcct ataatcccag cactttggga ggccgaggtg ggtggatcac atgaggtcag 305520
gagttcacaa ccagcctggc caacatagtg aaacgccgtc tttactacaa atacaaaaat 305580
tagccacgcg tggtggtggg tgcctgtaat cccagctact cgggaagctg aggcaggaga 305640
attgcttgaa cccaggaggc ggaggttgca gtgaaccaag atcgtgccac tgcactccaa 305700
cctgggtgac agagcaagac tccatcttag ataattaata ataataattt ggtctcgtgg 305760
acaccaaccc ccgcccccac gaagtgtttc agccatcccc agagtccaat accccttga 305820
gagcttctgt tctcacaaca gtacctgacc catagcaagc tactattgac tatcaccatt 305880
actactgtag cattaaggca aacattttga acaggtcttg ttccagacaa caggccctgc 305940
ttgagcttac cttgggtaag aaatctgcag actccagata gcaagacagg tgtaagtcct 306000
tctaaaataa tggtaagcca aatgtggtgg cacacacctg tagtcccagc tgttcaggag 306060
gctgaggcag gaggatcact tgagcccacg aggtcaagac cagctatgat cacacctgtg 306120
aataaccatt gcattccagc ctgggtgacg tagaaagatc ccatctctaa aaaaattaaa 306180
agtaaaaata aataaataaa ataatggcat ctaggaaaag atcagtccaa cgagaagtca 306240
aagttttgag gtcgagtgcg gtgtctgact cttgtaatct caacactttg ggagaatcac 306300
ttgaggccag tagttcaaga ccagcctggg caacatagca agacgctgtc tctaaaaaaa 306360
aaagtttgtt ttttttaagg ctgggtacag aggctcacgc ctgtaatccc agcactttgg 306420
gaggccaagg tgagcagatc accaagtcag gagtttgaga ccagcctggc caacatagtg 306480
aaaccctgtc tctactaaaa ataaaaaaat tagccaggtg tggtggtgca tgcctatatt 306540
cccagatact tggcaggctg aggcaggaaa atcgcttgaa cctgggaggc agaggttgca 306600
gtgagctgag attgcgtcac tgcactgcag cctgggcgac agagtgagac tacgtctcaa 306660
aaaaaaaaaa aaaaaaaaat ggaatggaag ggagggaggg aggggtttaa ctttctaacc 306720
aggcaatctg gcaaccacca caggcttcta aacaagctgc ccatccattg cagagctggc 306780
ctctggtccc cctcccatgg tgctggggtt gagtgtgtcc aggagccact ggagtaagcc 306840
agggtttgtg caattccctc tgctgtcaat gaggctgcag ccatctgtcc tcccaggaat 306900
gaagttcact accgaagccc cccatgagcc ctgaactcaa aggccaagtc tatgcccgag 306960
tgccaagagg tagacccaag gcctccacag tgcacatcat caggctagag tgttagttg  307019
```